US008283148B2

(12) United States Patent
Sorge et al.

(10) Patent No.: US 8,283,148 B2

(45) Date of Patent: *Oct. 9, 2012

(54) DNA POLYMERASE COMPOSITIONS FOR QUANTITATIVE PCR AND METHODS THEREOF

(75) Inventors: Joseph A. Sorge, Wilson, WY (US); Reinhold Dietrich Mueller, San Diego, CA (US); Gothami Padmabandu, San Diego, CA (US); Nick Roelofs, San Diego, CA (US); Holly H. Hogrefe, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 2021 days.

This patent is subject to a terminal disclaimer.

(21) Appl. No.: 10/734,563

(22) Filed: Dec. 12, 2003

(65) Prior Publication Data

US 2005/0069908 A1 Mar. 31, 2005

Related U.S. Application Data

(63) Continuation-in-part of application No. 10/408,601, filed on Apr. 7, 2003, now abandoned, which is a continuation-in-part of application No. 10/298,680, filed on Nov. 18, 2002, now abandoned, which is a continuation-in-part of application No. 10/280,962, filed on Oct. 25, 2002, now abandoned.

(51) Int. Cl.
*C12N 9/12* (2006.01)
*C12P 19/34* (2006.01)

(52) U.S. Cl. ...................................... 435/194; 435/91.1

(58) Field of Classification Search ........................ None
See application file for complete search history.

(56) References Cited

U.S. PATENT DOCUMENTS

| | | | | |
|---|---|---|---|---|
| 5,489,523 | A | 2/1996 | Mathur | 435/194 |
| 6,333,183 | B1 | 12/2001 | Evans et al. | 435/194 |
| 6,395,526 | B1 | 5/2002 | Uemori et al. | 435/194 |
| 6,607,883 | B1 | 8/2003 | Frey et al. | 435/6 |

FOREIGN PATENT DOCUMENTS

| | | | |
|---|---|---|---|
| EP | 0 870 832 | A1 | 10/1998 |
| EP | 0 693 078 | B1 | 6/1999 |
| EP | 0 922 765 | A1 | 6/1999 |
| EP | 1 088 891 | A1 | 4/2001 |
| EP | 1 132 474 | A1 | 9/2001 |
| JP | 2001-269188 | | 10/2001 |
| WO | WO 01/23583 | A2 | 4/2001 |
| WO | 0132887 | | 5/2001 |
| WO | WO 01/92501 | A1 | 12/2001 |
| WO | WO03/060144 | | 7/2003 |
| WO | WO03/089637 | | 10/2003 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

Arezi, B. et al., "Amplification efficiency of thermostable DNA polymerases", *Analytical Biochemistry*, 2003, 321:226-235.

Fogg, M.J. et. al., "The Structural Basis for Template Strand Uracil Recognition by Archaeal DNA Polymerases", *FASEB Summer Research Conference*, poster abstract, Jun. 2002, (20).

Hogrefe, H.H. et al., "Archael dUTPase enhances PCR amplifications with archael DNA polymerases by preventing dUTP incorporation", *PNAS*, 2002, 99(2):596-601.

Pavlov, A.R. et al., "Helix-hairpin-helix motifs confer salt resistance and processivity on chimeric DNA polymerases", *PNAS*, 2002, 99(21):13510-13515.

Evans, S.J. et. al., "Improving dideoxynucleotide-triphosphate utilisation by the hyper-thermophilic DNA polymerase from the archaeon *Pyrococcus furiosus", Nucleic Acids Research*, 2000, 28(5):1059-1066.

Greagg, M.A. et. al., "A read-ahead function in archaeal DNA polymerases detects promutagenic template-strand uracil", *Proceedings of the National Academy of Sciences USA*, 1999, 96(16):9045-9050.

Sakagacm, A.Y. et al., "Cautionary Note on the Use of dUMP-Containing PCR Primers with *Pfu* and $Vent_R$® DNA Polymerases", 1996, *BioTechniques*, 21:368-370.

Slupphaug, G. et al., "Low Incorporation of dUMP by Some Thermostable DNA Polymerases May Limit Their Use in PCR Amplifications", 1993, *Anal. Biochem*., 211:164-169.

Longo, M.C. et al., "Use of uracil DNA glycosylase to control carry-over contamination in polymerase chain reactions", 1990, *Gene*, 93:125-128.

International Search Report for PCT/US03/33997, dated Dec. 10, 2004.

Evans, et al. Improving dideoxynucleotide-triphosphate utilisation by the hyper-thermophilic DNA polymerase from the archaeon *Pyrococcus furiosus*. Nucleic Acids Research. Mar. 2000, vol. 28, No. 5, pp. 1059-1066.

Connolly et al., "Uracil Recognition by Archaeal Family B DNA Polymerase", Biochemical Society Transactions (2003), V. 31, Part 3, pp. 699-702.

Fogg et al., "Structural Basis for Uracil Recognition by Archaeal Family B DNA Polymerases", Nature Structural Biology (2002), V. 9, No. 12, pp. 922-927.

Gardner et al., "Determinants of Nucleotide Sugar Recognition in an Archaeon DNA Polymerase", Nucleic Acids Research (1999), V. 27, No. 12, pp. 2545-2553.

Supplementary European Search Report based on EP 03809647 dated Sep. 22, 2005.

Guo, et al. "Protein Tolerance to Random Amino Acid Change", (2004) Proc.Natl.Acad.Sci., vol. 101(25), pp. 9205-9210.

(Continued)

*Primary Examiner* — Richard Hutson

(57) ABSTRACT

The invention relates to the generation and characterization of Archaeal DNA polymerase mutants with deficient 3'-5' exonuclease activity and reduced base analog detection activity. The invention further provides for Archaeal DNA polymerase mutants with deficient 3'-5' exonuclease activity and reduced base analog detection activity containing additional mutations that modulate other DNA polymerase activities including DNA polymerization or reverse transcriptase activity. The invention also discloses methods and applications of DNA polymerases with deficient 3'-5' exonuclease activity and reduced base analog detection activity.

25 Claims, 62 Drawing Sheets

OTHER PUBLICATIONS

Bonnin, et al. "A Single Tyrosine Prevents Insertion of Ribonucleotides in the Eukaryotic-type Phi29 DNA Polymerase" (1999) J.Mol.Biol., vol. 291(1), pp. 241-251.

International Search Report received in PCT/US04/41899, dated Nov. 30, 2007.

Savino, C. et al., "Insights Into DNA Replication: The Crystal Structure of DNA Polymerase B1 from the Archaeon *Sulfolobus solfataricus*", Structure, vol. 12, 2001-2008, Nov. 2004.

* cited by examiner

Figure 1. Oligonucleotide Primers for QuikChange Mutagenesis

V93E#1

5'-gAACATCCCCAAgATgAACCCACTATTAgAgAAAAAg-3' (SEQ ID NO: 6)

V93E#2

5'-CTTTTTCTCTAATAgTgggTTCATCTTggggATgTTC-3' (SEQ ID NO: 7)

V93R#1

5'-gAACATCCCCAAgATAgACCCACTATTAgAgAAAAAg-3' (SEQ ID NO: 8)

V93R#2

5'-CTTTTTCTCTAATAgTgggTCTATCTTggggATgTTC-3' (SEQ ID NO: 9)

V93N#1

5'-gAACATCCCCAAgATAACCCCACTATTAgAgAAAAAg-3' (SEQ ID NO: 10)

V93N#2

5'-CTTTTTCTCTAATAgTggggTTATCTTggggATgTTC-3' (SEQ ID NO: 11)

V93H#1

5'-gAACATCCCCAAgATCACCCCACTATTAgAgAAAAAg-3' (SEQ ID NO: 12)

V93H#2

5'-CTTTTTCTCTAATAgTggggTgATCTTggggATgTTC-3' (SEQ ID NO: 13)

V93X (for saturation mutagenesis; obtained V93G and V93L mutants from library)

5'-(Phosphate)gAACATCCCCAAgATNNKCCCACTATTAgAgAAAAAg-3'

(SEQ ID NO: 14)

V93K#1

5'-gAACATCCCCAAgATAAACCCACTATTAgAg-3' (SEQ ID NO: 43)

V93K#2

5'-CTCTAATAgTgggTTTATCTTggggATgTTC-3' (SEQ ID NO: 44)

QCM#1 5'-(Phosphate)gAACATCCCCAAgATgCACCCACTATTAgAgAAAAAg-
(SEQ ID NO: 45)'
Alanine QCM#2 5'-(Phosphate)gAACATCCCCAAgATgACCCCACTATTAgAgAAAAAg-3'
(SEQ ID NO: 46)
Aspartic Acid QCM#3 5'-(Phosphate)gAACATCCCCAAgATTgCCCCCACTATTAgAgAAAAAg-3'
(SEQ ID NO: 47)
Cysteine QCM#4 5'-
(Phosphate)gAACATCCCCAAgATATACCCACTATTAgAgAAAAAg-3'
(SEQ ID NO: 48)
Isoleucine QCM#5 5'-(Phosphate)gAACATCCCCAAgATATgCCCACTATTAgAgAAAAAg-3'
(SEQ ID NO: 49)
Methionine QCM#6 5'-(Phosphate)gAACATCCCCAAgATTTCCCCACTATTAgAgAAAAAg-3'
(SEQ ID NO: 50)
Phenylalanine QCM#7 5'-(Phosphate)gAACATCCCCAAgATCCTCCCACTATTAgAgAAAAAg-3'
(SEQ ID NO: 51)
Proline QCM#8 5' Phosphate)gAACATCCCCAAgATAgCCCCACTATTAgAgAAAAAg-3'
(SEQ ID NO: 52)
Serine QCM#9 5'-(Phosphate)gAACATCCCCAAgATACACCCACTATTAgAgAAAAAg- 3'
(SEQ ID NO: 53)
Threonine QCM#10 5'-(Phosphate)gAACATCCCCAAgATTACCCCACTATTAgAgAAAAAg-3'
(SEQ ID NO: 54)
Tyrosine QCM#11 5'-(Phosphate)gAACATCCCCAAgATTggCCCACTATTAgAgAAAAAg-3'
(SEQ ID NO: 55)
Tryptophan Figure 3: Protein concentration, unit concentration, and specific activity of the purified Pfu V93R and V93E mutants.

| *Pfu* mutant | Protein concentration | PCR Unit concentrati | Specific activity (U/mg) |
|---|---|---|---|
| *Pfu* | 0.0258 µg/µl | 2.5U/µl | $9.7 \times 10^4$ |
| *Pfu* V93R | 45 µg/µl | 6250U/µl | $1.4 \times 10^5$ |
| *Pfu* V93E | 35 µg/µl | 6250U/µl | $1.8 \times 10^5$ |

FIGURE 6A

PFU DNA POLYMERASE (SEQ ID NO: 17)
V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93N MUTANT: GTT CAN BE MODIFIED TO BE = AAC, AAU (ALL CODONS FOR ASPARAGINE)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATGTTC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

KOD DNA POLYMERASE (SEQ ID NO: 18)
V93R MUTANT: GTC CAN BE MODIFIED TO BE = AGA, AGG, CGA, CGC, CGG, CGT (ALL POSSIBLE CODONS FOR ARGININE)
V93E MUTANT: GTC CAN BE MODIFIED TO BE = GAA, GAG (ALL CODONS FOR GLUTAMIC ACID)
V93D MUTANT: GTC CAN BE MODIFIED TO BE = GAT, GAC (ALL CODONS FOR ASPARTIC ACID)
V93K MUTANT: GTC CAN BE MODIFIED TO BE = AAA, AAG (ALL CODONS FOR LYSINE)
V93Q MUTANT: GTC CAN BE MODIFIED TO BE = CAA, CAG (ALL CODONS FOR GLUTAMINE)
V93N MUTANT: GTC CAN BE MODIFIED TO BE = AAC, AAU (ALL CODONS FOR ASPARAGINE)

ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACGTCC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CTTGA 2325

Vent DNA POLYMERASE (SEQ ID NO: 19)
V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93Q MUTANT: GTT CAN BE MODIFIED TO BE = CAA, CAG (ALL CODONS FOR GLUTAMINE)
V93N MUTANT: GTT CAN BE MODIFIED TO BE = AAC, AAU (ALL CODONS FOR ASPARAGINE)

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACGTTC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325

Deep Vent (SEQ ID NO: 20)

V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93Q MUTANT: GTT CAN BE MODIFIED TO BE = CAA, CAG (ALL CODONS FOR GLUTAMINE)
V93N MUTANT: GTT CAN BE MODIFIED TO BE = AAC, AAU (ALL CODONS FOR ASPARAGINE)

```
ATGATACTTG ACGCTGACTA CATCACCGAG GATGGGAAGC CGATTATAAG GATTTTCAAG     60
AAAGAAAACG GCGAGTTTAA GGTTGAGTAC GACAGAAACT TTAGACCTTA CATTTACGCT    120
CTCCTCAAAG ATGACTCGCA GATTGATGAG GTTAGGAAGA TAACCGCCGA GAGGCATGGG    180
AAGATAGTGA GAATTATAGA TGCCGAAAAG GTAAGGAAGA AGTTCCTGGG GAGGCCGATT    240
GAGGTATGGA GGCTGTACTT TGAACACCCT CAGGACGTTC CCGCAATAAG GGATAAGATA    300
AGAGAGCATT CCGCAGTTAT TGACATCTTT GAGTACGACA TTCCGTTCGC GAAGAGGTAC    360
CTAATAGACA AAGGCCTAAT TCCAATGGAA GGCGATGAAG AGCTCAAGTT GCTCGCATTT    420
GACATAGAAA CCCTCTATCA CGAAGGGGAG GAGTTCGCGA AGGGGCCCAT TATAATGATA    480
AGCTATGCTG ATGAGGAAGA AGCCAAAGTC ATAACGTGGA AAAAGATCGA TCTCCCGTAC    540
GTCGAGGTAG TTTCCAGCGA GAGGGAGATG ATAAAGCGGT TCCTCAAGGT GATAAGGGAG    600
AAAGATCCCG ATGTTATAAT TACCTACAAC GGCGATTCTT TCGACCTTCC CTATCTAGTT    660
AAGAGGGCCG AAAAGCTCGG GATAAAGCTA CCCCTGGGAA GGGACGGTAG TGAGCCAAAG    720
ATGCAGAGGC TTGGGGATAT GACAGCGGTG GAGATAAAGG GAAGGATACA CTTTGACCTC    780
TACCACGTGA TTAGGAGAAC GATAAACCTC CCAACATACA CCCTCGAGGC AGTTTATGAG    840
GCAATCTTCG GAAAGCCAAA GGAGAAAGTT TACGCTCACG AGATAGCTGA GGCCTGGGAG    900
ACTGGAAAGG GACTGGAGAG AGTTGCAAAG TATTCAATGG AGGATGCAAA GGTAACGTAC    960
GAGCTCGGTA GGGAGTTCTT CCCAATGGAG GCCCAGCTTT CAAGGTTAGT CGGCCAGCCC   1020
CTGTGGGATG TTTCTAGGTC TTCAACTGGC AACTTGGTGG AGTGGTACCT CCTCAGGAAG   1080
GCCTACGAGA GGAATGAATT GGCTCCAAAC AAGCCGGATG AGAGGGAGTA CGAGAGAAGG   1140
CTAAGGGAGA GCTACGCTGG GGGATACGTT AAGGAGCCGG AGAAAGGGCT CTGGGAGGGG   1200
TTAGTTTCCC TAGATTTCAG GAGCCTGTAC CCCTCGATAA TAATCACCCA TAACGTCTCA   1260
CCGGATACGC TGAACAGGGA AGGGTGTAGG GAATACGATG TCGCCCCAGA GGTTGGGCAC   1320
AAGTTCTGCA AGGACTTCCC GGGGTTTATC CCCAGCCTGC TCAAGAGGTT ATTGGATGAA   1380
AGGCAAGAAA TAAAAAGGAA GATGAAAGCT TCTAAAGACC CAATCGAGAA GAAGATGCTT   1440
GATTACAGGC AACGGGCAAT CAAAATCCTG GCAAACAGCT ATTATGGGTA TTATGGGTAC   1500
GCAAAAGCCC GTTGGTACTG TAAGGAGTGC GCAGAGAGCG TTACGGCCTG GGGGAGGGAA   1560
TATATAGAGT TCGTAAGGAA GGAACTGGAG GAAAAGTTCG GGTTCAAAGT CTTATACATA   1620
GACACAGATG GACTCTACGC CACAATTCCT GGGGCAAAAC CCGAGGAGAT AAAGAAGAAA   1680
GCCCTAGAGT TCGTAGATTA TATAAACGCC AAGCTCCCAG GGCTGTTGGA GCTTGAGTAC   1740
GAGGGCTTCT ACGTGAGAGG GTTCTTCGTG ACGAAGAAGA AGTATGCGTT GATAGATGAG   1800
GAAGGGAAGA TAATCACTAG GGGGCTTGAA ATAGTCAGGA GGGACTGGAG CGAAATAGCC   1860
AAAGAAACCC AAGCAAAAGT CCTAGAGGCT ATCCTAAAGC ATGGCAACGT TGAGGAGGCA   1920
GTAAAGATAG TTAAGGAGGT AACTGAAAAG CTGAGCAAGT ACGAAATACC TCCAGAAAAG   1980
CTAGTTATTT ACGAGCAGAT CACGAGGCCC CTTCACGAGT ACAAGGCTAT AGGTCCGCAC   2040
GTTGCCGTGG CAAAAAGGTT AGCCGCTAGA GGAGTAAAGG TGAGGCCTGG CATGGTGATA   2100
GGGTACATAG TGCTGAGGGG AGACGGGCCA ATAAGCAAGA GGGCTATCCT TGCAGAGGAG   2160
TTCGATCTCA GGAAGCATAA GTATGACGCT GAGTATTACA TAGAAAATCA GGTTTTACCT   2220
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAGTAA                2328
```

JDF-3 (SEQ ID NO: 21)

V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93Q MUTANT: GTT CAN BE MODIFIED TO BE = CAA, CAG (ALL CODONS FOR GLUTAMINE)
V93N MUTANT: GTT CAN BE MODIFIED TO BE = AAC, AAU (ALL CODONS FOR ASPARAGINE)

ATGATCCTTGACGTTGATTACATCACCGAGAATGGAAAGCCCGTCATCAGGGTCTTCAAGAAGGAGAACGGCGAGTT
CAGGATTGAATACGACCGCGAGTTCGAGCCCTACTTCTACGCGCTCCTCAGGGACGACTCTGCCATCGAAGAAATCA
AAAAGATAACCGCGGAGAGGCACGGCAGGGTCGTTAAGGTTAAGCGCGCGGAGAAGGTGAAGAAAAAGTTCCTCGGC
AGGTCTGTGGAGGTCTGGGTCCTCTACTTCACGCACCCGCAGGACGTTCCGGCAATCCGCGACAAAATAAGGAAGCA
CCCCGCGGTCATCGACATCTACGAGTACGACATACCCTTCGCCAAGCGCTACCTCATAGACAAGGGCCTAATCCCGA
TGGAAGGTGAGGAAGAGCTTAAACTCATGTCCTTCGACATCGAGACGCTCTACCACGAGGGAGAAGAGTTTGGAACC
GGGCCGATTCTGATGATAAGCTACGCCGATGAAAGCGAGGCGCGCGTGATAACCTGGAAGAAGATCGACCTTCCTTA
CGTTGAGGTTGTCTCCACCGAGAAGGAGATGATTAAGCGCTTCTTGAGGGTCGTTAAGGAGAAGGACCCGGACGTGC
TGATAACATACAACGGCGACAACTTCGACTTCGCCTACCTGAAAAAGCGCTGTGAGAAGCTTGGCGTGAGCTTTACC
CTCGGGAGGGACGGGAGCGAGCCGAAGATACAGCGCATGGGGGACAGGTTTGCGGTCGAGGTGAAGGGCAGGGTACA
CTTCGACCTTTATCCAGTCATAAGGCGCACCATAAACCTCCCGACCTACACCCTTGAGGCTGTATACGAGGCGGTTT
TCGGCAAGCCCAAGGAGAAGGTCTACGCCGAGGAGATAGCCACCGCCTGGGAGACCGGCGAGGGGCTTGAGAGGGTC
GCGCGCTACTCGATGGAGGACGCGAGGGTTACCTACGAGCTTGGCAGGGAGTTCTTCCCGATGGAGGCCCAGCTTTC
CAGGCTCATCGGCCAAGGCCTCTGGGACGTTTCCCGCTCCAGCACCGGCAACCTCGTCGAGTGGTTCCTCCTAAGGA
AGGCCTACGAGAGGAACGAACTCGCTCCCAACAAGCCCGACGAGAGGGAGCTGGCGAGGAGAAGGGGGGGCTACgcC
GGTGGCTACGTCAAGGAGCCGGAGCGGGGACTGTGGGACAATATCGTGTATCTAGACTTTCGTAGTCTCTACCCTTC
AATCATAATCACCCACAACGTCTCGCCAGATACGCTCAACCGCGAGGGGTGTAGGAGCTACGACGTTGCCCCCGAGG
TCGGTCACAAGTTCTGCAAGGACTTCCCCGGCTTCATTCCGAGCCTGCTCGGAAACCTGCTGGAGGAAAGGCAGAAG
ATAAAGAGGAAGATGAAGGCAACTCTCGACCCGCTGGAGAAGAATCTCCTCGATTACAGGCAACGCGCCATCAAGAT
TCTCGCCAACAGCTACTACGGCTACTACGGCTATGCCAGGGCAAGATGGTACTGCAGGGAGTGCGCCGAGAGCGTTA
CGGCATGGGGAAGGGAGTACATCGAAATGGTCATCAGAGAGCTTGAGGAAAAGTTCGGTTTTAAAGTCCTCTATGCA
GACACAGACGGTCTCCATGCCACCATTCCTGGAGCGGACGCTGAAACAGTCAAGAAAAAGGCAATGGAGTTCTTAAA
CTATATCAATCCCAAACTGCCCGGCCTTCTCGAACTCGAATACGAGGGCTTCTACGTCAGGGGCTTCTTCGTCACGA
AGAAAAAGTACGCGGTCATCGACGAGGAGGGCAAGATAACCACGCGCGGGCTTGAGATAGTCAGGCGCGACTGGAGC
GAGATAGCGAAGGAGACGCAGGCGAGGGTTTTGGAGGCGATACTCAGGCACGGTGACGTTGAAGAGGCCGTCAGAAT
TGTCAGGGAAGTCACCGAAAAGCTGAGCAAGTACGAGGTTCCGCCGGAGAAGCTGGTTATCCACGAGCAGATAACGC
GCGAGCTCAAGGACTACAAGGCCACCGGCCCGCACGTAGCCATAGCGAAgcGTTTGGCCGCCAGAGGTGTTAAAATC
CGGCCCGGAACTGTGATAAGCTACATCGTTCTGAAGGGCTCCGGAAGGATAGGCGACAGGGCGATTCCCTTCGACGA
GTTCGACCCGACGAAGCACAAGTACGATGCGGACTACTACATCGAGAACCAGGTTCTGCCGGCAGTTGAGAGAATCC
TCAGGGCCTTCGGCTACCGCAAGGAAGACCTGCGCTACCAGAAGACGAGGCAGGTCGGGCTTGGCGCGTGGCTGAAG
CCGAAGGGGAAGAAGAAGTGA

Tgo (SEQ ID NO: 22)

V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93Q MUTANT: GTT CAN BE MODIFIED TO BE = CAA, CAG (ALL CODONS FOR GLUTAMINE)
V93N MUTANT: GTT CAN BE MODIFIED TO BE = AAC, AAU (ALL CODONS FOR ASPARAGINE)

ATGATCCTCGATACAGACTACATAACTGAGGATGGAAAGCCCGTCATCAGGATCTTCAAGAAGGAGAACGGCGAGTT
CAAAATAGACTACGACAGAAACTTTGAGCCATACATCTACGCGCTCTTGAAGGACGACTCTGCGATTGAGGACGTCA
AGAAGATAACTGCCGAGAGGCACGGCACTACCGTTAGGGTTGTCAGGGCCGAGAAAGTGAAGAAGAAGTTCCTAGGC
AGGCCGATAGAGGTCTGGAAGCTCTACTTCACTCACCCCCAGGACGTTCCCGCAATCAGGGACAAGATAAAGGAGCA
TCCTGCCGTTGTGGACATCTACGAGTACGACATCCCCTTCGCGAAGCGCTACCTCATAGACAAAGGCTTAATCCCGA
TGGAGGGCGACGAGGAACTTAAGATGCTCGCCTTCGACATCGAGACGCTCTATCACGAGGGCGAGGAGTTCGCCGAA
GGGCCTATCCTGATGATAAGCTACGCCGACGAGGAAGGGGCGCGCGTTATTACCTGGAAGAATATCGACCTTCCCTA
TGTCGACGTCGTTTCCACCGAGAAGGAGATGATAAAGCGCTTCCTCAAGGTCGTCAAGGAAAAGGATCCCGACGTCC
TCATAACCTACAACGGCGACAACTTCGACTTCGCCTACCTCAAGAAGCGCTCCGAGAAGCTCGGAGTCAAGTTCATC
CTCGGAAGGGAAGGGAGCGAGCCGAAAATCCAGCGCATGGGCGATCGCTTTGCGGTGGAGGTCAAGGGAAGGATTCA
CTTCGACCTCTACCCCGTCATTAGGAGAACGATTAACCTCCCCACTTACACCCTTGAGGCAGTATATGAAGCCATCT
TTGGACAGCCGAAGGAGAAGGTCTACGCTGAGGAGATAGCGCAGGCCTGGGAAACGGGCGAGGGATTAGAAAGGGTG
GCCCGCTACTCGATGGAGGACGCAAAGGTAACCTATGAACTCGGAAAAGAGTTCTTCCCTATGGAAGCCCAGCTCTC
GCGCCTCGTAGGCCAGAGCCTCTGGGATGTATCTCGCTCGAGTACCGGAAACCTCGTCGAGTGGTTTTTGCTGAGGA
AGGCCTACGAGAGGAATGAACTTGCACCAAACAAGCCGGACGAGAGGGAGCTGGCAAGAAGAAGGGAGAGCTACGCG
GGTGGATACGTCAAGGAGCCCGAAAGGGGACTGTGGGAGAACATCGTGTATCTGGACTTCCGCTCCCTGTATCCTTC
GATAATAATCACCCATAACGTCTCCCCTGATACACTCAACAGGGAGGGTTGTGAGGAGTACGACGTGGCTCCTCAGG
TAGGCCATAAGTTCTGCAAGGACTTCCCCGGCTTCATCCCAAGCCTCCTCGGAGACCTCTTGGAGGAGAGACAGAAG
GTAAAGAAGAAGATGAAGGCCACTATAGACCCAATCGAGAAGAAACTCCTCGATTACAGGCAACGAGCAATCAAAAT
CCTTGCTAATAGCTTCTACGGTTACTACGGCTATGCAAAGGCCCGCTGGTACTGCAAGGAGTGCGCCGAGAGCGTTA
CCGCTTGGGGCAGGCAGTACATCGAGACCACGATAAGGGAAATAGAGGAGAAATTTGGCTTTAAAGTCCTCTACGCG
GACACAGATGGATTTTTCGCAACAATACCTGGAGCGGACGCCGAAACCGTCAAAAAGAAGGCAAAGGAGTTCCTGGA
CTACATCAACGCCAAACTGCCCGGCCTGCTCGAACTCGAATACGAGGGCTTCTACAAGCGCGGCTTCTTCGTGACGA
AGAAGAAGTACGCGGTTATAGACGAGGAGGACAAGATAACGACGCGCGGGCTTGAAATAGTTAGGCGTGACTGGAGC
GAGATAGCGAAGGAGACGCAGGCGAGGGTTCTTGAGGCGATACTAAAGCACGGTGACGTTGAAGAAGCGGTAAGGAT
TGTCAAAGAGGTTACGGAGAAGCTGAGCAAGTACGAGGTTCCACCGGAGAAGCTGGTCATCTACGAGCAGATAACCC
GCGACCTGAAGGACTACAAGGCCACCGGGCCGCATGTGGCTGTTGCAAAACGCCTCGCCGCAAGGGGGATAAAAATC
CGGCCCGGAACGGTCATAAGCTACATCGTGCTCAAAGGCTCGGGAAGGATTGGGGACAGGGCTATACCCTTTGACGA
ATTTGACCCGGCAAAGCACAAGTACGATGCAGAATACTACATCGAGAACCAGGTTCTTCCAGCTGTGGAGAGGATTC
TGAGGGCCTTTGGTTACCGTAAAGAAGATTTAAGGTATCAGAAAACGCGGCAGGTTGGCTTGGGGGCGTGGCTAAAA
CCTAAGACATGA

PFU DNA POLYMERASE (SEQ ID NO: 23)
G387P Mutant (CCN is the codon for Proline where N = C, G, A, or T)
V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93N MUTANT: GTT CAN BE MODIFIED TO BE = AAC, AAU (ALL CODONS FOR ASPARAGINE)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATGTTC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

PFU DNA POLYMERASE (SEQ ID NO: 24)
D141A/E143A Mutant (GCN is the codon for alanine where N = C, G, A, or T)
V93R MUTANT: GTT CAN BE MODIFIED TO BE = AGA, AGG, CGA, CGC, CGG, CGT (ALL POSSIBLE CODONS FOR ARGININE)
V93E MUTANT: GTT CAN BE MODIFIED TO BE = GAA, GAG (ALL CODONS FOR GLUTAMIC ACID)
V93D MUTANT: GTT CAN BE MODIFIED TO BE = GAT, GAC (ALL CODONS FOR ASPARTIC ACID)
V93K MUTANT: GTT CAN BE MODIFIED TO BE = AAA, AAG (ALL CODONS FOR LYSINE)
V93N MUTANT: GTT CAN BE MODIFIED TO BE = AAC, AAU (ALL CODONS FOR ASPARAGINE)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATGTTC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

PFU DNA POLYMERASE (SEQ ID NO: 25)
V93 DELETION MUTANT

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGAT---C CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

PFU DNA POLYMERASE (SEQ ID NO: 26)
D92-V93-P94 DELETION MUTANT

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAA         ACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
```

```
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

Figure 6B

>Pfu (SEQ ID NO: 27)

VALINE AT POSITION 93 MAY BE SUBSTITUTED BY ONE OF: R, E, D, K, OR N

MILDVDYITEEGKPVIRLFKKENGKFKIEHDRTFRPYIYALLRDDSKIEEVKKITGERHGKIVRIVDVEKVEKKFLG
KPITVWKLYLEHPQDVPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>DEEP VENT (SEQ ID NO: 28)

VALINE AT POSITION 93 MAY BE SUBSTITUTED BY ONE OF: R, E, D, K, Q, OR N

MILDADYITEDGKPIIRIFKKENGEFKVEYDRNFRPYIYALLKDDSQIDEVRKITAERHGKIVRIIDAEKVRKKFLG
RPIEVWRLYFEHPQDVPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTKQTGLTAWL
NIKKK

>TGO (SEQ ID NO: 29)

VALINE AT POSITION 93 MAY BE SUBSTITUTED BY ONE OF: R, E, D, K, Q, OR N

MILDTDYITEDGKPVIRIFKKENGEFKIDYDRNFEPYIYALLKDDSAIEDVKKITAERHGTTVRVVRAEKVKKKFLG
RPIEVWKLYFTHPQDVPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA

DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

>KOD (SEQ ID NO: 30)

VALINE AT POSITION 93 MAY BE SUBSTITUTED BY ONE OF: R, E, D, K, Q, OR N

MILDTDYITEDGKPVIRIFKKENGEFKIEYDRTFEPYFYALLKDDSAIEEVKKITAERHGTVVTVKRVEKVQKKFLG
RPVEVWKLYFTHPQDVPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT

>VENT (SEQ ID NO: 31)

VALINE AT POSITION 93 MAY BE SUBSTITUTED BY ONE OF: R, E, D, K, Q, OR N

MILDTDYITKDGKPIIRIFKKENGEFKIELDPHFQPYIYALLKDDSAIEEIKAIKGERHGKTVRVLDAVKVRKKFLG
REVEVWKLIFEHPQDVPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIQRMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

>JDF-3 (SEQ ID NO: 32)

VALINE AT POSITION 93 MAY BE SUBSTITUTED BY ONE OF: R, E, D, K, Q, OR N

MILDVDYITENGKPVIRVFKKENGEFRIEYDREFEPYFYALLRDDSAIEEIKKITAERHGRVVKVKRAEKVKKKFLG
RSVEVWVLYFTHPQDVPAIRDKIRKHPAVIDIYEYDIPFAKRYLIDKGLIPMEGEEELKLMSFDIETLYHEGEEFGT
GPILMISYADESEARVITWKKIDLPYVEVVSTEKEMIKRFLRVVKEKDPDVLITYNGDNFDFAYLKKRCEKLGVSFT
LGRDGSEPKIQRMGDRFAVEVKGRVHFDLYPVIRRTINLPTYTLEAVYEAVFGKPKEKVYAEEIATAWETGEGLERV
ARYSMEDARVTYELGREFFPMEAQLSRLIGQGLWDVSRSSTGNLVEWFLLRKAYERNELAPNKPDERELARRRGGYA
GGYVKEPERGLWDNIVYLDFRSLYPSIIITHNVSPDTLNREGCRSYDVAPEVGHKFCKDFPGFIPSLLGNLLEERQK
IKRKMKATLDPLEKNLLDYRQRAIKILANSYYGYYGYARARWYCRECAESVTAWGREYIEMVIRELEEKFGFKVLYA
DTDGLHATIPGADAETVKKKAMEFLNYINPKLPGLLELEYEGFYVRGFFVTKKKYAVIDEEGKITTRGLEIVRRDWS
EIAKETQARVLEAILRHGDVEEAVRIVREVTEKLSKYEVPPEKLVIHEQITRELKDYKATGPHVAIAKRLAARGVKI
RPGTVISYIVLKGSGRIGDRAIPFDEFDPTKHKYDADYYIENQVLPAVERILRAFGYRKEDLRYQKTRQVGLGAWLK
PKGKKK

>Pfu V93/G387P (SEQ ID NO: 33)

VALINE AT POSITION 93 MAY BE SUBSTITUTED BY ONE OF: R, E, D, K, OR N

MILDVDYITEEGKPVIRLFKKENGKFKIEHDRTFRPYIYALLRDDSKIEEVKKITGERHGKIVRIVDVEKVEKKFLG
KPITVWKLYLEHPQDVPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93/D141A/E143A (SEQ ID NO: 34)

VALINE AT POSITION 93 MAY BE SUBSTITUTED BY ONE OF: R, E, D, K, OR N

MILDVDYITEEGKPVIRLFKKENGKFKIEHDRTFRPYIYALLRDDSKIEEVKKITGERHGKIVRIVDVEKVEKKFLG
KPITVWKLYLEHPQDVPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu delta V93 (SEQ ID NO: 35)

MILDVDYITEEGKPVIRLFKKENGKFKIEHDRTFRPYIYALLRDDSKIEEVKKITGERHGKIVRIVDVEKVEKKFLG
KPITVWKLYLEHPQDPTIREKVREHPAVVDIFEYDIPFAKRYLIDKGLIPMEGEEELKILAFDIETLYHEGEEFGKG
PIIMISYADENEAKVITWKNIDLPYVEVVSSEREMIKRFLRIIREKDPDIIVTYNGDSFDFPYLAKRAEKLGIKLTI
GRDGSEPKMQRIGDMTAVEVKGRIHFDLYHVITRTINLPTYTLEAVYEAIFGKPKEKVYADEIAKAWESGENLERVA
KYSMEDAKATYELGKEFLPMEIQLSRLVGQPLWDVSRSSTGNLVEWFLLRKAYERNEVAPNKPSEEEYQRRLRESYT
GGFVKEPEKGLWENIVYLDFRALYPSIIITHNVSPDTLNLEGCKNYDIAPQVGHKFCKDIPGFIPSLLGHLLEERQK
IKTKMKETQDPIEKILLDYRQKAIKLLANSFYGYYGYAKARWYCKECAESVTAWGRKYIELVWKELEEKFGFKVLYI
DTDGLYATIPGGESEEIKKKALEFVKYINSKLPGLLELEYEGFYKRGFFVTKKRYAVIDEEGKVITRGLEIVRRDWS
EIAKETQARVLETILKHGDVEEAVRIVKEVIQKLANYEIPPEKLAIYEQITRPLHEYKAIGPHVAVAKKLAAKGVKI
KPGMVIGYIVLRGDGPISNRAILAEEYDPKKHKYDAEYYIENQVLPAVLRILEGFGYRKEDLRYQKTRQVGLTSWLN
IKKS //

>Pfu delta D92-V93-P94 (SEQ ID NO: 36)

MILDVDYITEEGKPVIRLFKKENGKFKIEHDRTFRPYIYALLRDDSKIEEVKKITGERHGKIVRIVDVEKVEKKFLG
KPITVWKLYLEHPQTIREKVREHPAVVDIFEYDIPFAKRYLIDKGLIPMEGEEELKILAFDIETLYHEGEEFGKGPI
IMISYADENEAKVITWKNIDLPYVEVVSSEREMIKRFLRIIREKDPDIIVTYNGDSFDFPYLAKRAEKLGIKLTIGR
DGSEPKMQRIGDMTAVEVKGRIHFDLYHVITRTINLPTYTLEAVYEAIFGKPKEKVYADEIAKAWESGENLERVAKY
SMEDAKATYELGKEFLPMEIQLSRLVGQPLWDVSRSSTGNLVEWFLLRKAYERNEVAPNKPSEEEYQRRLRESYTGG
FVKEPEKGLWENIVYLDFRALYPSIIITHNVSPDTLNLEGCKNYDIAPQVGHKFCKDIPGFIPSLLGHLLEERQKIK
TKMKETQDPIEKILLDYRQKAIKLLANSFYGYYGYAKARWYCKECAESVTAWGRKYIELVWKELEEKFGFKVLYIDT
DGLYATIPGGESEEIKKKALEFVKYINSKLPGLLELEYEGFYKRGFFVTKKRYAVIDEEGKVITRGLEIVRRDWSEI
AKETQARVLETILKHGDVEEAVRIVKEVIQKLANYEIPPEKLAIYEQITRPLHEYKAIGPHVAVAKKLAAKGVKIKP
GMVIGYIVLRGDGPISNRAILAEEYDPKKHKYDAEYYIENQVLPAVLRILEGFGYRKEDLRYQKTRQVGLTSWLNIK
KS >Pfu

Figure 6C-1 (SEQ ID NOS: 37[nt] and 38[aa])

5' atg atc ctc gat aca gac tac ata act gag gat gga aag ccc gtc atc 48
Met Ile Leu Asp Thr Asp Tyr Ile Thr Glu Asp Gly Lys Pro Val Ile
1 5 10 15 agg atc ttc aag aag gag aac ggc gag ttc aaa ata gac tac gac aga 96
Arg Ile Phe Lys Lys Glu Asn Gly Glu Phe Lys Ile Asp Tyr Asp Arg
20 25 30 aac ttt gag cca tac atc tac gcg ctc ttg aag gac gac tct gcg att 144
Asn Phe Glu Pro Tyr Ile Tyr Ala Leu Leu Lys Asp Asp Ser Ala Ile
35 40 45 gag gac gtc aag aag ata act gcc gag agg cac ggc act acc gtt agg 192
Glu Asp Val Lys Lys Ile Thr Ala Glu Arg His Gly Thr Thr Val Arg
50 55 60 gtt gtc agg gcc gag aaa gtg aag aag aag ttc cta ggc agg ccg ata 240
Val Val Arg Ala Glu Lys Val Lys Lys Lys Phe Leu Gly Arg Pro Ile
65 70 75 80 gag gtc tgg aag ctc tac ttc act cac ccc cag gac nnn ccc gca atc 288
Glu Val Trp Lys Leu Tyr Phe Thr His Pro Gln Asp Xaa Pro Ala Ile
85 90 95 agg gac aag ata aag gag cat cct gcc gtt gtg gac atc tac gag tac 336

Arg Asp Lys Ile Lys Glu His Pro Ala Val Val Asp Ile Tyr Glu Tyr
100 105 110 gac atc ccc ttc gcg aag cgc tac ctc ata gac aaa ggc tta atc ccg 384
Asp Ile Pro Phe Ala Lys Arg Tyr Leu Ile Asp Lys Gly Leu Ile Pro
115 120 125 atg gag ggc gac gag gaa ctt aag atg ctc gcc ttc gac atc gag acg 432
Met Glu Gly Asp Glu Glu Leu Lys Met Leu Ala Phe Asp Ile Glu Thr
130 135 140 ctc tat cac gag ggc gag gag ttc gcc gaa ggg cct atc ctg atg ata 480
Leu Tyr His Glu Gly Glu Glu Phe Ala Glu Gly Pro Ile Leu Met Ile
145 150 155 160 agc tac gcc gac gag gaa ggg gcg cgc gtt att acc tgg aag aat atc 528
Ser Tyr Ala Asp Glu Glu Gly Ala Arg Val Ile Thr Trp Lys Asn Ile
165 170 175 gac ctt ccc tat gtc gac gtc gtt tcc acc gag aag gag atg ata aag 576
Asp Leu Pro Tyr Val Asp Val Val Ser Thr Glu Lys Glu Met Ile Lys
180 185 190 cgc ttc ctc aag gtc gtc aag gaa aag gat ccc gac gtc ctc ata acc 624
Arg Phe Leu Lys Val Val Lys Glu Lys Asp Pro Asp Val Leu Ile Thr
195 200 205 tac aac ggc gac aac ttc gac ttc gcc tac ctc aag aag cgc tcc gag 672

Tyr Asn Gly Asp Asn Phe Asp Phe Ala Tyr Leu Lys Lys Arg Ser Glu
210 215 220 aag ctc gga gtc aag ttc atc ctc gga agg gaa ggg agc gag ccg aaa 720
Lys Leu Gly Val Lys Phe Ile Leu Gly Arg Glu Gly Ser Glu Pro Lys
225 230 235 240 atc cag cgc atg ggc gat cgc ttt gcg gtg gag gtc aag gga agg att 768
Ile Gln Arg Met Gly Asp Arg Phe Ala Val Glu Val Lys Gly Arg Ile
245 250 255 cac ttc gac ctc tac ccc gtc att agg aga acg att aac ctc ccc act 816
His Phe Asp Leu Tyr Pro Val Ile Arg Arg Thr Ile Asn Leu Pro Thr
260 265 270 tac acc ctt gag gca gta tat gaa gcc atc ttt gga cag ccg aag gag 864
Tyr Thr Leu Glu Ala Val Tyr Glu Ala Ile Phe Gly Gln Pro Lys Glu
275 280 285 aag gtc tac gct gag gag ata gcg cag gcc tgg gaa acg ggc gag gga 912
Lys Val Tyr Ala Glu Glu Ile Ala Gln Ala Trp Glu Thr Gly Glu Gly
290 295 300 tta gaa agg gtg gcc cgc tac tcg atg gag gac gca aag gta acc tat 960
Leu Glu Arg Val Ala Arg Tyr Ser Met Glu Asp Ala Lys Val Thr Tyr
305 310 315 320 gaa ctc gga aaa gag ttc ttc cct atg gaa gcc cag ctc tcg cgc ctc 1008

Glu Leu Gly Lys Glu Phe Phe Pro Met Glu Ala Gln Leu Ser Arg Leu
325 330 335 gta ggc cag agc ctc tgg gat gta tct cgc tcg agt acc gga aac ctc 1056
Val Gly Gln Ser Leu Trp Asp Val Ser Arg Ser Ser Thr Gly Asn Leu
340 345 350 gtc gag tgg ttt ttg ctg agg aag gcc tac gag agg aat gaa ctt gca 1104
Val Glu Trp Phe Leu Leu Arg Lys Ala Tyr Glu Arg Asn Glu Leu Ala
355 360 365 cca aac aag ccg gac gag agg gag ctg gca aga aga agg gag agc tac 1152
Pro Asn Lys Pro Asp Glu Arg Glu Leu Ala Arg Arg Arg Glu Ser Tyr
370 375 380 gcg ggt gga tac gtc aag gag ccc gaa agg gga ctg tgg gag aac atc 1200
Ala Gly Gly Tyr Val Lys Glu Pro Glu Arg Gly Leu Trp Glu Asn Ile
385 390 395 400 gtg tat ctg gac ttc cgc tcc ctg tat cct tcg ata ata atc acc cat 1248
Val Tyr Leu Asp Phe Arg Ser Leu Tyr Pro Ser Ile Ile Ile Thr His
405 410 415 aac gtc tcc cct gat aca ctc aac agg gag ggt tgt gag gag tac gac 1296
Asn Val Ser Pro Asp Thr Leu Asn Arg Glu Gly Cys Glu Glu Tyr Asp
420 425 430 gtg gct cct cag gta ggc cat aag ttc tgc aag gac ttc ccc ggc ttc 1344

Val Ala Pro Gln Val Gly His Lys Phe Cys Lys Asp Phe Pro Gly Phe
435 440 445 atc cca agc ctc ctc gga gac ctc ttg gag gag aga cag aag gta aag 1392
Ile Pro Ser Leu Leu Gly Asp Leu Leu Glu Glu Arg Gln Lys Val Lys
450 455 460 aag aag atg aag gcc act ata gac cca atc gag aag aaa ctc ctc gat 1440
Lys Lys Met Lys Ala Thr Ile Asp Pro Ile Glu Lys Lys Leu Leu Asp
465 470 475 480 tac agg caa cga gca atc aaa atc ctt gct aat agc ttc tac ggt tac 1488
Tyr Arg Gln Arg Ala Ile Lys Ile Leu Ala Asn Ser Phe Tyr Gly Tyr
485 490 495 tac ggc tat gca aag gcc cgc tgg tac tgc aag gag tgc gcc gag agc 1536
Tyr Gly Tyr Ala Lys Ala Arg Trp Tyr Cys Lys Glu Cys Ala Glu Ser
500 505 510 gtt acc gct tgg ggc agg cag tac atc gag acc acg ata agg gaa ata 1584
Val Thr Ala Trp Gly Arg Gln Tyr Ile Glu Thr Thr Ile Arg Glu Ile
515 520 525 gag gag aaa ttt ggc ttt aaa gtc ctc tac gcg gac aca gat gga ttt 1632
Glu Glu Lys Phe Gly Phe Lys Val Leu Tyr Ala Asp Thr Asp Gly Phe
530 535 540 ttc gca aca ata cct gga gcg gac gcc gaa acc gtc aaa aag aag gca 1680

Phe Ala Thr Ile Pro Gly Ala Asp Ala Glu Thr Val Lys Lys Lys Ala
545 550 555 560 aag gag ttc ctg gac tac atc aac gcc aaa ctg ccc ggc ctg ctc gaa 1728
Lys Glu Phe Leu Asp Tyr Ile Asn Ala Lys Leu Pro Gly Leu Leu Glu
565 570 575 ctc gaa tac gag ggc ttc tac aag cgc ggc ttc ttc gtg acg aag aag 1776
Leu Glu Tyr Glu Gly Phe Tyr Lys Arg Gly Phe Phe Val Thr Lys Lys
580 585 590 aag tac gcg gtt ata gac gag gag gac aag ata acg acg cgc ggg ctt 1824
Lys Tyr Ala Val Ile Asp Glu Glu Asp Lys Ile Thr Thr Arg Gly Leu
595 600 605 gaa ata gtt agg cgt gac tgg agc gag ata gcg aag gag acg cag gcg 1872
Glu Ile Val Arg Arg Asp Trp Ser Glu Ile Ala Lys Glu Thr Gln Ala
610 615 620 agg gtt ctt gag gcg ata cta aag cac ggt gac gtt gaa gaa gcg gta 1920
Arg Val Leu Glu Ala Ile Leu Lys His Gly Asp Val Glu Glu Ala Val
625 630 635 640 agg att gtc aaa gag gtt acg gag aag ctg agc aag tac gag gtt cca 1968
Arg Ile Val Lys Glu Val Thr Glu Lys Leu Ser Lys Tyr Glu Val Pro
645 650 655 ccg gag aag ctg gtc atc tac gag cag ata acc cgc gac ctg aag gac 2016

Pro Glu Lys Leu Val Ile Tyr Glu Gln Ile Thr Arg Asp Leu Lys Asp
660 665 670 tac aag gcc acc ggg ccg cat gtg gct gtt gca aaa cgc ctc gcc gca 2064
Tyr Lys Ala Thr Gly Pro His Val Ala Val Ala Lys Arg Leu Ala Ala
675 680 685 agg ggg ata aaa atc cgg ccc gga acg gtc ata agc tac atc gtg ctc 2112
Arg Gly Ile Lys Ile Arg Pro Gly Thr Val Ile Ser Tyr Ile Val Leu
690 695 700 aaa ggc tcg gga agg att ggg gac agg gct ata ccc ttt gac gaa ttt 2160
Lys Gly Ser Gly Arg Ile Gly Asp Arg Ala Ile Pro Phe Asp Glu Phe
705 710 715 720 gac ccg gca aag cac aag tac gat gca gaa tac tac atc gag aac cag 2208
Asp Pro Ala Lys His Lys Tyr Asp Ala Glu Tyr Tyr Ile Glu Asn Gln
725 730 735 gtt ctt cca gct gtg gag agg att ctg agg gcc ttt ggt tac cgt aaa 2256
Val Leu Pro Ala Val Glu Arg Ile Leu Arg Ala Phe Gly Tyr Arg Lys
740 745 750 gaa gat tta agg tat cag aaa acg cgg cag gtt ggc ttg ggg gcg tgg 2304
Glu Asp Leu Arg Tyr Gln Lys Thr Arg Gln Val Gly Leu Gly Ala Trp
755 760 765 cta aaa cct aag aca tga 2322

Leu Lys Pro Lys Thr

Tgo93 (R): nnn = AGA, AGG, CGA, CGC, CGG, CGT (R)

Tgo 93 (R) amino acid sequence

Tgo 93 (E): nnn = GAA, GAG (E)

Tgo 93 (E)amino acid sequence

Tgo93 (D): nnn = GAT, GAC (D)

Tgo 93 (D) amino acid sequence

Tgo93 (K): nnn = AAA, AAG (K)

Tgo 93 (K) amino acid sequence

Tgo93 (Q): nnn = CAA, CAG (Q)

Tgo 93 (Q) amino acid sequence

Tgo93 (N): nnn = AAC, AAU (N)

Tgo 93 (N) amino acid sequence

Figure 7A

ACCESSION AAA72101 Vent Thermococcus litoralis mildtdyitk dgkpiirifk kengefkiel dphfqpyiya llkddsaiee ikaikgerhg ktvrvldavk vrkkflgrev evwklifehp qdvpamrgki rehpavvdiy eydipfakry lidkglipme gdeelkllaf dietfyhegd efgkgeiimi syadeeearv itwknidlpy vdvvsnerem ikrfvqvvke kdpdviityn gdnfdlpyli kraeklgvrl vlgrdkehpe pkiqrmgdsf aveikgrihf dlfpvvrrti nlptytleav yeavlgktks klgaeeiaai weteesmkkl aqysmedara tyelgkeffp meaelaklig qsvwdvsrss tgnlvewyll rvayarnela pnkpdeeeyk rrlrttylgg yvkepekglw eniiyldfrs lypsiivthn vspdtlekeg cknydvapiv gyrfckdfpg fipsilgdli amrqdikkkm kstidpiekk mldyrqraik llansyygym gypkarwysk ecaesvtawg rhyiemtire ieekfgfkvl yadtdgfyat ipgekpelik kkakeflnyi nsklpgllel eyegfylrgf fvtkkryavi deegrittrg levvrrdwse iaketqakvl eailkegsve kavevvrdvv ekiakyrvpl eklviheqit rdlkdykaig phvaiakrla argikvkpgt iisyivlkgs gkisdrvill teydprkhky dpdyyienqv lpavlrilea fgyrkedlry qsskqtglda wlkr (SEQ ID NO. 83)

ACCESSION O33845 THEST THERMOCOCCUS SP.

mildtdyitk dgkpiirifk kengefkiel dphfqpyiya llkddsaide ikaikgerhg kivrvvdavk vkkkflgrdv evwklifehp qdvpalrgki rehpavidiy eydipfakry lidkglipme gdeelklmaf dietfyhegd efgkgeiimi syadeeearv itwknidlpy vdvvsnerem ikrfvqivre kdpdvlityn gdnfdlpyli kraeklgvtl llgrdkehpe pkihrmgdsf aveikgrihf dlfpvvrrti nlptytleav yeavlgktks klgaeeiaai weteesmkkl aqysmedara tyelgkeffp meaelaklig qsvwdvsrss tgnlvewyll rvayernela pnkpdeeeyr rrlrttylgg yvkeperglw eniayldfrc hpadtkvivk gkgivnisdv kegdyilgid gwqrvkkvwk yhyegklini nglkctpnhk vpvvtendrq trirdslaks flsgkvkgki ittklfekia efeknkpsee eilkgelsgi ilaegtllrk dieyfdssrg kkrishqyrv eitigeneke llerilyifd klfgirpsvk kkgdtnalki ttakkavylq ieellknies lyapavlrgf ferdatvnki rstivvtqgt nnkwkidiva klldslgipy sryeykyien gkeltkhile itgrdglilf qtlvgfisse knealekaie vremnrlknn sfynlstfev sseyykgevy dltlegnpyy fangilthns lypsiivthn vspdtlereg cknydvapiv gykfckdfpg fipsilgeli tmrqeikkkm katidpiekk mldyrqravk llansilpne wlpiiengev kfvkigefid rymeeqkdkv rtvdntevle vdnifafsln keskkseikk vkalirhkyk geayevelns grkihitrgh slftirngki keiwgeevkv gdliivpkkv klnekeavin ipelisklpd edtadvvmtt pvkgrknffk gmlrtlkwif geeskrirtf nrylfhleel gfvkllprgy evtdweglkr yrqlyeklvk nlryngnkre ylvrfndikd svscfprkel eewkigtxkg frxkcilkvd edfgkflgyy vsegyagaqk nktggmsysv klynenpnvl kdmkniaekf fgkvrvgknc vdipkkmayl lakslcgvta enkripsiif dssepvrwaf lrayfvgdgd ihpskrlrls tksellanql vfllnslgvs sikigfdsgv yrvyinedlp flqtsrqknt yypnlipkev leeifgrkfq knitfekfke ladsgkldkr kvklldflln gdivldrvkn vekreyegyv ydlsvednen flvgfgllya hnsyygymgy pkarwyskec aesvtawgrh yiemtikeie ekfgfkvlya dsvtgdteii vkrngriefv pieklfervd yrigekeyci ledvealtld nrgkliwkkv pyvmrhrakk kvyriwitns wyidvtedhs livaedglke arpmeiegks liatkddlsg veyikphaie eisyngyvyd ievegthrff angilvhntd gfyatipgek petikkkake flkyinsklp glleleyegf ylrgffvakk ryavideegr ittrglevvr rdwseiaket qakvleailk edsvekavei vkdvveeiak yqvpleklvi heqitkdlse ykaigphvai akrlaakgik vrpgtiisyi vlrgsgkisd rvillseydp kkhkydpdyy ienqvlpavl rileafgyrk edlkyqsskq vgldawlkk (SEQ ID NO. 84)

ACCESSION P77916 Pab Pyrococcus abyssi miidadyite dgkpiirifk kekgefkvey drtfrpyiya llkddsaide vkkitaerhg kivritevek vqkkflgrpi evwklylehp qdvpaireki rehpavvdif eydipfakry lidkgltpme gneeltflav dietlyhege efgkgpiimi syadeegakv itwksidlpy vevvsserem ikrlvkvire kdpdviityn gdnfdfpyll kraeklgikl plgrdnsepk mqrmgdslav eikgrihfdl fpvirrtinl ptytleavye aifgkskekv yaheiaeawe tgkglervak ysmedakvtf elgkeffpme aqlarlvgqp vwdvsrsstg nlvewfllrk ayernelapn kpdereyerr lresyeggyv kepekglweg ivsldfrsly psiiithnvs pdtlnrenck eydvapqvgh rfckdfpgfi psllgnllee rqkikkrmke skdpvekkll dyrqraikil ansyygyygy akarwyckec aesvtawgrq yidlvrrele srgfkvlyid tdglyatipg akheeikeka lkfveyinsk lpglleleye gfyargffvt kkkyalidee gkivtrglei vrrdwseiak etqakvleai lkhgnvdeav kivkevtekl skyeippekl viyeqitrpl seykaigphv avakrlaakg vkvkpgmvig yivlrgdgpi skraiaieef dpkkhkydae yyienqvlpa verilrafgy rkedlkyqkt kqvglgawlk f (SEQ ID NO. 85)

ACCESSION O59610 PYRHO Pyrococcus horikoshii mildadyite dgkpiirifk kengefkvey drnfrpyiya llrddsaide ikkitaqrhg kvvrivetek iqrkflgrpi evwklylehp qdvpairdki rehpavvdif eydipfakry lidkgltpme gnekltflav dietlyhege efgkgpvimi syadeegakv itwkkidlpy vevvsserem ikrlirvike kdpdviityn gdnfdfpyll kraeklgikl llgrdnsepk mqkmgdslav eikgrihfdl fpvirrtinl ptytleavye aifgkpkekv yadeiakawe tgeglervak ysmedakvty elgreffpme aqlarlvgqp vwdvsrsstg nlvewfllrk ayernelapn kpdekeyerr lresyeggyv kepekglweg ivsldfrsly psiiithnvs pdtlnregce eydvapkvgh rfckdfpgfi psllgqllee rqkikkrmke skdpvekkll dyrqraikil ansilpdewl pivenekvrf vkigdfidre ieenaervkr dgeteilevk dlkalsfnre tkkselkkvk alirhrysgk vysiklksgr rikitsghsl fsvkngklvk vrgdelkpgd lvvvpgrlkl peskqvlnlv elllklpeee tsnivmmipv kgrknffkgm lktlywifge gerprtagry lkhlerlgyv klkrrgcevl dweslkryrk lyetliknlk yngnsraymv efnslrdvvs lmpieelkew iigeprgpki gtfidvddsf akllgyyiss gdvekdrvkf hskdqnvled iaklaeklfg kvrrgrgyie vsgkishaif rvlaegkrip efiftspmdi kvaflkglng naeeltfstk sellvnqlil llnsigvsdi kiehekgvyr vyinkkessn gdivldsves ievekyegyv ydlsvednen flvgfgllya hnsyygyygy akarwyckec aesvtawgrq yidlvrrele argfkvlyid tdglyatipg vkdweevkrr alefvdyins klpgvleley egfyargffv tkkkyalide egkivtrgle ivrrdwseia ketqarvlea ilkhgnveea vkivkdvtek ltnyevppek lviyeqitrp ineykaigph vavakrlmar gikvkpgmvi gyivlrgdgp iskraisiee fdprkhkyda eyyienqvlp averilkafg ykredlrwqk tkqvglgawi kvkks (SEQ ID NO. 86)

ACCESSION P77932 PYRSE PYROCOCCUS SP.

miidadyite dgkpiirifk kekgefkvey drtfrpyiya llkddsaide vkkitaerhg kivritevek vqkkflgrpi evwklylehp qdvpaireki rehpavvdif eydipfakry lidkgltpme gneeltflav dietlyhege efgkgpiimi syadeegakv itwksidlpy vevvsserem ikrlvkvire kdpdviityn gdnfdfpyll kraeklgikl plgrdnsepk mqrmgdslav eikgrihfdl fpvirrtinl ptytleavye aifgkskekv yaheiaeawe tgkglervak ysmedakvtf elgkeffpme aqlarlvgqp vwdvsrsstg nlvewfllrk ayernelapn kpdereyerr lresyeggyv kepekglweg ivsldfrsly psiiithnvs pdtlnrenck eydvapqvgh rfckdfpgfi psllgnllee rqkikkrmke skdpvekkll dyrqraikil ansyygyygy akarwyckec aesvtawgrq yidlvrrele ssgfkvlyid tdglyatipg akpneikeka lkfveyinsk lpglleleye gfyargffvt kkkyalidee gkivtrglei vrrdwseiak etqakvleai lkhgnvdeav kivkevtekl skyeippekl viyeqitrpl seykaigphv avakrlaakg vkvkpgmvig yivlrgdgpi skraiaieef dpkkhkydae yyienqvlpa verilrafgy rkedlryqkt kqvglgawlk f (SEQ ID NO. 87)

ACCESSION AAA67131 DeepVent Pyrococcus sp.

mildadyite dgkpiirifk kengefkvey drnfrpyiya llkddsqide vrkitaerhg kivriidaek vrkkflgrpi
evwrlyfehp qdvpairdki rehsavidif eydipfakry lidkglipme gdeelkllaf dietlyhege efakgpiimi
syadeeeakv itwkkidlpy vevvsserem ikrflkvire kdpdviityn gdsfdlpylv kraeklgikl plgrdgsepk
mqrlgdmtav eikgrihfdl yhvirrtinl ptytleavye aifgkpkekv yaheiaeawe tgkglervak ysmedakvty
elgreffpme aqlsrlvgqp lwdvsrsstg nlvewyllrk ayernelapn kpdereyerr lresyaggyv kepekglweg
lvsldfrsly psiiithnvs pdtlnregcr eydvapevgh kfckdfpgfi psllkrllde rqeikrkmka skdpiekkml
dyrqraikil ansyygyygy akarwyckec aesvtawgre yiefvrkele ekfgfkvlyi dtdglyatip gakpeeikkk
alefvdyina klpglleley egfyvrgffv tkkkyalide egkiitrglc ivrrdwseia ketqakvlea ilkhgnveea
vkivkevtek lskyeippek lviyeqitrp lheykaigph vavakrlaar gvkvrpgmvi gyivlrgdgp iskrailaee
fdlrkhkyda eyyienqvlp avlrileafg yrkedlrwqk tkqtgltawl nikkk (SEQ ID NO. 88)

ACCESSION P80061 Pfu Pyrococcus furiosus mildvdyite egkpvirlfk kengkfkieh drtfrpyiya llrddskiee vkkitgerhg kivrivdvek vekkflgkpi
tvwklylehp qdvptirekv rehpavvdif eydipfakry lidkglipme geeelkilaf dietlyhege efgkgpiimi
syadeneakv itwknidlpy vevvsserem ikrflriire kdpdiivtyn gdsfdfpyla kraeklgikl tigrdgsepk
mqrigdmtav evkgrihfdl yhvitrtinl ptytleavye aifgkpkekv yadeiakawe sgenlervak ysmedakaty
elgkeflpme iqlsrlvgqp lwdvsrsstg nlvewfllrk ayernevapn kpseeeyqrr lresytggfv kepekglwen
ivyldfraly psiiithnvs pdtlnlegck nydiapqvgh kfckdipgfi psllghllee rqkiktkmke tqdpiekill
dyrqkaikll ansfygyygy akarwyckec aesvtawgrk yielvwkele ekfgfkvlyi dtdglyatip ggeseeikkk
alefvkyins klpglleley egfykrgffv tkkryavide egkvitrgle ivrrdwseia ketqarvlet ilkhgdveea
vrivkeviqk lanyeippek laiyeqitrp lheykaigph vavakklaak gvkikpgmvi gyivlrgdgp isnrailaee
ydpkkhkyda eyyienqvlp avlrilegfg yrkedlryqk trqvgltswl nikks (SEQ ID NO. 89)

> JDF-3 Thermococcus sp.

mildvdyitengkpvirvfkkengefrieydrefepyfyallrddsaieeikkitaerhgrvvkvkraekvkkkflgrsvevwvlyfthp
qdvpairdkirkhpavidiyeydipfakrylidkglipmegeeelklmsfdietlyhegeefgtgpilmisyadesearvitwkkidlpy
vevvstekemikrflrvvkekdpdvlityngdnfdfaylkkrceklgvsftlgrdgsepkiqrmgdrfavevkgrvhfdlypvirrtinl
ptytleavyeavfgkpkekvyaeeiatawetgeglervarysmedarvtyelgreffpmeaqlsrligqglwdvsrsstgnlvewfllrk
ayernelapnkpderelarrrggyaggyvkeperglwdnivyldfrslypsiiithnvspdtlnregcrsydvapevghkfckdfpgfip
sllgnlleerqkikrkmkatldpleknlldyrqraikilansyygyygyararwycrecaesvtawgreyiemvireleekfgfkvlyadt
dglhatipgadaetvkkkameflnyinpklpglleleyegfyvrgffvtkkkyavideegkittrgleivrrdwseiaketqarvleailrh
gdveeavrivrevteklskyevppeklviheqitrelkdykatgphvaiakrlaargvkirpgtvisyivlkgsgrigdraipfdefdptkh
kydadyyienqvlpaverilrafgyrkedlryqktrqvglgawlkpkgkkk(SEQ ID NO. 90)

ACCESSION Q56366 9degN THERMOCOCCUS SP. (STRAIN 9°N-7).

mildtdyite ngkpvirvfk kengefkiey drtfepyfya llkddsaied vkkvtakrhg tvvkvkraek vqkkflgrpi evwklyfnhp qdvpairdri rahpavvdiy eydipfakry lidkglipme gdeeltmlaf dietlyhege efgtgpilmi syadgsearv itwkkidlpy vdvvstekem ikrflrvvre kdpdvlityn gdnfdfaylk krceelgikf tlgrdgsepk iqrmgdrfav evkgrihfdl ypvirrtinl ptytleavye avfgkpkekv yaeeiaqawe sgeglervar ysmedakvty elgreffpme aqlsrligqs lwdvsrsstg nlvewfllrk aykrnelapn kpderelarr rggyaggyvk eperglwdni vyldfrslyp siiithnvsp dtlnregcke ydvapevghk fckdfpgfip sllgdlleer qkikrkmkat vdplekklld yrqraikila nsfygyygya karwyckeca esvtawgrey iemvirelee kfgfkvlyad tdglhatipg adaetvkkka keflkyinpk lpglleleye gfyvrgffvt kkkyavidee gkittrglei vrrdwseiak etqarvleai lkhgdveeav rivkevtekl skyevppekl viheqitrdl rdykatgphv avakrlaarg vkirpgtvis yivlkgsgri gdraipadef dptkhrydae yyienqvlpa verilkafgy rkedlryqkt kqvglgawlk vkgkk (SEQ ID NO. 91)

ACCESSION BAA06142 KOD Pyrococcus sp.

mildtdyite dgkpvirifk kengefkiey drtfepyfya llkddsaiee vkkitaerhg tvvtvkrvek vqkkflgrpv evwklyfthp qdvpairdki rehpavidiy eydipfakry lidkglvpme gdeelkmlaf dietlyhege efaegpilmi syadeegarv itwknvdlpy vdvvsterem ikrflrvvke kdpdvlityn gdnfdfaylk krceklginf algrdgsepk iqrmgdrfav evkgrihfdl ypvirrtinl ptytleavye avfgqpkekv yaeeittawe tgenlervar ysmedakvty elgkeflpme aqlsrligqs lwdvsrsstg nlvewfllrk ayernelapn kpdekelarr rqsyeggyvk eperglweni vyldfrchpa dtkvvvkgkg iinisevqeg dyvlgidgwq rvrkvweydy kgelvningl kctpnhklpv vtknerqtri rdslaksflt kkvkgkiitt plfyeigrat senipeeevl kgelagilla egtllrkdve yfdssrkkrr ishqyrveit igkdeeefrd rityiferlf gitpsisekk gtnavtlkva kknvylkvke imdnieslha psvlrgffeg dgsvnrvrrs ivatqgtkne wkiklvskll sqlgiphqty tyqyqengkd rsryileitg kdglilfqtl igfiserkna llnkaisqre mnnlenngfy rlsefnvste yyegkvydlt legtpyyfan gilthnslyp siiithnvsp dtlnregcke ydvapqvghr fckdfpgfip sllgdlleer qkikkkmkat idpierklld yrqraikila nsilpeewlp vleegevhfv rigelidrmm eenagkvkre getevlevsg levpsfnrrt nkaelkrvka lirhdysgkv ytirlksgrr ikitsghslf svrngelvev tgdelkpgdl vavprrlelp ernhvlnlve lllgtpeeet ldivmtipvk gkknffkgml rtlrwifgee krprtarryl rhledlgyvr lkkigyevld wdslknyrrl yealvenvry ngnkreylve fnsirdavgi mplkelkewk igtlngfrmr klievdesla kllgyyvseg yarkqrnpkn gwsysvklyn edpevlddme rlasrffgkv rrgrnyveip kkigyllfen mcgvlaenkr ipefvftspk gvrlaflegy figdgdvhpn krlrlstkse llanqlvlll nsvgvsavkl ghdsgvyrvy ineelpfvkl dkkknayysh vipkevlsev fgkvfqknvs pqtfrkmved grldpekaqr lswliegdvv ldrvesvdve dydgyvydls vednenflvg fglvyahnsy ygyygyarar wyckecaesv tawgreyitm tikeieekyg fkviysdtdg ffatipgada etvkkkamef lkyinaklpg aleleyegfy krgffvtkkk yavideegki ttrgleivrr dwseiaketq arvleallkd gdvekavriv kevteklsky evppeklvih eqitrdlkdy katgphvava krlaargvki rpgtvisyiv lkgsgrigdr aipfdefdpt khkydaeyyi enqvlpaver ilrafgyrke dlryqktrqv glsawlkpkg t (SEQ ID NO. 92)

ACCESSION 4699806 Tgo Thermococcus gorgonarius.

mildtdyite dgkpvirifk kengefkidy drnfepyiya llkddsaied vkkitaerhg ttvrvvraek vkkkflgrpi evwklyfthp qdvpairdki kehpavvdiy eydipfakry lidkglipme gdeelkmlaf dietlyhege efaegpilmi syadeegarv itwknidlpy vdvvstekem ikrflkvvke kdpdvlityn gdnfdfaylk krseklgvkf ilgregsepk iqrmgdrfav evkgrihfdl ypvirrtinl ptytleavye aifgqpkekv yaeeiaqawe tgeglervar ysmedakvty elgkeffpme aqlsrlvgqs lwdvsrsstg nlvewfllrk ayernelapn kpderelarr resyaggyvk eperglweni vyldfrslyp siiithnvsp dtlnregcee ydvapqvghk fckdfpgfip sllgdlleer qkvkkkmkat idpiekklld yrqraikila nsfygyygya karwyckeca esvtawgrqy iettireiee kfgfkvlyad tdgffatipg adaetvkkka kefldyinak lpglleleye gfykrgffvt kkkyavidee dkittrglei vrrdwseiak etqarvleai lkhgdveeav rivkevtekl skyevppekl viyeqitrdl kdykatgphv avakrlaarg ikirpgtvis yivlkgsgri gdraipfdef dpakhkydae yyienqvlpa verilrafgy rkedlryqkt rqvglgawlk pkt (SEQ ID NO. 93)

ACCESSION P74918 THEFM Thermococcus fumicolans mildtdyite dgrpvirvfk kengefkiey drdfepyiya llkddsaied vkkitasrhg ttvrvvragk vkkkflgrpi evwklyfthp qdvpairdki rehpavvdiy eydipfakry lidkglipme gdeelkmlaf dietlyhege efaegpilmi syadeegarv itwkkidlpy vdvvstekem ikrflkvvke kdpdvlityn gdnfdfaylk krseklgvkf ilgrdgsepk iqrmgdrfav evkgrihfdl ypvirhtinl ptytleavye aifgqpkekv yaeeiaqawe tgeglervar ysmedakvty elgreffpme aqlsrlvgqs fwdvsrsstg nlvewyllrk ayernelapn kpsgrelerr rggyaggyvk eperglweni ayldfrchpa dtkvivkgkg vvnisevreg dyvlgidgwq kvqrvweydy egelvningl kctpnhklpv vrrterqtai rdslaksflt kkvkgklitt plfekigkie redvpeeeil kgelagiila egtllrkdve yfdssrgkkr vshqyrveit vgaqeedfqr rivyiferlf gvtpsvyrkk ntnaitfkva kkevylrvre imdgienlha psvlrgffeg dgsvnkvrkt vvvnqgtnne wkievvskll nklgiphrry tydyterekt mtthileiag rdglilfqti vgfisteknm aleeairnre vnrlennafy tladftakte yykgkvydlt legtpyyfan gilthnslyp siiishnvsp dtlnregcge ydeapqvghr fckdfpgfip sllgdllder qkvkkhmkat vdpiekklld yrqraikila nsfygyygya karwyckeca esvtawgrqy iettmreiee kfgfkvlyad svtgdtevti rrngriefvp ieklfervdh rvgekeycvl ggvealtldn rgrlvwkkvp yvmrhktdkr iyrvwftnsw yldvtedhsl igylntskvk pgkplkerlv evkpeelggk vkslitpnrp iartikanpi avklweligl lvgdgnwggq snwakyyvgl scgldkaeie rkvlnplrea svisnyydks kkgdvsilsk wlagfmvkyf kdengnkaip sfmfnlprey ieaflrglfs adgtvslrrg ipeirltsvn relsdavrkl lwlvgvsnsl ftetkpnryl ekesgthsih vriknkhrfa drigflidrk stklsenlgg htnkkrayky dfdlvyprki eeitydgyvy dievegthrf fangilvhnt dgffatipga daetvkkkar eflnyinpkl pglleleyeg fyrrgffvtk kkyavideeg kittrgleiv rrdwsevake tqarvleail rhgdveeavr ivkevtekls kyevppeklv iheqitrelk dykatgphva iakrlaargi kvrpgtvisy ivlkgsgrig drtipfdefd ptkhrydaey yienqvlpav erilkafgyk kedlryqktr qvglgawlkm gkk (SEQ ID NO. 94)

ACCESSION O27276 METTH Methanobacterium thermoautotrophicum medyrmvlld idyvtvdevp virlfgkdks ggnepiiahd rsfrpyiyai ptdldeclre leelelekle vkemrdlgrp teviriefrh pqdvpkirdr irdlesvrdi rehdipfyrr ylidksivpm eelefqgvev dsapsvttdv rtvevtgrvq stgsgahgld ilsfdievrn phgmpdpekd eivmigvagn mgyesvista gdhldfvevv ederellerf aeividkkpd ilvgynsdnf dfpyitrraa ilgaeldlgw dgskirtmrr gfanataikg tvhvdlypvm rrymnldryt lervyqelfg eekidlpgdr lweywdrdel rdelfrysld dvvathriae kilplnlelt rlvgqplfdi srmatgqqae wflvrkayqy gelvpnkpsq sdfssrrgrr avggyvkepe kglhenivqf dfrslypsii isknispdtl tddeesecyv apeygyrfrk sprgfvpsvi geilservri keemkgsddp merkilnvqq ealkrlantm ygvygysrfr wysmecaeai tawgrdyikk tiktaeefgf htvyadtdgf yatyrg (SEQ ID NO. 95)

ACCESSION Q58295 Metja Methanococcus jannaschii mgmsmgkiki dalidntykt iedkaviyly linsilkdrd fkpyfyvelh kekvenedie kikefllknd llkfveniev vkkiilrkek evikiiathp qkvpklrkik eceivkeiye hdipfakryl idneiipmty wdfenkkpvs ieipklksva fdmevynrdt epnperdpil masfwdengg kvitykefnh pnievvknek elikkiietl keydviytyn gdnfdfpylk arakiygidi nlgkdgeelk ikrggmeyrs yipgrvhidl ypisrrllkl tkytledvvy nlfgieklki phtkivdywa nndktlieys lqdakytyki gkyffplevm fsrivnqtpf eitrmssgqm veyllmkraf kenmivpnkp deeeyrrrvl ttyeggyvke pekgmfedii smdfrchpkg tkvvvkgkgi vniedvkegn yvlgidgwqk vkkvwkyeye gelinvnglk ctpnhkiplr ykikhkkink ndylvrdiya kslltkfkge gklilckdfe tignyekyin dmdedfilks eligillaeg hllrrdieyf dssrgkkris hqyrveitvn edekdfieki kyifkklfny elyvrrkkgt kaitlgcakk diylkieeil knkekylpna ilrgffegdg yvntvrravv vnqgtnnydk ikfiaslldr lgikysfyty syeergkklk ryvieifskg dlikfsilis fisrrknnll neiirqktly kigdygfydl ddvcvslesy kgevydltle grpyyfangi lthnslypsi iisynispdt ldceccktvs ekilghwfck kkeglipktl rnlierrini krrmkkmaei geineeynll dyeqkslkil ansilpdeyl tiieedgikv vkigeyiddl mrkhkdkikf sgiseiletk nlktfsfdki tkkceikkvk alirhpyfgk aykiklrsgr tikvtrghsl fkyengkive vkgddvrfgd livvpkkltc vdkevvinip krlinadeee ikdlvitkhk dkaffvklkk tlediennkl kvifddcily lkelglidyn iikkinkvdi kildeekfka ykkyfdtvie hgnfkkgrcn iqyikikdyi anipdkefed ceigaysgki nallkldekl akflgffvtr grlkkqklkg etvyeisvyk slpeyqkeia etfkevfgag smvkdkvtmd nkivylvlky ifkcgdkdkk hipeelflas esviksfldg flkakknshk gtstfmakde kylnqlmilf nlvgiptrft pvknkgyklt lnpkygtvkd lmldevkeie afeysgyvyd lsvednenfl vnniyahnsv ygylafprar fysrecaeiv tylgrkyile tvkeaekfgf kvlyidtdgf yaiwkekisk eelikkamef veyinsklpg tmelefegyf krgifvtkkr yalidengrv tvkglefvrr dwsniakitq rrvleallve gsiekakkii qdvikdlrek kikkedliiy tqltkdpkey kttaphveia kklmregkri kvgdiigyii vkgtksiser aklpeevdid didvnyyidn qilppvlrim eavgvsknel kkegaqltld kffk (SEQ ID NO. 96)

ACCESSION B56277 POC Pyrodictium occultum mtetiefvll dssyeilgke pvvilwgitl dgkrvvlldh rfrpyfyali argyedmvee iaasirrlsv vkspiidakp ldkryfgrpr kavkittmip esvrhyreav kkiegvedsl eadirfamry lidkrlypft vyripvedag rnpgfrvdrv ykvagdpepl aditridlpp mrlvafdiev ysrrgspnpa rdpviivslr dsegkerlie aeghddrrvl refveyvraf dpdiivgyns nhfdwpylme rarrlgikld vtrrvgaept tsvyghvsvq grlnvdlydy aeempeikmk tleevaeylg vmkkservii ewwripeywd dekkrqller yalddvraty glaekmlpfa iqlstvtgvp ldqvgamgvg frlewylmra aydmnelvpn rverrgesyk gavvlkplkg vhenvvvldf ssmypsimik ynvgpdtivd dpsecpkygg cyvapevghr frrsppgffk tvlenllklr rqvkekmkef ppdspeyrly derqkalkvl anasygymgw sharwyckrc aeavtawgrn liltaieyar klglkviygd tdslfvvydk ekvekliefv ekelgfeiki dkiykkvfft eakkryvgll edgridivgf eavrgdwcel akevqekaae ivlntgnvdk aisyirevik qlregkvpit kliiwktlsk rieeyehdap hvmaarrmke agyevspgdk vgyvivkgsg svssraypyf mvdpstidvn yyidhqivpa alrilsyfgv tekqlkaaat vqrslfdffa skk (SEQ ID NO. 97)

ACCESSION BAA81109 ApeI Aeropyrum pernix mrgstpviil wgrgadgsrv vvfygefrpy fyvlpdgsvg ldqlaamirr lsrpsspils vervrrrfig revealkvtt lvpasvreyr eavrrlggvr dvleadipfa lrfiidfnly pmrwyvaevr evavphgysv draytlsgdi redetriqed plkglrvmaf dievyskmrt pdpkkdpvim iglqqaggei eileaedrsd kkviagfver vksidpdviv gynqnrfdwp ylverarvlg vklavgrrsv epqpglyghy svsgrlnvdl ldfaeelhev kvktleevad ylgvvkiger vtlewwqige ywddpskrei lrkylrddvr stmglaekfl pfgaelsqvs glpldqvmaa svgfrlewrl ireaaklgel vpnrverseg ryagaivlrp kpgvhediav ldfasmypni mvkynvgpdt lvrpgeeyge eevytapevg hkfrksppgf fkkilerfls wrrqirsemk khppdspeyk llderqkaik llanasygym gwpharwycr ecaeavtawg rsiirtairk agelgleviy gdtdslfvkn dpekverlir fveeelgfdi kvdkvyrrvf fteakkryvg ltvdgkidvv gfeavrgdws elaketqfkv aeivlktgsv deavdyvrni ieklrrgqvd mrklviwktl trppsmyear qphvtaallm eragikvepg akigyvvtkg sgplytrakp yfmaskeevd veyyvdkqvv paalrilqyf gvtekrlkgg grqstlldfm rrgk (SEQ ID NO. 98)

ACCESSION O29753 ARCFU Archaeoglobus fulgidus mervegwlid adyetiggka vvrlwckddq gifvaydynf dpyfyvigvd edilknaats trreviklks fekaqlktlg revegyivya hhpqhvpklr dylsqfgdvr eadipfayry lidkdlacmd giaiegekqg gvirsykiek veriprmefp elkmlvfdce mlssfgmpep ekdpiivisv ktndddeiil tgderkiisd fvkliksydp diivgynqda fdwpylrkra erwnipldvg rdgsnvvfrg grpkitgrln vdlydiamri sdikikklen vaeflgtkie iadieakdiy rywsrgekek vlnyarqdai ntyliakell pmhyelskmi rlpvddvtrm grgkqvdwll lseakkigei apnppehaes yegafvlepe rglhenvacl dfasmypsim iafnispdty gcrddcyeap evghkfrksp dgffkrilrm liekrrelkv elknlspess eyklldikqq tlkvltnsfy gymgwnlarw ychpcaeatt awgrhfirts akiaesmgfk vlygdtdsif vtkagmtked vdrlidklhe elpiqievde yysaiffvek kryagltedg rlvvkglevr rgdwcelakk vqrevievil keknpekals lvkdvilrik egkvsleevv iykgltkkps kyesmqahvk aalkaremgi iypvsskigy vivkgsgnig draypidlie dfdgenlrik tksgieikkl dkdyyidnqi ipsvlriler fgyteaslkg ssqmsldsff s (SEQ ID NO. 99)

ACCESSION 6435708 Desulfurococcus sp. Tok.

mildadyite dgkpvirvfk kekgefkidy drdfepyiya llkddsaied ikkitaerhg ttvrvtraer vkkkflgrpv evwklyfthp qdvpairdki rehpavvdiy eydipfakry lidrglipme gdeelrmlaf dietlyhege efgegpilmi syadeegarv itwknidlpy vesvstekem ikrflkviqe kdpdvlityn gdnfdfaylk krsemlgvkf ilgrdgsepk iqrmgdrfav evkgrihfdl ypvirrtinl ptytletvye pvfgqpkekv yaeeiarawe sgeglervar ysmedakaty elgkeffpme aqlsrlvgqs lwdvsrsstg nlvewfllrk ayerndvapn kpderelarr tesyaggyvk epekglweni vyldykslyp siiithnvsp dtlnregcre ydvapqvghr fckdfpgfip sllgdlleer qkvkkkmkat vdpierklld yrqraikila nsyygyyaya narwycreca esvtawgrqy iettmreiee kfgfkvlyad tdgffatipg adaetvknka keflnyinpr lpglleleye gfyrrgffvt kkkyavidee dkittrglei vrrdwseiak etqarvleai lkhgdveeav rivkevtekl srhevppekl viyeqitrdl rsyratgphv avakrlaarg ikirpgtvis yivlkgpgrv gdraipfdef dpakhrydae yyienqvlpa verilrafgy rkedlryqkt kqaglgawlk pkt (SEQ ID NO. 100)

ACCESSION Q56366 9oN-7 mildtdyite ngkpvirvfk kengefkiey drtfepyfya llkddsaied vkkvtakrhg tvvkvkraek vqkkflgrpi evwklyfnhp qdvpairdri rahpavvdiy eydipfakry lidkglipme gdeeltmlaf dietlyhege efgtgpilmi syadgsearv itwkkidlpy vdvvstekem ikrflrvvre kdpdvlityn gdnfdfaylk krceelgikf tlgrdgsepk iqrmgdrfav evkgrihfdl ypvirrtinl ptytleavye avfgkpkekv yaeeiaqawe sgeglervar ysmedakvty elgreffpme aqlsrligqs lwdvsrsstg nlvewfllrk aykrnelapn kpderelarr rggyaggyvk eperglwdni vyldfrslyp siiithnvsp dtlnregcke ydvapevghk fckdfpgfip sllgdlleer qkikrkmkat vdplekklld yrqraikila nsfygyygya karwyckeca esvtawgrey iemvirelee kfgfkvlyad tdglhatipg adaetvkkka keflkyinpk lpglleleye gfyvrgffvt kkkyavidee gkittrglei vrrdwseiak etqarvleai lkhgdveeav rivkevtekl skyevppekl viheqitrdl rdykatgphv avakrlaarg vkirpgtvis yivlkgsgri gdraipadef dptkhrydae yyienqvlpa verilkafgy rkedlryqkt kqvglgawlk vkgkk (SEQ ID NO. 101)

ACCESSION O29753 Afu mervegwlid adyetiggka vvrlwckddq gifvaydynf dpyfyvigvd edilknaats trreviklks fekaqlktlg revegyivya hhpqhvpklr dylsqfgdvr eadipfayry lidkdlacmd giaiegekqg gvirsykiek veriprmefp elkmlvfdce mlssfgmpep ekdpiivisv ktndddeiil tgderkiisd fvkliksydp diivgynqda fdwpylrkra erwnipldvg rdgsnvvfrg grpkitgrln vdlydiamri sdikikklen vaeflgtkie iadieakdiy rywsrgekek vlnyarqdai ntyliakell pmhyelskmi rlpvddvtrm grgkqvdwll lseakkigei apnppehaes yegafvlepe rglhenvacl dfasmypsim iafnispdty gcrddcyeap evghkfrksp dgffkrilrm liekrrelkv elknlspess eyklldikqq tlkvltnsfy gymgwnlarw ychpcaeatt awgrhfirts akiaesmgfk vlygdtdsif vtkagmtked vdrlidklhe elpiqievde yysaiffvek kryagltedg rlvvkglevr rgdwcelakk vqrevievil keknpekals lvkdvilrik egkvsleevv iykgltkkps kyesmqahvk aalkaremgi iypvsskigy vivkgsgnig draypidlie dfdgenlrik tksgieikkl dkdyyidnqi ipsvlriler fgyteaslkg ssqmsldsff s (SEQ ID NO. 102)

ACCESSION P52025 Mvo mdldynskdl cidmyykncg lkkpeinlqk ecefkpyfyv dtsepkeiyd yldglnqeid lkklepefen ntslkvqdli tnieiiekiv ysdyilngkd isevsdfknk kerkickvyv kypnhvkiir eyfkefgksy efdipflrry midqdivpsa kysednkidn sipelnciaf dmelyckkep nakkdpiimv nlfskdyqkv itykkfense yngcvdyvkd ekeliqktie ilkqydviyt yngdnfdfpy lkkraniyei eldfdnasns qqpqiikisk gginrkskip giihidlypi arkllnltky klenvvqelf kinkeavdyg dipkmweted ttllryayed alytykmgny flpleimfsr ivnqplydts rmnssqmvef lllkrsfeqn mispnrpsss syrerakfsy eggyvreplk giqedivsld fmslypsili shnispetvi yeekerenme lgiipktlne llsrrkhikm llkdkiqkne fdeeysrleh eqksikvlan shygylafpm arwysdkcae mvtglgrkyi qetiekaeef gfkviyadtd gfyakwdydk lqkgkkeend ksdklsnlpk lskeeliilt kkflkginee lpegmelefe ghfkrglfvt kkkyaliedd ghivvkglev vrrdwsniak dtqqaviral ledgdvnlak kiikntidnl kkgnidkndl lihtqltkni eeykstaphi evakkikqrg dsvrvgdvis yiivkgsrsi seraelleya gdydinyyid nqvlppviri meslgisede lknsgkqfkl dqfm (SEQ ID NO. 103)

ACCESSION AAF27815 melkvwpldi tyavvgsvpe irifgilssg ervvlidrsf kpyfyvdcav cepaalktal srvapiddvq iverrflgrs kkflkviaki pedvrklrea amsiprvsgv yeadirfymr ymidmgvvpc swnvaeveeg grlggiptyv vsqwygideg fppslkvmaf dievynergs pdpirdpvvm laiktndghe evfeasgkdd rgvvrafvdf irsydpdviv gynsngfdwp ylverakavg vplkvdrlsn ppqqsvyghw sivgranvdl yniveefpei klktldrvae yfgvmkreer vlipghkiye ywkdpnkrpl lkryvlddvr stlgladkll pfliqlssvs glpldqvaaa svgnrvewml lryayrlgev apnreereye pykgaivlep kpgmyedvlv ldfssmypni mmkynlspdt ylepgepdpp egvnvapevg hrfrrsppgf vpqvlkslve lrkavreeak kyppdspefk ilderqralk vmanaiygyl gwvgarwykr evaesvtafa railkdvieq arrlgivvvy gdtdslfvkk hgdvdkliky veekygidik vdkdyakvlf teakkryagl lrdgridivg fevvrgdwse lakdvqlrvi eiilksrdiv earhgvikyi reiierlkny kfniddliiw ktldkeldey kaypphvhaa qilkrhgyrv gkgttigyvi vkggekvser alpyillddi kkididyyie rqiipaalri aevigvkesd lktgrmersl ldfls (SEQ ID NO. 104)

ACCESSION AAC62712 Csy mtvqdaveip psllvsatyd sqagavvlkf yepesqkivh wtdntghkpy cytrqppsel gelegredvl gteqvmrhdl iadkdvpvtk itvadplaig gtnseksirn imdtwesdik yyenylydks lvvgryysvs ggkviphdmp isdevklalk sllwdkvvde gmadrkefre fiagwadlln qpiprirrls fdievdseeg ripdpkisdr rvtavgfaat dglkqvfvlr sgaeegengv tpgvevvfyd keadmirdal svigsypfvl tyngddfdmp ymlnrarrlg vsdsdiplym mrdsatlrhg vhldlyrtfs nrsfqlyafa akytdyslns vtkamlgegk vdygvklgdl tlyqtanycy hdarltlels tfgneilmdl lvvtsriarm piddmsrmgv sqwirsllyy ehrqrnalip rrdelegrsr evsndavikd kkfrgglvve peegihfdvt vmdfaslyps iikvrnlsye tvrcvhaeck kntipdtnhw vctknnglts miigslrdlr vnyykslsks tsiteeqrqq ytvisqalkv vlnasygvmg aeifplyflp aaeattavgr yiimqtishc eqmgvrvlyg dtdslfikdp eerqiheive hakkehgvel evdkeyryvv lsnrkknyfg vtragkvdvk gltgkkshtp pfikelfysl ldilsgvese defesakmri skaiaacgkr leerqiplvd lafnvmiska pseyvktvpq hiraarllen arevkkgdii syvkvmnktg vkpvemarag evdtskylef mestldqlts smgldfdeil gkpkqtgmeq fffk (SEQ ID NO. 105)

ACCESSION P95690 Sac mskqatlfdf sikkneskeq tnqesvevpk qtanrtkiew ikeaedgkvy fllqvdydgk ksravcklyd kegkkiyimq desghkpyfl tdidpdkvnk itkvvrdpsf dhlelinkvd pytgkkirlt kivvkdplav rrnrsslpka yeahikyynn yvydnglipg liykvnkgkl tqlnpelkge eineikklsd ayemtketvn dwipiletev pdikrvsldi evytpnrgri pdperaefpi isvalagndg skivlalkre dvnsdfskkd gvqveifdse kkllarlfei ireypmlltf ngddfdipyi yfralrlnfs peevpldvvs gegkflagih idlykfffnr avsiyafegk yseyslyava tallgiskvk ldtfisfmdi dklieynlrd aeitlklttf nnnlvlklmv llarisklgl eeltrtevst wiknlyyweh rkrnwliplk eeilvrsnqv ktaavikgkk ykgavvidpp agvyfnvvvl dfaslypsii knwnisyeti eidectkkvw vedetgeklh yvcmdkpgit avyqglirdf rvkvykkkak ysniseeqrs lydvvqramk vfinatygvf gaenfplyap avaesvtaig ryiitttykq aeklnlkviy gdtdslflyn ptkdkleeli kfvkqnfnld levdntykyv aysglkknyf gvypdgktei kgmlakkrnt pefikkefae iknmlaslns pndipevknk leikikdiyy klrnkgynld dlafrimlsk pldsytkntp qhvkaglqlr afgvnvlprd vimfvkvksk dgvkayqlak iseidiekyv etlrttfeqi lkafgiswde ivstisidsf fgskk (SEQ ID NO. 106)

ACCESSION BAA23994 Soh marqitlfdf tlkkeqnkde srkeeiphan ineerrkpke wikeaeegks yfllqvdydg kkskaickly dketkkiyil ydntghkpyf ltdidpekvn kipkvvrdps fdhletviki dpysgnkikl tkivvkdpla vrrnrnsvpk ayeahikyfn nyiydlglip glpyvvkkgk leqlrpelkg eevdeirkaf adsdemtkea vndwipifes evpdvkrvai dievytpikg ripdpekaef piisislagn dgtkrvlvll redvnsqitk hdvivetfks erelirrffd iildypiilt fngddfdipy iyyralklnf tpeeipfdii ndegkylagi hidlykfffn rairnyafeg kyneynldav atallgmskv kldtlisfld ldklieynsr daeitlkltt fnnnlvwkli illariskmg leeltrtevs twiknlyywe hrrrnwlipl keeiltrssq iktaaiikgk rykgavvidp pagvffnvvv ldfaslypsi irnwnisyet vdvencknke yvrdetgevl hyickdkpgi tavitgllrd frvkvykkka ksqniseeqr svydvvqram kvfinatygv fgaenfplya pavaesvtai gryvitttvn ycrsiglqvl ygdtdsmflw npskekleei ikfvkgkfgl dlevdkvykf vafsglkkny lgvypdgktd ikgmlakkrn tpefikkefn evkqlvttin spddipkird qleykikeiy eklrhkgynl delafrvmls kplesytknt pqhvkaalql rsygvmvlpr diimfvkvks kdgvkpvqla klseidvdky idavrstfeq ilkafgliga nllqllsils lt (SEQ ID NO. 107)

ACCESSION P26811 Sso mtkqltlfdi psskpakseq ntqqsqqsap veekkvvrre wleeaqenki yfllqvdydg kkgkavcklf dketqkiyal ydntghkpyf lvdlepdkvg kipkivrdps fdhietvski dpytwnkfkl tkivvrdpla vrrlrndvpk ayeahikyfn nymydiglip gmpyvvkngk lesvylslde kdveeikkaf adsdemtrqm avdwlpifet eipkikrvai dievytpvkg ripdsqkaef piisialags dglkkvlvln rndvnegsvk ldgisverfn teyellgrff dilleypivl tfngddfdlp yiyfralklg yfpeeipidv agkdeakyla glhidlykff fnkavrnyaf egkyneynld avakallgts kvkvdtlisf ldveklieyn frdaeitlql ttfnndltmk livlfsrisr lgieeltrte istwvknlyy wehrkrnwli plkeeilaks snirtsalik gkgykgavvi dppagiffni tvldfaslyp siirtwnlsy etvdiqqckk pyevkdetge vlhivcmdrp gitavitgll rdfrvkiykk kaknpnnsee qkllydvvqr amkvfinaty gvfgaetfpl yapavaesvt algryvitst vkkareeglt vlygdtdslf llnppknsle niikwvkttf nldlevdkty kfvafsglkk nyfgvyqdgk vdikgmlvkk rntpefvkkv fnevkelmis inspndvkei krkivdvvkg syeklknkgy nldelafkvm lskpldaykk ntpqhvkaal qlrpfgvnvl prdiiyyvkv rskdgvkpvq lakvteidae kylealrstf eqilrafgvs wdeiaatmsi dsffsypskg ns (SEQ ID NO. 108)

Figure 7B

Alignment (DIALIGN format):

```
Pfu      1   MILDVDYITE EGKPVIRLFK KENGKFKIEH DRTFRPYIYA LLRDDSKIEE
Tgo      1   MILDTDYITE DGKPVIRIFK KENGEFKIDY DRNFEPYIYA LLKDDSAIED
KOD      1   MILDTDYITE DGKPVIRIFK KENGEFKIEY DRTFEPYFYA LLKDDSAIEE
Vent     1   MILDTDYITK DGKPIIRIFK KENGEFKIEL DPHFQPYIYA LLKDDSAIEE
Deep     1   MILDADYITE DGKPIIRIFK KENGEFKVEY DRNFRPYIYA LLKDDSQIDE
JDF-3    1   MILDVDYITE NGKPVIRVFK KENGEFRIEY DREFEPYFYA LLRDDSAIEE

                                                        V93
Pfu      51  VKKITGERHG KIVRIVDVEK VEKKFLGKPI TVWKLYLEHP QDVPTIREKV
Tgo      51  VKKITAERHG TTVRVVRAEK VKKKFLGRPI EVWKLYFTHP QDVPAIRDKI
KOD      51  VKKITAERHG TVVTVKRVEK VQKKFLGRPV EVWKLYFTHP QDVPAIRDKI
Vent     51  IKAIKGERHG KTVRVLDAVK VRKKFLGREV EVWKLIFEHP QDVPAMRGKI
Deep     51  VRKITAERHG KIVRIIDAEK VRKKFLGRPI EVWRLYFEHP QDVPAIRDKI
JDF-3    51  IKKITAERHG RVVKVKRAEK VKKKFLGRSV EVWVLYFTHP QDVPAIRDKI

                                                        DXE (exo I)
Pfu      101 REHPAVVDIF EYDIPFAKRY LIDKGLIPME GEEELKILAF DIETLYHEGE
Tgo      101 KEHPAVVDIY EYDIPFAKRY LIDKGLIPME GDEELKMLAF DIETLYHEGE
KOD      101 REHGAVIDIY EYDIPFAKRY LIDKGLVPME GDEELKMLAF DIQTLYHEGE
Vent     101 REHPAVVDIY EYDIPFAKRY LIDKGLIPME GDEELKLLAF DIETFYHEGD
Deep     101 REHSAVIDIF EYDIPFAKRY LIDKGLIPME GDEELKLLAF DIETLYHEGE
JDF-3    101 RKHPAVIDIY EYDIPFAKRY LIDKGLIPME GEEELKLMSF DIETLYHEGE
                        111        121        131        141-143

Pfu      151 EFGKGPIIMI SYADENEAKV ITWKNIDLPY VEVVSSEREM IKRFLRIIRE
Tgo      151 EFAEGPILMI SYADEEGARV ITWKNIDLPY VDVVSTEKEM IKRFLKVVKE
KOD      151 EFAEGPILMI SYADEEGARV ITWKNVDLPY VDVVSTEREM IKRFLRVVKE
Vent     151 EFGKGEIIMI SYADEEEARV ITWKNIDLPY VDVVSNEREM IKRFvQVVKE
Deep     151 EFAKGPIIMI SYADEEEAKV ITWKKIDLPY VEVVSSEREM IKRFLKVIRE
JDF-3    151 EFGTGPILMI SYADESEARV ITWKKIDLPY VEVVSTEKEM IKRFLRVVKE

                     NX2-3FD (exo II)
Pfu      201 KDPDIIVTYN GDSFDFPYLA KRAEKLGIKL TIGRDGS--E PKMQRIGDMT
Tgo      201 KDPDVLITYN GDNFDFAYLK KRSEKLGVKF ILGREGS--E PKIQRMGDRF
KOD      201 KDPDVLITYN GDNFDFAYLK KRCEKLGINF ALGRDGS--E PKIQRMGDRF
Vent     201 KDPDVIITYN GDNFDLPYLI KRAEKLGVRL VLGRDkehpE PKIQRMGDSF
Deep     201 KDPDVIITYN GDSFDLPYLV KRAEKLGIKL PLGRDGS--E PKMQRLGDMT
JDF-3    201 KDPDVLITYN GDNFDFAYLK KRCEKLGVSF TLGRDGS--E PKIQRMGDRF
                 210-215                 231        239

Pfu      249 AVEVKGRIHF DLYHVITRTI NLPTYTLEAV YEAIFGKPKE KVYADEIAKA
Tgo      249 AVEVKGRIHF DLYPVIRRTI NLPTYTLEAV YEAIFGQPKE KVYAEEIAQA
KOD      249 AVEVKGRIHF DLYPVIRRTI NLPTYTLEAV YEAVFGQPKE KVYAEEITPA
```

| | | |
|---|---|---|
| Vent | 251 | AVEIKGRIHF DLFPVVRRTI NLPTYTLEAV YEAVLGKTKS KLGAEEIAAI |
| Deep | 249 | AVEIKGRIHF DLYHVIRRTI NLPTYTLEAV YEAIFGKPKE KVYAHEIAEA |
| JDF-3 | 249 | AVEVKGRVHF DLYPVIRRTI NLPTYTLEAV YEAVFGKPKE KVYAEEIATA |

$YX_3D$ (exo III)

| | | |
|---|---|---|
| Pfu | 299 | WESGENLERV AKYSMEDAKA TYELGKEFLP MEIQLSRLVG QPLWDVSRSS |
| Tgo | 299 | WETGEGLERV ARYSMEDAKV TYELGKEFFP MEAQLSRLVG QSLWDVSRSS |
| KOD | 299 | WETGENLERV ARYSMEDAKV TYELGKEFLP MEAQLSRLIG QSLWDVSRSS |
| Vent | 301 | WETEESMKKL AQYSMEDARA TYELGKEFFP MEAELAKLIG QSVWDVSRSS |
| Deep | 299 | WETGKGLERV AKYSMEDAKV TYELGREFFP MEAQLSRLVG QPLWDVSRSS |
| JDF-3 | 299 | WETGEGLERV ARYSMEDARV TYELGREFFP MEAQLSRLIG QGLWDVSRSS |

311-315

| | | |
|---|---|---|
| Pfu | 349 | TGNLVEWFLL RKAYERNEVA PNKPSEEEYQ RRLRESYTGG FVKEPEKGLW |
| Tgo | 349 | TGNLVEWFLL RKAYERNELA PNKPDERELA RR-RESYAGG YVKEPERGLW |
| KOD | 349 | TGNLVEWFLL RKAYERNELA PNKPDEKELA RR-RQSYEGG YVKEPERGLW |
| Vent | 351 | TGNLVEWYLL RVAYARNELA PNKPDEEEYK RRLRTTYLGG YVKEPEKGLW |
| Deep | 349 | TGNLVEWYLL RKAYERNELA PNKPDEREYE RRLRESYAGG YVKEPEKGLW |
| JDF-3 | 349 | TGNLVEWFLL RKAYERNELA PNKPDERELA RR-RggYAGG YVKEPERGLW |

| | | |
|---|---|---|
| Pfu | 399 | ENIVYLDFRA LYPSIIITHN VSPDTLNLEG CKNYDIAPQV GHKFCKDIPG |
| Tgo | 398 | ENIVYLDFRS LYPSIIITHN VSPDTLNREG CEEYDVAPQV GHKFCKDFPG |
| KOD | 398 | ENIVYLDFRS LYPSIIITHN VSPDTLNREG CKEYDVAPQV GHRFCKDFPG |
| Vent | 401 | ENIIYLDFRS LYPSIIVTHN VSPDTLEKEG CKNYDVAPIV GYRFCKDFPG |
| Deep | 399 | EGLVSLDFRS LYPSIIITHN VSPDTLNREG CREYDVAPEV GHKFCKDFPG |
| JDF-3 | 398 | DNIVYLDFRS LYPSIIITHN VSPDTLNREG CRSYDVAPEV GHKFCKDFPG |

| | | |
|---|---|---|
| Pfu | 449 | FIPSLLGHLL EERQKIKTKM KETQDPIEKI LLDYRQKAIK LLANSFYGYY |
| Tgo | 448 | FIPSLLGDLL EERQKVKKKM KATIDPIEKK LLDYRQRAIK ILANSFYGYY |
| KOD | 448 | FIPSLLGDLL EERQKIKKKM KATIDPIERK LLDYRQRAIK ILANSYYGYY |
| Vent | 451 | FIPSILGDLI AMRQDIKKKM KSTIDPIEKK MLDYRQRAIK LLANSYYGYM |
| Deep | 449 | FIPSLLKRLL DERQEIKRKM KASKDPIEKK MLDYRQRAIK ILANSYYGYY |
| JDF-3 | 448 | FIPSLLGNLL EERQKIKRKM KATLDPLEKN LLDYRQRAIK ILANSYYGYY |

| | | |
|---|---|---|
| Pfu | 499 | GYAKARWYCK ECAESVTAWG RKYIELVWKE LEEKFGFKVL YIDTDGLYAT |
| Tgo | 498 | GYAKARWYCK ECAESVTAWG RQYIETTIRE IEEKFGFKVL YADTDGFFAT |
| KOD | 498 | GYARARWYCK ECAESVTAWG REYITMTIKE IEEKYGFKVI YSDTDGFFAT |
| Vent | 501 | GYPKARWYSK ECAESVTAWG RHYIEMTIRE IEEKFGFKVL YADTDGFYAT |
| Deep | 499 | GYAKARWYCK ECAESVTAWG REYIEFVRKE LEEKFGFKVL YIDTDGLYAT |
| JDF-3 | 498 | GYARARWYCR ECAESVTAWG REYIEMVIRE LEEKFGFKVL YADTDGLHAT |

| | | |
|---|---|---|
| Pfu | 549 | IPGGESEEIK KKALEFVKYI NSKLPGLLEL EYEGFYKRGF FVTKKRYAVI |
| Tgo | 548 | IPGADAETVK KKAKEFLDYI NAKLPGLLEL EYEGFYKRGF FVTKKKYAVI |

| | | | | | | | |
|---|---|---|---|---|---|---|---|
| KOD | 548 | IPGADAETVK | KKAMEFLNYI | NAKLPGALEL | EYEGFYKRGF | FVTKKKYAVI | |
| Vent | 551 | IPGEKPELIK | KKAKEFLNYI | NSKLPGLLEL | EYEGFYLRGF | FVTKKRYAVI | |
| Deep | 549 | IPGAKPEEIK | KKALEFVDYI | NAKLPGLLEL | EYEGFYVRGF | FVTKKKYALI | |
| JDF-3 | 548 | IPGADAETVK | KKAMEFLNYI | NPKLPGLLEL | EYEGFYVRGF | FVTKKKYAVI | |

| | | | | | | |
|---|---|---|---|---|---|---|
| Pfu | 599 | DEEGKVITRG | LEIVRRDWSE | IAKETQARVL | ETILKHGDVE | EAVRIVKEVI |
| Tgo | 598 | DEEDKITTRG | LEIVRRDWSE | IAKETQARVL | EAILKHGDVE | EAVRIVKEVT |
| KOD | 598 | DEEGKITTRG | LEIVRRDWSE | IAKETQARVL | EALLKDGDVE | KAVRIVKEVT |
| Vent | 601 | DEEGRITTRG | LEVVRRDWSE | IAKETQAKVL | EAILKEGSVE | KAVEVVRDVV |
| Deep | 599 | DEEGKIITRG | LEIVRRDWSE | IAKETQAKVL | EAILKHGNVE | EAVKIVKEVT |
| JDF-3 | 598 | DEEGKITTRG | LEIVRRDWSE | IAKETQARVL | EAILRHGDVE | EAVRIVREVT |

| | | | | | | |
|---|---|---|---|---|---|---|
| Pfu | 649 | QKLANYEIPP | EKLAIYEQIT | RPLHEYKAIG | PHVAVAKKLA | AKGVKIKPGM |
| Tgo | 648 | EKLSKYEVPP | EKLVIYEQIT | RDLKDYKATG | PHVAVAKRLA | ARGIKIRPGT |
| KOD | 648 | EKLSKYEVPP | EKLVIHEQIT | RDLKDYKATG | PHVAVAKRLA | ARGVKIRPGT |
| Vent | 651 | EKIAKYRVPL | EKLVIHEQIT | RDLKDYKAIG | PHVAIAKRLA | ARGIKVKPGT |
| Deep | 649 | EKLSKYEIPP | EKLVIYEQIT | RPLHEYKAIG | PHVAVAKRLA | ARGVKVRPGM |
| JDF-3 | 648 | EKLSKYEVPP | EKLVIHEQIT | RELKDYKATG | PHVAIAKRLA | ARGVKIRPGT |

| | | | | | | |
|---|---|---|---|---|---|---|
| Pfu | 699 | VIGYIVLRGD | GPISNRAILA | EEYDPKKHKY | DAEYYIENQV | LPAVLRILEG |
| Tgo | 698 | VISYIVLKGS | GRIGDRAIPF | DEFDPAKHKY | DAEYYIENQV | LPAVERILRA |
| KOD | 698 | VISYIVLKGS | GRIGDRAIPF | DEFDPTKHKY | DAEYYIENQV | LPAVERILRA |
| Vent | 701 | IISYIVLKGS | GKISDRVILL | TEYDPRKHKY | DPDYYIENQV | LPAVLRILEA |
| Deep | 699 | VIGYIVLRGD | GPISKRAILA | EEFDLRKHKY | DAEYYIENQV | LPAVLRILEA |
| JDF-3 | 698 | VISYIVLKGS | GRIGDRAIPF | DEFDPTKHKY | DADYYIENQV | LPAVERILRA |

| | | | | | |
|---|---|---|---|---|---|
| Pfu | 749 | FGYRKEDLRY | QKTRQVGLTS | WLNIKKs-- |
| Tgo | 748 | FGYRKEDLRY | QKTRQVGLGA | WLKPKt--- |
| KOD | 748 | FGYRKEDLRY | QKTRQVGLSA | WLKPKGt-- |
| Vent | 751 | FGYRKEDLRY | QSSKQTGLDA | WLKr----- |
| Deep | 749 | FGYRKEDLRW | QKTKQTGLTA | WLNIKKk-- |
| JDF-3 | 748 | FGYRKEDLRY | QKTRQVGLGA | WLKPKGkkk |

Alignment (FASTA format):

>Pfu
MILDVDYITEEGKPVIRLFKKENGKFKIEHDRTFRPYIYALLRDDSKIEE
VKKITGERHGKIVRIVDVEKVEKKFLGKPITVWKLYLEHPQDVPTIREKV
REHPAVVDIFEYDIPFAKRYLIDKGLIPMEGEEELKILAFDIETLYHEGE
EFGKGPIIMISYADENEAKVITWKNIDLPYVEVVSSEREMIKRFLRIIRE
KDPDIIVTYNGDSFDFPYLAKRAEKLGIKLTIGRDGS--EPKMQRIGDMT
AVEVKGRIHFDLYHVITRTINLPTYTLEAVYEAIFGKPKEKVYADEIAKA

WESGENLERVAKYSMEDAKATYELGKEFLPMEIQLSRLVGQPLWDVSRSS
TGNLVEWFLLRKAYERNEVAPNKPSEEEYQRRLRESYTGGFVKEPEKGLW
ENIVYLDFRALYPSIIITHNVSPDTLNLEGCKNYDIAPQVGHKFCKDIPG
FIPSLLGHLLEERQKIKTKMKETQDPIEKILLDYRQKAIKLLANSFYGYY
GYAKARWYCKECAESVTAWGRKYIELVWKELEEKFGFKVLYIDTDGLYAT
IPGGESEEIKKKALEFVKYINSKLPGLLELEYEGFYKRGFFVTKKRYAVI
DEEGKVITRGLEIVRRDWSEIAKETQARVLETILKHGDVEEAVRIVKEVI
QKLANYEIPPEKLAIYEQITRPLHEYKAIGPHVAVAKKLAAKGVKIKPGM
VIGYIVLRGDGPISNRAILAEEYDPKKHKYDAEYYIENQVLPAVLRILEG
FGYRKEDLRYQKTRQVGLTSWLNIKKs--

>Tgo
MILDTDYITEDGKPVIRIFKKENGEFKIDYDRNFEPYIYALLKDDSAIED
VKKITAERHGTTVRVVRAEKVKKKFLGRPIEVWKLYFTHPQDVPAIRDKI
KEHPAVVDIYEYDIPFAKRYLIDKGLIPMEGDEELKMLAFDIETLYHEGE
EFAEGPILMISYADEEGARVITWKNIDLPYVDVVSTEKEMIKRFLKVVKE
KDPDVLITYNGDNFDFAYLKKRSEKLGVKFILGREGS--EPKIQRMGDRF
AVEVKGRIHFDLYPVIRRTINLPTYTLEAVYEAIFGQPKEKVYAEEIAQA
WETGEGLERVARYSMEDAKVTYELGKEFFPMEAQLSRLVGQSLWDVSRSS
TGNLVEWFLLRKAYERNELAPNKPDERELARR-RESYAGGYVKEPERGLW
ENIVYLDFRSLYPSIIITHNVSPDTLNREGCEEYDVAPQVGHKFCKDFPG
FIPSLLGDLLEERQKVKKKMKATIDPIEKKLLDYRQRAIKILANSFYGYY
GYAKARWYCKECAESVTAWGRQYIETTIREIEEKFGFKVLYADTDGFFAT
IPGADAETVKKKAKEFLDYINAKLPGLLELEYEGFYKRGFFVTKKKYAVI
DEEDKITTRGLEIVRRDWSEIAKETQARVLEAILKHGDVEEAVRIVKEVT
EKLSKYEVPPEKLVIYEQITRDLKDYKATGPHVAVAKRLAARGIKIRPGT
VISYIVLKGSGRIGDRAIPFDEFDPAKHKYDAEYYIENQVLPAVERILRA
FGYRKEDLRYQKTRQVGLGAWLKPKt---

>KOD
MILDTDYITEDGKPVIRIFKKENGEFKIEYDRTFEPYFYALLKDDSAIEE
VKKITAERHGTVVTVKRVEKVQKKFLGRPVEVWKLYFTHPQDVPAIRDKI
REHGAVIDIYEYDIPFAKRYLIDKGLVPMEGDEELKMLAFDIQTLYHEGE
EFAEGPILMISYADEEGARVITWKNVDLPYVDVVSTEREMIKRFLRVVKE
KDPDVLITYNGDNFDFAYLKKRCEKLGINFALGRDGS--EPKIQRMGDRF
AVEVKGRIHFDLYPVIRRTINLPTYTLEAVYEAVFGQPKEKVYAEEITPA
WETGENLERVARYSMEDAKVTYELGKEFLPMEAQLSRLIGQSLWDVSRSS
TGNLVEWFLLRKAYERNELAPNKPDEKELARR-RQSYEGGYVKEPERGLW
ENIVYLDFRSLYPSIIITHNVSPDTLNREGCKEYDVAPQVGHRFCKDFPG
FIPSLLGDLLEERQKIKKKMKATIDPIERKLLDYRQRAIKILANSYYGYY
GYARARWYCKECAESVTAWGREYITMTIKEIEEKYGFKVIYSDTDGFFAT
IPGADAETVKKKAMEFLNYINAKLPGALELEYEGFYKRGFFVTKKKYAVI
DEEGKITTRGLEIVRRDWSEIAKETQARVLEALLKDGDVEKAVRIVKEVT
EKLSKYEVPPEKLVIHEQITRDLKDYKATGPHVAVAKRLAARGVKIRPGT
VISYIVLKGSGRIGDRAIPFDEFDPTKHKYDAEYYIENQVLPAVERILRA
FGYRKEDLRYQKTRQVGLSAWLKPKGt--

>Vent
MILDTDYITKDGKPIIRIFKKENGEFKIELDPHFQPYIYALLKDDSAIEE
IKAIKGERHGKTVRVLDAVKVRKKFLGREVEVWKLIFEHPQDVPAMRGKI
REHPAVVDIYEYDIPFAKRYLIDKGLIPMEGDEELKLLAFDIETFYHEGD
EFGKGEIIMISYADEEEARVITWKNIDLPYVDVVSNEREMIKRFvQVVKE
KDPDVIITYNGDNFDLPYLIKRAEKLGVRLVLGRDkehpEPKIQRMGDSF
AVEIKGRIHFDLFPVVRRTINLPTYTLEAVYEAVLGKTKSKLGAEEIAAI
WETEESMKKLAQYSMEDARATYELGKEFFPMEAELAKLIGQSVWDVSRSS
TGNLVEWYLLRVAYARNELAPNKPDEEEYKRRLRTTYLGGYVKEPEKGLW
ENIIYLDFRSLYPSIIVTHNVSPDTLEKEGCKNYDVAPIVGYRFCKDFPG
FIPSILGDLIAMRQDIKKKMKSTIDPIEKKMLDYRQRAIKLLANSYYGYM
GYPKARWYSKECAESVTAWGRHYIEMTIREIEEKFGFKVLYADTDGFYAT IPGEKPELIKKKAKEFLNYINSKLPGLLELEYEGFYLRGFFVTKKRYAVI
DEEGRITTRGLEVVRRDWSEIAKETQAKVLEAILKEGSVEKAVEVVRDVV
EKIAKYRVPLEKLVIHEQITRDLKDYKAIGPHVAIAKRLAARGIKVKPGT
IISYIVLKGSGKISDRVILLTEYDPRKHKYDPDYYIENQVLPAVLRILEA
FGYRKEDLRYQSSKQTGLDAWLKr------

>Deep
MILDADYITEDGKPIIRIFKKENGEFKVEYDRNFRPYIYALLKDDSQIDE
VRKITAERHGKIVRIIDAEKVRKKFLGRPIEVWRLYFEHPQDVPAIRDKI
REHSAVIDIFEYDIPFAKRYLIDKGLIPMEGDEELKLLAFDIETLYHEGE
EFAKGPIIMISYADEEEAKVITWKKIDLPYVEVVSSEREMIKRFLKVIRE
KDPDVIITYNGDSFDLPYLVKRAEKLGIKLPLGRDGS--EPKMQRLGDMT
AVEIKGRIHFDLYHVIRRTINLPTYTLEAVYEAIFGKPKEKVYAHEIAEA
WETGKGLERVAKYSMEDAKVTYELGREFFPMEAQLSRLVGQPLWDVSRSS
TGNLVEWYLLRKAYERNELAPNKPDEREYERRLRESYAGGYVKEPEKGLW
EGLVSLDFRSLYPSIIITHNVSPDTLNREGCREYDVAPEVGHKFCKDFPG
FIPSLLKRLLDERQEIKRKMKASKDPIEKKMLDYRQRAIKILANSYYGYY
GYAKARWYCKECAESVTAWGREYIEFVRKELEEKFGFKVLYIDTDGLYAT
IPGAKPEEIKKKALEFVDYINAKLPGLLELEYEGFYVRGFFVTKKKYALI
DEEGKIITRGLEIVRRDWSEIAKETQAKVLEAILKHGNVEEAVKIVKEVT
EKLSKYEIPPEKLVIYEQITRPLHEYKAIGPHVAVAKRLAARGVKVRPGM
VIGYIVLRGDGPISKRAILAEEFDLRKHKYDAEYYIENQVLPAVLRILEA
FGYRKEDLRWQKTKQTGLTAWLNIKKk--

>JDF-3
MILDVDYITENGKPVIRVFKKENGEFRIEYDREFEPYFYALLRDDSAIEE
IKKITAERHGRVVKVKRAEKVKKKFLGRSVEVWVLYFTHPQDVPAIRDKI
RKHPAVIDIYEYDIPFAKRYLIDKGLIPMEGEEELKLMSFDIETLYHEGE
EFGTGPILMISYADESEARVITWKKIDLPYVEVVSTEKEMIKRFLRVVKE
KDPDVLITYNGDNFDFAYLKKRCEKLGVSFTLGRDGS--EPKIQRMGDRF
AVEVKGRVHFDLYPVIRRTINLPTYTLEAVYEAVFGKPKEKVYAEEIATA
WETGEGLERVARYSMEDARVTYELGREFFPMEAQLSRLIGQGLWDVSRSS
TGNLVEWFLLRKAYERNELAPNKPDERELARR-RggYAGGYVKEPERGLW
DNIVYLDFRSLYPSIIITHNVSPDTLNREGCRSYDVAPEVGHKFCKDFPG
FIPSLLGNLLEERQKIKRKMKATLDPLEKNLLDYRQRAIKILANSYYGYY
GYARARWYCRECAESVTAWGREYIEMVIRELEEKFGFKVLYADTDGLHAT
IPGADAETVKKKAMEFLNYINPKLPGLLELEYEGFYVRGFFVTKKKYAVI
DEEGKITTRGLEIVRRDWSEIAKETQARVLEAILRHGDVEEAVRIVREVT
EKLSKYEVPPEKLVIHEQITRELKDYKATGPHVAIAKRLAARGVKIRPGT
VISYIVLKGSGRIGDRAIPFDEFDPTKHKYDADYYIENQVLPAVERILRA
FGYRKEDLRYQKTRQVGLGAWLKPKGkkk Sequence tree:

Tree constructed using UPGMA

```
(((Pfu        :0.000998,
Deep        :0.000998):0.000080,
((Tgo        :0.000905,
KOD        :0.000905):0.000032,
JDF-3        :0.000937):0.000141):0.000067,
Vent        :0.001144);
```

Alignment (DIALIGN format):

```
Pfu      1   MILDVDYITE EGKPVIRLFK KENGKFKIEH DRTFRPYIYA LLRDDSKIEE
Tgo      1   MILDTDYITE DGKPVIRIFK KENGEFKIDY DRNFEPYIYA LLKDDSAIED
KOD      1   MILDTDYITE DGKPVIRIFK KENGEFKIEY DRTFEPYFYA LLKDDSAIEE
Vent     1   MILDTDYITK DGKPIIRIFK KENGEFKIEL DPHFQPYIYA LLKDDSAIEE
Deep     1   MILDADYITE DGKPIIRIFK KENGEFKVEY DRNFRPYIYA LLKDDSQIDE
JDF-3    1   MILDVDYITE NGKPVIRVFK KENGEFRIEY DREFEPYFYA LLRDDSAIEE

Pfu     51   VKKITGERHG KIVRIVDVEK VEKKFLGKPI TVWKLYLEHP QDVPTIREKV
Tgo     51   VKKITAERHG TTVRVVRAEK VKKKFLGRPI EVWKLYFTHP QDVPAIRDKI
KOD     51   VKKITAERHG TVVTVKRVEK VQKKFLGRPV EVWKLYFTHP QDVPAIRDKI
Vent    51   IKAIKGERHG KTVRVLDAVK VRKKFLGREV EVWKLIFEHP QDVPAMRGKI
Deep    51   VRKITAERHG KIVRIIDAEK VRKKFLGRPI EVWRLYFEHP QDVPAIRDKI
JDF-3   51   IKKITAERHG RVVKVKRAEK VKKKFLGRSV EVWVLYFTHP QDVPAIRDKI

Pfu    101   REHPAVVDIF EYDIPFAKRY LIDKGLIPME GEEELKILAF DIETLYHEGE
Tgo    101   KEHPAVVDIY EYDIPFAKRY LIDKGLIPME GDEELKMLAF DIETLYHEGE
KOD    101   REHGAVIDIY EYDIPFAKRY LIDKGLVPME GDEELKMLAF DIQTLYHEGE
Vent   101   REHPAVVDIY EYDIPFAKRY LIDKGLIPME GDEELKLLAF DIETFYHEGD
Deep   101   REHSAVIDIF EYDIPFAKRY LIDKGLIPME GDEELKLLAF DIETLYHEGE
JDF-3  101   RKHPAVIDIY EYDIPFAKRY LIDKGLIPME GEEELKLMSF DIETLYHEGE

Pfu    151   EFGKGPIIMI SYADENEAKV ITWKNIDLPY VEVVSSEREM IKRFLRIIRE
Tgo    151   EFAEGPILMI SYADEEGARV ITWKNIDLPY VDVVSTEKEM IKRFLKVVKE
KOD    151   EFAEGPILMI SYADEEGARV ITWKNVDLPY VDVVSTEREM IKRFLRVVKE
Vent   151   EFGKGEIIMI SYADEEEARV ITWKNIDLPY VDVVSNEREM IKRFvQVVKE
Deep   151   EFAKGPIIMI SYADEEEAKV ITWKKIDLPY VEVVSSEREM IKRFLKVIRE
JDF-3  151   EFGTGPILMI SYADESEARV ITWKKIDLPY VEVVSTEKEM IKRFLRVVKE

Pfu    201   KDPDIIVTYN GDSFDFPYLA KRAEKLGIKL TIGRDGS--E PKMQRIGDMT
Tgo    201   KDPDVLITYN GDNFDFAYLK KRSEKLGVKF ILGREGS--E PKIQRMGDRF
KOD    201   KDPDVLITYN GDNFDFAYLK KRCEKLGINF ALGRDGS--E PKIQRMGDRF
Vent   201   KDPDVIITYN GDNFDLPYLI KRAEKLGVRL VLGRDkehpE PKIQRMGDSF
Deep   201   KDPDVIITYN GDSFDLPYLV KRAEKLGIKL PLGRDGS--E PKMQRLGDMT
JDF-3  201   KDPDVLITYN GDNFDFAYLK KRCEKLGVSF TLGRDGS--E PKIQRMGDRF

Pfu    249   AVEVKGRIHF DLYHVITRTI NLPTYTLEAV YEAIFGKPKE KVYADEIAKA
Tgo    249   AVEVKGRIHF DLYPVIRRTI NLPTYTLEAV YEAIFGQPKE KVYAEEIAQA
KOD    249   AVEVKGRIHF DLYPVIRRTI NLPTYTLEAV YEAVFGQPKE KVYAEEITPA
```

| | | |
|---|---|---|
| Vent | 251 | AVEIKGRIHF DLFPVVRRTI NLPTYTLEAV YEAVLGKTKS KLGAEEIAAI |
| Deep | 249 | AVEIKGRIHF DLYHVIRRTI NLPTYTLEAV YEAIFGKPKE KVYAHEIAEA |
| JDF-3 | 249 | AVEVKGRVHF DLYPVIRRTI NLPTYTLEAV YEAVFGKPKE KVYAEEIATA |

| | | |
|---|---|---|
| Pfu | 299 | WESGENLERV AKYSMEDAKA TYELGKEFLP MEIQLSRLVG QPLWDVSRSS |
| Tgo | 299 | WETGEGLERV ARYSMEDAKV TYELGKEFFP MEAQLSRLVG QSLWDVSRSS |
| KOD | 299 | WETGENLERV ARYSMEDAKV TYELGKEFLP MEAQLSRLIG QSLWDVSRSS |
| Vent | 301 | WETEESMKKL AQYSMEDARA TYELGKEFFP MEAELAKLIG QSVWDVSRSS |
| Deep | 299 | WETGKGLERV AKYSMEDAKV TYELGREFFP MEAQLSRLVG QPLWDVSRSS |
| JDF-3 | 299 | WETGEGLERV ARYSMEDARV TYELGREFFP MEAQLSRLIG QGLWDVSRSS |

| | | |
|---|---|---|
| Pfu | 349 | TGNLVEWFLL RKAYERNEVA PNKPSEEEYQ RRLRESYTGG FVKEPEKGLW |
| Tgo | 349 | TGNLVEWFLL RKAYERNELA PNKPDERELA RR-RESYAGG YVKEPERGLW |
| KOD | 349 | TGNLVEWFLL RKAYERNELA PNKPDEKELA RR-RQSYEGG YVKEPERGLW |
| Vent | 351 | TGNLVEWYLL RVAYARNELA PNKPDEEEYK RRLRTTYLGG YVKEPEKGLW |
| Deep | 349 | TGNLVEWYLL RKAYERNELA PNKPDEREYE RRLRESYAGG YVKEPEKGLW |
| JDF-3 | 349 | TGNLVEWFLL RKAYERNELA PNKPDERELA RR-RggYAGG YVKEPERGLW |

DXXSLYPSII (Region II)

| | | |
|---|---|---|
| Pfu | 399 | ENIVYLDFRA LYPSIIITHN VSPDTLNLEG CKNYDIAPQV GHKFCKDIPG |
| Tgo | 398 | ENIVYLDFRS LYPSIIITHN VSPDTLNREG CEEYDVAPQV GHKFCKDFPG |
| KOD | 398 | ENIVYLDFRS LYPSIIITHN VSPDTLNREG CKEYDVAPQV GHRFCKDFPG |
| Vent | 401 | ENIIYLDFRS LYPSIIVTHN VSPDTLEKEG CKNYDVAPIV GYRFCKDFPG |
| Deep | 399 | EGLVSLDFRS LYPSIIITHN VSPDTLNREG CREYDVAPEV GHKFCKDFPG |
| JDF-3 | 398 | DNIVYLDFRS LYPSIIITHN VSPDTLNREG CRSYDVAPEV GHKFCKDFPG |

| | | |
|---|---|---|
| Pfu | 449 | FIPSLLGHLL EERQKIKTKM KETQDPIEKI LLDYRQKAIK LLANSFYGYY |
| Tgo | 448 | FIPSLLGDLL EERQKVKKKM KATIDPIEKK LLDYRQRAIK ILANSFYGYY |
| KOD | 448 | FIPSLLGDLL EERQKIKKKM KATIDPIERK LLDYRQRAIK ILANSYYGYY |
| Vent | 451 | FIPSILGDLI AMRQDIKKKM KSTIDPIEKK MLDYRQRAIK LLANSYYGYM |
| Deep | 449 | FIPSLLKRLL DERQEIKRKM KASKDPIEKK MLDYRQRAIK ILANSYYGYY |
| JDF-3 | 448 | FIPSLLGNLL EERQKIKRKM KATLDPLEKN LLDYRQRAIK ILANSYYGYY |

| | | |
|---|---|---|
| Pfu | 499 | GYAKARWYCK ECAESVTAWG RKYIELVWKE LEEKFGFKVL YIDTDGLYAT |
| Tgo | 498 | GYAKARWYCK ECAESVTAWG RQYIETTIRE IEEKFGFKVL YADTDGFFAT |
| KOD | 498 | GYARARWYCK ECAESVTAWG REYITMTIKE IEEKYGFKVI YSDTDGFFAT |
| Vent | 501 | GYPKARWYSK ECAESVTAWG RHYIEMTIRE IEEKFGFKVL YADTDGFYAT |
| Deep | 499 | GYAKARWYCK ECAESVTAWG REYIEFVRKE LEEKFGFKVL YIDTDGLYAT |
| JDF-3 | 498 | GYARARWYCR ECAESVTAWG REYIEMVIRE LEEKFGFKVL YADTDGLHAT |

| | | |
|---|---|---|
| Pfu | 549 | IPGGESEEIK KKALEFVKYI NSKLPGLLEL EYEGFYKRGF FVTKKRYAVI |
| Tgo | 548 | IPGADAETVK KKAKEFLDYI NAKLPGLLEL EYEGFYKRGF FVTKKKYAVI |

| | | |
|---|---|---|
| KOD | 548 | IPGADAETVK KKAMEFLNYI NAKLPGALEL EYEGFYKRGF FVTKKKYAVI |
| Vent | 551 | IPGEKPELIK KKAKEFLNYI NSKLPGLLEL EYEGFYLRGF FVTKKRYAVI |
| Deep | 549 | IPGAKPEEIK KKALEFVDYI NAKLPGLLEL EYEGFYVRGF FVTKKKYALI |
| JDF-3 | 548 | IPGADAETVK KKAMEFLNYI NPKLPGLLEL EYEGFYVRGF FVTKKKYAVI |

| | | |
|---|---|---|
| Pfu | 599 | DEEGKVITRG LEIVRRDWSE IAKETQARVL ETILKHGDVE EAVRIVKEVI |
| Tgo | 598 | DEEDKITTRG LEIVRRDWSE IAKETQARVL EAILKHGDVE EAVRIVKEVT |
| KOD | 598 | DEEGKITTRG LEIVRRDWSE IAKETQARVL EALLKDGDVE KAVRIVKEVT |
| Vent | 601 | DEEGRITTRG LEVVRRDWSE IAKETQAKVL EAILKEGSVE KAVEVVRDVV |
| Deep | 599 | DEEGKIITRG LEIVRRDWSE IAKETQAKVL EAILKHGNVE EAVKIVKEVT |
| JDF-3 | 598 | DEEGKITTRG LEIVRRDWSE IAKETQARVL EAILRHGDVE EAVRIVREVT |

| | | |
|---|---|---|
| Pfu | 649 | QKLANYEIPP EKLAIYEQIT RPLHEYKAIG PHVAVAKKLA AKGVKIKPGM |
| Tgo | 648 | EKLSKYEVPP EKLVIYEQIT RDLKDYKATG PHVAVAKRLA ARGIKIRPGT |
| KOD | 648 | EKLSKYEVPP EKLVIHEQIT RDLKDYKATG PHVAVAKRLA ARGVKIRPGT |
| Vent | 651 | EKIAKYRVPL EKLVIHEQIT RDLKDYKAIG PHVAIAKRLA ARGIKVKPGT |
| Deep | 649 | EKLSKYEIPP EKLVIYEQIT RPLHEYKAIG PHVAVAKRLA ARGVKVRPGM |
| JDF-3 | 648 | EKLSKYEVPP EKLVIHEQIT RELKDYKATG PHVAIAKRLA ARGVKIRPGT |

| | | |
|---|---|---|
| Pfu | 699 | VIGYIVLRGD GPISNRAILA EEYDPKKHKY DAEYYIENQV LPAVLRILEG |
| Tgo | 698 | VISYIVLKGS GRIGDRAIPF DEFDPAKHKY DAEYYIENQV LPAVERILRA |
| KOD | 698 | VISYIVLKGS GRIGDRAIPF DEFDPTKHKY DAEYYIENQV LPAVERILRA |
| Vent | 701 | IISYIVLKGS GKISDRVILL TEYDPRKHKY DPDYYIENQV LPAVLRILEA |
| Deep | 699 | VIGYIVLRGD GPISKRAILA EEFDLRKHKY DAEYYIENQV LPAVLRILEA |
| JDF-3 | 698 | VISYIVLKGS GRIGDRAIPF DEFDPTKHKY DADYYIENQV LPAVERILRA |

| | | |
|---|---|---|
| Pfu | 749 | FGYRKEDLRY QKTRQVGLTS WLNIKKs-- |
| Tgo | 748 | FGYRKEDLRY QKTRQVGLGA WLKPKt--- |
| KOD | 748 | FGYRKEDLRY QKTRQVGLSA WLKPKGt-- |
| Vent | 751 | FGYRKEDLRY QSSKQTGLDA WLKr----- |
| Deep | 749 | FGYRKEDLRW QKTKQTGLTA WLNIKKk-- |
| JDF-3 | 748 | FGYRKEDLRY QKTRQVGLGA WLKPKGkkk |

Alignment (FASTA format):

>Pfu
MILDVDYITEEGKPVIRLFKKENGKFKIEHDRTFRPYIYALLRDDSKIEE
VKKITGERHGKIVRIVDVEKVEKKFLGKPITVWKLYLEHPQDVPTIREKV
REHPAVVDIFEYDIPFAKRYLIDKGLIPMEGEEELKILAFDIETLYHEGE
EFGKGPIIMISYADENEAKVITWKNIDLPYVEVVSSEREMIKRFLRIIRE
KDPDIIVTYNGDSFDFPYLAKRAEKLGIKLTIGRDGS--EPKMQRIGDMT
AVEVKGRIHFDLYHVITRTINLPTYTLEAVYEAIFGKPKEKVYADEIAKA

WESGENLERVAKYSMEDAKATYELGKEFLPMEIQLSRLVGQPLWDVSRSS
TGNLVEWFLLRKAYERNEVAPNKPSEEEYQRRLRESYTGGFVKEPEKGLW
ENIVYLDFRALYPSIIITHNVSPDTLNLEGCKNYDIAPQVGHKFCKDIPG
FIPSLLGHLLEERQKIKTKMKETQDPIEKILLDYRQKAIKLLANSFYGYY
GYAKARWYCKECAESVTAWGRKYIELVWKELEEKFGFKVLYIDTDGLYAT
IPGGESEEIKKKALEFVKYINSKLPGLLELEYEGFYKRGFFVTKKRYAVI
DEEGKVITRGLEIVRRDWSEIAKETQARVLETILKHGDVEEAVRIVKEVI
QKLANYEIPPEKLAIYEQITRPLHEYKAIGPHVAVAKKLAAKGVKIKPGM
VIGYIVLRGDGPISNRAILAEEYDPKKHKYDAEYYIENQVLPAVLRILEG
FGYRKEDLRYQKTRQVGLTSWLNIKKs—

>Tgo
MILDTDYITEDGKPVIRIFKKENGEFKIDYDRNFEPYIYALLKDDSAIED
VKKITAERHGTTVRVVRAEKVKKKFLGRPIEVWKLYFTHPQDVPAIRDKI
KEHPAVVDIYEYDIPFAKRYLIDKGLIPMEGDEELKMLAFDIETLYHEGE
EFAEGPILMISYADEEGARVITWKNIDLPYVDVVSTEKEMIKRFLKVVKE
KDPDVLITYNGDNFDFAYLKKRSEKLGVKFILGREGS—EPKIQRMGDRF
AVEVKGRIHFDLYPVIRRTINLPTYTLEAVYEAIFGQPKEKVYAEEIAQA
WETGEGLERVARYSMEDAKVTYELGKEFFPMEAQLSRLVGQSLWDVSRSS
TGNLVEWFLLRKAYERNELAPNKPDERELARR-RESYAGGYVKEPERGLW
ENIVYLDFRSLYPSIIITHNVSPDTLNREGCEEYDVAPQVGHKFCKDFPG
FIPSLLGDLLEERQKVKKKMKATIDPIEKKLLDYRQRAIKILANSFYGYY
GYAKARWYCKECAESVTAWGRQYIETTIREIEEKFGFKVLYADTDGFFAT
IPGADAETVKKKAKEFLDYINAKLPGLLELEYEGFYKRGFFVTKKKYAVI
DEEDKITTRGLEIVRRDWSEIAKETQARVLEAILKHGDVEEAVRIVKEVT
EKLSKYEVPPEKLVIYEQITRDLKDYKATGPHVAVAKRLAARGIKIRPGT
VISYIVLKGSGRIGDRAIPFDEFDPAKHKYDAEYYIENQVLPAVERILRA
FGYRKEDLRYQKTRQVGLGAWLKPKt---

>KOD
MILDTDYITEDGKPVIRIFKKENGEFKIEYDRTFEPYFYALLKDDSAIEE
VKKITAERHGTVVTVKRVEKVQKKFLGRPVEVWKLYFTHPQDVPAIRDKI
REHGAVIDIYEYDIPFAKRYLIDKGLVPMEGDEELKMLAFDIQTLYHEGE
EFAEGPILMISYADEEGARVITWKNVDLPYVDVVSTEREMIKRFLRVVKE
KDPDVLITYNGDNFDFAYLKKRCEKLGINFALGRDGS—EPKIQRMGDRF
AVEVKGRIHFDLYPVIRRTINLPTYTLEAVYEAVFGQPKEKVYAEEITPA
WETGENLERVARYSMEDAKVTYELGKEFLPMEAQLSRLIGQSLWDVSRSS
TGNLVEWFLLRKAYERNELAPNKPDEKELARR-RQSYEGGYVKEPERGLW
ENIVYLDFRSLYPSIIITHNVSPDTLNREGCKEYDVAPQVGHRFCKDFPG
FIPSLLGDLLEERQKIKKKMKATIDPIERKLLDYRQRAIKILANSYYGYY
GYARARWYCKECAESVTAWGREYITMTIKEIEEKYGFKVIYSDTDGFFAT
IPGADAETVKKKAMEFLNYINAKLPGALELEYEGFYKRGFFVTKKKYAVI
DEEGKITTRGLEIVRRDWSEIAKETQARVLEALLKDGDVEKAVRIVKEVT
EKLSKYEVPPEKLVIHEQITRDLKDYKATGPHVAVAKRLAARGVKIRPGT
VISYIVLKGSGRIGDRAIPFDEFDPTKHKYDAEYYIENQVLPAVERILRA
FGYRKEDLRYQKTRQVGLSAWLKPKGt—

>Vent
MILDTDYITKDGKPIIRIFKKENGEFKIELDPHFQPYIYALLKDDSAIEE
IKAIKGERHGKTVRVLDAVKVRKKFLGREVEVWKLIFEHPQDVPAMRGKI
REHPAVVDIYEYDIPFAKRYLIDKGLIPMEGDEELKLLAFDIETFYHEGD
EFGKGEIIMISYADEEEARVITWKNIDLPYVDVVSNEREMIKRFvQVVKE
KDPDVIITYNGDNFDLPYLIKRAEKLGVRLVLGRDkehpEPKIQRMGDSF
AVEIKGRIHFDLFPVVRRTINLPTYTLEAVYEAVLGKTKSKLGAEEIAAI
WETEESMKKLAQYSMEDARATYELGKEFFPMEAELAKLIGQSVWDVSRSS
TGNLVEWYLLRVAYARNELAPNKPDEEEYKRRLRTTYLGGYVKEPEKGLW
ENIIYLDFRSLYPSIIVTHNVSPDTLEKEGCKNYDVAPIVGYRFCKDFPG
FIPSILGDLIAMRQDIKKKMKSTIDPIEKKMLDYRQRAIKLLANSYYGYM
GYPKARWYSKECAESVTAWGRHYIEMTIREIEEKFGFKVLYADTDGFYAT IPGEKPELIKKKAKEFLNYINSKLPGLLELEYEGFYLRGFFVTKKRYAVI
DEEGRITTRGLEVVRRDWSEIAKETQAKVLEAILKEGSVEKAVEVVRDVV
EKIAKYRVPLEKLVIHEQITRDLKDYKAIGPHVAIAKRLAARGIKVKPGT
IISYIVLKGSGKISDRVILLTEYDPRKHKYDPDYYIENQVLPAVLRILEA
FGYRKEDLRYQSSKQTGLDAWLKr------

>Deep
MILDADYITEDGKPIIRIFKKENGEFKVEYDRNFRPYIYALLKDDSQIDE
VRKITAERHGKIVRIIDAEKVRKKFLGRPIEVWRLYFEHPQDVPAIRDKI
REHSAVIDIFEYDIPFAKRYLIDKGLIPMEGDEELKLLAFDIETLYHEGE
EFAKGPIIMISYADEEEAKVITWKKIDLPYVEVVSSEREMIKRFLKVIRE
KDPDVIITYNGDSFDLPYLVKRAEKLGIKLPLGRDGS--EPKMQRLGDMT
AVEIKGRIHFDLYHVIRRTINLPTYTLEAVYEAIFGKPKEKVYAHEIAEA
WETGKGLERVAKYSMEDAKVTYELGREFFPMEAQLSRLVGQPLWDVSRSS
TGNLVEWYLLRKAYERNELAPNKPDEREYERRLRESYAGGYVKEPEKGLW
EGLVSLDFRSLYPSIIITHNVSPDTLNREGCREYDVAPEVGHKFCKDFPG
FIPSLLKRLLDERQEIKRKMKASKDPIEKKMLDYRQRAIKILANSYYGYY
GYAKARWYCKECAESVTAWGREYIEFVRKELEEKFGFKVLYIDTDGLYAT
IPGAKPEEIKKKALEFVDYINAKLPGLLELEYEGFYVRGFFVTKKKYALI
DEEGKIITRGLEIVRRDWSEIAKETQAKVLEAILKHGNVEEAVKIVKEVT
EKLSKYEIPPEKLVIYEQITRPLHEYKAIGPHVAVAKRLAARGVKVRPGM
VIGYIVLRGDGPISKRAILAEEFDLRKHKYDAEYYIENQVLPAVLRILEA
FGYRKEDLRWQKTKQTGLTAWLNIKKk--

>JDF-3
MILDVDYITENGKPVIRVFKKENGEFRIEYDREFEPYFYALLRDDSAIEE
IKKITAERHGRVVKVKRAEKVKKKFLGRSVEVWVLYFTHPQDVPAIRDKI
RKHPAVIDIYEYDIPFAKRYLIDKGLIPMEGEEELKLMSFDIETLYHEGE
EFGTGPILMISYADESEARVITWKKIDLPYVEVVSTEKEMIKRFLRVVKE
KDPDVLITYNGDNFDFAYLKKRCEKLGVSFTLGRDGS--EPKIQRMGDRF
AVEVKGRVHFDLYPVIRRTINLPTYTLEAVYEAVFGKPKEKVYAEEIATA
WETGEGLERVARYSMEDARVTYELGREFFPMEAQLSRLIGQGLWDVSRSS
TGNLVEWFLLRKAYERNELAPNKPDERELARR-RggYAGGYVKEPERGLW
DNIVYLDFRSLYPSIIITHNVSPDTLNREGCRSYDVAPEVGHKFCKDFPG
FIPSLLGNLLEERQKIKRKMKATLDPLEKNLLDYRQRAIKILANSYYGYY
GYARARWYCRECAESVTAWGREYIEMVIRELEEKFGFKVLYADTDGLHAT
IPGADAETVKKKAMEFLNYINPKLPGLLELEYEGFYVRGFFVTKKKYAVI
DEEGKITTRGLEIVRRDWSEIAKETQARVLEAILRHGDVEEAVRIVREVT
EKLSKYEVPPEKLVIHEQITRELKDYKATGPHVAIAKRLAARGVKIRPGT
VISYIVLKGSGRIGDRAIPFDEFDPTKHKYDADYYIENQVLPAVERILRA
FGYRKEDLRYQKTRQVGLGAWLKPKGkkk Sequence tree:

Tree constructed using UPGMA (((Pfu :0.000998,
Deep :0.000998) :0.000080,
((Tgo :0.000905,
KOD :0.000905) :0.000032,
JDF-3 :0.000937) :0.000141) :0.000067,
Vent :0.001144);

Results: *Pfu* V93K and V93R mutants show significantly improved dUTP incorporation compared to wild type *Pfu*. In contrast, the *Pfu* V93W, V93Y, and V93M mutants show little-to-no improvement in dUTP incorporation.

Results: The *Pfu* V93D and V93R mutants show significantly improved dUTP incorporation compared to wild type *Pfu*.

Results: The *Pfu* V93N mutant shows a very small improvement in dUTP incorporation compared to wild type *Pfu*. In contrast, the *Pfu* V93G mutant shows little-to-no improvement.

Figure 9: Polymerase activity and Temperature optimum of Pfu N terminal truncation mutants

| Pfu clone # | Truncated after Pfu residue | Relative DNA polymerase activity | Temperature Optimum |
|---|---|---|---|
| 61 | H30 | Moderate | 65° |
| 72 | V66 | Similar to wild type | 70° |
| 81 | P128 | Low | Not tested |
| 92 | I158 | Low | Not tested |
| 3 | G125 | Similar to wild type | Not tested |
| 13/14 | K201 | low | 65° |

Figure 10. Oligonucleotide Primers for QuikChange Mutagenesis

KOD V93 mutations

V93Q KOD 5'- CTCATCCG CAGGACCAGC CAGCGATAAG GGACAAG-3' (SEQ ID NO: 56)

V93R KOD 5'- CTCATCCG CAGGACCGTC CAGCGATAAG GGACAAG-3' (SEQ ID NO: 57)

V93K KOD 5'- CTCATCCG CAGGACAAAC CAGCGATAAG GGACAAG-3' (SEQ ID NO: 58)

V93N KOD 5'- CTCATCCG CAGGACAATC CAGCGATAAG GGACAAG-3' (SEQ ID NO: 59)

V93E KOD 5'- CTCATCCG CAGGACGAGC CAGCGATAAG GGACAAG-3' (SEQ ID NO: 60)

V93D KOD 5'- CTCATCCG CAGGACGATC CAGCGATAAG GGACAAG-3' (SEQ ID NO: 61)

Tgo V93 mutations

(SEQ ID NO: 62)

V93Q Tgo 5'-CAC CCC CAG GAC CAA CCC GCA ATC AGG GAC AAG G-3'

(SEQ ID NO: 63)

V93R Tgo 5'-CAC CCC CAG GAC AGA CCC GCA ATC AGG GAC AAG G-3'

(SEQ ID NO: 64)

V93N Tgo 5'-CAC CCC CAG GAC AAT CCC GCA ATC AGG GAC AAG G-3'

(SEQ ID NO: 65)

V93K Tgo 5'-CAC CCC CAG GAC AAA CCC GCA ATC AGG GAC AAG G-3'

(SEQ ID NO: 66)

V93E Tgo 5'-CAC CCC CAG GAC GAA CCC GCA ATC AGG GAC AAG G-3'

(SEQ ID NO: 67)

V93D Tgo 5'-CAC CCC CAG GAC GAC CCC GCA ATC AGG GAC AAG G-3'

JDF-3 V93 mutations

(SEQ ID NO: 68)

V93Q JDF-3 5′-ACG CAC CCG CAG GAC CAA CCG GCA ATC CGC GAC 3′

(SEQ ID NO: 69)

V93R JDF-3 5′-ACG CAC CCG CAG GAC CGT CCG GCA ATC CGC GAC 3′

(SEQ ID NO: 70)

V93E JDF-3 5′-ACG CAC CCG CAG GAC GAG CCG GCA ATC CGC GAC 3′

(SEQ ID NO: 71)

V93D JDF-3 5′-ACG CAC CCG CAG GAC GAT CCG GCA ATC CGC GAC 3′

(SEQ ID NO: 72)

V93K JDF-3 5′-ACG CAC CCG CAG GAC AAA CCG GCA ATC CGC GAC 3′

***Pfu* deletions**

(SEQ ID NO: 73)

Δ93 Pfu : 5′- GAA CAT CCC CAA GAT CCC ACT ATT AGA G-3′

(SEQ ID NO: 74)

Δ92-94 Pfu : 5′- GAA CAT CCC CAA ACT ATT AGA G-3′

Fig. 11. Uracil Insensitivity of KOD V93 mutants
T-/dU-primers and dUTP/TTP incorporation:
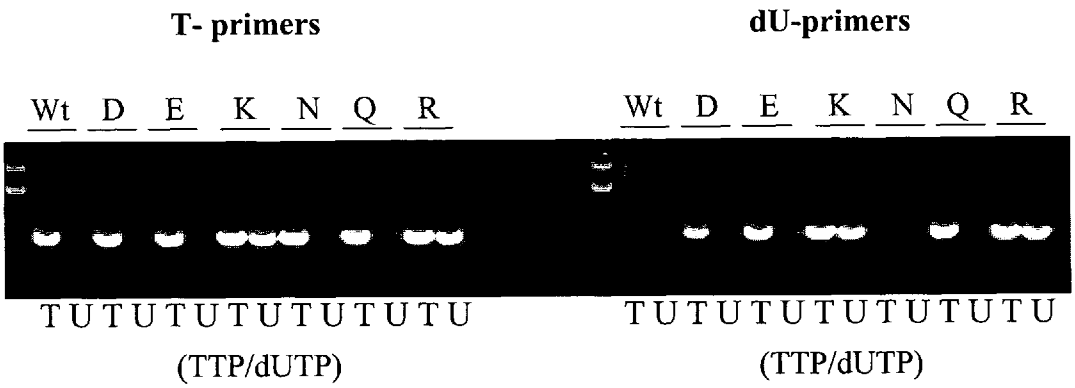
| | With regular primers | | With U primers | |
|---|---|---|---|---|
| | dNTP | dGCAU | dNTP | dGCAU |
| KOD WT | + | - | - | - |
| KOD V93D | + | - | + | - |
| KOD V93E | + | - | + | - |
| KOD V93K | + | + | + | + |
| KOD V93N | + | - | - | - |
| KOD V93Q | + | - | + | - |
| KOD V93R | + | + | + | + |

Fig. 12. Uracil Insensitivity of Tgo V93 mutants
T-primers and dUTP/TTP incorporation:
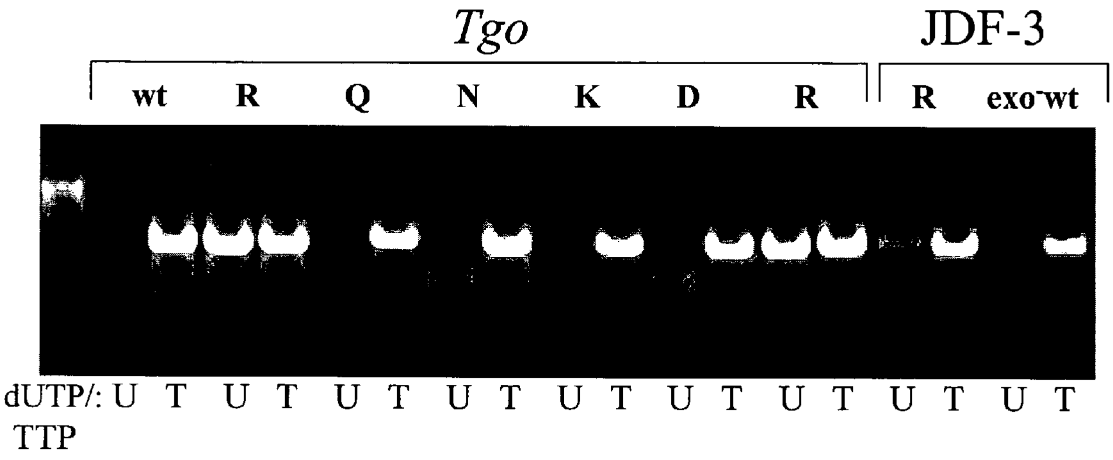

Fig. 13. Uracil Insensitivity of JDF-3 V93 mutants
T-primers and dUTP/TTP incorporation:
M wt N Q K D R
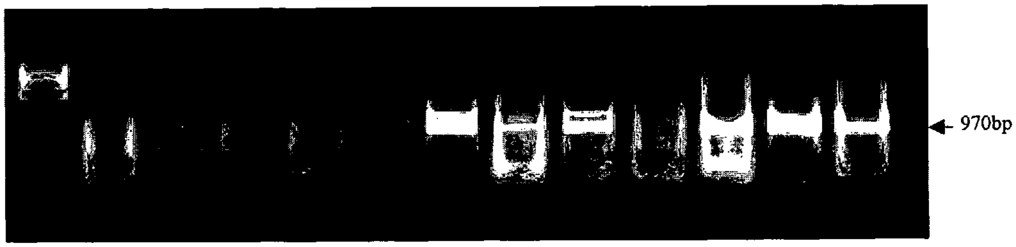
dUTP/: U T U T U T U T U T U T
TTP
T-/dU-primers and dUTP/TTP incorporation:
Wt V93R
Primers: T U T U
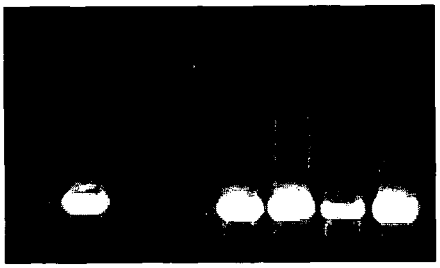
dUTP/: U T U T U T U T
TTP

**Fig. 14. Uracil Sensitivity of *Pfu* deletion mutants**
T-primers and dUTP/TTP incorporation:
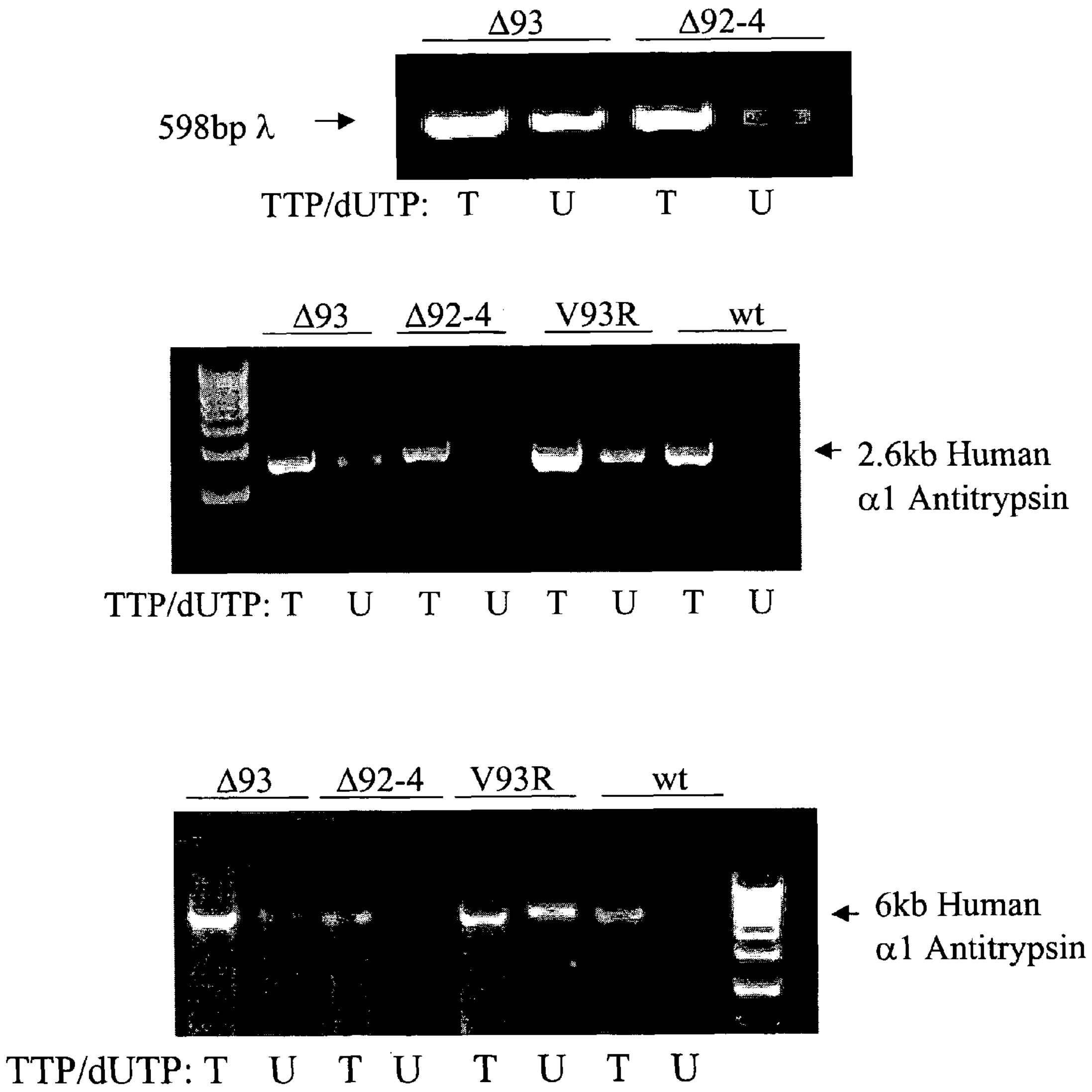

Amplification Plot for Comparison of Three Polymerases in QRT-PCR

* FM = FEN-1

Semi-log Amplification Plots Comparing Pfu V93R and Pfu V93R exo- Containing QPCR Reactions

| | V93R exo- | V93Rexo- | V93R | V93R | PlatinumTaq | AmpliTaq |
|---|---|---|---|---|---|---|
| Units | 1.25 | 2.5 | 1.25 | 2.5 | 1.25 | 1.25 |
| Avg Ct | 22.2 | 22.2 | 23.5 | 23.2 | 24.3 | 23.6 |
| | | | | | | |

Pfn V93R exo -*Multiplex-ATP2B1 and TfR*

| | Target amt | TfR | ATP2B1 | TfR + ATP2B1 |
|---|---|---|---|---|
| Pfn V93R exo | 100ng | **22.8** | | **22.7** |
| | | | 30.9 | 30.8 |
| ABI MM | 100ng | **24.6** | | **25.3** |
| (TaqMan) | | | 30.3 | 30.1 |

DNA POLYMERASE COMPOSITIONS FOR QUANTITATIVE PCR AND METHODS THEREOF

RELATED APPLICATIONS

The present application claims priority under 35 U.S.C. §120 as a continuation in part of U.S. patent application with Ser. No. 10/408,601, filed Apr. 7, 2003, which is a continuation in part of U.S. application Ser. No. 10/298,680, filed Nov. 18, 2002, which is a continuation in part of U.S. application Ser. No. 10/280,962, Filed Oct. 25, 2002. The entirety of each of the above applications is hereby incorporated by reference.

FIELD OF THE INVENTION

The invention relates to mutant Archaeal DNA polymerases with deficient 3'-5' exonuclease activity and/or reduced base analog detection activity, and the uses thereof.

BACKGROUND

DNA polymerases synthesize DNA molecules in the 5' to 3' direction from deoxynucleoside triphosphates (nucleotides) using a complementary template DNA strand and a primer by successively adding nucleotides to the free 3'-hydroxyl group of the growing strand. The template strand determines the order of addition of nucleotides via Watson-Crick base pairing. In cells, DNA polymerases are involved in DNA repair synthesis and replication (Kornberg, 1974, In DNA Synthesis. W. H. Freeman, San Francisco).

Archaeal DNA polymerases have a 3' to 5' exonuclease activity and a DNA synthesis activity. Many molecular cloning techniques and protocols involve the synthesis of DNA in in vitro reactions catalyzed by DNA polymerases. Sometimes, mutant forms of DNA polymerases are desired for particular uses. For example, DNA polymerases are used in DNA labelling and DNA sequencing reactions, using either 35S-, 32P- or 33P-labelled nucleotides. Most of these enzymes require a template and primer, and synthesize a product whose sequence is complementary to that of the template. The 5' to 3' exonuclease activity of An Archaeal DNA polymerases is often troublesome in these reactions because it degrades the 5' terminus of primers that are bound to the DNA templates and removes 5' phosphates from the termini of DNA fragments that are to be used as substrates for ligation. The use of DNA polymerase for these labelling and sequencing reactions thus may depend upon the removal of the 5' to 3' exonuclease activity.

DNA processivity is performed by heat denaturation of a DNA template containing the target sequence, annealing of a primer to the DNA strand and extension of the annealed primer with a DNA polymerase. The concept of net DNA processivity is the ratio of DNA synthesis activity versus 3'-5' exonuclease activity (for reviews, see, e.g., Kelman et al., 1998 *Processivity of DNA polymerases: two mechanisms, one goal*. Structure 6(2):121-5; Wyman and Botchan, 1995, *DNA replication. A familiar ring to DNA polymerase processivity*. Curr Biol. 5(4):334-7; and Von Hippel et al., 1994, *On the processivity of polymerases*. Ann NY Acad Sci. 726:118-31). DNA synthesis activity acts to polymerize nucleotides while 3'-5' exonuclease has an editing or proof-reading function to enhance the fidelity of the synthesis. Thus highly efficient DNA synthesis is generally achieved at the expense of high fidelity and vice versa. The 3'-to-5' exonuclease activity of many DNA polymerases may, therefore, be disadvantageous in situations where one is trying to achieve net synthesis of DNA and/or where fidelity is not of primary concern.

Archaeal family B DNA polymerases are uniquely able to recognize unrepaired uracil in a template strand and stall polymerization upstream of the lesion, thereby preventing the irreversible fixation of an G-C to A-T mutation (Fogg et al., 2002, Nat Struct Biol. 9(12):922-7). Uracil detection is thought to represent the first step in a pathway to repair DNA cytosine deamination (dCMP→dUMP) in archaea (Greagg et al, 1999, PNAS USA, 96:9405). Stalling of DNA synthesis opposite uracil has significant implications for high-fidelity PCR amplification with Archaeal DNA polymerases. Techniques requiring dUTP (e.g., dUTP/UDG decontamination methods, Longo et al. 1990, Gene, 93:125) or uracil-containing oligonucleotides can not be performed with proofreading DNA polymerases (Slupphaug et al. 1993, Anal. Biochem., 211:164; Sakaguchi et al. 1996, Biotechniques, 21:368). But more importantly, uracil stalling has been shown to compromise the performance of Archaeal DNA polymerases under standard PCR conditions (Hogrefe et al. 2002, PNAS USA, 99:596).

During PCR amplification, a small amount of dCTP undergoes deamination to dUTP (% dUTP varies with cycling time), and is subsequently incorporated by Archaeal DNA polymerases. Once incorporated, uracil-containing DNA inhibits Archaeal DNA polymerases, limiting their efficiency. We found that adding a thermostable dUTPase (dUTP→dUMP+$PP_i$) to amplification reactions carried out with Pfu, KOD, Vent, and Deep Vent DNA polymerases significantly increases PCR product yields by preventing dUTP incorporation (Hogrefe et al. 2002, Supra). Moreover, the target-length capability of Pfu DNA polymerase is dramatically improved in the presence of dUTPase (from <2 kb to 14 kb), indicating that uracil poisoning severely limits long-range PCR due to the use of prolonged extension times (1-2 min per kb @72° C.) that promote dUTP formation.

In addition to dUTP incorporation, uracil may also arise as a result of cytosine deamination in template DNA. The extent to which cytosine deamination occurs during temperature cycling has not been determined; however, any uracil generated would presumably impair the PCR performance of Archaeal DNA polymerases. Uracil arising from cytosine deamination in template DNA is unaffected by adding dUTPase, which only prevents incorporation of dUTP (created by dCTP deamination). Adding enzymes such as uracil DNA glycosylase (UGD), which excise uracil from the sugar backbone of DNA, or mismatch-specific UDGs (MUG), which additionally excise G:T mismatches, is one way to eliminate template uracil that impedes polymerization.

Alternatively, the problem of uracil stalling may be overcome by introducing mutations or deletions in Archaeal DNA polymerases that reduce, or ideally, eliminate uracil detection, and therefore, allow synthesis to continue opposite incorporated uracil (non-mutagenic uracil) and deaminated cytosine (pro-mutagenic uracil). Such mutants would be expected to produce higher product yields and amplify longer targets compared to wild type Archaeal DNA polymerases. Moreover, mutants that lack uracil detection should be compatible with dUTP/UNG decontamination methods employed in real-time Q-PCR.

It is sometimes desired for a DNA polymerase or a reverse transcriptase to have a high processivity. Processivity is a measurement of the ability of a DNA polymerase to incorporate one or more deoxynucleotides into a primer template molecule without the DNA polymerase dissociating from that molecule. DNA polymerases having low processivity, such as the Klenow fragment of DNA polymerase I of *E. coli*, will dissociate after about 5-40 nucleotides are incorporated on average. Other polymerases, such as T7 DNA polymerase in the presence of thioredoxin, are able to incorporate many thousands of nucleotides prior to dissociating. In the absence of thioredoxin such a T7 DNA polymerase has a much lower processivity. Processivity factors have been identified to increase the processivity of a DNA polymerase (e.g., see Carson D R, Christman M F. 2001, Proc Natl Acad Sci U S A. 98(15):8270-5).

U.S. Pat. No. 5,972,603 teaches a chimeric DNA polymerase having a DNA polymerase domain and a processivity factor binding domain not naturally associated with the DNA polymerase domain, where the processivity factor binding domain binds thioredoxin.

U.S. patent application with Ser. No. 2002/0119467 describes a method for increasing the processivity of reverse transcriptase (RT) *E. coli* DNA polymerase and T7 DNA polymerase using a polynucleotide binding protein such as Ncp7, recA, SSB and T4gp32.

There is therefore a need for thermostable DNA polymerases that can amplify DNA in the presence of dUTP without compromising proofreading or polymerization activity and efficiency. There is also a need for thermostable DNA polymerases that can amplify DNA efficiently without the proof checking function of 3'-5' exonuclease activity so that the thermostable DNA polymerase exhibits increased processivity.

SUMMARY OF THE INVENTION

The present invention provides an Archaeal DNA polymerase comprising an amino acid sequence selected from SEQ ID NOs. 83-108, and further comprising at lease one amino acid mutation in exoI motif and another amino acid mutation at V93, where the Archaeal DNA polymerase is deficient in 3'-5' exonuclease activity.

The present invention provides an Archaeal DNA polymerase comprising an amino acid sequence selected from SEQ ID NOs. 83-108, and further comprising at lease one amino acid mutation in exoII motif and another amino acid mutation at V93, where the Archaeal DNA polymerase is deficient in 3'-5' exonuclease activity.

The present invention also provides an Archaeal DNA polymerase comprising an amino acid sequence selected from SEQ ID NOs. 83-108, and further comprising at lease one amino acid mutation in exo III motif and another amino acid mutation at V93, where the Archaeal DNA polymerase is deficient in 3'-5' exonuclease activity.

The present invention further provides an Archaeal DNA polymerase comprising an amino acid sequence selected from SEQ ID NOs. 83-108, and further comprising at lease one amino acid mutation in each of exo I and exo III motifs and another amino acid mutation at V93, where the Archaeal DNA polymerase is deficient in 3'-5' exonuclease activity.

In addition, the present invention provides an Archaeal DNA polymerase comprising an amino acid sequence selected from SEQ ID NOs. 83-108, and further comprising at lease one amino acid mutation in each of exo II and exo III motifs and another amino acid mutation at V93, where the Archaeal DNA polymerase is deficient in 3'-5' exonuclease activity.

The present invention provides an Archaeal DNA polymerase comprising an amino acid sequence selected from SEQ ID NOs. 83-108, and further comprising at lease one amino acid mutation in each of exo I and exoII motifs and another amino acid mutation at V93, where the Archaeal DNA polymerase is deficient in 3'-5' exonuclease activity.

The present invention provides an Archaeal DNA polymerase comprising an amino acid sequence selected from SEQ ID NOs. 83-108, and further comprising at lease one amino acid mutation in each of exoI, exo II, and exoIII motifs and another amino acid mutation at V93, where the Archaeal DNA polymerase is deficient in 3'-5' exonuclease activity.

Preferably, the mutant Archaeal DNA polymerase of the present invention is selected from the group consisting of: KOD, Pfu, and JDF-3 DNA polymerase.

Also preferably, the mutation at position V93, is a Valine to Arginine substitution, a Valine to Glutamic acid substitution, a Valine to Lysine substitution, a Valine to Aspartic acid substitution, a Valine to Glutamine substitution, or a Valine to Asparagine substitution.

Preferably, the mutation in exo I motif is selected from the group consisting of: aspartic acid (D) to threonine (T), aspartic acid (D) to alanine (A) and glutamic acid (E) to alanine (A).

The present invention provides an isolated polynucleotide comprising a nucleotide sequence encoding a mutant Archaeal DNA polymerase of the present invention as described above.

The present invention provides a composition comprising a mutant Archaeal DNA polymerase as described above.

Preferably, the composition of the present invention also contains an enzyme with reverse transcriptase activity.

The present invention provides a kit comprising a mutant Archaeal DNA polymerase as described above and packaging material therefor.

The kit may further contain an enzyme with reverse transcriptase activity.

Preferably, the enzyme with reverse transcriptase is a second mutant DNA polymerase.

More preferably, the enzyme with reverse transcriptase is the mutant Archaeal DNA polymerase which contains an increased reverse transcriptase activity.

The composition or kit of the present invention may further comprise a PCR additive.

The present invention provides a method for DNA synthesis comprising: (a) providing a mutant Archaeal DNA polymerase; and (b) contacting the mutant Archaeal DNA polymerase with a polynucleotide template to permit DNA synthesis. The present invention further provides a method for determining the abundance of a polynucleotide template, comprising (a) providing a mutant Archaeal DNA polymerase; (b) contacting the mutant Archaeal DNA polymerase with the polynucleotide template to produce amplified product; and (c) determining the abundance of the amplified product, where the abundance of the amplified product is indicative of the abundance of the polynucleotide template.

Preferably, the polynucleotide template is a RNA molecule, and where the RNA molecule is reverse transcribed into cDNA before the contacting step (b).

Also preferably, the RNA is reverse transcribed by an enzyme with reverse transcriptase activity.

More preferably, the RNA is reverse transcribed by the mutant Archaeal DNA polymerase which also contains an increased reverse transcriptase activity.

BRIEF DESCRIPTION OF THE DRAWINGS

FIG. 1: Oligonucleotide Primers for QuikChange Mutagenesis (SEQ ID Nos: 6-14, 43-55) according to one embodiment of the invention.

(b) PCR Amplification of Pfu V93R exo-mutant extract in the presence of 100% dUTP according to one embodiment of the invention.

FIG. 3: Protein concentration, unit concentration, and specific activity of the purified Pfu V93R and V93E exo-mutants according to one embodiment of the invention.

Figure 4:
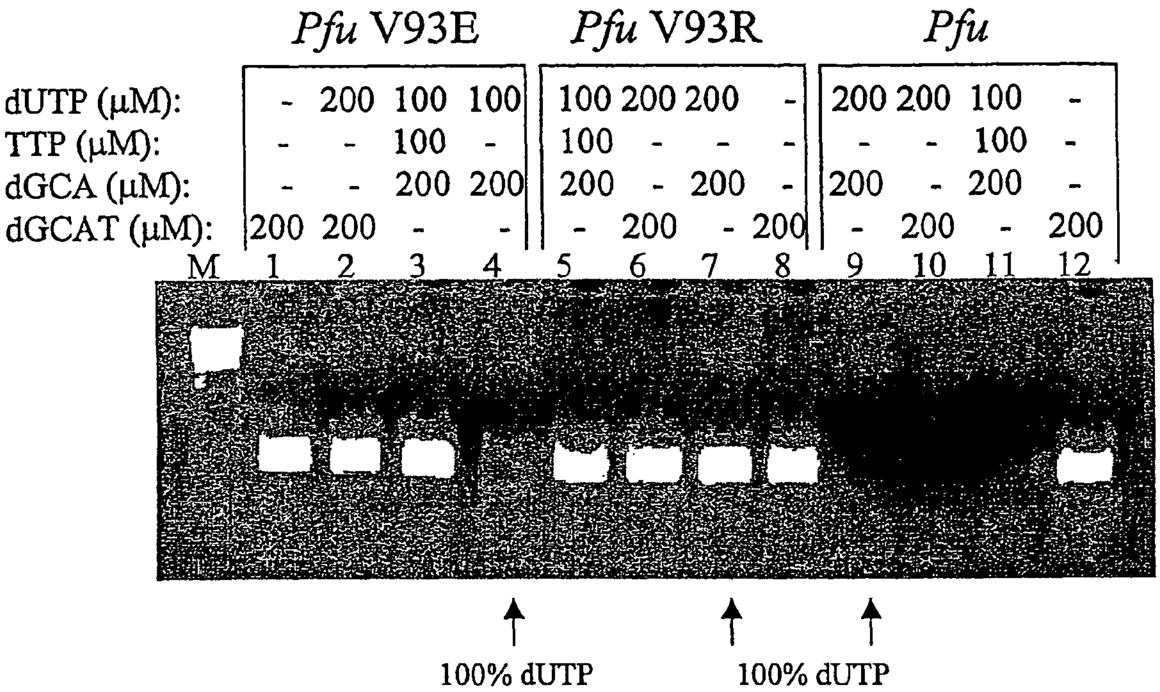

FIG. 4: Comparison of the efficacy of PCR amplification of Pfu DNA polymerase mutants and wt enzyme in the presence of different TTP:dUTP concentration ratios.

Figure 5:
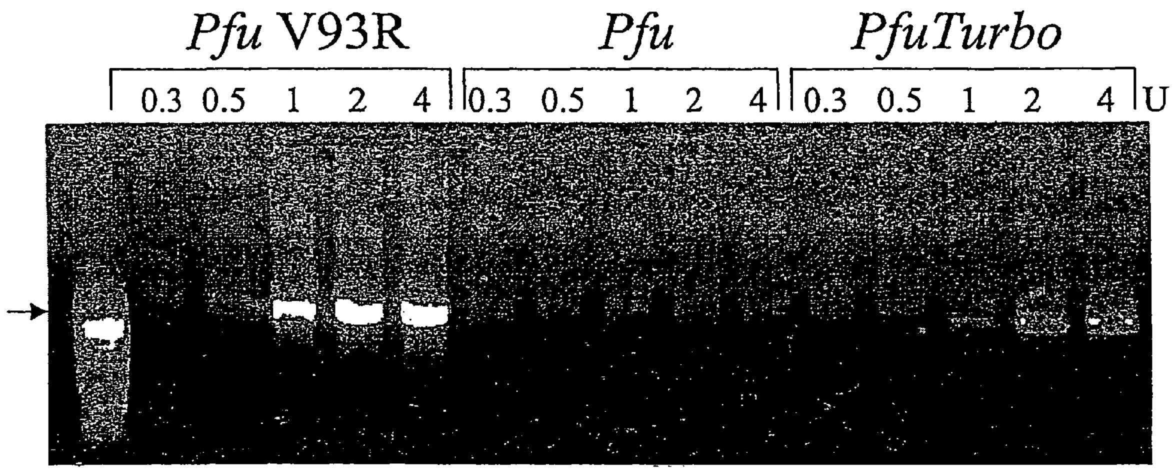

FIG. 5: Comparison of the efficacy of "long" PCR amplification of Pfu DNA polymerase mutants and wt enzyme.

FIG. 6: 6A. DNA sequence of example mutant Archaeal DNA polymerases according to one embodiment of the invention.

6B. Amino acid sequence of example mutant Archaeal DNA polymerases according to one embodiment of the invention

6C. DNA and Amino acid sequence of mutant Tgo DNA polymerase according to one embodiment of the invention FIG. 7: 7A. Amino acid sequence of example wild type DNA polymerase according to one embodiment of the invention (SEQ ID NOs. 83-108).

7B Amino acid sequence alignment of example wild-type Archaeal DNA polymerases according to one embodiment of the invention: Pfu: SEQ ID NO: 27; Tgo: SEQ ID NO: 29; KOD: SEQ ID NO: 30; Vent: SEQ ID NO: 31; Deep: SEQ ID NO: 28; JDF-3: SEQID NO: 32.

FIG. 8: dUTP incorporation of Pfu mutants compared to wild type Pfu DNA polymerase according to one embodiment of the invention.

8A. dUTP incorporation of Pfu mutants V93W, V93Y, V93M, V93K and V93R compared to wild type Pfu DNA polymerase

8B. dUTP incorporation of the Pfu V93D and V93R mutants compared to wild type Pfu DNA polymerase.

8C. dUTP incorporation of the Pfu V93N and V93G mutant compared to wild type Pfu DNA polymerase FIG. 9: DNA polymerase activity of N-terminal Pfu DNA polymerase truncation mutants according to one embodiment of the invention.

FIG. 10: Oligonucleotide Primers for QuikChange Mutagenesis (SEQ ID Nos: 56-74).

FIG. 11: DNA polymerase activity of KOD V93 exo-polymerase mutants according to one embodiment of the invention.

FIG. 12: DNA polymerase activity of Tgo V93 exo-DNA polymerase mutants and comparison with JDF-3 V93 exo-polymerase mutants according to one embodiment of the invention.

FIG. 13: DNA polymerase activity of JDF-3 polymerase mutants according to one embodiment of the invention.

FIG. 14: DNA polymerase activity of Pfu polymerase deletion mutants according to one embodiment of the invention.

Figure 15:
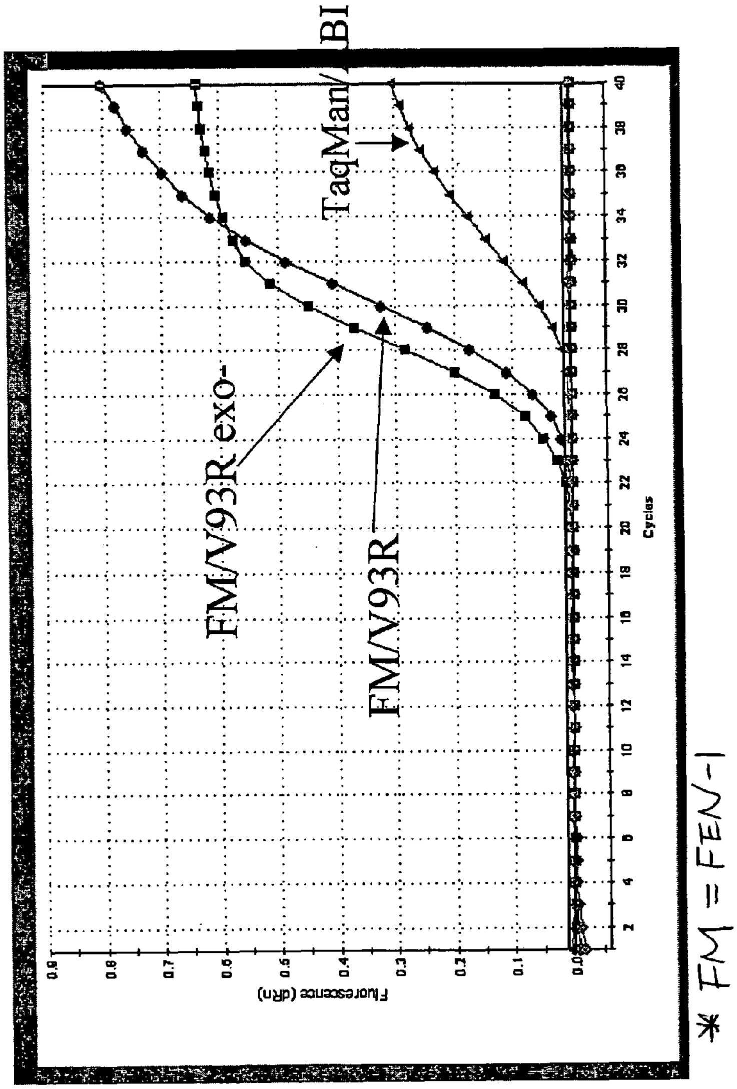

FIG. 15: An amplification plot for comparison of three polymerases in RT-QPCR according to one embodiment of the invention.

Figure 16:
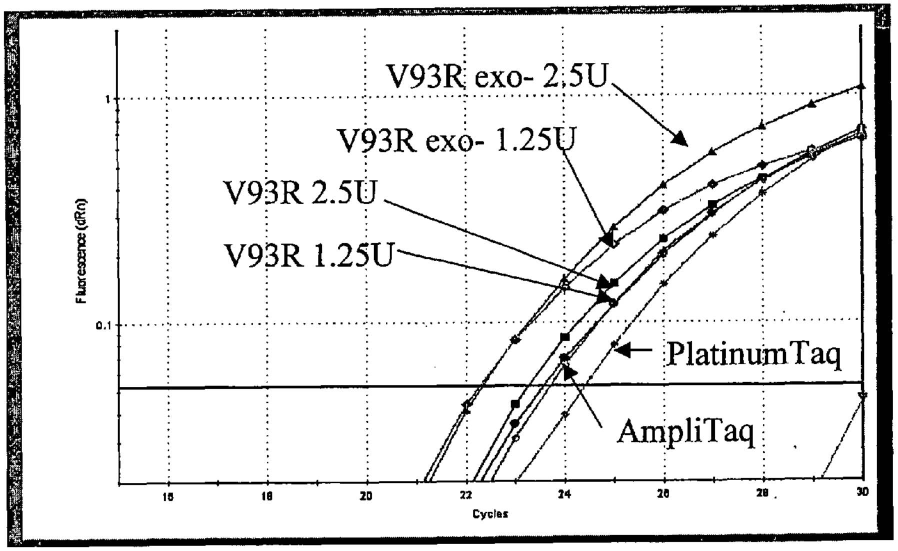

FIG. 16: A semi-log amplification plot comparing Pfu V93R and Pfu V93R exo-QPCR according to one embodiment of the invention.

Figure 17:
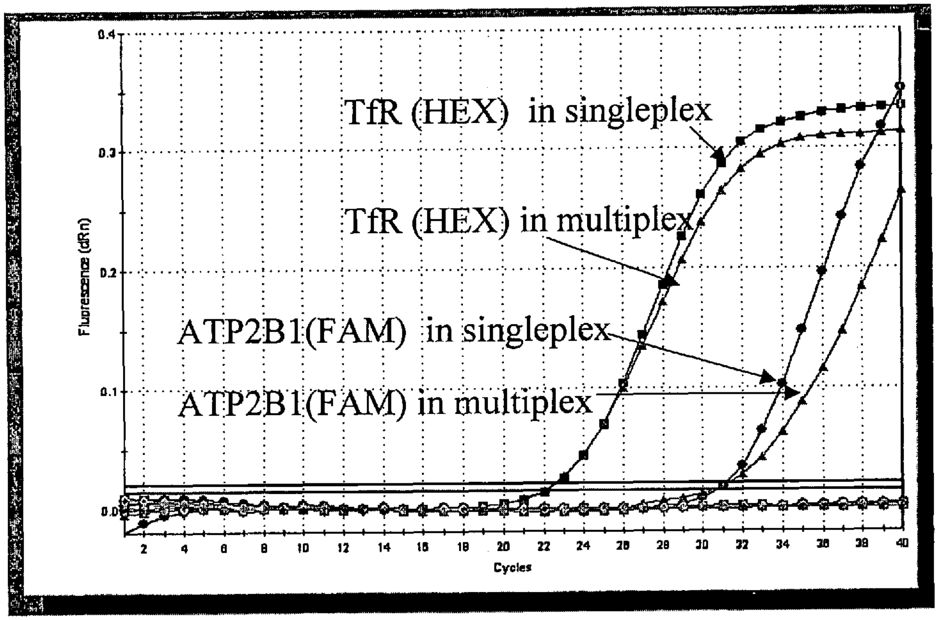

FIG. 17: An amplification plot comparing Pfu V93R and other DNA polymerase in multiplexing QPCR according to one embodiment of the invention.

DETAILED DESCRIPTION

Definitions

The invention contemplates A mutant DNA polymerase that exhibits deficient 3'-5' exonuclease activity and/or reduced base analog detection (for example, reduced detection of a particular base analog such as uracil or inosine or reduced detection of at least two base analogs).

Unless defined otherwise, the scientific and technological terms and nomenclature used herein have the same meaning as commonly understood by a person of ordinary skill to which this invention pertains. Generally, the procedures for molecular biology methods and the like are common methods used in the art. Such standard techniques can be found in reference manuals such as for example Sambrook et al. (1989, *Molecular Cloning—A Laboratory Manual*, Cold Spring Harbor Laboratories) and Ausubel et al. (1994, *Current Protocols in Molecular Biology*, Wiley, N.Y).

As used herein, "Archaeal" DNA polymerase refers to DNA polymerases that belong to either the Family B/pol I-type group (e.g., Pfu, KOD, Pfx, Vent, Deep Vent, Tgo, Pwo) or the pol II group (e.g., *Pyrococcus furiosus* DP1/DP2 2-subunit DNA polymerase). In one embodiment, "Archaeal" DNA polymerase refers to thermostable Archaeal DNA polymerases (PCR-able) and include, but are not limited to, DNA polymerases isolated from *Pyrococcus* species (*furiosus*, species GB-D, *woesii, abysii, horikoshii*), *Thermococcus* species (*kodakaraensis* KODI, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of>70-80° C. Appropriate PCR enzymes from the Archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche). Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995

As used herein, "mutant" polymerase refers to an Archaeal DNA polymerase, as defined herein, comprising one or more mutations that alter one or more activities of the DNA polymerase, for example, DNA polymerization, 3'-5' exonuclease activity or base analog detection activities. In one embodiment, the "mutant" polymerase of the invention refers to a DNA polymerase containing one or more mutations that reduce one or more base analog detection activities of the DNA polymerase. In a preferred embodiment, the "mutant" polymerase of the invention has a reduced uracil detection activity. In a preferred embodiment, the "mutant" polymerase of the invention has a reduced inosine detection activity. In another preferred embodiment, the "mutant" polymerase of the invention has a reduced uracil and inosine detection activity. A "mutant" polymerase as defined herein, includes a polymerase comprising one or more amino acid substitutions, one or more amino acid insertions, a truncation or an internal deletion.

A "mutant" polymerase as defined herein also includes a chimeric polymerase wherein any of the single, double or triple mutant Archaeal DNA polymerases described herein, any mutant Archaeal DNA polymerases comprising an insertion, described herein, or any of the truncated, or deleted mutant Archaeal DNA polymerases described herein, occur in combination with a polypeptide that increases processivity, thereby forming a chimera, as defined herein. A polypeptide that increases processivity is described in U.S. patent application with Ser. No. 10/408,601, WO 01/92501 A1 and Pavlov et al., 2002, Proc. Natl. Acad. Sci. USA, 99:13510-13515, herein incorporated by reference in their entirety.

A "chimera" as defined herein, is a fusion of a first amino acid sequence (protein) comprising a wild type or mutant ARCHAEAL DNA polymerase of the invention, joined to a second amino acid sequence defining a polypeptide that increases processivity, wherein the first and second amino acids are not found in the same relationship in nature. A "chimera" according to the invention contains two or more amino acid sequences (for example a sequence encoding a wild type or mutant ARCHAEAL DNA polymerase and a polypeptide that increases processivity) from unrelated proteins, joined to form a new functional protein. A chimera of the invention may present a foreign polypeptide which is found (albeit in a different protein) in an organism which also expresses the first protein, or it may be an "interspecies", "intergenic", etc. fusion of protein structures expressed by different kinds of organisms. The invention encompasses chimeras wherein the polypeptide that increases processivity and/or efficiency is joined N-terminally or C-terminally to a wild-type Archaeal DNA polymerase or to any of the mutant Archaeal DNA polymerases described herein.

As used herein, "joined" refers to any method known in the art for functionally connecting polypeptide domains, including without limitation recombinant fusion with or without intervening domains, intein-mediated fusion, non-covalent association, and covalent bonding, including disulfide bonding, hydrogen bonding, electrostatic bonding, and conformational bonding.

As used herein, "mutation" refers to a change introduced into a wild type DNA sequence that changes the amino acid sequence encoded by the DNA, including, but not limited to, substitutions, insertions, deletions or truncations. The consequences of a mutation include, but are not limited to, the creation of a new character, property, function, or trait not found in the protein encoded by the parental DNA, including, but not limited to, N terminal truncation, C terminal truncation or chemical modification. A "mutation," according to the present invention, may be created by genetic modification or chemical modification.

As used herein, "corresponding" refers to sequence similarity in a comparison of two or more nucleic acids or polypeptides, where functionally equivalent domains or sub-sequences are identified; such functionally equivalent domains or sub-sequences or amino acids within such a domain or sub-sequence are said to "correspond". That is, two or more sequences are compared through a comparative alignment analysis in which an entire sequence is examined for regions of sequence that are similar or identical, and thus regions likely to be functionally equivalent to regions from the other sequence(s) are identified.

As used herein in reference to comparisons of an amino acid, amino acid sequence, or protein domain, the term "similar" refers to amino acids or domains that although not identical, represent "conservative" differences. By "conservative" is meant that the differing amino acid has like characteristics with the amino acid in the corresponding or reference sequence. Typical conservative substitutions are among Ala, Val, Leu and Ile; among Ser and Thr; among the acidic residues Asp and Glu; among Asn and Gln; and among the basic residues Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "functionally equivalent" means that a given motif, region, or amino acid within a motif or region performs the same function with regard to the overall function of the enzyme as a motif, region or amino acid within a motif or region performs in another enzyme.

As used herein, "3' to 5' exonuclease deficient" or "3' to 5' exo-" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, for example, 0.03%, 0.05%, 0.1%, 1%, 5%, 10%, 20% or even up to 50% of the exonuclease activity relative to the parental enzyme. Methods used to generate and characterize 3'-5' exonuclease DNA polymerases including the D141A and E143A mutations as well as other mutations that reduce or eliminate 3'-5' exonuclease activity are disclosed in the pending U.S. patent application Ser. No. 09/698,341 (Sorge et al; filed Oct. 27, 2000). Additional mutations that reduce or eliminate 3' to 5' exonuclease activity are known in the art and contemplated herein.

As used herein, "base analogs" refer to bases that have undergone a chemical modification as a result of the elevated temperatures required for PCR reactions. In a preferred embodiment, "base analog" refers to uracil that is generated by deamination of cytosine. In another preferred embodiment, "base analog" refers to inosine that is generated by deamination of adenine.

As used herein, "reduced base analog detection" refers to a DNA polymerase with a reduced ability to recognize a base analog, for example, uracil or inosine, present in a DNA template. In this context, mutant DNA polymerase with "reduced" base analog detection activity is a DNA polymerase mutant having a base analog detection activity which is lower than that of the wild-type enzyme, i.e., having less than 10% (e.g., less than 8%, 6%, 4%, 2% or less than 1%) of the base analog detection activity of that of the wild-type enzyme. base analog detection activity may be determined according to the assays similar to those described for the detection of DNA polymerases having a reduced uracil detection as described in Greagg et al. (1999) Proc. Natl. Acad. Sci. 96, 9045-9050 and Example 3. Alternatively, "reduced" base analog detection refers to a mutant DNA polymerase with a reduced ability to recognize a base analog, the "reduced" recognition of a base analog being evident by an increase in the amount of >10 Kb PCR of at least 10%, preferably 50%, more preferably 90%, most preferably 99% or more, as compared to a wild type DNA polymerase without a reduced base analog detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

As used herein, "reduced uracil detection" refers to a DNA polymerase with a reduced ability to recognize a uracil base present in a DNA template. In this context, mutant DNA polymerase with "reduced" uracil detection activity is a DNA polymerase mutant having a uracil detection activity which is lower than that of the wild-type enzyme, i.e., having less than 10% (e.g., less than 8%, 6%, 4%, 2% or less than 1%) of the uracil detection activity of that of the wild-type enzyme. Uracil detection activity may be determined according to the assays described in Greagg et al. (1999) Proc. Natl. Acad. Sci. 96, 9045-9050 and as described herein below. Alternatively, "reduced" uracil detection refers to a mutant DNA polymerase with a reduced ability to recognize uracil, the "reduced" recognition of uracil being evident by an increase in the amount of >10 Kb PCR of at least 10%, preferably 50%, more preferably 90%, most preferably 99% or more, as compared to a wild type DNA polymerase without a reduced uracil detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

As used herein, the terms "reverse transcription activity" and "reverse transcriptase activity" are used interchangeably to refer to the ability of an enzyme (e.g., a reverse transcriptase or a DNA polymerase) to synthesize a DNA strand (i.e., cDNA) utilizing an RNA strand as a template. Methods for measuring RT activity are provided in the examples herein below and also are well known in the art. For example, the Quan-T-RT assay system is commercially available from Amersham (Arlington Heights, Ill.) and is described in Bosworth, et al., Nature 1989, 341:167-168.

As used herein, the term "increased reverse transcriptase activity" refers to the level of reverse transcriptase activity of a mutant enzyme (e.g., a DNA polymerase) as compared to its wild-type form. A mutant enzyme is said to have an "increased reverse transcriptase activity" if the level of its reverse transcriptase activity (as measured by methods described herein or known in the art) is at least 20% or more than its wild-type form, for example, at least 25%, 30%, 40%, 50%, 60%, 70%, 80%, 90%, 100% more or at least 2-fold, 3-fold, 4-fold, 5-fold, or 10-fold or more.

As used herein, "synthesis" refers to any in vitro method for making new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

"DNA synthesis", according to the invention, includes, but is not limited to, PCR, the labelling of polynucleotide (i.e., for probes and oligonucleotide primers), polynucleotide sequencing.

As used herein, "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. "DNA polymerase" catalyzes the polymerization of deoxynucleotides. In a preferred embodiment, the "DNA polymerase" of the invention is an Archaeal DNA polymerase. A "DNA polymerase" useful according to the invention includes, but is not limited to those included in the section of the present specification entitled "Polymerases".

As used herein, "polypeptide that increases processivity and/or efficiency" refers to a domain that is a protein or a region of a protein or a protein complex, comprising a polypeptide sequence, or a plurality of peptide sequences wherein that region increases processivity, as defined herein, or increases salt resistance, as defined herein. A "polypeptide that increases processivity and/or efficiency useful according to the invention includes but is not limited to any of the domains included in Pavlov et al., supra or WO 01/92501, for example Sso7d, Sac7d, HMF-like proteins, PCNA homologs, and helix-hairpin-helix domains, for example derived from Topoisomerase V.

As used herein, "processivity" refers to the ability of a polynucleotide modifying enzyme, for example a polymerase, to remain attached to the template or substrate and perform multiple modification reactions. "Modification reactions" include but are not limited to polymerization, and exonucleolytic cleavage. "Processivity" also refers to the ability of a polynucleotide modifying enzyme, for example a polymerase, to modify relatively long (for example 0.5-1 kb, 1-5 kb or 5 kb or more) tracts of nucleotides. "Processivity" also refers to the ability of a polynucleotide modifying enzyme, for example a DNA polymerase, to perform a sequence of polymerization steps without intervening dissociation of the enzyme from the growing DNA chains. "Processivity" can depend on the nature of the polymerase, the sequence of a DNA template, and reaction conditions, for example, salt concentration, temperature or the presence of specific proteins.

As used herein, "increased processivity" refers to an increase of 5-10%, preferably 10-50%, more preferably 50-100% or more, as compared to a wild type or mutant ARCHAEAL DNA polymerase that lacks a polypeptide that increases processivity as defined herein. Methods for measuring processivity of a DNA polymerase are generally known in the art, e.g., as described in Sambrook et al. 1989, In Molecular Cloning, 2nd Edition, CSH Press, 7.79-7.83 and 13.8, and as described in U.S. patent application with Ser. No. 2002/0119467, hereby incorporated by reference. Processivity and increased processivity can be measured according the methods defined herein and in Pavlov et al., supra and WO 01/92501 A1. Processivity can also be measured by any known method in the art, e.g., as described in U.S. Pat. No. 5,972,603, the entirety of which is incorporated herein by reference.

As used herein, the term "efficiency" of a DNA polymerase refers to a rate at which the DNA polymerase incorporates a nucleotide into a polynucleotide, or it may be defined as $N=No(1+E)^{CT}$ as described in "Amplification efficiency of thermostable DNA polymerases" Anal/Biochem. 321 (2003) 226-235 (incorporated herein by reference). Methods for measuring the rate of incorporation are described herein below and are generally known in the art, e.g., as described in Leung et al. (1989) Technique 1:11-15 and Caldwell et al. (1992) PCR Methods Applic. 2:28-33, hereby incorporated by reference.

The term "efficiency" may be also defined in terns of $N=No(1+E)^{CT}$. Methods for calculating efficiency this way are known in the art, e.g., as described in Arezi et al., 2003 Analytical Biochem. 321:226/235, hereby incorporated by reference. Theoretically, the amount of product doubles during each PCR cycle; in other words, $N=No2^n$, where N is the number of amplified molecules, No is the initial number of molecules, and n is the number of amplification cycles. Experimentally, amplification efficiency (E) is less than perfect, ranging from 0 to 1, and therefore the real PCR equation is $N=No(1+E)^n$. At threshold cycle, where the emission intensity of the amplification product measured by a real-time PCR instrument (such as the Mx4000 Multiplex Quantitative PCR System; Stratagene, La Jolla, Calif.) is recorded as statistically significant above the background noise, the PCR equation transforms into $N=No(1+E)^{CT}$. This equation can also be written as log N=log No+$C_T$ log(1+E), and therefore $C_T$ is proportional to the negative of the log of the initial target copy number. thus, the plot of $C_T$ versus the log of initial target copy number is a straight line, with a slope of −[1/log(1+E)] corresponding to amplification efficiency via the equation $E=10^{[-1/slope]}-1$.

As used herein, "increased efficiency" refers to an increase of 5-10%, preferably 10-50%, more preferably 50-100% or more, as compared to a wild type archaeal DNA polymerase.

As used herein, "increased salt resistance" refers to a polymerase that exhibits >50% activity at a salt concentration that is know to be greater than the maximum salt concentration at which the wild-type polymerase is active. The maximum salt concentration differs for each polymerase and is known in the art, or can be experimentally determined according to methods in the art. For example, Pfu is inhibited at 30 mM (in PCR) so a Pfu enzyme with increased salt resistance would have significant activity (>50%) at salt concentrations above 30 mM. A polymerase with increased salt resistance that is a chimera comprising a polypeptide that increases salt resistance, as defined herein, is described in Pavlov et al. supra and WO 01/92501 A1.

As used herein, a DNA polymerase with a "reduced DNA polymerization activity" is a DNA polymerase mutant comprising a DNA polymerization activity which is lower than that of the wild-type enzyme, e.g., comprising less than 10% DNA (e.g., less than 8%, 6%, 4%, 2% or less than 1%) polymerization activity of that of the wild-type enzyme. Methods used to generate characterize Pfu DNA polymerases with reduced DNA polymerization activity are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

As used herein, "thermostable" refers to an enzyme which is stable and active at temperatures as great as preferably between about 90-100° C. and more preferably between about 70-98° C. to heat as compared, for example, to a non-thermostable form of an enzyme with a similar activity. For example, a thermostable polynucleotide polymerase derived from thermophilic organisms such as *P. furiosus, M. jannaschii, A. fulgidus* or *P. horikoshii* are more stable and active at elevated temperatures as compared to a polynucleotide polymerase from *E. coli*. A representative thermostable polynucleotide polymerase isolated from *P. furiosus* (Pfu) is described in Lundberg et al., 1991, *Gene,* 108:1-6. Additional representative temperature stable polymerases include, e.g., polymerases extracted from the thermophilic bacteria *Thermusflavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus.*

Temperature stable polymerases are preferred in a thermocycling process wherein double stranded polynucleotides are denatured by exposure to a high temperature (about 95° C.) during the PCR cycle.

As used herein, the term "template DNA molecule" refers to that strand of a polynucleotide from which a complementary polynucleotide strand is synthesized by a DNA polymerase, for example, in a primer extension reaction.

As used herein, the term "template dependent manner" is intended to refer to a process that involves the template dependent extension of a primer molecule (e.g., DNA synthesis by DNA polymerase). The term "template dependent manner" refers to polynucleotide synthesis of RNA or DNA wherein the sequence of the newly synthesised strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

As used herein, an "amplified product" refers to the double strand polynucleotide population at the end of a PCR amplification reaction. The amplified product contains the original polynucleotide template and polynucleotide synthesized by DNA polymerase using the polynucleotide template during the PCR reaction.

As used herein, the term "abundance of polynucleotide" refers to the amount of a particular target polynucleotide sequence present in an amplification reaction, either before (e.g., the amount of the template polynucleotide), during (e.g., as in real-time PCR), or after the amplification (e.g., the amount of amplified product). The amount is generally measured as a relative amount in terms of concentration or copy number of the target sequence relative to the amount of a standard of known concentration or copy number. Alternatively, the amount in one unknown sample is measured relative to the amount in another unknown sample. As used herein, abundance of a polynucleotide is measured on the basis of the intensity of a detectable label, most often a fluorescent label. The methods of the invention permit one to extrapolate the relative amount of one or more target sequences in a polynucleotide sample from the amplification profile of that target sequence or sequences from that sample.

The term "fidelity" as used herein refers to the accuracy of DNA polymerization by template-dependent DNA polymerase. The fidelity of a DNA polymerase is measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate of $5\times10^{-6}$ per base pair or lower. The fidelity or error rate of a DNA polymerase may be measured using assays known to the art. For example, the error rates of DNA polymerase mutants can be tested using the lacI PCR fidelity assay described in Cline, J., Braman, J. C., and Hogrefe, H. H. (96) NAR 24:3546-3551. Briefly, a 1.9 kb fragment encoding the lacIOlacZα target gene is amplified from pPRIAZ plasmid DNA using 2.5 U DNA polymerase (i.e. amount of enzyme necessary to incorporate 25 nmoles of total dNTPs in 30 min. at 72° C.) in the appropriate PCR buffer. The lacI-containing PCR products are then cloned into lambda GT 10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per bp per duplication (MF/bp/d), where bp is the number of detectable sites in the lacI gene sequence (349) and d is the number of effective target doublings. For each DNA polymerase mutant, at least two independent PCR amplifications are performed.

As used herein, "polynucleotide template" or "target polynucleotide template" or "template" refers to a polynucleotide containing an amplified region. The "amplified region," as used herein, is a region of a polynucleotide that is to be either synthesized by polymerase chain reaction (PCR). For example, an amplified region of a polynucleotide template resides between two sequences to which two PCR primers are complementary to.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

As used herein, the term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibits a reduced uracil detection activity.

As used herein, "additive" refers to a reagent which can increase the processivity, efficiency, or heat or salt stability, including but not limited to, Pfu dUTPase (PEF), PCNA, RPA, ssb, antibodies, DMSO, betaine, 3'-5' exonuclease (e.g., Pfu G387P), Ncp7, recA, T4gp32.

As used herein "FEN-1 nuclease" refers to thermostable FEN-1 endonucleases useful according to the invention and include, but are not limited to, FEN-1 endonuclease purified from the "hyperthermophiles", e.g., from *M. jannaschii, P. furiosus* and *P. woesei*. See U.S. Pat. No. 5,843,669, hereby incorporated by reference.

According to the methods of the present invention, the addition of FEN-1 in the amplification reaction dramatically increases the efficiency of PCR amplification. 400 ng to 4000 ng of FEN-1 may be used in each amplification reaction. Preferably 400-1000 ng, more preferably, 400-600 ng of FEN-1 is used in the amplification reaction. In a preferred embodiment of the invention, 400 ng FEN-1 is used.

As used herein, a "PCR enhancing factor" or a "Polymerase Enhancing Factor" (PEF) refers to a complex or protein possessing polynucleotide polymerase enhancing activity including, but not limited to, PCNA, RFC, helicases etc (Hogrefe et al., 1997, Strategies 10:93-96; and U.S. Pat. No. 6,183,997, both of which are hereby incorporated by reference).

Amino acid residues identified herein are preferred in the natural L-configuration. In keeping with standard polypeptide nomenclature, J. Biol. Chem., 243:3557-3559, 1969, abbreviations for amino acid residues are as shown in the following Table I.

TABLE I

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

Misincorporation, base deamination and other base modifications greatly increase as a consequence of PCR reaction conditions, for example, elevated temperature. This results in the progressive accumulation of base analogs (for example uracil or inosine) in the PCR reaction that ultimately inhibit Archaeal proofreading DNA polymerases, such as Pfu, Vent and Deep Vent DNA polymerases, severely limiting their processivity and/or efficiency.

The present invention provides a remedy to the above problem of PCR reactions by disclosing compositions for Archaeal DNA polymerase mutants which increase PCR amplification processivity and/or efficiency and there uses thereof in PCR, including quantitative PCR and quantitative RT-PCR.

The mutant Archaeal DNA polymerases of the invention may provide for the use of fewer units of polymerase, may allow assays to be done using shorter extension times and/or may provide greater success in achieving higher yields and or longer products.

Archaeal DNA Polymerases

There are 2 different classes of DNA polymerases which have been identified in archaea: 1. Family B/pol I type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol I or pol II) can be derived from archaea with optimal growth temperatures that are similar to the desired assay temperatures.

Thermostable Archaeal DNA polymerases include, but are not limited to polymerases isolated from *Pyrococcus* species (*furiosus*, species GB-D, *woesii, abysii, horikoshii*), *Thermococcus* species (*kodakaraensis* KOD 1, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the Archaeal pol I DNA polymerase group are commercially available, including Pfu (Stratagene), KOD (Toyobo), Pfx (Life Technologies, Inc.), 9°N-7 (New England Biolabs, Inc), Vent (Tli) (New England BioLabs), Deep Vent (PGB-D) (New England BioLabs), Afu from *Archaeoglobus fulgidus* (e.g., Chalov et al., 2002, Dokl Biochem Biophys. 382:53-5), Mvo (Koniskyet al., 1994, J. Bacteriol. 176: 6402-6403), DTok (Bergseid, M., Scott, B. R., Mathur, S., Nielson, K. B., Shoemaker, D., Mathur, E. J. 1992, Strategies 5, 50), Pis (Kahler et al., 2000, J. Bacteriol. 182 655-663), Csy (Schleperet al., 1998, J. Bacteriol. 180 (19), 5003-5009), Sac (Datukishvili et al., 1996, Gene 177 (1-2), 271-273), Soh (Iwai et al., 2000, DNA Res. 7 (4), 243-251), Sso (Pisani et al., 1992, Nucleic Acids Res. 20 (11), 2711-2716), Poc (Uemori et al., 1995, J. Bacteriol. 177 (8), 2164-2177), Ape (Kawarabayasi et al., 1999, DNA Res. 6 (2), 83-101), Tgo (Roche), and Pwo (Roche).

Additional Archaeal DNA polymerases related to those listed above are described in table 1 and in the following references: Archaea: A Laboratory Manual (Robb, F. T. and Place, A. R., eds.), Cold Spring Harbor Laboratory Press, Cold Spring Harbor, N.Y., 1995 and *Thermophilic Bacteria* (Kristjansson, J. K.,ed.) CRC Press, Inc., Boca Raton, Fla., 1992.

The invention therefore provides for thermostable Archaeal DNA polymerases of either Family B/pol I type or pol II type with a reduced base analog detection activity.

TABLE II

Protein sequences for Archaeal DNA polymerases as represented by their accession numbers. Polynucleotide coding sequences can be found in references or nucleotide accession numbers identified in the Genbank database through the protein sequence accession numbers.

| | |
|---|---|
| Vent | *Thermococcus litoralis* |
| ACCESSION | AAA72101 |
| PID | g348689 |
| VERSION | AAA72101.1 GI: 348689 |
| DBSOURCE | locus THCVDPE accession M74198.1 |
| THEST | *THERMOCOCCUS* SP. (STRAIN TY) |
| ACCESSION | O33845 |
| PID | g3913524 |
| VERSION | O33845 GI: 3913524 |
| DBSOURCE | swissprot: locus DPOL__THEST, accession O33845 |
| Pab | *Pyrococcus abyssi* |
| ACCESSION | P77916 |
| PID | g3913529 |
| VERSION | P77916 GI: 3913529 |
| DBSOURCE | swissprot: locus DPOL__PYRAB, accession P77916 |
| PYRHO | *Pyrococcus horikoshii* |
| ACCESSION | O59610 |
| PID | g3913526 |
| VERSION | O59610 GI: 3913526 |
| DBSOURCE | swissprot: locus DPOL__PYRHO, accession O59610 |
| PYRSE | *PYROCOCCUS* SP. (STRAIN GE23) |
| ACCESSION | P77932 |
| PID | g3913530 |
| VERSION | P77932 GI: 3913530 |
| DBSOURCE | swissprot: locus DPOL__PYRSE, accession P77932 |
| DeepVent | *Pyrococcus* sp. |
| ACCESSION | AAA67131 |
| PID | g436495 |
| VERSION | AAA67131.1 GI: 436495 |

TABLE II-continued

Protein sequences for Archaeal DNA polymerases as represented by their accession numbers. Polynucleotide coding sequences can be found in references or nucleotide accession numbers identified in the Genbank database through the protein sequence accession numbers.

| | |
|---|---|
| DBSOURCE | locus PSU00707 accession U00707.1 |
| Pfu | *Pyrococcus furiosus* |
| ACCESSION | P80061 |
| PID | g399403 |
| VERSION | P80061 GI: 399403 |
| DBSOURCE | swissprot: locus DPOL__PYRFU, accession P80061 |
| JDF-3 | *Thermococcus* sp. |
| Unpublished | |
| Baross gi\|2097756\|pat\|US\|5602011\|12 Sequence 12 from patent U.S. Pat. No. 5602011 | |
| 9degN | *THERMOCOCCUS* SP. (STRAIN 9°N-7). |
| ACCESSION | Q56366 |
| PID | g3913540 |
| VERSION | Q56366 GI: 3913540 |
| DBSOURCE | swissprot: locus DPOL__THES9, accession Q56366 |
| KOD | *Pyrococcus* sp. |
| ACCESSION | BAA06142 |
| PID | g1620911 |
| VERSION | BAA06142.1 GI:1620911 |
| DBSOURCE | locus PYWKODPOL accession D29671.1 |
| Tgo | *Thermococcus gorgonarius.* |
| ACCESSION | 4699806 |
| PID | g4699806 |
| VERSION | GI:4699806 |
| DBSOURCE | pdb: chain 65, release Feb 23, 1999 |
| THEFM | *Thermococcus fumicolans* |
| ACCESSION | P74918 |
| PID | g3913528 |
| VERSION | P74918 GI:3913528 |
| DBSOURCE | swissprot: locus DPOL__THEFM, accession P74918 |
| METTH | *Methanobacterium thermoautotrophicum* |
| ACCESSION | O27276 |
| PID | g3913522 |
| VERSION | O27276 GI:3913522 |
| DBSOURCE | swissprot: locus DPOL__METTH, accession O27276 |
| Metja | *Methanococcus jannaschii* |
| ACCESSION | Q58295 |
| PID | g3915679 |
| VERSION | Q58295 GI:3915679 |
| DBSOURCE | swissprot: locus DPOL__METJA, accession Q58295 |
| POC | *Pyrodictium occultum* |
| ACCESSION | B56277 |
| PID | g1363344 |
| VERSION | B56277 GI:1363344 |
| DBSOURCE | pir: locus B56277 |
| ApeI | *Aeropyrum pernix* |
| ACCESSION | BAA81109 |
| PID | g5105797 |
| VERSION | BAA81109.1 GI:5105797 |
| DBSOURCE | locus AP000063 accession AP000063.1 |
| ARCFU | *Archaeoglobus fulgidus* |
| ACCESSION | O29753 |
| PID | g3122019 |
| VERSION | O29753 GI:3122019 |
| DBSOURCE | swissprot: locus DPOL__ARCFU, accession O29753 |
| *Desulfurococcus* sp. Tok. | |
| ACCESSION | 6435708 |
| PID | g64357089 |
| VERSION | GT:6435708 |
| 9oN-7 | |
| ACCESSION | Q56366 |
| VERSION | Q56366 GI:3913540 |
| Afu | |
| ACCESSION | O29753 |
| VERSION | O29753 GI:3122019 |
| Mvo | |
| ACCESSION | P52025 |
| VERSION | P52025 GI:1706513 |
| ACCESSION | AAF27815 |
| VERSION | AAF27815.1 GI:6752664 |
| Csy | |
| ACCESSION | AAC62712 |

TABLE II-continued

| Protein sequences for Archaeal DNA polymerases as represented by their accession numbers. Polynucleotide coding sequences can be found in references or nucleotide accession numbers identified in the Genbank database through the protein sequence accession numbers. | |
|---|---|
| VERSION | AAC62712.1 GI:3599407 |
| Sac | |
| ACCESSION | P95690 |
| VERSION | P95690 GI:3913538 |
| Soh | |
| ACCESSION | BAA23994 |
| VERSION | BAA23994.1 GI:2696625 |
| Sso | |
| ACCESSION | P26811 |
| VERSION | P26811 GI:12643274 |

Mutant DNA Polymerases

3 '-5' Exonuclease Deficient

In one embodiment, the mutant DNA polymerase is a mutant with deficient 3'-5' exonuclease activity.

DNA polymerases lacking 3'-5' exonuclease (proofreading) activity are preferred for applications requiring nucleotide analog incorporation (e.g., DNA sequencing) to prevent removal of nucleotide analogs after incorporation. The 3'-5' exonuclease activity associated with proofreading DNA polymerases can be reduced or abolished by mutagenesis. Sequence comparisons have identified three conserved motifs (exo I (DXE), II ($NX_{2-3}$(F/Y)D), III ($YX_3D$)) in the 3'-5' exonuclease domain of DNA polymerases (reviewed V. Derbyshire, J. K. Pinsonneault, and C. M. Joyce, *Methods Enzymol.* 262, 363 (1995)). For example, replacement of any of the conserved aspartic or glutamic acid residues with alanine has been shown to abolish the exonuclease activity of numerous DNA polymerases, including Archaeal DNA polymerases such as Vent (H. Kong, R. B. Kucera, and W. E. Jack, *J. Biol. Chem.* 268, 1965 (1993)) and Pfu (Stratagene, unpublished). It is understood, according to the present invention, that other amino acids within or outside the exonuclease motifs may also be mutated to render the DNA polymerase deficient in 3'-5' exonuclease activity (e.g., by affecting the tertiary structure of the exonuclease domain). Conservative substitutions lead to reduced exonuclease activity, as shown for mutants of the Archaeal 9° N-7 DNA polymerase (M. W. Southworth, H. Kong, R. B. Kucera, J. Ware, H. Jannasch, and F. B. Perler, *Proc. Natl. Acad. Sci.* 93, 5281 (1996)).

In one embodiment, a 3'-5' exonuclease deficient JDF-3, KOD, or Pfu DNA polymerase is produced.

In one embodiment of the invention, the mutant DNA polymerase contains a mutation at a position corresponding to D141 and/or E143 of JDF-3 DNA polymerase.

JDF-3 DNA polymerase mutants exhibiting substantially reduced 3'-5' exonuclease activity (e.g., with one or more mutations as D141A, D141N, D141S, D141T, D141E and E143A) were prepared by introducing amino acid substitutions at the conserved 141D or 143E residues in the exo I domain, as described in U.S. patent application with Ser. No. 10/223,650, hereby incorporated by reference.

It is appreciated that one skilled in the art would be able to make an Archaeal DNA polymerase with deficient 3'-5' exonuclease activity by comparing the sequence of the Archaeal DNA polymerase with the sequence of JDF-3 DNA polymerase and by mutating the amino acids within the corresponding conserved exo I, II, or III motifs. In addition, it is also appreciated that one skilled in the art would be able to make an Archaeal DNA polymerase with deficient 3'-5' exonuclease activity by mutating one or more amino acid within the corresponding exo I, II, and III motifs.

Assays for DNA polymerase activity and 3'-5' exonuclease activity can be found in *DNA Replication 2nd Ed.*, Kornberg and Baker, supra; *Enzymes*, Dixon and Webb, Academic Press, San Diego, Calif. (1979), as well as other publications available to the person of ordinary skill in the art.

Suitable exonuclease activity assays include one described in Hogrefe et al (Hogrefe et 20 al., 2001, Methods in Enzymology, 343:91-116, incorporated by reference). Another assay employs double-stranded λ DNA, which has been uniformly labeled with $^3$H S-adenosyl methionine (NEN #NET-155) and Sss I methylase (NEB), and then restriction digested with Pal I (Kong et al., 1993, J. Biol. Chem. 268:1965). Using double-stranded labeled DNA templates, one can determine specificity by measuring whether cpms decrease (3'-5' exonuclease) with the addition of dNTPs (10-100 μM). A typical exonuclease reaction cocktail consists of 1× reaction buffer and 20 μg/ml $^3$H-labeled digested double-stranded λ DNA (~$10^6$ cpms/ml), prepared as described (Kong et al., supra). Exonuclease activity can be measured in the appropriate PCR buffer or in a universal assay buffer such as 70 mM Tris HCl (pH 8.8), 2 mM $MgCl_2$, 0.1% Triton-X, and 100 μg/ml BSA.

Percent exonuclease activity can be determined as: (corrected cpms for mutants)/(corrected cpms for wt DNA polymerase). To more precisely quantify % activity, cpms released can be converted into units of exonuclease activity. One unit of exonuclease activity is defined as the amount of enzyme that catalyzes the acid-solubilization of 10 nmoles of total dNMPs in 30 minutes at a defined temperature. To determine units, background (average "minimum cpms" value) is first subtracted from the average sample cpms. Nmoles dNMPs released is calculated using the following equation:

$$\frac{(\text{corrected sample cpms})}{\text{total cpms}} \times \frac{(\text{ng } DNA)}{\text{reaction}} \times \frac{(1 \text{ nmole } dNMP)}{(330 \text{ ng } dNMP)}$$

Units of exonuclease activity (in 30 minutes) can then be determined as:

$$\frac{(\text{nmoles } dNMPs \text{ released per hr})}{2} \times \frac{(1 \text{ unit})}{(10 \text{ nmoles } dNMPs \text{ released})}$$

Exonuclease specific activity (U/mg) can be extrapolated from the slope of the linear portion of units versus enzyme amount plots. Finally, % activity can be determined as:

$$\frac{\text{specific exonuclease activity } (U/mg) \text{ of mutant } DNA \text{ polymerase}}{\text{specific exonuclease activity } (U/mg) \text{ of wt } DNA \text{ polymerase}}$$

In addition to the substrate described above, exonuclease activity can be also be quantified using [$^3$H]-*E. coli* genomic DNA (NEN #NET561; 5.8 μCi/μg), a commercially-available substrate. A typical exonuclease reaction cocktail consists of 25 ng/ml $^3$H-labeled *E. coli* genomic DNA and 975 ng/ml cold *E. coli* genomic DNA in 1× reaction buffer. Assays are performed as described above.

Reduced Uracil Base Detection

In one embodiment of the invention, the Archaeal polymerase is a mutant polymerase having reduced uracil base detection.

Examination of Archaeal DNA polymerases revealed the presence of a distinct "pocket" located on a surface-exposed face toward the outer edge of the polymerases (Fogg, et al., 2002, Nature structural Biology, 9:922-927, hereby incorporated by reference in its entirety). The pocket is formed entirely by residues from four conserved segments in the Archaeal DNA polymerase sequences. Corresponding to Pfu DNA polymerase sequence, the base of the pocket is formed by the main chain and side chains of amino acids Pro36, Tyr 37, and Ile 38, one face of the pocket is formed by amino acids 90-97, another face is formed by residues 111-116, and by Pro 115.

An wild type Archaeal DNA polymerase or an Archaeal DNA polymerase with deficient 3'-5' exonuclease activity may be mutated at or more amino acid positions corresponding to Pro36, Tyr 37, Ile 38, amino acids 90-97, residues 111-116, and Pro 115 in wild type Pfu DNA polymerase, e.g., as described in U.S. patent application with Ser. No. 10/408,601, filed Apr. 7, 2003, hereby incorporated by reference in its entirety.

In one embodiment of the invention, the mutant DNA polymerase is encoded by a polynucleotide sequence selected from SEQ ID Nos 17-24, wherein the codon encoding amino acid residue Valine at position 93 is replaced by the one of the following codons:

Codons encoding Arginine: AGA, AGG, CGA, CGC, CGG, CGT

Codons encoding Glutamic acid: GAA, GAG

Codons encoding Aspartic acid: GAT, GAC

Codons encoding Lysine: AAA, AAG

Codons encoding Glutamine: CAA, CAG

Codons encoding Asparagine AAC, AAU

In one embodiment, a mutant DNA polymerase has an amino acid sequence selected from the sequences of SEQ ID NOS: 27-34, wherein Valine at position 93 is replaced by one of Arginine, Glutamic acid, Aspartic acid, Lysine, Glutamine, and Asparagine.

Alternatively, the mutant DNA polymerase may be a Pfu DNA polymerase having a deletion of Valine at position 93 as shown in SEQ ID NO: 35, or alternatively, having a deletion of Aspartic acid at position 92, Valine at position 93, and Proline at position 94 as shown in SEQ ID NO: 36. Similarly, the mutant DNA polymerase may be a Pfu DNA polymerase having a deletion of the codon GTT encoding Valine at position 93 as shown in SEQ ID NO: 25, or alternatively having a deletion of the successive codons GAT, GTT, and CCC which encode residues Aspartic acid, Valine, and Proline at positions 92, 93, and 94 respectively as shown in SEQ ID NO: 26.

In one embodiment, a Pfu, KOD or JDF-3 DNA polymerase mutants exhibiting substantially reduced 3'-5' exonuclease activity (e.g., with one or more mutations as D141A, D141N, D141S, D141T, D141E and E143A) are mutated to further comprise one or more mutations at corresponding positions to Pro36, Tyr 37, Ile 38, amino acids 90-97, residues 111-116, and Pro 115 of wild type Pfu DNA polymerase.

The present invention encompass making an Archaeal DNA polymerase with reduced uracil base detection by comparing the sequence of the Archaeal DNA polymerase with th e sequence of Pfu DNA polymerase and by mutating the amino acids within the corresponding conserved residues within the pocket forming amino acids. In addition, one skilled in the art would be able to make an Archaeal DNA polymerase with reduced uracil base detection by mutating one or more amino acid within these amino acid positions.

Increased Reverse Transcriptase Activity

Amino acid changes at the position corresponding to L408 of JDF-3 Family B DNA polymerase which lead to increased reverse transcriptase activity tend to introduce cyclic side chains, such as phenylalanine, tryptophan, histidine or tyrosine as described in U.S. patent application with Ser. No. 10/435,766, hereby incorporated by reference. While the amino acids with cyclic side chains are demonstrated herein to increase the reverse transcriptase activity of Archaeal Family B DNA polymerases, other amino acid changes at the LYP motif are contemplated to have effects on the reverse transcriptase activity. Thus, in order to modify the reverse transcriptase activity of another Archaeal Family B DNA polymerase, one would first look to modify the LYP motif of Region II, particularly the L or other corresponding amino acid of the LYP motif, first substituting cyclic side chains and assessing reverse transcriptase activity relative to wild-type as disclosed herein below in "Methods of Evaluating Mutants for Increased RT Activity." If necessary or if desired, one can subsequently modify the same position in the LYP motif with additional amino acids and similarly assess the effect on activity. Alternatively, or in addition, one can modify the other positions in the LYP motif and similarly assess the reverse transcriptase activity.

Methods for assaying reverse transcriptase (RT) activity based on the RNA-dependent synthesis of DNA have been well known in the art, e.g., as described in U.S. Pat. No. 3,755,086; Poiesz et al., (1980) Proc. Natl. Acad. Sci. USA, 77: 1415; Hoffman et al., (1985) Virology 147: 326; all hereby incorporated by reference.

Recently, highly sensitive PCR based assays have been developed that can detect RNA-dependent DNA polymerase in the equivalent of one to ten particles (Silver et al. (1993) Nucleic Acids Res. 21: 3593-4; U.S. Pat. No. 5,807,669). One such assay, designated as PBRT (PCR-based reverse transcriptase), has been used to detect RT activity in a variety of samples (Pyra et al. (1994) Proc. Natl. Acad. Sci. USA 51: 1544-8; Boni, et al. (1996) J. Med. Virol. 49: 23-28). This assay is $10^6$-$10^7$ more sensitive than the conventional RT assay.

Other useful RT assays include, but are not limited to, one-step fluorescent probe product-enhanced reverse transcriptase assay described in Hepler, R. W., and Keller, P. M. (1998). Biotechniques 25(1), 98-106; an improved product enhanced reverse transcriptase assay described in Chang, A., Ostrove, J. M., and Bird, R. E. (1997) J Virol Methods 65(1), 45-54; an improved non-radioisotopic reverse transcriptase assay described in Nakano et al., (1994) Kansenshogaku Zasshi 68(7), 923-3 1; a highly sensitive qualitative and quantitative detection of reverse transcriptase activity as described in Yamamoto, S., Folks, T. M., and Heneine, W. (1996) J Virol Methods 61(1-2), 135-43, all references hereby incorporated by reference.

RT activity can be measured using radioactive or non-radioactive labels.

In one embodiment, 1 μl of appropriately purified DNA polymerase mutant or diluted bacterial extract (i.e., heat-treated and clarified extract of bacterial cells expressing a cloned polymerase or mutated cloned polymerase) is added to 10 μl of each nucleotide cocktail (200 μM dATP, 200 μM dGTP, 200 μM dCTP and 5 μCi/ml α-$^{33}$P dCTP and 200 μM dTTP, a RNA template, 1× appropriate buffer, followed by incubation at the optimal temperature for 30 minutes (e.g., 72° C. for Pfu DNA polymerase), for example, as described in Hogrefe et al., 2001, Methods in Enzymology, 343:91-116.

Extension reactions are then quenched on ice, and 5 μl aliquots are spotted immediately onto DE81 ion-exchange filters (2.3 cm; Whatman #3658323). Unincorporated label is removed by 6 washes with 2×SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms" (wash filters as above). Cpms bound is proportional to the amount of RT activity present per volume of bacterial extract or purified DNA polymerase.

In another embodiment, the RT activity is measured by incorporation of non-radioactive digoxigenin labeled dUTP into the synthesized DNA and detection and quantification of the incorporated label essentially according to the method described in Holtke, H.-J.; Sagner, G; Kessler, C. and Schmitz, G. (1992) Biotechniques 12, 104-113. The reaction is performed in a reaction mixture consists of the following components: 1 μg of polydA-$(dT)_{15}$, 33 μM of dTTP, 0.36 μM of labeled-dUTP, 200 mg/ml BSA, 10 mM Tris-HCl, pH 8.5, 20 mM KCl, 5 mM $MgCl_2$, 10 mM DTE and various amounts of DNA polymerase. The samples are incubated for 30 min. at 50° C., the reaction is stopped by addition of 2μ 5 M EDTA, and the tubes placed on ice. After addition of 8 μl 5 M NaCl and 150 μl of Ethanol (precooled to −20° C.) the DNA is precipitated by incubation for 15 min on ice and pelleted by centrifugation for 10 min at 13000×rpm and 4° C. The pellet is washed with 100 μl of 70% Ethanol (precooled to −20° C.) and 0.2 M NaCl, centrifuged again and dried under vacuum.

The pellets are dissolved in 50 μl Tris-EDTA (10 mM/0.1 mM; pH 7.5). 5 μl of the sample are spotted into a well of a nylon membrane bottomed white microwave plate (Pall Filtrationstechnik GmbH, Dreieich, FRG, product no: SM045BWP). The DNA is fixed to the membrane by baking for 10 min. at 70° C. The DNA loaded wells are filled with 100 μl of 0.45 μm-filtrated 1% blocking solution (100 mM maleic acid, 150 mM NaCl, 1% (w/v) casein, pH 7.5). All following incubation steps are done at room temperature. After incubation for 2 min. the solution is sucked through the membrane with a suitable vacuum manifold at −0.4 bar. After repeating the washing step, the wells are filled with 100 μl of a 1:10,000-dilution of Anti-digoxigenin-AP, Fab fragments (Boehringer Mannheim, FRG, no: 1093274) diluted in the above blocking solution. After incubation for 2 min. and sucking this step is repeated once. The wells are washed twice under vacuum with 200 μl each time washing-buffer 1 (100 mM maleic-acid, 150 mM NaCl, 0.3%(v/v) Tween.™. 20, pH 7.5). After washing another two times under vacuum with 200 μl each time washing-buffer 2 (10 mM Tris-HCl, 100 mM NaCl, 50 mM $MgCl_2$, pH 9.5) the wells are incubated for 5 min with 50 μl of CSPD™ (Boehringer Mannheim, no: 1655884), diluted 1:100 in washing-buffer 2, which serves as a chemiluminescent substrate for the alkaline phosphatase. The solution is sucked through the membrane and after 10 min incubation the RLU/s (Relative Light Unit per second) are detected in a Luminometer e.g. MicroLumat LB 96 P (EG&G Berthold, Wilbad, FRG). With a serial dilution of Taq DNA polymerase a reference curve is prepared from which the linear range serves as a standard for the activity determination of the DNA polymerase to be analyzed.

U.S. Pat. No. 6,100,039 (incorporated hereby by reference) describes another useful process for detecting reverse transcriptase activity using fluorescence polarization: the reverse transcriptase activity detection assays are performed using a Beacon™ 2000 Analyzer. The following reagents are purchased from commercial sources: fluorescein-labeled oligo dA-F (Bio.Synthesis Corp., Lewisville, Tex.), AMV Reverse Transcriptase (Promega Corp., Madison, Wis.), and Polyadenylic Acid Poly A (Pharmacia Biotech, Milwaukee, Wis.). The assay requires a reverse trancriptase reaction step followed by a fluorescence polarization-based detection step. The reverse transcriptase reactions are completed using the directions accompanying the kit. In the reaction 20 ng of Oligo (dT) were annealed to 1 μg of Poly A at 70° C. for 5 minutes. The annealed reactions are added to an RT mix containing RT buffer and dTTP nucleotides with varying units of reverse transcriptase (30, 15, 7.5, 3.8, and 1.9 Units/Rxn). Reactions are incubated at 37° C. in a water bath. 5 μl aliquots are quenched at 5, 10, 15, 20, 25, 30, 45, and 60 minutes by adding the aliquots to a tube containing 20 μl of 125 mM NaOH. For the detection step, a 75 μl aliquot of oligo dA-F in 0.5 M Tris, pH 7.5, is added to each quenched reaction. The samples are incubated for 10 minutes at room temperature. Fluorescence polarization in each sample was measured using the Beacon™ 2000 Analyzer.

Additional Mutations

The mutant DNA polymerase of the present invention may contain additional mutations.

In one embodiment, the mutant DNA polymerase of the present invention contains a mutation which reduces its analog discrimination activity as described in U.S. application with Ser. No. 10/223,650, hereby incorporated by reference in its entirety.

In another embodiment, the mutant DNA polymerase of the present invention contains a mutation which reduces its polymerization activity as described in U.S. patent application with Ser. No. Ser. No. 10/227,110, hereby incorporated by reference.

In another embodiment, the mutant DNA polymerase of the present invention is a chimeric protein, e.g., as described in U.S. patent application with Ser. No. 10/324,846, hereby incorporated by reference in its entirety.

In another embodiment, the mutant DNA polymerase of the present invention also contains a mutation which increases the RT activity.

Preparing Mutant DNA Polymerase

Cloned wild-type DNA polymerases may be modified to generate forms exhibiting deficient 3'-5' exonuclease and/or reduced base analog detection activity (as well as other modified activities) by a number of methods. These include the methods described below and other methods known in the art. Any proofreading Archaeal DNA polymerase can be used to prepare for DNA polymerase with reduced base analog detection activity in the invention.

Genetic Modifications-Mutagenesis

Direct comparison of DNA polymerases from diverse organisms indicates that the domain structure of these enzymes is highly conserved and in many instances, it is possible to assign a particular function to a well-defined domain of the enzyme. The conserved exo motifs and the uracil pocket among the Archaeal DNA polymerases provide a useful model to direct genetic modifications for preparing DNA polymerase with desired activity.

The preferred method of preparing a DNA polymerase with desired activity, e.g., deficient 3'-5' exo activity and/or reduced base analog detection activity is by genetic modification (e.g., by modifying the DNA sequence of a wild-type DNA polymerase, or a mutant DNA polymerase). A number of methods are known in the art that permit the random as well as targeted mutation of DNA sequences (see for example, Ausubel et. al. *Short Protocols in Molecular Biology* (1995) 3$^{rd}$ Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition DNA polymerases with deficient 3'-5' exo activity and/or reduced base analog detection activity may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of mutant Archaeal DNA polymerases exhibiting reduced uracil detection activity is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 μg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 μM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C; followed by 5-10 cycles of 1 min at 94° C, 2 min at 54° C. and The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Methods of random mutagenesis, which will result in a panel of mutants bearing one or more randomly situated mutations, exist in the art. Such a panel of mutants may then be screened for those exhibiting reduced uracil detection activity relative to the wild-type polymerase (e.g., by measuring the incorporation of 10 nmoles of dNTPs into polymeric form in 30 minutes in the presence of 200 μM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

A person of average skill in the art having the benefit of this disclosure will recognize that polymerases with deficient 3'-5' exo activity and/or reduced uracil detection derived from JDF-3 or PFU or other exo+DNA polymerases including Vent DNA polymerase, JDF-3 DNA polymerase, Tgo DNA polymerase, and the like may be suitably used in the subject compositions.

In one embodiment, the invention provides DNA polymerase selected from Pfu, Tgo, JDF-3 and KOD comprising one or more mutations at V93, and which demonstrate reduced uracil detection activity.

In another embodiment, the invention provides DNA polymerase selected from Pfu, Tgo, JDF-3 and KOD comprising one or more mutations at D141 and/or E143, which is deficient in 3'-5' exonuclease activity.

In another embodiment, the invention provides DNA polymerase selected from Pfu, Tgo, JDF-3 and KOD comprising one or more mutations at V93, and which demonstrate reduced uracil detection activity, and further comprising one or more mutations at D141 and/or E143, which is deficient in 3'-5' exonuclease activity.

In another embodiment, the invention provides DNA polymerase selected from Pfu, Tgo, JDF-3 and KOD comprising one or more mutations at V93, and which demonstrate reduced uracil detection activity, and further comprising one or more mutations at D141 and/or E143, which is deficient in 3'-5' exonuclease activity, as well as a mutation at L408, which has an increased reverse transcriptase activity.

The enzyme of the subject composition may comprise DNA polymerases that have not yet been isolated.

In preferred embodiments of the invention, the mutant Pfu DNA polymerase harbors an amino acid substitution at amino acid position, V93. In a preferred embodiment, the mutant Pfu DNA polymerase of the invention contains a Valine to Arginine, Valine to Glutamic acid, Valine to Lysine, Valine to Aspartic Acid, or Valine to Asparagine substitution at amino acid position 93.

The invention further provides for mutant Archaeal DNA polymerases with reduced base analog detection activity that contains a Valine to Arginine, Valine to Glutamic acid, Valine to Lysine, Valine to Aspartic Acid, Valine to Glutamine, or Valine to Asparagine substitution at amino acid position 93. In particular, FIG. 6 shows mutant Archaeal DNA polymerases of the invention with reduced base analog detection activity.

According to the invention, V93 mutant Pfu DNA polymerases with reduced uracil detection activity may contain one or more additional mutations that reduce or abolish one or more additional activities of V93 Pfu DNA polymerases, e.g., DNA polymerization activity or 3'-5' exonuclease activity. In one embodiment, the V93 mutant Pfu DNA polymerase according to the invention contains one or more mutations that renders the DNA polymerase 3'-5' exonuclease deficient. In another embodiment, the V93 mutant Pfu DNA polymerase according to the invention contains one or more mutations that the DNA polymerization activity of the V93 Pfu DNA polymerase.

In another embodiment, a mutant Archaeal dna polymerase is a chimera that further comprises a polypeptide that increases processivity and/or increases salt resistance. A polypeptide useful according to the invention and methods of preparing chimeras are described in WO 01/92501 A1 and Pavlov et al., 2002, Proc. Natl. Acad. Sci USA, 99:13510-13515. Both references are herein incorporated in their entirety.

The invention provides for V93Rmutant Pfu DNA polymerases with reduced uracil detection activity containing one or mutations that reduce DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

In a preferred embodiment, the invention provides for a V93R/G387P, V93E/G387P, V93D/G387P, V93K/G387P and V93N/G387P double mutant Pfu DNA polymerase with reduced DNA polymerization activity and reduced uracil detection activity.

The invention further provides for V93R, V93E, V93D, V93K and V93N mutant Pfu DNA polymerases with reduced uracil detection activity containing one or mutations that reduce or eliminate 3'-5' exonuclease activity as disclosed in the pending U.S. patent application Ser. No. 09/698,341 (Sorge et al; filed Oct. 27, 2000).

In a preferred embodiment, the invention provides for a V93R/D141A/E143A triple mutant Pfu DNA polymerase with reduced 3'-5' exonuclease activity and reduced uracil detection activity.

The invention further provides for combination of one or more mutations that may increase or eliminate base analog detection activity of an Archaeal DNA polymerase.

DNA polymerases containing additional mutations are generated by site directed mutagenesis using the Pfu DNA polymerase or Pfu V93R cDNA as a template DNA molecule, according to methods that are well known in the art and are described herein.

Methods used to generate Pfu DNA polymerases with reduced DNA polymerization activity are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

Methods for generating 3'-5' exonuclease deficient Pfu are disclosed in U.S. Pat. No. 5,489,523, incorporated herein by reference.

Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000). A person skilled in the art in possession of the V93 Pfu DNA polymerase cDNA and the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into the V93 Pfu DNA polymerase cDNA, as disclosed in the pending U.S. patent application Ser. No. 09/698,341, using established site directed mutagenesis methodology.

Such methods (e.g., for Pfu and JDF-3) can be readily used to generate other 3'-5' exonuclease deficient archaeal DNA polymerase. Sequence alignment techniques are known in the art and are taught herein. One skilled in the art would appreciate the teaching of the present invention and can identify amino acid sequences to mutate by aligning Pfu or JDF-3 sequence with another archaeal DNA polymerase.

Methods of preparing chimeras according to the invention are described in WO 01/92501 A1 and Pavlov et al., 2002, Proc. Natl. Acad. Sci USA, 99:13510-13515. Both references are herein incorporated in their entirety.

In one embodiment, the Pfu mutants are expressed and purified as described in U.S. Pat. No. 5,489,523, hereby incorporated by reference in its entirety.

Methods of Evaluating Mutants for Reduced Base Analog Detection Activity and 3'-5' Exonuclease Activity, etc.

Random or site-directed mutants generated as known in the art or as described herein and expressed in bacteria may be screened for reduced uracil detection activity by several different assays. Embodiments for the expression of mutant and wild type enzymes is described herein. In one method, $exo^+$ DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) Gene 97:119-123). For this approach, lambda phage clones are plated at a density of 10-20 plaques per square centimeter and replica plated. Proteins present in the plaques are transferred to filters and moistened with polymerase screening buffer (50 mM Tris (pH 8.0), 7 mM $MgCl_2$, 3 mM β-ME). The filters are kept between layers of plastic wrap and glass while the host cell proteins are heat-inactivated by incubation at 65° C. for 30 minutes. The heat-treated filters are then transferred to fresh plastic wrap and approximately 35 μl of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 μg/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 200 μM dATP, 200 μM dGTP, 200 μM dCTP and 5 μCi/ml α-$^{33}$P dCTP and 200 μM dUTP or 200 μM dTTP. The filters, in duplicate, are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label in the presence of 200 μM dUTP or 200 μM dTTP are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measurement of the polymerization activity of the polymerase in the presence of 200 μM dUTP as compared to the polymerase activity of the same mutant polymerase in the presence of 200 μM dTTP. A plaque comprising a mutant DNA polymerase with reduced uracil detection activity as compared to that of the wild-type enzyme can then be identified and further tested in primer extension assays in which template dependent DNA synthesis is measured in the presence of 200 μM dUTP. For example, 1 μl of appropriately diluted bacterial extract (i.e., heat-treated and clarified extract of bacterial cells expressing a cloned polymerase or mutated cloned polymerase) is added to 10 μl of each nucleotide cocktail (200 μM dATP, 200 μM dGTP, 200 μM dCTP and 5 μCi/ml α-$^{33}$P dCTP, $^3$H-dCTP and 200 μM dUTP or 200 μM dTTP, activated calf thymus DNA, 1× appropriate buffer (see above)), followed by incubation at the optimal temperature for 30 minutes (e.g., 73° C. for Pfu DNA polymerase), for example, as described in Hogrefe et al., 2001, Methods in Enzymology, 343:91-116. Extension reactions are then quenched on ice, and 5 μl aliquots are spotted immediately onto DE81 ion-exchange filters (2.3 cm; Whatman #3658323). Unincorporated label is removed by 6 washes with 2×SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms" (wash filters as above). Cpms bound is proportional to the amount of polymerase activity present per volume of bacterial extract. Mutants that can incorporate significant radioactivity in the presence of dUTP are selected for further analysis.

Mutant DNA polymerases with reduced uracil recognition can also be identified as those that can synthesize PCR products in the presence of 100% dUTP(See Example 3).

The "uracil detection" activity can also be determined using the long range primer extension assay on single uracil templates as described by Greagg et al., (1999) Proc. Natl. Acad. Sci. 96, 9045-9050. Briefly, the assay requires a 119-mer template that is generated by PCR amplification of a segment of pUC19 spanning the polylinker cloning site. PCR primer sequences are:

```
A, GACGTTGTAAAACGACGGCCAGU;          (SEQ ID NO: 3)

B, ACGTTGTAAAACGACGGCCAGT;           (SEQ ID NO: 4)
and

C, CAATTTCACACAGGAAACAGCTATGACCATG.  (SEQ ID NO: 5)
```

The 119-mer oligonucleotide incorporating either a U or T nucleotide 23 bases from the terminus of one strand, was synthesized by using Taq polymerase under standard PCR conditions, using primer C and either primer A or primer B. PCR products are then purified on agarose gels and extracted by using Qiagen columns.

For long range primer extension, primer C is annealed to one strand of the 119-bp PCR product by heating to 65° C. in reaction buffer and cooling to room temperature. The dNTPs, [α-[$^{32}$P] dATP, and 5 units of DNA polymerase (Pfu, Taq and mutant Pfu DNA polymerase to be tested) are added in polymerase reaction buffer (as specified by the suppliers of each polymerase) to a final volume of 20 μl, and the reaction is allowed to proceed for 60 min at 55° C. Reaction products are subjected to electrophoresis in a denaturing acrylamide gel and scanned and recorded on a Fuji FLA-2000 phosphorimager. The ability of the DNA polymerases from the thermophilic archaea *Pyrococcus furiosus* (Pfu) and the test mutant Pfu DNA polymerase to extend a primer across a template containing a single deoxyuridine can then be determined and directly compared.

The 3' to 5' exonuclease activity of purified Archaeal DNA polymerase (e.g., Pfu, KOD, or JDF-3 DNA polymerase) may be assayed according to methods known in the art, e.g., as described herein above, and in U.S. Pat. No. 5,489,523, incorporated herein by reference.

For example, a sample containing 0.01 to 0.1 unit of DNA polymerase activity is admixed in a 25 μl exonuclease reaction admixture containing 40 mM Tris-Cl, pH 7.5, 10 mM $MgCl_2$, 2.5 μg of Taq I restriction endonuclease-digested Lambda DNA fragments filled in with $^3$H-dGTP and $^3$H-dCTP. The labelled DNA substrate was prepared by digesting 1 mg lambda gt10 with 1000 units Taq I at 68° C. for 3 hrs in 1× Universal Buffer (Stratagene), followed by filling in the 3' recessed ends with 25 μCi each of $^3$H -dGTP and $^3$H -dCTP using 50 units of Sequenase (USB; United States Biochemicals, Inc.); the labelled fragments were separated from unincorporated nucleotides by passage through a NucTrap column (Stratagene) following the manufacturer's instructions. After a 30 min incubation of the endonuclease reaction admixture at 72° C., the reaction was terminated by addition of 5 μl of 15 mg/ml BSA and 13 μl of 50% trichloroacetic acid, and incubated on ice for 30 min to precipitate the nucleic acids. The precipitated nucleic acids were then centrifuged at 9000×g for 5 min, and 25 μl of the resulting supernatant was removed for scintillation counting. All reactions were performed in triplicate. One unit of exonuclease activity catalyzes the acid solubilization of 10 nmole of total nucleotides in 30 min at 72° C.

The polymerization activity of any of the above enzymes can be defined by means well known in the art. One unit of DNA polymerization activity of conventional DNA polymerase, according to the subject invention, is defined as the amount of enzyme which catalyzes the incorporation of 10 nmoles of total deoxynucleotides (dNTPs) into polymeric form in 30 minutes at optimal temperature (e.g., 72° C. for Pfu DNA polymerase).

Expression of Wild-Type or Mutant Enzymes According to the Invention

Methods known in the art may be applied to express and isolate the mutated forms of DNA polymerase (i.e., the second enzyme) according to the invention. The methods described here can be also applied for the expression of wild-type enzymes useful (e.g., the first enzyme) in the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argu, ileY, leuW, and proL tRNA genes), allowing high efficiency expression of cloned protein genes, for example, cloned Archaeal enzyme genes (several BL21 -CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, *PCR Meth. & App.* 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

The invention further provides for mutant V93R, V93E, V93D, V93K or V93N Pfu DNA polymerases that contain one or more additional mutations with improved reverse transcriptase activity, as described in U.S. application with Ser. No. 10/435,766, hereby incorporated by reference.

DNA Polymerase blend and PCR Additives

The invention further provides for compositions in which any of the Archaeal mutant DNA polymerases are mixed with either a second DNA polymerase (either wild type or another mutant DNA polymerase). For example, a mutant DNA polymerase with deficient 3'-5' exonuclease activity and reduced uracil detection activity (or additionally with increased reverse transcriptase activity) may be mixed with:

a.) an Archaeal DNA polymerase with reduced polymerization activity b) a wild type DNA polymerase with no 3'-5' exonuclease activity, e.g., Taq polymerase c) a polymerase chimera (e.g., Pfu chimera as as described in WO 01/92501 A1 or Pavlov et al. supra)

d) a reverse transcriptase, such as HIV, HTLV-I, HTLV-II, FeLV, FIV, SIV, AMV, MMTV, and MoMuLV reverse transcriptases.

The present invention also provides a composition containing one mutant archaeal DNA polymerase with no 3'-5' exonuclease activity and another mutant archaeal DNA polymerase with 3'-5' exonuclease activity.

Preferably, both the mutant archaeal DNA polymerase with no 3'-5' exonuclease activity and the other mutant archaeal DNA polymerase with 3'-5' exonuclease activity contain a mutation at V93.

The present invention also provides compositions which contain the mutant DNA polymerase and an PCR additive, such as one or more selected from the group consisting of: Pfu dUTPase (PEF), PCNA, RPA, ssb, antibodies, DMSO, betaine, 3'-5' exonuclease (e.g., Pfu G387P), Ncp7, recA, and T4gp32, e.g., as described in U.S. patent application with Ser. No. 20020119467, hereby incorporated by reference in its entirety.

The addition of NCp7 to a reverse transcription reaction, significantly increases the processivity of the reverse transcriptase enzyme. Hence, it is expected that a number of other general RNA binding proteins will have the same effect. Non-limiting examples of such RNA binding proteins, include nucleocapsid proteins from other retroviruses (Ncp7 is derived from HIV-1), p50 (a protein which possesses strong, but non-specific, RNA-binding activity and is associated with cytoplasmic mRNA), the FRGY 2 protein from *Xenopus oocytes*, La antigen, and polypyrimidine tract binding protein (hnRNP I/PTB) (Ghetti et al., 1992 Nucl. Acid. Res. 20: 3671-3678; Dreyfuss et al., 1993, Annu. Rev. Biochem. 62: 289-321; Chang et al., 1994, J. Virol. 68:7008-7020; and Spirin, 1998, In Hershey et al., (Eds), Translational Control, Cold Spring Harbor Laboratory press, Cold Spring Harbor, N.Y. pp. 319-334).

Similarly, although the improvement in the processivity of a RNA-dependent polymerase has been demonstrated with reverse transcriptase, the present invention should not be so limited. A recent report has demonstrated that a single missense mutation with the catalytic fragment of Moloney murine leukemia virus (MMLV) RT (the parental RT from which superscript is derived) is sufficient to convert this enzyme from a RNA-dependent DNA polymerase to a RNA-dependent RNA polymerase (Giao et al., 1997, Proc. Nati. Acad. Sci. USA 94: 407-411). It is thus expected that general RNA binding proteins will also stimulate the processivity of RNA-dependent RNA polymerases given that the inhibitory features of "difficult" RNA template will be present. Other examples of RNA-dependent RNA polymerases include the polymerases of all members of the picomavirus family which copy their mRNAs directly into ds RNA genome from a single stranded mRNA template.

In addition, it is expected that general DNA binding proteins will stimulate the processivity of DNA-dependent DNA polymerases and DNA-dependent RNA polymerase. While the methods of the instant invention have been demonstrated with rec A protein and single-strand DNA binding protein (SSB), other general DNA binding proteins could also be used as stimulators. A non-limiting example of a general DNA binding protein is the gene 32 product of T4 bacteriophage (T4gp32). Hence, it is expected that a number of other general DNA binding proteins will be able to stimulate, for example, T7DNA polymerase processivity during second strand synthesis when generating a cDNA library. Non-limiting examples of other general DNA binding proteins, include: ssCRE-BP/Pur.varies. (a protein isolated from rat lung); Hbsu (an essential nucleoid-associated protein from *Bacillus subtilis*); uvs.sup.y (a gene product of bacteriophage T4); replication protein A (a heterotrimeric ss DNA binding protein in eukaryotes); the BALF2 gene product of Epstein-Barr virus; the yeast RAD51 gene product; the SSB of *Bacillus subtilis* phage phi 29; and the SSB of adenovirus (Wei et al., 1998, Ipn. J. Pharmacol. 78: 418-42; Kohler et al., 1998, Mol. Gen. Genet. 260: 487-491; Sweezy et al., 1999, Biochemistry 38: 936-944; Brill et al., 1998, Mol. Cel. Biol. 18: 7225-7234; Tsurumi et al., 1998, J. Gen. Virol, 79: 1257-1264; Namsaraev et al., 1997, Mol. Cell. Biol. 17: 5359-5368; Soengas et al., 1997, J. Biol. Chem. 272: 303-310; and Kanellopoulos et al., 1995, J. Struct. Biol. 115: 113-116).

In addition non-limiting examples of DNA-dependent DNA polymerases which could benefit from the processivity enhancing methods and compositions of the present invention include *E. coli* DNA polymerase, the klenow fragment of *E. coli* DNA polymerase, Vent polymerase, Pfu polymerase, Bst DNA polymerase, and any other thermophilic DNA polymerase. Also, as pertaining to CDNA systhesis, *E. coli* DNA polymerase (see FIG. 1), T4 DNA polymerase, and thermophilic DNA polymerases have all been used to generate second strand product depending on the strategy being undertaken (In cDNA Library Protocols, 1997, Cowell et al., (eds). Humana Press, Totowa, N.J.).

In addition, a composition containing the mutant DNA polymerase of the present invention may also contain additives like antibodies for increased specificity (for hot start PCR, described in Borns et al. (2001) Strategies 14, pages 5-8 and also in manual accompanying commercially available kit, Stratagene Catalogue # 600320), DMSO for GC-rich PCR or single stranded DNA binding protein for higher specificity (commercially available, Stratagene Catalog # 600201), dUTP and/or uracil N-glycosylase.

Applications of the Subject Invention

In one aspect, the invention provides a method for DNA synthesis using the compositions of the subject invention. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

A. Application in Amplification Reactions

"Polymerase chain reaction" or "PCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 μl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

The enzymes provided herein are also useful for dUTP/UNG cleanup methods that require PCR enzymes that incorporate dUTP (Longo et al., Supra).

In addition, Mutations that reduce uracil sensitivity are expected to improve the success rate of long-range amplification (higher yield, longer targets amplified). It is expected that mutations eliminating uracil detection will also increase the error rate of Archaeal DNA polymerases. If uracil stalling contributes to fidelity by preventing synthesis opposite pro-mutagenic uracil (arising from cytosine deamination), then uracil insensitive mutants are likely to exhibit a higher GC→TA transition mutation rate. It is therefore envisioned that optimal PCR performance and fidelity may be achieved by adding to uracil-insensitive Archaeal DNA polymerase mutants either thermostable exonucleases (e.g., polymerase reduced proofreading DNA polymerases, exonuclease III) or additional mutations that increase fidelity.

1. Thermostable Enzymes

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

2. PCR Reaction Mixture

In addition to the subject enzyme mixture, one of average skill in the art may also employ other PCR parameters to increase the fidelity of synthesis/amplification reaction. It has been reported PCR fidelity may be affected by factors such as changes in dNTP concentration, units of enzyme used per reaction, pH, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increases non-specific annealing and produced undesirable PCR products (gives multiple bands in gel). When non-specific amplification occurs, $Mg^{2+}$ may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication 2$^{nd}$ edition*, supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 μM to 2 mM each is suitable, and 100-600 μM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 μM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 μM) may therefore reduce error rate. PCR reaction for amplifying larger size template may need more dNTPs.

One suitable buffering agent is Tris-HCl, preferably pH 8.3, although the pH may be in the range 8.0-8.8. The Tris-HCl concentration is from 5-250 mM, although 10-100 mM is most preferred. A preferred buffering agent is Bicine-KOH, preferably pH 8.3, although pH may be in the range 7.8-8.7. Bicine acts both as a pH buffer and as a metal buffer. Tricine may also be used.

PCR is a very powerful tool for DNA amplification and therefore very little template DNA is needed. However, in some embodiments, to reduce the likelihood of error, a higher DNA concentration may be used, though too many templates may increase the amount of contaminants and reduce efficiency.

Usually, up to 3 μM of primers may be used, but high primer to template ratio can results in non-specific amplification and primer-dimer formation. Therefore it is usually necessary to check primer sequences to avoid primer-dimer formation.

The invention provides for Pfu V93R, V93E, V93K, V93D, or V93N DNA polymerases with reduced uracil detection activity that enhance PCR of GC rich DNA templates by minimizing the effect of cytosine deamination in the template and by allowing the use of higher denaturation times and denaturation temperatures.

3. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycle can be increased if the number of template DNA is very low, and decreased if high amount of template DNA is used.

4. PCR Enhancing Factors and Additives

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reaction. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 μg/μl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentration of each additive mentioned above.

The invention provides for additive including, but not limited to antibodies (for hot start PCR) and ssb (higher specificity). The invention also contemplates mutant ARCHAEAL DNA polymerases in combination with accessory factors, for example as described in U.S. Pat. No. 6,333,158, and WO 01/09347 A2, hereby incorporated by reference in its entirety.

Various specific PCR amplification applications are available in the art (for reviews, see for example, Erlich, 1999, *Rev Immunogenet.,* 1:127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications including, but are not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention.

B. Application in Quantitative PCR and Quantitative RT-PCR

A typical PCR reaction includes multiple amplification steps, or cycles that selectively amplify a target nucleic acid species. A full description of the PCR process, and common variations thereof, such as quantitative PCR (QPCR), real-time QPCR, reverse transcription PCR (RT-PCR) and quantitative reverse transcription PCR (QRT-PCR) is beyond the scope of this disclosure and these methods are well-described in the art and have been broadly commercialized.

The present invention may be used to perform any of the above PCR methods known in the art (e.g., as reviewed in Joyce et al. (2002, Methods Mol Biol. 193:83-92), Klein (2002, Trends Mol Med. 8(6):257-60), Wittwer et al. (2001, Methods. 25(4):430-42), Freeman et al. (1999, Biotechniques. 26(1):112-22, 124-5), hereby incorporated by reference.

Reverse transcription of an RNA template into cDNA is an integral part of many techniques used in molecular biology. Accordingly, the reverse transcription procedures, compositions, and kits provided in the present invention find a wide variety of uses. For example, it is contemplated that the reverse transcription procedures and compositions of the present invention are utilized to produce cDNA inserts for cloning into cDNA library vectors (e.g., lambda gt10 [Huynh et al., In DNA Cloning Techniques: A Practical Approach, D. Glover, ed., IRL Press, Oxford, 49, 1985], lambda gt11 [Young and Davis, Proc. Nat'l. Acad. Sci., 80:1194, 1983], pBR322 [Watson, Gene 70:399-403, 1988], pUC19 [Yarnisch-Perron et al., Gene 33:103-119, 1985], and M13 [Messing et al., Nucl. Acids. Res. 9:309-321, 1981]). The present invention also finds use for identification of target RNAs in a sample via RT-PCR (e.g., U.S. Pat. No. 5,322,770, incorporated herein by reference). Additionally, the present invention finds use in providing cDNA templates for techniques such as differential display PCR (e.g., Liang and Pardee, Science 257(5072):967-71 (1992). The DNA polymerase with increased RT activity, compositions or kits comprising such polymerase can be applied in any suitable applications, including, but not limited to the following examples.

1. Reverse Transcription

The present invention contemplates the use of thermostable DNA polymerase for reverse transcription reactions. Accordingly, in some embodiments of the present invention, thermostable DNA polymerases having increased RT activity are provided. In some embodiments, the thermostable DNA polymerase is selected from the DNA polymerases listed in Tables II-IV, for example, a Pfu or a JDF-3 DNA polymerase.

In some embodiments of the present invention, where a DNA polymerase with increased RT activity is utilized to reverse transcribe RNA, the reverse transcription reaction is conducted at about 50° C. to 80° C., preferably about 60° C. to 75° C. Optimal reaction temperature for each DNA polymerase is know in the art and may be relied upon as the optimal temperature for the mutant DNA polymerases of the present invention. Preferred conditions for reverse transcription are 1×MMLV RT buffer (50 mM Tris pH 8.3, 75 mM KCl, 10 mM DTT, 3 mM $MgCl_2$), containing 20% DMSO.

In still further embodiments, reverse transcription of an RNA molecule by a DNA polymerase with increased RT activity results in the production of a cDNA molecule that is substantially complementary to the RNA molecule. In other embodiments, the DNA polymerase with increased RT activity then catalyzes the synthesis of a second strand DNA complementary to the cDNA molecule to form a double stranded DNA molecule. In still further embodiments of the present invention, the DNA polymerase with increased RT activity catalyzes the amplification of the double stranded DNA molecule in a PCR as described below. In some embodiments, PCR is conducted in the same reaction mix as the reverse transcriptase reaction (i.e., a single tube reaction is performed). In other embodiments, PCR is performed in a separate reaction mix on an aliquot removed from the reverse transcription reaction (i.e., a two tube reaction is performed).

In another embodiment, the DNA polymerase mutants of the invention can be used for labeling cDNA for microarray analysis, e.g., with fluorescent labels such as Cy3, Cy5 or other labels. It is contemplated that DNA polymerase mutants as described herein would have the advantage of more efficient labeling or more uniform incorporation of labeled nucleotides relative to wild-type enzymes.

2. QPCR and RT_QPCR

The mutant DNA polymerase of the present invention is generally applicable to QPCR or RT-QPCR.

A quantitative reverse transcriptase polymerase chain reaction (RT-QPCR) method is provided for rapidly and accurately detecting low abundance RNA species in a population of RNA molecules (for example, and without limitation, total RNA or mRNA), including the steps of: a) incubating an RNA sample with a reverse transcriptase and a high concentration of a target sequence-specific reverse transcriptase primer under conditions suitable to generate cDNA; b) subsequently adding suitable polymerase chain reaction (PCR) reagents to the reverse transcriptase reaction, including a high concentration of a PCR primer set specific to the cDNA and a thermostable DNA polymerase to the reverse transcriptase reaction, and c) cycling the PCR reaction for a desired number of cycles and under suitable conditions to generate PCR product ("amplicons") specific to the cDNA. By temporally separating the reverse transcriptase and the PCR reactions, and by using reverse transcriptase-optimized and PCR-optimized primers, excellent specificity is obtained. The reaction is conducted in a single tube (all tubes, containers, vials, cells and the like in which a reaction is performed may be referred to herein, from time to time, generically, as a "reaction vessel"), removing a source of contamination typically found in two-tube reactions. The high concentration primers permit very rapid QRT-PCR reactions, typically on the order of 20 minutes from the beginning of the reverse transcriptase reaction to the end of a 40 cycle PCR reaction. The realization of such a rapid QRT-PCR experiment is assisted by the availability of thermal cycling devices capable of generating a thermal ramp rate (delta T) of at least about 5° C. per second.

The reaction c) may be performed in the same tube as the reverse transcriptase reaction by adding sufficient reagents to the reverse transcriptase (RT) reaction to create good, or even optimal conditions for the PCR reaction to proceed. A single tube may be loaded, prior to the running of the reverse transcriptase reaction, with: 1) the reverse transcriptase reaction mixture, and 2) the PCR reaction mixture to be mixed with the cDNA mixture after the reverse transcriptase reaction is completed. The reverse transcriptase reaction mixture and the PCR reaction mixture may be physically separated by a solid, or semi-solid (including amorphous, glassy substances and waxy) barrier of a composition that melts at a temperature greater than the incubation temperature of the reverse transcriptase reaction, but below the denaturing temperature of the PCR reaction. The barrier composition may be hydrophobic in nature and forms a second phase with the RT and PCR reaction mixtures when in liquid form. One example of such a barrier composition is wax beads, commonly used in PCR reactions, such as the AMPLIWAX PCR GEM products commercially available from Applied Biosystems of Foster City, Calif. and the STRATASPHERE Magnesium Wax Beads, commercially available from Stratagene of La Jolla, Calif.

In one type of two-step process, the first step involves synthesis of first strand cDNA with a reverse transcriptase, following by a second PCR step. In certain protocols, these steps are carried out in separate reaction tubes. In these two tube protocols, following reverse transcription of the initial RNA template in the first tube, an aliquot of the resultant product is then placed into the second PCR tube and subjected to PCR amplification.

In a second type of two-step process, both RT and PCR are carried out in the same tube using a compatible RT and PCR buffer. Typically, reverse transcription is carried out first, followed by addition of PCR reagents to the reaction tube and subsequent PCR.

Reverse transcription is commonly performed with viral reverse transcriptases isolated from Avian myeloblastosis virus (AMV-RT) or Moloney murine leukemia virus (MMLV-RT), which are active in the presence of magnesium ions.

The mutant DNA polymerase may be used in performing two-step RT-QPCR, in which RT is performed by a conventional reverse transcriptase and the quantitative PCR is performed by a mutant DNA polymerase of the present invention.

A variety of one-step RT-PCR protocols have been developed, see Blain & Goff, J. Biol. Chem. (1993) 5: 23585-23592; Blain & Goff, J. Virol. (1995) 69:4440-4452; Sellner et al., J. Virol. Method. (1994) 49:47-58; PCR, Essential Techniques (ed. J. F. Burke, J. Wiley & Sons, New York) (1996) pp61-63; 80-81.

Some one-step systems are commercially available, for example, SuperScript One-Step RT-PCR System description on the world-wide web at lifetech.com/world_whatsnew/archive/$nz_{1-3}$.html; Access RT-PCR System and Access RT-PCR Introductory System described on the world wide web at promega.com/tbs/tb220/tb220.html; AdvanTaq & AdvanTaq Plus PCR kits and User Manual available at www.clontech.com, and ProSTAR™ HF single-tube RT-PCR kit (Stratagene, Catalog No. 600164, information available on the world wide web at stratagene.com).

Certain RT-PCR methods use an enzyme blend or enzymes with both reverse transcriptase and DNA polymerase or exonuclease activities, e.g., as described in U.S. Pat. Nos. 6,468,775; 6,399,320; 5,310,652; 6,300,073; patent application No. U.S. 2002/0119465A1; EP 1,132,470A1 and WO 00/71739A1, all of which are incorporated herein by reference.

The reverse transcription and PCR may also be performed in a single step reaction using a mutant DNA polymerase of the present invention which also contains an increased reverse transcriptase activity.

As used herein, "quantitative PCR (QPCR)" refers to a PCR amplification which is used to determine the abundance of polynucleotide as described herein above. To determine the abundance of a specific polynucleotide present in a PCR reaction, this method usually utilizes a labeling dye which fluoresces in proportion to the amount of target DNA species that is produced by the PCR reaction.

According to one embodiment of the present invention, the quantitative PCR methods may amplify, in the presence of Mg ions, a target nucleic acid by using dATF, dGTP, dCTP, dTTP or dUTP, a target nucleic acid (DNA or RNA), a mutant DNA polymerase of the invention, a primer, and a nucleic acid labeled with a fluorescent dye or an intercalator while repeatedly changing the temperature between low and high levels, and monitor increases in fluorescence emission from the fluorescent dye in real time in the course of the amplification.

In the case of a fluorescent probe, the reaction fluoresces in relative proportion to the quantity of DNA product produced.

TaqMan is a homogenous assay for detecting polynucleotides (U.S. Pat. No. 5,723,591). In this assay, two PCR primers flank a central probe oligonucleotide. The probe oligonucleotide contains two fluorescent moieties. During the polymerization step of the PCR process, the polymerase cleaves the probe oligonucleotide. The cleavage causes the two fluorescent moieties to become physically separated, which causes a change in the wavelength of the fluorescent emission. As more PCR product is created, the intensity of the novel wavelength increases. The TaqMan.™. procedure (Applied Biosystems, CA) describes one such fluorescent methodology for performing Quantitative PCR. Briefly described, this system integrates the use of a detectable reporter construct, or probe, which comprises both a fluorescent label molecule and a quencher molecule. Ordinarily, the quencher nullifies the majority of fluorescence which may be emitted by the probe. During the amplification process, however, the quencher molecule is released from the probe allowing the fluorescent label to be detected. The quantity or intensity of fluorescence may then be correlated with the amount of product formed in the reaction. Using this information, calculations can be made to determine the initial quantity of template present. Quantitation in this manner is useful in applications including: determination of levels/concentrations of specific DNA and RNA sequences in tissue samples, identification of viral loads, genotyping, and numerous other applications. For additional information regarding the fundamental concepts of quantitative PCR the reader is directed to Allelic Discrimination by Nick-Translation PCR with Fluorogenic Probes, L. G. Lee, C. R. Connell, and W. Bloch, Nucleic Acids Research 21:3761-3766, 1993 and PCR Technology: Principles and Applications for DNA Amplification. Karl Drlica, John Wiley and Sons, 1997.

Molecular beacons are an alternative to TaqMan (U.S. Pat. Nos. 6,277,607; 6,150,097; 6,037,130) for the detection of polynucleotides. Molecular beacons are oligonucleotide hairpins which undergo a conformational change upon binding to a perfectly matched template. The conformational change of the oligonucleotide increases the physical distance between a fluorophore moiety and a quencher moiety present on the oligonucleotide. This increase in physical distance causes the effect of the quencher to be diminished, thus increasing the signal derived from the fluorophore.

U.S. Pat. No. 6,174,670B1 discloses methods of monitoring hybridization during a polymerase chain reaction which are achieved with rapid thermal cycling and use of double stranded DNA dyes or specific hybridization probes in the presence of a fluorescence resonance energy transfer pair—fluorescein and Cy5.3 or Cy5.5. The method amplifies the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair such that upon hybridization of the two probes with the target sequence, the donor fluorophore interacts with the acceptor fluorophore to generate a detectable signal. The sample is then excited with light at a wavelength absorbed by the donor fluorophore and the fluorescent emission from the fluorescence energy transfer pair is detected for the determination of that target amount.

There are also several other fluorescent and enzymatic PCR technologies, such as Scorpions™, Sunrise™ primers, and DNAzymes, for polynucleotide detection, where each polynucleotide to be detected requires a different oligonucleotide probe and two different fluorescent moieties.

In addition, QPCR may also be performed according to methods as described in U.S. Patent Application with Ser. No. 60/435,484, hereby incorporated by reference in its entirety.

In one embodiment, the mutant DNA polymerase is used in a method for detecting the amount of a target polynucleotide in an amplification reaction mixture, comprising: (a) providing a forward and a reverse primer which amplify the target polynucleotide in the amplification reaction mixture; (b) providing to the reaction mixture a target-hybridizing probe 1 comprising a target binding sequence (P1-DNA) which hybridizes to one strand of the target polynucleotide and a probe binding sequence (P1-P) which does not hybridize to the target polynucleotide, and a target-hybridizing probe 2 comprising a target binding sequence (P2-DNA) which hybridizes, in close proximity, to the same strand of the target polynucleotide and a probe binding sequence (P2-P) which does not hybridize to the target polynucleotide; (c) providing to the reaction mixture a non-target-hybridizing universal probe 3 labeled with label A and a non-target-hybridizing universal probe 4 labeled with label B, where the universal probe 3 hybridize to the P1-P sequence and the universal probe 4 hybridizes to the P2-P sequence, and where the label A interact with the label B to generate a signal; and (d) detecting the generated signal which is indicative as to the amount of the polynucleotide in the sample.

C. Application in Direct Cloning of PCR Amplified Product

It is understood that the amplified product produced using the subject enzyme can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) disclose methods for direct cloning of PCR products using a DNA polymerase which takes advantage of the single 3'-deoxy-adenosine monophosphate (dAMP) residues attached to the 3' termini of PCR generated polynucleotides. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directly ligated into vectors containing single 3'dT overhangs. Archaeal DNA polymerase, on the other hand, lacks terminal transferase activity, and thus produces blunt-ended PCR products that are efficiently cloned into blunt-ended vectors.

In one embodiment, the invention provides for a PCR product, generated in the presence of a mutant DNA polymerase of the present invention, that is subsequently incubated with Taq DNA polymerase in the presence of dATP at 72° C. for 15-30 minutes. Addition of 3'-dAMP to the ends of the amplified DNA product then permits cloning into TA cloning vectors according to methods that are well known to a person skilled in the art.

D. Application in DNA Sequencing

The invention further provides for dideoxynucleotide DNA sequencing methods using thermostable DNA polymerases having a reduced base analog detection activity to catalyze the primer extension reactions. Methods for dideoxynucleotide DNA sequencing are well known in the art and are disclosed in U.S. Pat. Nos. 5,075,216, 4,795,699 and 5,885,813, the contents of which are hereby incorporated in their entirety.

E. Application in Mutagenesis

The mutant Archaeal DNA polymerases of the invention, preferably V93R Pfu DNA polymerase, also provide enhanced efficacy for PCR-based or linear amplification-based mutagenesis. The invention therefore provides for the use of the mutant Archaeal DNA polymerases with reduced base analog detection activity for site-directed mutagenesis and their incorporation into commercially available kits, for example, QuikChange Site-directed Mutagenesis, QuikChange Multi-Site-Directed Mutagenesis (Stratagene). Site-directed mutagenesis methods and reagents are disclosed in the pending U.S. patent application Ser. No. 10/198,449 (Hogrefe et al.; filed Jul. 18, 2002), the contents of which are hereby incorporated in its entirety. The invention also encompasses Mutazyme (exo$^-$ Pfu in combination with PEF, GeneMorph Kit). The GeneMorph kits are disclosed in the pending U.S. patent application Ser. No. 10/154,206 (filed May 23, 2002), the contents of which are hereby incorporated in its entirety.

All of the mutant Archaeal DNA polymerases contemplated herein are useful for PCR and RT-PCR.

Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

The invention contemplates a kit comprising a combination of a mutant ARCHAEAL DNA polymerase of the invention, and another mutant or wild type DNA polymerase.

The invention contemplates a kit comprising a combination of a mutant Archaeal DNA polymerase of the invention, and a PCR additive.

EXAMPLES

Example 1

Construction of Tgo, Pfu, KOD or JDF-3 DNA Polymerase Mutants with Deficient 3'-5' Exonuclease Activity and Reduced Uracil Detection In one embodiment of the invention, Tgo, Pfu, KOD or JDF-3 DNA polymerase mutants exhibiting substantially reduced 3'-5' exonuclease activity are prepared by introducing amino acid substitutions at the conserved 141D or 143E residues in the exo I domain. Using the CHAMELEON® Double-Stranded, Site-Directed Mutagenesis Kit (Stratagene), the following mutants are constructed: D141A, D141N, D141S, D141T, D141E and E143A for Tgo, Pfu, KOD or JDF-3 DNA polymerases.

To analyze Tgo, Pfu, KOD, JDF-3 mutant proteins, the DNA sequence encoding each of Tgo, Pfu, KOD, and JDF-3 DNA polymerases is PCR amplified using primers GGG AAA CAT ATG ATC CTT GAC GTT GAT TAC (SEQ ID NO: 109; where NdeI site in bold and start codon underlined) and GGG AAA GGA TCC TCA CTT CTT CTT CCC CTT C (SEQ ID NO: 110; where BamHI site shown in bold type). The PCR products are digested, purified, and ligated into a high expression level vector using standard methods. Plasmid clones are transformed into BL21(DE3). Recombinant bacterial clones are grown using standard procedures and polymerase mutants are expressed in the absence of induction. The exonuclease and polymerase activities of recombinant clones are assayed using bacterial lysates. Typically, crude extracts are heated at 70° C. for 15-30 minutes and then centrifuged to obtain a cleared lysate.

The combination exonuclease mutant D141A+E143A is also made as described above herein in the description.

The D141T, E143A, D141A or D141A+E143A double mutants which exhibits significantly reduced 3'-5' exo activity may be chosen for further mutagenesis. For experiment or applications requiring maximal elimination of 3' to 5' exonuclease activity, the double mutant D141A+E143A is preferred.

Additional mutations are introduced into Tgo, Pfu, KOD or JDF-3 DNA polymerase exo-mutants that are likely to reduce uracil detection, while having minimal effects on polymerase or proofreading activity. With the QuikChange Multi kit, specific point mutations (e.g., V93E, H, K, R, and N) are introduced by incorporating one phosphorylated mutagenic primer or by selecting random mutants from a library of Tgo, Pfu, KOD or JDF-3 DNA V93 variants, created by incorporating a degenerate codon (V93G and L). Clones are sequenced to identify the incorporated mutations.

For example, Valine 93 in Tgo, Pfu, KOD or JDF-3 DNA DNA polymerase may be substituted with Glycine (G), asparagine (N), arginine [R], glutamic acid (E), histidine (H), and leucine (L) using the QuikChange primer sequences listed in FIG. 1.

Example 2

Preparation of Bacterial Extracts Containing Mutant Pfu, KOD or JDF-3 DNA Polymerases Plasmid DNA is purified with the StrataPrep® Plasmid Miniprep Kit (Stratagene), and used to transform BL26-CodonPlus-RIL cells. Ampicillin resistant colonies are grown up in 1-5 liters of LB media containing Turbo Amp™ (100 μg/μl) and chloramphenicol (30 μg/μl) at 30° C. with moderate aeration. The cells are collected by centrifugation and stored at −80° C. until use.

Cell pellets (12-24 grams) are resuspended in 3 volumes of lysis buffer (buffer A: 50 mM Tris HCl (pH 8.2), 1 mM EDTA, and 10 mM βME). Lysozyme (1 mg/g cells) and PMSF (1 mM) were added and the cells were lysed for 1 hour at 4° C. The cell mixture is sonicated, and the debris removed by centrifugation at 15,000 rpm for 30 minutes (4° C.). Tween 20 and Igepal CA-630 are added to final concentrations of 0.1% and the supernatant is heated at 72° C. for 10 minutes. Heat denatured *E. coli* proteins are then removed by centrifugation at 15,000 rpm for 30 minutes (4° C.).

Example 3

Evaluate 3'-5' Exonuclease Activity and Assessment of dUTP Incorporation by PCR There are several methods of measuring 3' to 5' exonuclease activity known in the art, including that of Kong et al. (Kong et al., 1993, J. Biol. Chem. 268: 1965) and that of Southworth et al. (Southworth et al., 1996, Proc. Natl. Acad. Sci. U.S.A. 93: 5281), the full contents of both of which are hereby incorporated by reference. For example, the exonuclease activity of wild type and active JDF-3 mutant polymerases as measured by the Kong et al. method were as follows: (other DNA polymerase mutants may be measured similarly)

Exo Activity (U/mg):

| | |
|---|---|
| Wt | 915 |
| D141A | 7 |
| D141N | 953 |
| D141S | 954 |
| D141T | 0.5 |

-continued

| | |
|---|---|
| D141E | 940 |
| E143A | 0.3 |

Partially-purified mutant preparations (heat-treated bacterial extracts) are assayed for dUTP incorporation during PCR. For example, a 2.3 kb fragment containing the Pfu pol gene was from plasmid DNA using PCR primers: (FPfuLIC) 5'-gACgACgACAAgATgATTTTAgATgTggAT-3' (SEQ ID NO:1) and (RPfuLIC) 5'-ggAACAAgACCCgTCTAg-gATTTTTTAATg-3' (SEQ ID NO: 2). Amplification reactions consisted of 1× cloned Pfu PCR buffer, 7 ng plasmid DNA, 100 ng of each primer, 2.5 U of Pfu mutant (or wild type Pfu), and 200 μM each dGTP, dCTP, and dATP. To assess relative dUTP incorporation, various amounts of dUTP (0-400 μM) and/or TTP (0-200 μM) were added to the PCR reaction cocktail. The amplification reactions were cycled as described in example 6. Other DNA polymerase mutants may be similarly tested.

Figure 2:
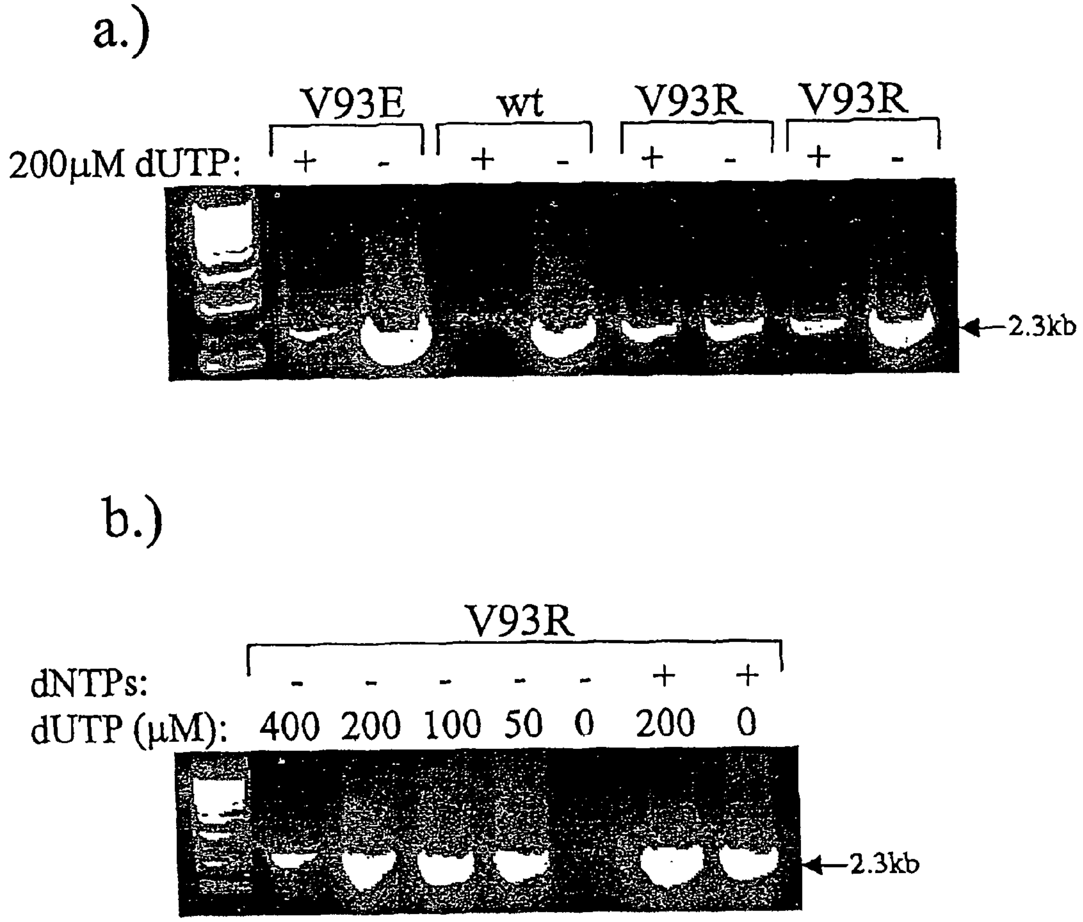
FIG. 2: (a) dUTP incorporation of V93E and V93R exo-mutants compared to wild type Pfu DNA polymerase according to one embodiment of the invention.

Partially-purified preparations of the V93E and V93R mutants showed improved dUTP incorporation compared to wild type Pfu (FIG. 2*a*). Each mutant successfully amplified a 2.3 kb target in the presence of 200 μM dUTP (plus 200 μM each TTP, dATP, dCTP, dGTP). In contrast, extracts containing the Pfu V93N, V93G, V93H, and V93L mutants showed little-to-no amplification in the presence of 200 μM dUTP, similar to wild type Pfu (data not shown). Additional testing showed that the Pfu V93R mutant extract amplified the 2.3 kb target in the presence of 100% dUTP (0% TTP)(FIG. 2*b*).

KOD: Partially-purified preparations of KOD V93D, E, K, Q, and R showed reduced uracil sensitivity as evidenced by successful amplification of the 970 bp amplicon using dU-containing primers and TTP (FIG. 11). In contrast, wild type KOD and the KOD V93N mutant were unable to amplify using dU-primers and TTP. Only the KOD V93K and V93R mutants showed complete or nearly complete elimination of uracil sensitivity as shown by successful amplification in the presence of 100% dUTP (FIG. 11). In contrast, the KOD V93D, E, and Q substitutions only partially reduce uracil sensitivity since these mutants are unable to amplify in the presence of 100% dUTP.

The rationale for determining relative uracil sensitivity using PCR assays is as follows. Successful amplification with dU-primers indicates that reduction in uracil sensitivity is sufficient to allow the mutants to polymerize past the nine uracils in the PCR primers (to create the primer annealing sites). However, mutants that successfully amplify in the presence of 100% dUTP, must lack or almost completely lack uracil sensitivity, since they must polymerize past numerous uracils (~230 uracils per strand; 925 bp segment synthesized with 25% T content) in the template strand.

Tgo: Only the Tgo V93R mutant successfully amplified the 0.97 kb amplicon in the presence of 100% dUTP (FIG. 12), indicating that the arginine substitution was most effective in reducing uracil sensitivity.

JDF-3: Only the JDF-3 V93R and V93K mutants successfully amplified the 0.97 kb amplicon in the presence of 100% dUTP (FIG. 12), indicating that the arginine and lysine substitutions were the most effective in reducing uracil sensitivity. Product yields with 100% dUTP were noticeably lower than yields with 100% TTP suggesting that in JDF-3, the V93R mutation does not completely eliminate uracil sensitivity (FIG. 13). In contrast, Pfu V93R, Tgo V93R, and KOD V93R produce similar yields with TTP and dUTP, indicating that uracil sensitivity is almost completely eliminated.

Pfu deletions. We constructed deletions (92,92,94, 92-93, 93-94, 92-94) and insertions (1-3 glycines between D92 and V93) in Pfu centering around V93. Only the Pfu delta V93 and delta D92-V93-P94 mutants showed a reduction in uracil sensitivity (FIG. 14). Based on amplification of 0.6 kb, 2.6 kb, and 6 kb genomic amplicons, relative uracil sensitivity was determined as follows: (least sensitive/highest dTUP incorporation) Pfu V93R>Pfu delta 93>Pfu delta 92-94>wild type Pfu (most sensitive/no dUTP incorporation).

Example 4

Purification of DNA Polymerase Mutants

Bacterial expression of Pfu mutants. Pfu mutants (Tgo, or KOD or JDF-3 mutants) can be purified as described in U.S. Pat. No. 5,489,523 (purification of the exo$^-$ Pfu D141A/E143A DNA polymerase mutant) or as follows. Clarified, heat-treated bacterial extracts were chromatographed on a Q-Sepharose™ Fast Flow column (~20 ml column), equilibrated in buffer B (buffer A plus 0.1% (v/v) Igepal CA-630, and 0.1% (v/v) Tween 20). Flow-through fractions were collected and then loaded directly onto a P11 Phosphocellulose column (~20 ml), equilibrated in buffer C (same as buffer B, except pH 7.5). The column was washed and then eluted with a 0-0.7M KCl gradient/Buffer C. Fractions containing Pfu DNA polymerase mutants (95 kD by SDS-PAGE) were dialyzed overnight against buffer D (50 mM Tris HCl (pH 7.5), 5 mM βME, 5% (v/v) glycerol, 0.2% (v/v) Igepal CA-630, 0.2% (v/v) Tween 20, and 0.5M NaCl) and then applied to a Hydroxyapatite column (~5 ml), equilibrated in buffer D. The column was washed and Pfu DNA polymerase mutants were eluted with buffer D2 containing 400 mM $KPO_4$, (pH 7.5), 5 mM βME, 5% (v/v) glycerol, 0.2% (v/v) Igepal CA-630, 0.2% (v/v) Tween 20, and 0.5 M NaCl. Purified proteins were spin concentrated using Centricon YM30 devices, and exchanged into Pfu final dialysis buffer (50 mM Tris-HCl (pH 8.2), 0.1 mM EDTA, 1 mM dithiothreitol (DTT), 50% (v/v) glycerol, 0.1% (v/v) Igepal CA-630, and 0.1% (v/v) Tween 20).

Protein samples were evaluated for size, purity, and approximate concentration by SDS-PAGE using Tris-Glycine 4-20% acrylamide gradient gels. Gels were stained with silver stain or Sypro Orange (Molecular Probes). Protein concentration was determined relative to a BSA standard (Pierce) using the BCA assay (Pierce).

Results: Pfu exo-D141A/E143A mutants with additional V93E or V93R mutations were purified to 90% purity as determined by SDS-PAGE.

Example 5

Determining Mutant Polymerase Unit Concentration and Specific Activity

The unit concentration of purified Pfu mutant preparations was determined by PCR. In this assay, a 500 bp lacZ target is amplified from transgenic mouse genomic DNA using the forward primer: 5'-GACAGTCACTCCGGCCCG-3' (SEQ ID NO:15) and the reverse primer: 5'-CGACGACTCGTGGAGCCC-3' (SEQ ID NO: 16). Amplification reactions consisted of 1× cloned Pfu PCR buffer, 10 ng genomic DNA, 150 ng each primer, 200 μM each dNTP, and varying amounts of either wild type Pfu (1.25 U to 5 U) or Pfu mutant (0.625-12.5 U). Amplification was performed using a RoboCycler® temperature cycler (Stratagene) with the following program: (1 cycle) 95° C. for 2 minute; (30 cycles) 95° C. for 1 minute, 58° C. for 1 minute, 72° C. for 1.5 minutes; (1 cycle) 72° C. for 7 minutes. PCR products were examined on 1% agarose gels containing ethidium bromide.

Results: FIG. 3 contains a table listing the protein concentration, unit concentration, and specific activity of the purified Pfu V93R and V93E mutants.

The purified mutants were also re-assayed to assess dUTP incorporation during PCR, according to the method described in Example 3. FIG. 4 shows that the Pfu V93R mutant produces similar yields of the 500 bp amplicon in the presence of 100% TTP (lane 8), 50% TTP:50% dUTP (lane 5), and 100% dUTP (lane 7), while the Pfu V93E mutant produces high yields in the presence of 100% TTP (lane 1) and 50% TTP:50% dUTP (lane 3) and lower yields in the presence of 100% dUTP (lane 4). In contrast, cloned Pfu can only amplify in the presence of 100% TTP (lane 12). These results indicate that the V93R and V93E mutations significantly improve dUTP incorporation compared to wild type Pfu, and that the V93R mutation appear to be superior to the V93E mutation with respect to reducing uracil detection.

Example 6

PCR Amplification with Purified DNA Polymerase Mutants

PCR reactions are conducted under standard conditions in cloned Pfu PCR buffer (10 mM KCl, 10 mM $(NH_4)_2SO_4$, 20 mM Tris HCl (pH 8.8), 2mM Mg $SO_4$, 0.1% Triton X-100, and 100 μg/ml BSA) with various amounts of cloned Pfu, PfuTurbo, or mutant Pfu DNA polymerase. For genomic targets 0.3-9 kb in length, PCR reactions contained 100 ng of human genomic DNA, 200 μM each dNTP, and 100 ng of each primer. For genomic targets >9 kb in length, PCR reactions contained 250 ng of human genomic DNA, 500 μM each dNTP, and 200 ng of each primer.

Table 3—Cycling Conditions:

TABLE 4

| Amplicon | PCR primers | Cycling conditions |
|---|---|---|
| 0.6 kb lambda | F: 5'-GGAATGAAGTTATCCCCGCTTCCCC<br>(SEQ ID NO: 41)<br>R: 5'-CCAGTTCATTCAGCGTATTCAG-3'<br>(SEQ ID NO: 42) | 93° C. 1 min (1x)<br>93° C. 1 min, 60° C.<br>40 s, 72° C. 1 min (30x)<br>72° C. 10 min (1x) |
| 0.97 lambda | FU: 5'-GGAAUGAAGUUAUCCCCGCUUCCCC-<br>(SEQ ID NO: 75)<br>RU: 5'-CCAGGUCUCCAGCGUGCCCA-3'<br>(SEQ ID NO: 76)<br>FT: 5'-GGAATGAAGTTATCCCCGCTTCCCC<br>(SEQ ID NO: 77) | 93° C. 1 min (1x)<br>93° C. 1 min, 60° C.<br>50 s, 72° C. 1 min (30x)<br>72° C. 10 min (1x) |

TABLE 4-continued

| Amplicon | PCR primers | Cycling conditions |
|---|---|---|
| | RT: 5'-CCAGGTCTCCAGCGTGCCCA-3'<br>(SEQ ID NO: 78) | |
| 2.6 kb<br>Human genomic<br>(α1 anti-trypsin) | F: 5'GAG GAG AGC AGG AAA GGT GGA AC<br>(SEQ ID NO: 79)<br>R: 5'TGC AGA GCG ATT ATT CAG GAA TGC<br>(SEQ ID NO: 80) | 95° C. 2 min (1x)<br>95° C. 40 s, 58° C. 30 s,<br>72° C. 3 min (30x)<br>72° C. 7 min (1x) |
| 6 kb<br>Human genomic<br>(α1 anti-trypsin) | F: 5'GAG GAG AGC AGG AAA GGT GGA AC<br>(SEQ ID NO: 81)<br>R: 5'GAG CAA TGG TCA AAG TCA ACG TCA TCC ACA GC<br>(SEQ ID NO: 82) | 92° C. 2 min (1x)<br>92° C. 10 s, 58° C. 30 s,<br>68° C. 12 min (10x)<br>92° C. 10 s, 58° C. 30 s,<br>68° C. 12 min plus<br>10 s/cycle (20x)<br>68° C. 10 min (1x) |

Pfu mutants are described here as examples, but the same protocol can be used for PCR by other DNA polymerase mutants (e.g., KOD and JDF-3). Comparisons were carried out to determine if mutations that improve dUTP incorporation, and hence reduce uracil detection, also improve PCR performance. In FIG. 5, a 12 kb target was amplified from human genomic DNA using 2 min per kb extension times. Under these conditions, 1 U, 2 U, and 4 U of the Pfu V93R mutant successfully amplified the target, while the same amount of cloned Pfu could not. In comparison, PfuTurbo successfully amplified the long target; however, PCR product yields were significantly lower than those produced with the V93R mutant (FIG. 5). Similar experiments employing 1 min per kb extension times showed that the 12 kb target could be amplified in high yield with 5 U and 10 U of Pfu V93R and amplified in low yield with 10 U of PfuTurbo (data not shown). In total, these results demonstrate that the V93R mutation dramatically improves the PCR performance of Pfu DNA polymerase.

Similar testing of the purified Pfu V93E mutant showed that although the V93E mutation improves dUTP incorporation (FIG. 2), this mutant is not robust enough to amplify the long 12 kb amplicon when assayed using enzyme amounts between 0.6 U and 10 U (data not shown). In comparison, the product was successfully amplified using 10 U of PfuTurbo (data not shown).

Figure 8A:
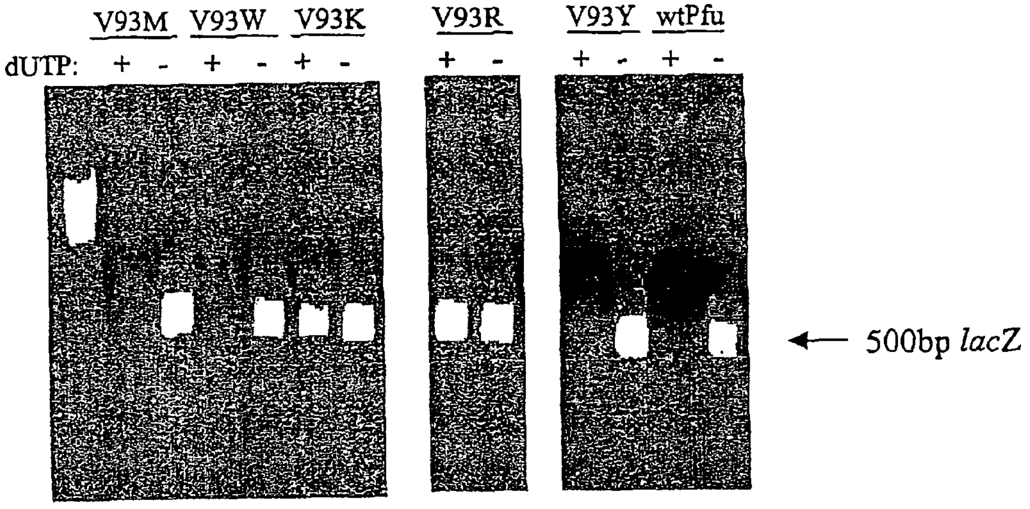
Figure 8B:
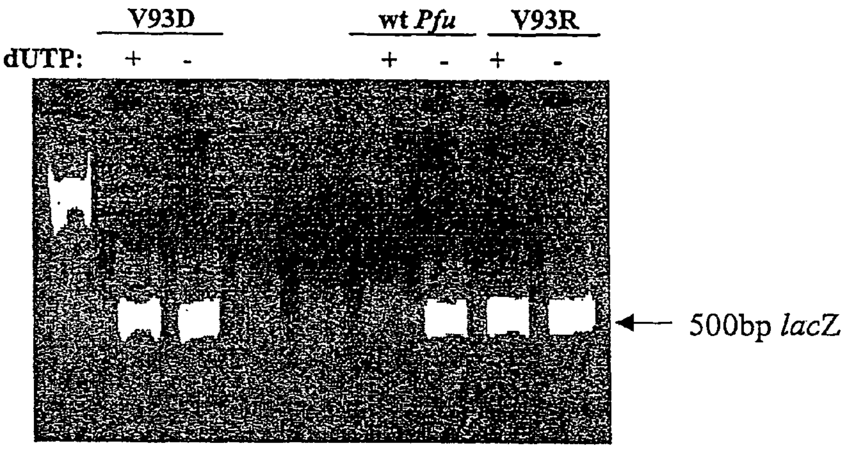
Figure 8C:
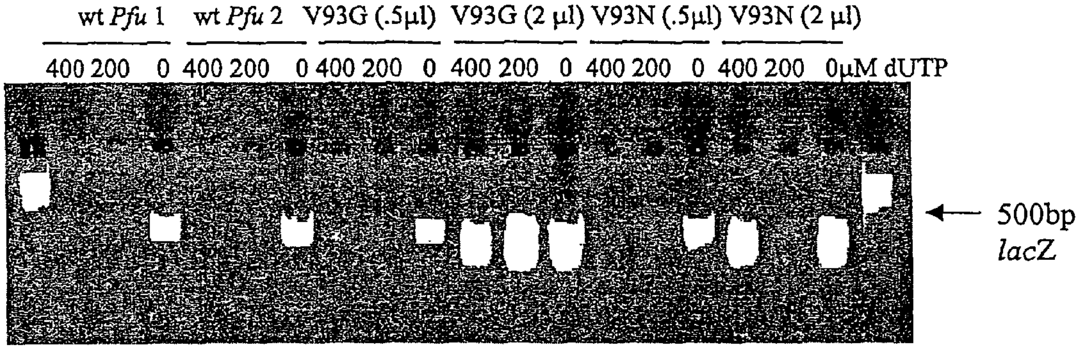

FIG. 8 shows the results of additional Pfu mutations on dUTP incorporation. Pfu V93K and V93R mutants show significantly improved dUTP incorporation compared to wild type Pfu. In contrast, the Pfu V93W, V93 V93W, V93Y and V93M mutants showed little to no improvement in dUTP incorporation (see FIG. 8A). In addition, both V93D and V93R mutants showed significantly improved dUTP incorporation, compared to wild type (FIG. 8B), while the V93N mutation showed a very small improvement in dTUP incorporation (FIG. 8C). The Pfu V93G mutation showed little to no improvement in dUTP incorporation.

Example 7

Construction of Pfu DNA Polymerase Deletion and Insertion Mutants

Mutants with altered polymerization activity may also be constructed using the exo- and/or V93 mutants obtained. For example, insertions and deletions were introduced in Pfu DNA polymerase in the region around V93 using the QuikChange Multi Site-Directed Mutagenesis Kit (Stratagene). FIG. 10 lists the primer sequences employed to generate useful mutations. Clones were sequenced to identify the incorporated mutations.

The following Pfu mutants were constructed: deletions of residues 93, 92, 94, 92-93, 93-94, and 92-94, and insertions of one, two, or three glycines between residues 92 and 93.

Example 8

Quantitative PCR Using Mutant DNA Polymerase of the Present Invention

PCR reactions may be set up as described above in Example 6. A Taqman probe (labeled) may be added as described by Applied Biosystems (CA). an oligonucleotide probe containing a reporter molecule-quencher molecule pair that specifically anneals to a region of a target polynucleotide “downstream”, i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a mutant DNA polymerase of the present invention, the probe anneals to the template where it is digested by the 5' to 3' exonuclease activity of the polymerase. As a result of the probe being digested, the reporter molecule is effectively separated from the quencher molecule such that the quencher molecule is no longer close enough to the reporter molecule to quench the reporter molecule’s fluorescence. Thus, as more and more probes are digested during amplification, the number of reporter molecules in solution increases, thus resulting in an increasing number of unquenched reporter molecules which produce a stronger and stronger fluorescent signal. are labeled with a fluorophore and a quencher of that fluorophore, respectively. In the absence of target polynucleotide, the complementary sequences on either end of the molecule permit stem formation, bringing the labeled ends of the molecule together, so that fluorescence from the fluorophore is quenched. In the presence of the target polynucleotide, which bears sequence complementary to the loop and part of the stem structure of the beacon probe, the intermolecular hybridization of the probe to the target is energetically favored over intramolecular stem-loop formation, resulting in the separation of the fluorophore and the quencher, so that fluorescent signal is emitted upon excitation of the fluorophore. The more target present, the more probe hybridizes to it, and the more fluorophore is freed from quenching, providing a read out of the amplification process in real time.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. An Archaeal DNA polymerase comprising at least one amino acid mutation in the exoI motif and an amino acid mutation at V93 of SEQ ID NO:89 or a corresponding residue in an amino acid sequence selected from SEQ ID NOs: 83-88 or SEQ ID NOs:90-102, wherein said Archaeal DNA polymerase is deficient in 3'-5' exonuclease activity.

2. An Archaeal DNA polymerase comprising at least one amino acid mutation in the exoII motif and an amino acid mutation at V93 of SEQ ID NO:89 or a corresponding residue in an amino acid sequence selected from SEQ ID NOs:83-88 or SEQ ID NOs:90-102, wherein said Archaeal DNA polymerase is deficient in 3'-5' exonuclease activity.

3. An Archaeal DNA polymerase comprising at least one amino acid mutation in the exo III motif and an amino acid mutation at V93 of SEQ ID NO:89 or a corresponding residue in an amino acid sequence selected from SEQ ID NOs:83-88 or SEQ ID NOs:90-102, wherein said Archaeal DNA polymerase is deficient in 3'-5' exonuclease activity.

4. An Archaeal DNA polymerase comprising at least one amino acid mutation in each of the exo I and exo III motifs and an amino acid mutation at V93 of SEQ ID NO:89 or a corresponding residue in an amino acid sequence selected from SEQ ID NOs:83-88 or SEQ ID NOs:90-102, wherein said Archaeal DNA polymerase is deficient in 3'-5' exonuclease activity.

5. An Archaeal DNA polymerase comprising at least one amino acid mutation in each of the exo II and exo III motifs and an amino acid mutation at V93 of SEQ ID NO:89 or a corresponding residue in an amino acid sequence selected from SEQ ID NOs:83-88 or SEQ ID NOs:90-102, wherein said Archaeal DNA polymerase is deficient in 3'-5' exonuclease activity.

6. An Archaeal DNA polymerase comprising at least one amino acid mutation in each of the exo I and exoII motifs and an amino acid mutation at V93 of SEQ ID NO:89 or a corresponding residue in an amino acid sequence selected from SEQ ID NOs:83-88 or SEQ ID NOs:90-102, wherein said Archaeal DNA polymerase is deficient in 3'-5' exonuclease activity.

7. An Archaeal DNA polymerase comprising at least one amino acid mutation in each of the exoI, exo II, and exoIII motifs and an amino acid mutation at V93 of SEQ ID NO:89 or a corresponding residue in an amino acid sequence selected from SEQ ID NOs: 83-88 or SEQ ID NOs:90-102, wherein said Archaeal DNA polymerase is deficient in 3'-5' exonuclease activity.

8. The mutant Archaeal DNA polymerase of any of claims 1-7, wherein said mutant Archaeal DNA polymerase is selected from the group consisting of: KOD, Pfu, and JDF-3 DNA polymerase.

9. The mutant Archaeal DNA polymerase of any of claims 1-7, wherein said mutation at position V93, is a Valine to Arginine substitution, a Valine to Glutamic acid substitution, a Valine to Lysine substitution, a Valine to Aspartic acid substitution, a Valine to Glutamine substitution, or a Valine to Asparagine substitution.

10. The mutant Archaeal DNA polymerase of any of claims 1-7, wherein said mutation in exo I motif is selected from the group consisting of: aspartic acid (D) to threonine (T), aspartic acid (D) to alanine (A) and glutamic acid (E) to alanine (A).

11. A composition comprising a mutant Archaeal DNA polymerase of any of claims 1-7.

12. The composition of claim 11, further comprising an enzyme with reverse transcriptase activity.

13. The composition of claim 12, wherein said enzyme with reverse transcriptase is a second mutant DNA polymerase.

14. The composition of claim 12, wherein said enzyme with reverse transcriptase is the mutant Archaeal DNA polymerase which contains an increased reverse transcriptase activity.

15. The composition of claim 11, further comprising a PCR additive.

16. A kit comprising a mutant Archaeal DNA polymerase of any of claims 1-7 and packaging material therefor.

17. The kit of claim 16, further comprising an enzyme with reverse transcriptase activity.

18. The kit of claim 17, wherein said enzyme with reverse transcriptase is a second mutant DNA polymerase.

19. The kit of claim 17, wherein said enzyme with reverse transcriptase is the mutant Archaeal DNA polymerase which contains an increased reverse transcriptase activity.

20. The kit of claim 16, further comprising a PCR additive.

21. A method for DNA synthesis comprising:

(a) providing a mutant Archaeal DNA polymerase of any of claims 1-7; and (b) contacting said mutant Archaeal DNA polymerase with a polynucleotide template to permit DNA synthesis.

22. A method for determining the abundance of a polynucleotide template, comprising (a) providing a mutant Archaeal DNA polymerase of any of claims 1-7;

(b) contacting said mutant Archaeal DNA polymerase with said polynucleotide template to produce amplified product; and (c) determining the abundance of said amplified product, wherein said abundance of said amplified product is indicative of the abundance of said polynucleotide template.

23. The method of claim 22, wherein said polynucleotide template is a RNA molecule, and wherein said RNA molecule is reverse transcribed into cDNA before the contacting step (b).

24. The method of claim 23, wherein said RNA is reverse transcribed by an enzyme with reverse transcriptase activity.

25. The method of claim 24, wherein said RNA is reverse transcribed by said mutant Archaeal DNA polymerase which also contains an increased reverse transcriptase activity.

* * * * *

UNITED STATES PATENT AND TRADEMARK OFFICE

CERTIFICATE OF CORRECTION

PATENT NO. : 8,283,148 B2
APPLICATION NO. : 10/734563
DATED : October 9, 2012
INVENTOR(S) : Joseph A. Sorge et al.

It is certified that error appears in the above-identified patent and that said Letters Patent is hereby corrected as shown below:

On the face page, in field (56), under "Other Publications", in column 2, line 10, delete "Archael" and insert -- Archaeal --, therefor.

On the face page, in field (56), under "Other Publications", in column 2, line 11, delete "archael" and insert -- archaeal --, therefor.

Signed and Sealed this
First Day of January, 2013

David J. Kappos
*Director of the United States Patent and Trademark Office*

SEQUENCE LISTING

<160> NUMBER OF SEQ ID NOS: 110

<210> SEQ ID NO 1
<211> LENGTH: 30
<212> TYPE: DNA
<213> ORGANISM: Artificial sequence
<220> FEATURE:
<223> OTHER INFORMATION: primer

<400> SEQUENCE: 1
gacgacgaca agatgatttt agatgtggat 30

<210> SEQ ID NO 2
<211> LENGTH: 30
<212> TYPE: DNA
<213> ORGANISM: Artificial sequence
<220> FEATURE:
<223> OTHER INFORMATION: primer

<400> SEQUENCE: 2
ggaacaagac ccgtctagga ttttttaatg 30

<210> SEQ ID NO 3
<211> LENGTH: 23
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (23)..(23)
<223> OTHER INFORMATION: n = Uracil

<400> SEQUENCE: 3
gacgttgtaa aacgacggcc agn 23

<210> SEQ ID NO 4
<211> LENGTH: 22
<212> TYPE: DNA
<213> ORGANISM: Artificial sequence
<220> FEATURE:
<223> OTHER INFORMATION: primer

<400> SEQUENCE: 4
acgttgtaaa acgacggcca gt 22

<210> SEQ ID NO 5
<211> LENGTH: 31
<212> TYPE: DNA
<213> ORGANISM: Artificial sequence
<220> FEATURE:
<223> OTHER INFORMATION: primer

<400> SEQUENCE: 5
caatttcaca caggaaacag ctatgaccat g 31

<210> SEQ ID NO 6
<211> LENGTH: 37
<212> TYPE: DNA
<213> ORGANISM: Artificial sequence
<220> FEATURE:
<223> OTHER INFORMATION: primer

<400> SEQUENCE: 6
gaacatcccc aagatgaacc cactattaga gaaaaag 37

<210> SEQ ID NO 7
<211> LENGTH: 37
<212> TYPE: DNA
<213> ORGANISM: Artificial sequence
<220> FEATURE:
<223> OTHER INFORMATION: primer

<400> SEQUENCE: 7
ctttttctct aatagtgggt tcatcttggg gatgttc 37

<210> SEQ ID NO 8
<211> LENGTH: 37
<212> TYPE: DNA
<213> ORGANISM: Artificial sequence
<220> FEATURE:
<223> OTHER INFORMATION: primer

<400> SEQUENCE: 8
gaacatcccc aagatagacc cactattaga gaaaaag 37

<210> SEQ ID NO 9
<211> LENGTH: 37
<212> TYPE: DNA
<213> ORGANISM: Artificial sequence
<220> FEATURE:
<223> OTHER INFORMATION: primer

<400> SEQUENCE: 9
ctttttctct aatagtgggt ctatcttggg gatgttc 37

<210> SEQ ID NO 10
<211> LENGTH: 37
<212> TYPE: DNA
<213> ORGANISM: Artificial sequence
<220> FEATURE:
<223> OTHER INFORMATION: primer

<400> SEQUENCE: 10
gaacatcccc aagataaccc cactattaga gaaaaag 37

<210> SEQ ID NO 11
<211> LENGTH: 37
<212> TYPE: DNA
<213> ORGANISM: Artificial sequence
<220> FEATURE:
<223> OTHER INFORMATION: primer

<400> SEQUENCE: 11
ctttttctct aatagtgggg ttatcttggg gatgttc 37

<210> SEQ ID NO 12
<211> LENGTH: 37
<212> TYPE: DNA
<213> ORGANISM: Artificial sequence
<220> FEATURE:
<223> OTHER INFORMATION: primer

<400> SEQUENCE: 12
gaacatcccc aagatcaccc cactattaga gaaaaag 37

<210> SEQ ID NO 13
<211> LENGTH: 37
<212> TYPE: DNA
<213> ORGANISM: Artificial sequence
<220> FEATURE:
<223> OTHER INFORMATION: primer

<400> SEQUENCE: 13 cttttctct aatagtgggg tgatcttggg gatgttc 37

<210> SEQ ID NO 14
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (16)..(17)
<223> OTHER INFORMATION: n= A, T, G or C

<400> SEQUENCE: 14
gaacatcccc aagatnnkcc cactattaga gaaaaag 37

<210> SEQ ID NO 15
<211> LENGTH: 18
<212> TYPE: DNA
<213> ORGANISM: Artificial sequence
<220> FEATURE:
<223> OTHER INFORMATION: primer

<400> SEQUENCE: 15
gacagtcact ccggcccg 18

<210> SEQ ID NO 16
<211> LENGTH: 18
<212> TYPE: DNA
<213> ORGANISM: Artificial sequence
<220> FEATURE:
<223> OTHER INFORMATION: primer

<400> SEQUENCE: 16
cgacgactcg tggagccc 18

<210> SEQ ID NO 17
<211> LENGTH: 2328
<212> TYPE: DNA
<213> ORGANISM: Pyrococcus furiosus

<400> SEQUENCE: 17
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacgggga aaggcatgga 180 aagattgtga gaattgttga tgtagagaag gttgagaaaa agtttctcgg caagcctatt 240
accgtgtgga aactttattt ggaacatccc caagatgttc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat tcgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaatttttg gaaagccaaa ggagaaggta tacgccgacg agatagcaaa agcctgggaa 900
agtggagaga accttgagag agttgccaaa tactcgatgg aagatgcaaa ggcaacttat 960
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacagg tggattcgtt aaagagccag aaaaggggtt gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg ggaagaaag 1560 tacatcgagt tagtatggaa ggagctcgaa gaaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328

<210> SEQ ID NO 18
<211> LENGTH: 2325
<212> TYPE: DNA
<213> ORGANISM: Pyrococcus sp.

<400> SEQUENCE: 18
atgatcctcg acactgacta cataaccgag gatggaaagc ctgtcataag aattttcaag 60
aaggaaaacg gcgagtttaa gattgagtac gaccggactt ttgaacccta cttctacgcc 120
ctcctgaagg acgattctgc cattgaggaa gtcaagaaga taaccgccga gaggcacggg 180
acggttgtaa cggttaagcg ggttgaaaag gttcagaaga agttcctcgg gagaccagtt 240
gaggtctgga aactctactt tactcatccg caggacgtcc cagcgataag ggacaagata 300
cgagagcatc cagcagttat tgacatctac gagtacgaca tacccttcgc caagcgctac 360

-continued

```
ctcatagaca agggattagt gccaatggaa ggcgacgagg agctgaaaat gctcgccttc    420
gacattgaaa ctctctacca tgagggcgag gagttcgccg aggggccaat ccttatgata    480
agctacgccg acgaggaagg ggccagggtg ataacttgga agaacgtgga tctcccctac    540
gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg gacggataca cttcgatctc    780
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg gagacctcct agaggagagg   1380
cagaagataa agaagaagat gaaggccacg attgacccga tcgagaggaa gctcctcgat   1440
tacaggcaga gggccatcaa gatcctggca aacagctact acggttacta cggctatgca   1500
agggcgcgct ggtactgcaa ggagtgtgca gagagcgtaa cggcctgggg aagggagtac   1560
ataacgatga ccatcaagga gatagaggaa aagtacggct ttaaggtaat ctacagcgac   1620
accgacggat tttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca aacgcggctt cttcgtcacg aagaagaagt atgcggtgat agacgaggaa   1800
ggcaagataa caacgcgcgg acttgagatt gtgaggcgtg actggagcga gatagcgaaa   1860
gagacgcagg cgagggttct tgaagctttg ctaaaggacg gtgacgtcga gaaggccgtg   1920
aggatagtca aagaagttac cgaaaagctg agcaagtacg aggttccgcc ggagaagctg   1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                   2325
```

<210> SEQ ID NO 19
<211> LENGTH: 2325
<212> TYPE: DNA
<213> ORGANISM: Thermococcus litoralis

<400> SEQUENCE: 19

```
atgatactgg acactgatta cataacaaaa gatggcaagc ctataatccg aatttttaag     60
aaagagaacg gggagtttaa aatagaactt gaccctcatt ttcagcccta tatatatgct    120
cttctcaaag atgactccgc tattgaggag ataaaggcaa taaagggcga gagacatgga    180
```

-continued

```
aaaactgtga gagtgctcga tgcagtgaaa gtcaggaaaa aatttttggg aagggaagtt    240
gaagtctgga agctcatttt cgagcatccc caagacgttc cagctatgcg ggcaaaata     300
agggaacatc cagctgtggt tgacatttac gaatatgaca taccctttgc caagcgttat    360
ctcatagaca agggcttgat tcccatggag ggagacgagg agcttaagct ccttgccttt    420
gatattgaaa cgttttatca tgagggagat gaatttggaa agggcgagat aataatgatt    480
agttatgccg atgaagaaga ggccagagta atcacatgga aaaatatcga tttgccgtat    540
gtcgatgttg tgtccaatga aagagaaatg ataaagcgtt ttgttcaagt tgttaaagaa    600
aaagaccccg atgtgataat aacttacaat ggggacaatt ttgatttgcc gtatctcata    660
aaacgggcag aaaagctggg agttcggctt gtcttaggaa gggacaaaga acatcccgaa    720
cccaagattc agaggatggg tgatagtttt gctgtggaaa tcaagggtag aatccacttt    780
gatcttttcc cagttgtgcg aaggacgata aacctcccaa cgtatacgct tgaggcagtt    840
tatgaagcag ttttaggaaa aaccaaaagc aaattaggag cagaggaaat tgccgctata    900
tgggaaacag aagaaagcat gaaaaaacta gcccagtact caatggaaga tgctagggca    960
acgtatgagc tcgggaagga attcttcccc atggaagctg agctggcaaa gctgataggt   1020
caaagtgtat gggacgtctc gagatcaagc accggcaacc tcgtggagtg gtatctttta   1080
agggtggcat acgcgaggaa tgaacttgca ccgaacaaac ctgatgagga agagtataaa   1140
cggcgcttaa gaacaactta cctgggagga tatgtaaaag agccagaaaa aggtttgtgg   1200
gaaaatatca tttatttgga tttccgcagt ctgtaccctt caataatagt tactcacaac   1260
gtatccccag ataccctgga aaaagagggc tgtaagaatt acgatgttgc tccgatagta   1320
ggatataggt tctgcaagga ctttccgggc tttattccct ccatactcgg ggacttaatt   1380
gcaatgaggc aagatataaa gaagaaaatg aaatccacaa ttgacccgat cgaaaagaaa   1440
atgctcgatt ataggcaaag ggctattaaa ttgcttgcaa acagctatta cggctatatg   1500
gggtatccta aggcaagatg gtactcgaag gaatgtgctg aaagcgttac cgcatggggg   1560
agacactaca tagagatgac gataagagaa atagaggaaa agttcggctt taaggttctt   1620
tatgcggaca ctgacggctt ttatgccaca atacccgggg aaaagcctga actcattaaa   1680
aagaaagcca aggaattcct aaactacata aactccaaac ttccaggtct gcttgagctt   1740
gagtatgagg gcttttactt gagaggattc tttgttacaa aaaagcgcta tgcagtcata   1800
gatgaagagg gcaggataac aacaaggggc ttggaagtag taaggagaga ttggagtgag   1860
atagctaagg agactcaggc aaaggtttta gaggctatac ttaaagaggg aagtgttgaa   1920
aaagctgtag aagttgttag agatgttgta gagaaaatag caaaatacag ggttccactt   1980
gaaaagcttg ttatccatga gcagattacc agggatttaa aggactacaa agccattggc   2040
cctcatgtcg cgatagcaaa aagacttgcc gcaagaggga taaaagtgaa accgggcaca   2100
ataataagct atatcgttct caaagggagc ggaaagataa gcgataggt aattttactt    2160
acagaatacg atcctagaaa acacaagtac gatccggact actacataga aaaccaagtt   2220
ttgccggcag tacttaggat actcgaagcg tttggataca gaaaggagga tttaaggtat   2280
caaagctcaa aacaaaccgg cttagatgca tggctcaaga ggtag                   2325
```

<210> SEQ ID NO 20
<211> LENGTH: 2328
<212> TYPE: DNA
<213> ORGANISM: Pyrococcus sp.

<400> SEQUENCE: 20

-continued

```
atgatacttg acgctgacta catcaccgag gatgggaagc cgattataag gattttcaag      60
aaagaaaacg gcgagtttaa ggttgagtac gacagaaact ttagacctta catttacgct     120
ctcctcaaag atgactcgca gattgatgag gttaggaaga taaccgccga gaggcatggg     180
aagatagtga gaattataga tgccgaaaag gtaaggaaga agttcctggg gaggccgatt     240
gaggtatgga ggctgtactt tgaacaccct caggacgttc ccgcaataag ggataagata     300
agagagcatt ccgcagttat tgacatcttt gagtacgaca ttccgttcgc gaagaggtac     360
ctaatagaca aaggcctaat tccaatggaa ggcgatgaag agctcaagtt gctcgcattt     420
gacatagaaa ccctctatca cgaaggggag gagttcgcga aggggcccat tataatgata     480
agctatgctg atgaggaaga agccaaagtc ataacgtgga aaaagatcga tctcccgtac     540
gtcgaggtag tttccagcga gagggagatg ataaagcggt tcctcaaggt gataagggag     600
aaagatcccg atgttataat tacctacaac ggcgattctt tcgaccttcc ctatctagtt     660
aagagggccg aaaagctcgg gataaagcta cccctgggaa gggacggtag tgagccaaag     720
atgcagaggc ttggggatat gacagcggtg gagataaagg gaaggataca ctttgacctc     780
taccacgtga ttaggagaac gataaacctc ccaacataca ccctcgaggc agtttatgag     840
gcaatcttcg gaaagccaaa ggagaaagtt tacgctcacg agatagctga ggcctgggag     900
actggaaagg gactggagag agttgcaaag tattcaatgg aggatgcaaa ggtaacgtac     960
gagctcggta gggagttctt cccaatggag gcccagcttt caaggttagt cggccagccc    1020
ctgtgggatg tttctaggtc ttcaactggc aacttggtgg agtggtacct cctcaggaag    1080
gcctacgaga ggaatgaatt ggctccaaac aagccggatg agagggagta cgagagaagg    1140
ctaagggaga gctacgctgg gggatacgtt aaggagccgg agaaagggct ctgggagggg    1200
ttagtttccc tagatttcag gagcctgtac ccctcgataa taatcaccca taacgtctca    1260
ccggatacgc tgaacaggga agggtgtagg gaatacgatg tcgccccaga ggttgggcac    1320
aagttctgca aggacttccc ggggtttatc cccagcctgc tcaagaggtt attggatgaa    1380
aggcaagaaa taaaaaggaa gatgaaagct tctaaagacc caatcgagaa gaagatgctt    1440
gattacaggc aacgggcaat caaaatcctg gcaaacagct attatgggta ttatgggtac    1500
gcaaaagccc gttggtactg taaggagtgc gcagagagcg ttacggcctg gggggaggaa    1560
tatatagagt tcgtaaggaa ggaactggag gaaaagttcg ggttcaaagt cttatacata    1620
gacacagatg gactctacgc cacaattcct ggggcaaaac ccgaggagat aaagaagaaa    1680
gccctagagt tcgtagatta tataaacgcc aagctcccag ggctgttgga gcttgagtac    1740
gagggcttct acgtgagagg gttcttcgtg acgaagaaga agtatgcgtt gatagatgag    1800
gaagggaaga taatcactag ggggcttgaa atagtcagga gggactggag cgaaatagcc    1860
aaagaaaccc aagcaaaagt cctagaggct atcctaaagc atggcaacgt tgaggaggca    1920
gtaaagatag ttaaggaggt aactgaaaag ctgagcaagt acgaaatacc tccagaaaag    1980
ctagttattt acgagcagat cacgaggccc cttcacgagt acaaggctat aggtccgcac    2040
gttgccgtgg caaaaaggtt agccgctaga ggagtaaagg tgaggcctgg catggtgata    2100
gggtacatag tgctgagggg agacgggcca ataagcaaga gggctatcct tgcagaggag    2160
ttcgatctca ggaagcataa gtatgacgct gagtattaca tagaaaatca ggttttacct    2220
gccgttctta gaatattaga ggcctttggg tacaggaaag aagacctcag gtggcagaag    2280
actaaacaga caggtcttac ggcatggctt aacatcaaga agaagtaa                 2328
```

-continued

<210> SEQ ID NO 21
<211> LENGTH: 2331
<212> TYPE: DNA
<213> ORGANISM: Thermococcus sp.

<400> SEQUENCE: 21

```
atgatccttg acgttgatta catcaccgag aatggaaagc ccgtcatcag ggtcttcaag      60
aaggagaacg gcgagttcag gattgaatac gaccgcgagt tcgagcccta cttctacgcg     120
ctcctcaggg acgactctgc catcgaagaa atcaaaaaga taaccgcgga gaggcacggc     180
agggtcgtta aggttaagcg cgcggagaag gtgaagaaaa agttcctcgg caggtctgtg     240
gaggtctggg tcctctactt cacgcacccg caggacgttc cggcaatccg cgacaaaata     300
aggaagcacc ccgcggtcat cgacatctac gagtacgaca taccettcgc caagcgctac     360
ctcatagaca agggcctaat cccgatggaa ggtgaggaag agcttaaact catgtccttc     420
gacatcgaga cgctctacca cgagggagaa gagtttggaa ccgggccgat tctgatgata     480
agctacgccg atgaaagcga ggcgcgcgtg ataacctgga agaagatcga ccttccttac     540
gttgaggttg tctccaccga gaaggagatg attaagcgct tcttgagggt cgttaaggag     600
aaggacccgg acgtgctgat aacatacaac ggcgacaact tcgacttcgc ctacctgaaa     660
aagcgctgtg agaagcttgg cgtgagcttt accctcggga gggacgggag cgagccgaag     720
atacagcgca tgggggacag gtttgcggtc gaggtgaagg gcagggtaca cttcgacctt     780
tatccagtca taaggcgcac cataaacctc ccgacctaca cccttgaggc tgtatacgag     840
gcggttttcg gcaagcccaa ggagaaggtc tacgccgagg agatagccac cgcctgggag     900
accggcgagg ggcttgagag ggtcgcgcgc tactcgatgg aggacgcgag ggttacctac     960
gagcttggca gggagttctt cccgatggag gcccagcttt ccaggctcat cggccaaggc    1020
ctctgggacg tttcccgctc cagcaccggc aacctcgtcg agtggttcct cctaaggaag    1080
gcctacgaga ggaacgaact cgctcccaac aagcccgacg agagggagct ggcgaggaga    1140
aggggggggct acgccggtgg ctacgtcaag gagccggagc ggggactgtg ggacaatatc    1200
gtgtatctag actttcgtag tctctaccct tcaatcataa tcacccacaa cgtctcgcca    1260
gatacgctca accgcgaggg gtgtaggagc tacgacgttg cccccgaggt cggtcacaag    1320
ttctgcaagg acttccccgg cttcattccg agcctgctcg gaaacctgct ggaggaaagg    1380
cagaagataa agaggaagat gaaggcaact ctcgacccgc tggagaagaa tctcctcgat    1440
tacaggcaac gcgccatcaa gattctcgcc aacagctact acggctacta cggctatgcc    1500
agggcaagat ggtactgcag ggagtgcgcc gagagcgtta cggcatgggg aagggagtac    1560
atcgaaatgg tcatcagaga gcttgaggaa aagttcggtt ttaaagtcct ctatgcagac    1620
acagacggtc tccatgccac cattcctgga gcggacgctg aaacagtcaa gaaaaaggca    1680
atggagttct taaactatat caatcccaaa ctgcccggcc ttctcgaact cgaatacgag    1740
ggcttctacg tcaggggctt cttcgtcacg aagaaaaagt acgcggtcat cgacgaggag    1800
ggcaagataa ccacgcgcgg gcttgagata gtcaggcgcg actggagcga gatagcgaag    1860
gagacgcagg cgagggtttt ggaggcgata ctcaggcacg gtgacgttga agaggccgtc    1920
agaattgtca gggaagtcac cgaaaagctg agcaagtacg aggttccgcc ggagaagctg    1980
gttatccacg agcagataac gcgcgagctc aaggactaca aggccaccgg cccgcacgta    2040
gccatagcga agcgtttggc cgccagaggt gttaaaatcc ggcccggaac tgtgataagc    2100
tacatcgttc tgaagggctc cggaaggata ggcgacaggg cgattccctt cgacgagttc    2160
gacccgacga agcacaagta cgatgcggac tactacatcg agaaccaggt tctgccggca    2220
```

gttgagagaa tcctcagggc cttcggctac cgcaaggaag acctgcgcta ccagaagacg 2280
aggcaggtcg ggcttggcgc gtggctgaag ccgaagggga agaagaagtg a 2331

<210> SEQ ID NO 22
<211> LENGTH: 2322
<212> TYPE: DNA
<213> ORGANISM: Thermococcus gorgonaius

<400> SEQUENCE: 22
atgatcctcg atacagacta cataactgag gatggaaagc ccgtcatcag gatcttcaag 60
aaggagaacg gcgagttcaa aatagactac gacagaaact ttgagccata catctacgcg 120
ctcttgaagg acgactctgc gattgaggac gtcaagaaga taactgccga gaggcacggc 180
actaccgtta gggttgtcag ggccgagaaa gtgaagaaga agttcctagg caggccgata 240
gaggtctgga agctctactt cactcacccc caggacgttc ccgcaatcag ggacaagata 300
aaggagcatc ctgccgttgt ggacatctac gagtacgaca tccccttcgc gaagcgctac 360
ctcatagaca aaggcttaat cccgatggag ggcgacgagg aacttaagat gctcgccttc 420
gacatcgaga cgctctatca cgagggcgag gagttcgccg aagggcctat cctgatgata 480
agctacgccg acgaggaagg ggcgcgcgtt attacctgga agaatatcga ccttccctat 540
gtcgacgtcg tttccaccga gaaggagatg ataaagcgct tcctcaaggt cgtcaaggaa 600
aaggatcccg acgtcctcat aacctacaac ggcgacaact tcgacttcgc ctacctcaag 660
aagcgctccg agaagctcgg agtcaagttc atcctcggaa gggaagggag cgagccgaaa 720
atccagcgca tgggcgatcg ctttgcggtg gaggtcaagg gaaggattca cttcgacctc 780
taccccgtca ttaggagaac gattaacctc cccacttaca cccttgaggc agtatatgaa 840
gccatctttg gacagccgaa ggagaaggtc tacgctgagg agatagcgca ggcctgggaa 900
acgggcgagg gattagaaag ggtggcccgc tactcgatgg aggacgcaaa ggtaacctat 960
gaactcggaa aagagttctt ccctatggaa gcccagctct cgcgcctcgt aggccagagc 1020
ctctgggatg tatctcgctc gagtaccgga aacctcgtcg agtggttttt gctgaggaag 1080
gcctacgaga ggaatgaact tgcaccaaac aagccggacg agagggagct ggcaagaaga 1140
agggagagct acgcgggtgg atacgtcaag gagcccgaaa ggggactgtg ggagaacatc 1200
gtgtatctgg acttccgctc cctgtatcct tcgataataa tcacccataa cgtctcccct 1260
gatacactca acagggaggg ttgtgaggag tacgacgtgg ctcctcaggt aggccataag 1320
ttctgcaagg acttccccgg cttcatccca agcctcctcg gagacctctt ggaggagaga 1380
cagaaggtaa agaagaagat gaaggccact atagacccaa tcgagaagaa actcctcgat 1440
tacaggcaac gagcaatcaa aatccttgct aatagcttct acggttacta cggctatgca 1500
aaggcccgct ggtactgcaa ggagtgcgcc gagagcgtta ccgcttgggg caggcagtac 1560
atcgagacca cgataaggga aatagaggag aaatttggct ttaaagtcct ctacgcggac 1620
acagatggat ttttcgcaac aatacctgga gcggacgccg aaaccgtcaa aaagaaggca 1680
aaggagttcc tggactacat caacgccaaa ctgcccggcc tgctcgaact cgaatacgag 1740
ggcttctaca agcgcggctt cttcgtgacg aagaagaagt acgcggttat agacgaggag 1800
gacaagataa cgacgcgcgg gcttgaaata gttaggcgtg actggagcga gatagcgaag 1860
gagacgcagg cgagggttct tgaggcgata ctaaagcacg gtgacgttga agaagcggta 1920
aggattgtca aagaggttac ggagaagctg agcaagtacg aggttccacc ggagaagctg 1980
gtcatctacg agcagataac ccgcgacctg aaggactaca aggccaccgg gccgcatgtg 2040

-continued

```
gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacat ga                      2322
```

<210> SEQ ID NO 23
<211> LENGTH: 2328
<212> TYPE: DNA
<213> ORGANISM: Pyrococcus furiosus
<220> FEATURE:
<221> NAME/KEY: misc_feature
<222> LOCATION: (1161)..(1161)
<223> OTHER INFORMATION: n = A, T, G or C

<400> SEQUENCE: 23

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacggggga aaggcatgga    180

aagattgtga gaattgttga tgtagagaag gttgagaaaa agtttctcgg caagcctatt    240

accgtgtgga aactttattt ggaacatccc caagatgttc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gatatagaaa ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacacc nggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg ggggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740
```

```
gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328
```

```
<210> SEQ ID NO 24
<211> LENGTH: 2328
<212> TYPE: DNA
<213> ORGANISM: Pyrococcus furiosus
<220> FEATURE:
<221> NAME/KEY: misc_feature
<222> LOCATION: (423)..(423)
<223> OTHER INFORMATION: n= A, T, G or C
<220> FEATURE:
<221> NAME/KEY: misc_feature
<222> LOCATION: (429)..(429)
<223> OTHER INFORMATION: n= A, T, G or C

<400> SEQUENCE: 24
```

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga    180

aagattgtga gaattgttga tgtagagaag gttgagaaaa agtttctcgg caagcctatt    240

accgtgtgga aactttattt ggaacatccc caagatgttc ccactattag agaaaaagtt    300

agagaacatc cagcagttgt ggacatcttc gaatacgata ttccatttgc aaaagagatac    360

ctcatcgaca aaggcctaat accaatggag ggggaagaag agctaaagat tcttgccttc    420

gcnatagcna ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320
```

```
aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg gggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328
```

<210> SEQ ID NO 25
<211> LENGTH: 2325
<212> TYPE: DNA
<213> ORGANISM: Pyrococcus furiosus

<400> SEQUENCE: 25

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga   180

aagattgtga gaattgttga tgtagagaag gttgagaaaa agtttctcgg caagcctatt    240

accgtgtgga aactttattt ggaacatccc caagatccca ctattagaga aaaagttaga    300

gaacatccag cagttgtgga catcttcgaa tacgatattc catttgcaaa gagatacctc    360

atcgacaaag gcctaatacc aatggagggg gaagaagagc taaagattct tgccttcgat    420

atagaaaccc tctatcacga aggagaagag tttggaaaag gcccaattat aatgattagt    480

tatgcagatg aaaatgaagc aaaggtgatt acttggaaaa acatagatct tccatacgtt    540

gaggttgtat caagcgagag agagatgata aagagatttc tcaggattat cagggagaag    600

gatcctgaca ttatagttac ttataatgga gactcattcg cattcccata tttagcgaaa    660

agggcagaaa aacttgggat taaattaacc attggaagag atggaagcga gcccaagatg    720

cagagaatag gcgatatgac ggctgtagaa gtcaagggaa gaatacattt cgacttgtat    780

catgtaataa caaggacaat aaatctccca acatacacac tagaggctgt atatgaagca    840

atttttggaa agccaaagga gaaggtatac gccgacgaga tagcaaaagc ctgggaaagt    900

ggagagaacc ttgagagagt tgccaaatac tcgatggaag atgcaaaggc aacttatgaa    960

ctcgggaaag aattccttcc aatggaaatt cagctttcaa gattagttgg acaaccttta   1020

tgggatgttt caaggtcaag cacagggaac cttgtagagt ggttcttact taggaaagcc   1080

tacgaaagaa acgaagtagc tccaaacaag ccaagtgaag aggagtatca aagaaggctc   1140
```

agggagagct acacaggtgg attcgttaaa gagccagaaa aggggttgtg ggaaaacata 1200
gtatacctag attttagagc cctatatccc tcgattataa ttacccacaa tgtttctccc 1260
gatactctaa atcttgaggg atgcaagaac tatgatatcg ctcctcaagt aggccacaag 1320
ttctgcaagg acatccctgg ttttatacca agtctcttgg gacatttgtt agaggaaaga 1380
caaaagatta agacaaaaat gaaggaaact caagatccta tagaaaaaat actccttgac 1440
tatagacaaa aagcgataaa actcttagca aattctttct acggatatta tggctatgca 1500
aaagcaagat ggtactgtaa ggagtgtgct gagagcgtta ctgcctgggg aagaaagtac 1560
atcgagttag tatggaagga gctcgaagaa aagtttggat ttaaagtcct ctacattgac 1620
actgatggtc tctatgcaac tatcccagga ggagaaagtg aggaaataaa gaaaaaggct 1680
ctagaatttg taaaatacat aaattcaaag ctccctggac tgctagagct tgaatatgaa 1740
gggttttata agaggggatt cttcgttacg aagaagaggt atgcagtaat agatgaagaa 1800
ggaaaagtca ttactcgtgg tttagagata gttaggagag attggagtga aattgcaaaa 1860
gaaactcaag ctagagtttt ggagacaata ctaaaacacg gagatgttga agaagctgtg 1920
agaatagtaa aagaagtaat acaaaagctt gccaattatg aaattccacc agagaagctc 1980
gcaatatatg agcagataac aagaccatta catgagtata aggcgatagg tcctcacgta 2040
gctgttgcaa agaaactagc tgctaaagga gttaaaataa agccaggaat ggtaattgga 2100
tacatagtac ttagaggcga tggtccaatt agcaataggg caattctagc tgaggaatac 2160
gatcccaaaa agcacaagta tgacgcagaa tattacatgg agaaccaggt tcttccagcg 2220
gtacttagga tattggaggg atttggatac agaaaggaag acctcagata ccaaaagaca 2280
agacaagtcg gcctaacttc ctggcttaac attaaaaaat cctag 2325

<210> SEQ ID NO 26
<211> LENGTH: 2319
<212> TYPE: DNA
<213> ORGANISM: Pyrococcus furiosus

<400> SEQUENCE: 26
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacgggggga aaggcatgga 180 aagattgtga gaattgttga tgtagagaag gttgagaaaa agtttctcgg caagcctatt 240
accgtgtgga aactttattt ggaacatccc caaactatta gagaaaaagt tagagaacat 300
ccagcagttg tggacatctt cgaatacgat attccatttg caaagagata cctcatcgac 360
aaaggcctaa taccaatgga gggggaagaa gagctaaaga ttcttgcctt cgatatagaa 420
accctctatc acgaaggaga agagtttgga aaaggcccaa ttataatgat tagttatgca 480
gatgaaaatg aagcaaaggt gattacttgg aaaaacatag atcttccata cgttgaggtt 540
gtatcaagcg agagagagat gataaagaga tttctcagga ttatcaggga gaaggatcct 600
gacattatag ttacttataa tggagactca ttcgcattcc catatttagc gaaaagggca 660
gaaaaacttg ggattaaatt aaccattgga agagatggaa gcgagcccaa gatgcagaga 720
ataggcgata tgacggctgt agaagtcaag ggaagaatac atttcgactt gtatcatgta 780
ataacaagga caataaatct cccaacatac acactagagg ctgtatatga agcaattttt 840
ggaaagccaa aggagaaggt atacgccgac gagatagcaa aagcctggga aagtggagag 900
aaccttgaga gagttgccaa atactcgatg gaagatgcaa aggcaactta tgaactcggg 960

```
aaagaattcc ttccaatgga aattcagctt tcaagattag ttggacaacc tttatgggat   1020

gtttcaaggt caagcacagg gaaccttgta gagtggttct tacttaggaa agcctacgaa   1080

agaaacgaag tagctccaaa caagccaagt gaagaggagt atcaaagaag gctcagggag   1140

agctacacag gtggattcgt taaagagcca gaaaaggggt tgtgggaaaa catagtatac   1200

ctagatttta gagccctata tccctcgatt ataattaccc acaatgtttc tcccgatact   1260

ctaaatcttg agggatgcaa gaactatgat atcgctcctc aagtaggcca caagttctgc   1320

aaggacatcc ctggttttat accaagtctc ttgggacatt tgttagagga aagacaaaag   1380

attaagacaa aaatgaagga aactcaagat cctatagaaa aaatactcct tgactataga   1440

caaaaagcga taaaactctt agcaaattct ttctacggat attatggcta tgcaaaagca   1500

agatggtact gtaaggagtg tgctgagagc gttactgcct ggggaagaaa gtacatcgag   1560

ttagtatgga aggagctcga agaaaagttt ggatttaaag tcctctacat tgacactgat   1620

ggtctctatg caactatccc aggaggagaa agtgaggaaa taaagaaaaa ggctctagaa   1680

tttgtaaaat acataaattc aaagctccct ggactgctag agcttgaata tgaagggttt   1740

tataagaggg gattcttcgt tacgaagaag aggtatgcag taatagatga agaaggaaaa   1800

gtcattactc gtggtttaga gatagttagg agagattgga gtgaaattgc aaaagaaact   1860

caagctagag ttttggagac aatactaaaa cacggagatg ttgaagaagc tgtgagaata   1920

gtaaaagaag taatacaaaa gcttgccaat tatgaaattc caccagagaa gctcgcaata   1980

tatgagcaga taacaagacc attacatgag tataaggcga taggtcctca cgtagctgtt   2040

gcaaagaaac tagctgctaa aggagttaaa ataaagccag gaatggtaat tggatacata   2100

gtacttagag gcgatggtcc aattagcaat agggcaattc tagctgagga atacgatccc   2160

aaaaagcaca agtatgacgc agaatattac atggagaacc aggttcttcc agcggtactt   2220

aggatattgg agggatttgg atacagaaag gaagacctca gataccaaaa gacaagacaa   2280

gtcggcctaa cttcctggct taacattaaa aaatcctag                          2319


<210> SEQ ID NO 27
<211> LENGTH: 775
<212> TYPE: PRT
<213> ORGANISM: Pyrococcus furiosus

<400> SEQUENCE: 27

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
```

-continued

```
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560
```

-continued

```
Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775
```

<210> SEQ ID NO 28
<211> LENGTH: 775
<212> TYPE: PRT
<213> ORGANISM: Pyrococcus sp.

<400> SEQUENCE: 28

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160
```

-continued

```
Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590
```

```
Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775


<210> SEQ ID NO 29
<211> LENGTH: 773
<212> TYPE: PRT
<213> ORGANISM: thermococcus gorgonarius

<400> SEQUENCE: 29

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190
```

```
Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
```

```
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 30
<211> LENGTH: 774
<212> TYPE: PRT
<213> ORGANISM: Pyrococcus sp.

<400> SEQUENCE: 30

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
```

-continued

```
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640
```

Arg Ile Val Lys Glu Val Thr Glu Lys Leu Ser Lys Tyr Glu Val Pro
645 650 655

Pro Glu Lys Leu Val Ile His Glu Gln Ile Thr Arg Asp Leu Lys Asp
660 665 670

Tyr Lys Ala Thr Gly Pro His Val Ala Val Ala Lys Arg Leu Ala Ala
675 680 685

Arg Gly Val Lys Ile Arg Pro Gly Thr Val Ile Ser Tyr Ile Val Leu
690 695 700

Lys Gly Ser Gly Arg Ile Gly Asp Arg Ala Ile Pro Phe Asp Glu Phe
705 710 715 720

Asp Pro Thr Lys His Lys Tyr Asp Ala Glu Tyr Tyr Ile Glu Asn Gln
725 730 735

Val Leu Pro Ala Val Glu Arg Ile Leu Arg Ala Phe Gly Tyr Arg Lys
740 745 750

Glu Asp Leu Arg Tyr Gln Lys Thr Arg Gln Val Gly Leu Ser Ala Trp
755 760 765

Leu Lys Pro Lys Gly Thr
770

<210> SEQ ID NO 31
<211> LENGTH: 774
<212> TYPE: PRT
<213> ORGANISM: thermococcus litoralis

<400> SEQUENCE: 31

Met Ile Leu Asp Thr Asp Tyr Ile Thr Lys Asp Gly Lys Pro Ile Ile
1 5 10 15

Arg Ile Phe Lys Lys Glu Asn Gly Glu Phe Lys Ile Glu Leu Asp Pro
20 25 30

His Phe Gln Pro Tyr Ile Tyr Ala Leu Leu Lys Asp Asp Ser Ala Ile
35 40 45

Glu Glu Ile Lys Ala Ile Lys Gly Glu Arg His Gly Lys Thr Val Arg
50 55 60

Val Leu Asp Ala Val Lys Val Arg Lys Lys Phe Leu Gly Arg Glu Val
65 70 75 80

Glu Val Trp Lys Leu Ile Phe Glu His Pro Gln Asp Val Pro Ala Met
85 90 95

Arg Gly Lys Ile Arg Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Leu Leu Ala Phe Asp Ile Glu Thr
130 135 140

Phe Tyr His Glu Gly Asp Glu Phe Gly Lys Gly Glu Ile Ile Met Ile
145 150 155 160

Ser Tyr Ala Asp Glu Glu Glu Ala Arg Val Ile Thr Trp Lys Asn Ile
165 170 175

Asp Leu Pro Tyr Val Asp Val Val Ser Asn Glu Arg Glu Met Ile Lys
180 185 190

Arg Phe Val Gln Val Val Lys Glu Lys Asp Pro Asp Val Ile Ile Thr
195 200 205

Tyr Asn Gly Asp Asn Phe Asp Leu Pro Tyr Leu Ile Lys Arg Ala Glu
210 215 220

Lys Leu Gly Val Arg Leu Val Leu Gly Arg Asp Lys Glu His Pro Glu
225 230 235 240

-continued

```
Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670
```

Leu Lys Asp Tyr Lys Ala Ile Gly Pro His Val Ala Ile Ala Lys Arg
675 680 685

Leu Ala Ala Arg Gly Ile Lys Val Lys Pro Gly Thr Ile Ile Ser Tyr
690 695 700

Ile Val Leu Lys Gly Ser Gly Lys Ile Ser Asp Arg Val Ile Leu Leu
705 710 715 720

Thr Glu Tyr Asp Pro Arg Lys His Lys Tyr Asp Pro Asp Tyr Tyr Ile
725 730 735

Glu Asn Gln Val Leu Pro Ala Val Leu Arg Ile Leu Glu Ala Phe Gly
740 745 750

Tyr Arg Lys Glu Asp Leu Arg Tyr Gln Ser Ser Lys Gln Thr Gly Leu
755 760 765

Asp Ala Trp Leu Lys Arg
770

<210> SEQ ID NO 32
<211> LENGTH: 776
<212> TYPE: PRT
<213> ORGANISM: Thermococcus sp.

<400> SEQUENCE: 32

Met Ile Leu Asp Val Asp Tyr Ile Thr Glu Asn Gly Lys Pro Val Ile
1 5 10 15

Arg Val Phe Lys Lys Glu Asn Gly Glu Phe Arg Ile Glu Tyr Asp Arg
20 25 30

Glu Phe Glu Pro Tyr Phe Tyr Ala Leu Leu Arg Asp Asp Ser Ala Ile
35 40 45

Glu Glu Ile Lys Lys Ile Thr Ala Glu Arg His Gly Arg Val Val Lys
50 55 60

Val Lys Arg Ala Glu Lys Val Lys Lys Lys Phe Leu Gly Arg Ser Val
65 70 75 80

Glu Val Trp Val Leu Tyr Phe Thr His Pro Gln Asp Val Pro Ala Ile
85 90 95

Arg Asp Lys Ile Arg Lys His Pro Ala Val Ile Asp Ile Tyr Glu Tyr
100 105 110

Asp Ile Pro Phe Ala Lys Arg Tyr Leu Ile Asp Lys Gly Leu Ile Pro
115 120 125

Met Glu Gly Glu Glu Glu Leu Lys Leu Met Ser Phe Asp Ile Glu Thr
130 135 140

Leu Tyr His Glu Gly Glu Glu Phe Gly Thr Gly Pro Ile Leu Met Ile
145 150 155 160

Ser Tyr Ala Asp Glu Ser Glu Ala Arg Val Ile Thr Trp Lys Lys Ile
165 170 175

Asp Leu Pro Tyr Val Glu Val Val Ser Thr Glu Lys Glu Met Ile Lys
180 185 190

Arg Phe Leu Arg Val Val Lys Glu Lys Asp Pro Asp Val Leu Ile Thr
195 200 205

Tyr Asn Gly Asp Asn Phe Asp Phe Ala Tyr Leu Lys Lys Arg Cys Glu
210 215 220

Lys Leu Gly Val Ser Phe Thr Leu Gly Arg Asp Gly Ser Glu Pro Lys
225 230 235 240

Ile Gln Arg Met Gly Asp Arg Phe Ala Val Glu Val Lys Gly Arg Val
245 250 255

His Phe Asp Leu Tyr Pro Val Ile Arg Arg Thr Ile Asn Leu Pro Thr
260 265 270

```
Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
```

-continued 690 695 700

Lys Gly Ser Gly Arg Ile Gly Asp Arg Ala Ile Pro Phe Asp Glu Phe
705 710 715 720

Asp Pro Thr Lys His Lys Tyr Asp Ala Asp Tyr Tyr Ile Glu Asn Gln
725 730 735

Val Leu Pro Ala Val Glu Arg Ile Leu Arg Ala Phe Gly Tyr Arg Lys
740 745 750

Glu Asp Leu Arg Tyr Gln Lys Thr Arg Gln Val Gly Leu Gly Ala Trp
755 760 765

Leu Lys Pro Lys Gly Lys Lys Lys
770 775

<210> SEQ ID NO 33
<211> LENGTH: 775
<212> TYPE: PRT
<213> ORGANISM: Pyrococcus furiosus

<400> SEQUENCE: 33

Met Ile Leu Asp Val Asp Tyr Ile Thr Glu Glu Gly Lys Pro Val Ile
1 5 10 15

Arg Leu Phe Lys Lys Glu Asn Gly Lys Phe Lys Ile Glu His Asp Arg
20 25 30

Thr Phe Arg Pro Tyr Ile Tyr Ala Leu Leu Arg Asp Asp Ser Lys Ile
35 40 45

Glu Glu Val Lys Lys Ile Thr Gly Glu Arg His Gly Lys Ile Val Arg
50 55 60

Ile Val Asp Val Glu Lys Val Glu Lys Lys Phe Leu Gly Lys Pro Ile
65 70 75 80

Thr Val Trp Lys Leu Tyr Leu Glu His Pro Gln Asp Val Pro Thr Ile
85 90 95

Arg Glu Lys Val Arg Glu His Pro Ala Val Val Asp Ile Phe Glu Tyr
100 105 110

Asp Ile Pro Phe Ala Lys Arg Tyr Leu Ile Asp Lys Gly Leu Ile Pro
115 120 125

Met Glu Gly Glu Glu Glu Leu Lys Ile Leu Ala Phe Asp Ile Glu Thr
130 135 140

Leu Tyr His Glu Gly Glu Glu Phe Gly Lys Gly Pro Ile Ile Met Ile
145 150 155 160

Ser Tyr Ala Asp Glu Asn Glu Ala Lys Val Ile Thr Trp Lys Asn Ile
165 170 175

Asp Leu Pro Tyr Val Glu Val Val Ser Ser Glu Arg Glu Met Ile Lys
180 185 190

Arg Phe Leu Arg Ile Ile Arg Glu Lys Asp Pro Asp Ile Ile Val Thr
195 200 205

Tyr Asn Gly Asp Ser Phe Asp Phe Pro Tyr Leu Ala Lys Arg Ala Glu
210 215 220

Lys Leu Gly Ile Lys Leu Thr Ile Gly Arg Asp Gly Ser Glu Pro Lys
225 230 235 240

Met Gln Arg Ile Gly Asp Met Thr Ala Val Glu Val Lys Gly Arg Ile
245 250 255

His Phe Asp Leu Tyr His Val Ile Thr Arg Thr Ile Asn Leu Pro Thr
260 265 270

Tyr Thr Leu Glu Ala Val Tyr Glu Ala Ile Phe Gly Lys Pro Lys Glu
275 280 285

Lys Val Tyr Ala Asp Glu Ile Ala Lys Ala Trp Glu Ser Gly Glu Asn

-continued

```
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720
```

```
Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775
```

<210> SEQ ID NO 34
<211> LENGTH: 775
<212> TYPE: PRT
<213> ORGANISM: Pyrococcus furiosus

<400> SEQUENCE: 34

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320
```

```
Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750
```

Lys Glu Asp Leu Arg Tyr Gln Lys Thr Arg Gln Val Gly Leu Thr Ser
755 760 765

Trp Leu Asn Ile Lys Lys Ser
770 775

<210> SEQ ID NO 35
<211> LENGTH: 774
<212> TYPE: PRT
<213> ORGANISM: Pyrococcus furiosus

<400> SEQUENCE: 35

Met Ile Leu Asp Val Asp Tyr Ile Thr Glu Glu Gly Lys Pro Val Ile
1 5 10 15

Arg Leu Phe Lys Lys Glu Asn Gly Lys Phe Lys Ile Glu His Asp Arg
20 25 30

Thr Phe Arg Pro Tyr Ile Tyr Ala Leu Leu Arg Asp Asp Ser Lys Ile
35 40 45

Glu Glu Val Lys Lys Ile Thr Gly Glu Arg His Gly Lys Ile Val Arg
50 55 60

Ile Val Asp Val Glu Lys Val Glu Lys Lys Phe Leu Gly Lys Pro Ile
65 70 75 80

Thr Val Trp Lys Leu Tyr Leu Glu His Pro Gln Asp Pro Thr Ile Arg
85 90 95

Glu Lys Val Arg Glu His Pro Ala Val Val Asp Ile Phe Glu Tyr Asp
100 105 110

Ile Pro Phe Ala Lys Arg Tyr Leu Ile Asp Lys Gly Leu Ile Pro Met
115 120 125

Glu Gly Glu Glu Glu Leu Lys Ile Leu Ala Phe Asp Ile Glu Thr Leu
130 135 140

Tyr His Glu Gly Glu Glu Phe Gly Lys Gly Pro Ile Ile Met Ile Ser
145 150 155 160

Tyr Ala Asp Glu Asn Glu Ala Lys Val Ile Thr Trp Lys Asn Ile Asp
165 170 175

Leu Pro Tyr Val Glu Val Val Ser Ser Glu Arg Glu Met Ile Lys Arg
180 185 190

Phe Leu Arg Ile Ile Arg Glu Lys Asp Pro Asp Ile Ile Val Thr Tyr
195 200 205

Asn Gly Asp Ser Phe Asp Phe Pro Tyr Leu Ala Lys Arg Ala Glu Lys
210 215 220

Leu Gly Ile Lys Leu Thr Ile Gly Arg Asp Gly Ser Glu Pro Lys Met
225 230 235 240

Gln Arg Ile Gly Asp Met Thr Ala Val Glu Val Lys Gly Arg Ile His
245 250 255

Phe Asp Leu Tyr His Val Ile Thr Arg Thr Ile Asn Leu Pro Thr Tyr
260 265 270

Thr Leu Glu Ala Val Tyr Glu Ala Ile Phe Gly Lys Pro Lys Glu Lys
275 280 285

Val Tyr Ala Asp Glu Ile Ala Lys Ala Trp Glu Ser Gly Glu Asn Leu
290 295 300

Glu Arg Val Ala Lys Tyr Ser Met Glu Asp Ala Lys Ala Thr Tyr Glu
305 310 315 320

Leu Gly Lys Glu Phe Leu Pro Met Glu Ile Gln Leu Ser Arg Leu Val
325 330 335

Gly Gln Pro Leu Trp Asp Val Ser Arg Ser Ser Thr Gly Asn Leu Val
340 345 350

-continued

```
Glu Trp Phe Leu Leu Arg Lys Ala Tyr Glu Arg Asn Glu Val Ala Pro
        355                 360                 365

Asn Lys Pro Ser Glu Glu Glu Tyr Gln Arg Arg Leu Arg Glu Ser Tyr
    370                 375                 380

Thr Gly Gly Phe Val Lys Glu Pro Glu Lys Gly Leu Trp Glu Asn Ile
385                 390                 395                 400

Val Tyr Leu Asp Phe Arg Ala Leu Tyr Pro Ser Ile Ile Ile Thr His
                405                 410                 415

Asn Val Ser Pro Asp Thr Leu Asn Leu Glu Gly Cys Lys Asn Tyr Asp
            420                 425                 430

Ile Ala Pro Gln Val Gly His Lys Phe Cys Lys Asp Ile Pro Gly Phe
        435                 440                 445

Ile Pro Ser Leu Leu Gly His Leu Leu Glu Glu Arg Gln Lys Ile Lys
    450                 455                 460

Thr Lys Met Lys Glu Thr Gln Asp Pro Ile Glu Lys Ile Leu Leu Asp
465                 470                 475                 480

Tyr Arg Gln Lys Ala Ile Lys Leu Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Lys Tyr Ile Glu Leu Val Trp Lys Glu Leu
        515                 520                 525

Glu Glu Lys Phe Gly Phe Lys Val Leu Tyr Ile Asp Thr Asp Gly Leu
    530                 535                 540

Tyr Ala Thr Ile Pro Gly Gly Glu Ser Glu Glu Ile Lys Lys Lys Ala
545                 550                 555                 560

Leu Glu Phe Val Lys Tyr Ile Asn Ser Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Arg Tyr Ala Val Ile Asp Glu Glu Gly Lys Val Ile Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Thr Ile Leu Lys His Gly Asp Val Glu Glu Ala Val
625                 630                 635                 640

Arg Ile Val Lys Glu Val Ile Gln Lys Leu Ala Asn Tyr Glu Ile Pro
                645                 650                 655

Pro Glu Lys Leu Ala Ile Tyr Glu Gln Ile Thr Arg Pro Leu His Glu
            660                 665                 670

Tyr Lys Ala Ile Gly Pro His Val Ala Val Ala Lys Lys Leu Ala Ala
        675                 680                 685

Lys Gly Val Lys Ile Lys Pro Gly Met Val Ile Gly Tyr Ile Val Leu
    690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
                725                 730                 735

Val Leu Pro Ala Val Leu Arg Ile Leu Glu Gly Phe Gly Tyr Arg Lys
            740                 745                 750

Glu Asp Leu Arg Tyr Gln Lys Thr Arg Gln Val Gly Leu Thr Ser Trp
        755                 760                 765

Leu Asn Ile Lys Lys Ser
```

770

<210> SEQ ID NO 36
<211> LENGTH: 772
<212> TYPE: PRT
<213> ORGANISM: Pyrococcus furiosus

<400> SEQUENCE: 36

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Thr Ile Arg Glu Lys
                85                  90                  95

Val Arg Glu His Pro Ala Val Val Asp Ile Phe Glu Tyr Asp Ile Pro
            100                 105                 110

Phe Ala Lys Arg Tyr Leu Ile Asp Lys Gly Leu Ile Pro Met Glu Gly
        115                 120                 125

Glu Glu Glu Leu Lys Ile Leu Ala Phe Asp Ile Glu Thr Leu Tyr His
    130                 135                 140

Glu Gly Glu Glu Phe Gly Lys Gly Pro Ile Ile Met Ile Ser Tyr Ala
145                 150                 155                 160

Asp Glu Asn Glu Ala Lys Val Ile Thr Trp Lys Asn Ile Asp Leu Pro
                165                 170                 175

Tyr Val Glu Val Val Ser Ser Glu Arg Glu Met Ile Lys Arg Phe Leu
            180                 185                 190

Arg Ile Ile Arg Glu Lys Asp Pro Asp Ile Ile Val Thr Tyr Asn Gly
        195                 200                 205

Asp Ser Phe Asp Phe Pro Tyr Leu Ala Lys Arg Ala Glu Lys Leu Gly
    210                 215                 220

Ile Lys Leu Thr Ile Gly Arg Asp Gly Ser Glu Pro Lys Met Gln Arg
225                 230                 235                 240

Ile Gly Asp Met Thr Ala Val Glu Val Lys Gly Arg Ile His Phe Asp
                245                 250                 255

Leu Tyr His Val Ile Thr Arg Thr Ile Asn Leu Pro Thr Tyr Thr Leu
            260                 265                 270

Glu Ala Val Tyr Glu Ala Ile Phe Gly Lys Pro Lys Glu Lys Val Tyr
        275                 280                 285

Ala Asp Glu Ile Ala Lys Ala Trp Glu Ser Gly Glu Asn Leu Glu Arg
    290                 295                 300

Val Ala Lys Tyr Ser Met Glu Asp Ala Lys Ala Thr Tyr Glu Leu Gly
305                 310                 315                 320

Lys Glu Phe Leu Pro Met Glu Ile Gln Leu Ser Arg Leu Val Gly Gln
                325                 330                 335

Pro Leu Trp Asp Val Ser Arg Ser Ser Thr Gly Asn Leu Val Glu Trp
            340                 345                 350

Phe Leu Leu Arg Lys Ala Tyr Glu Arg Asn Glu Val Ala Pro Asn Lys
        355                 360                 365

Pro Ser Glu Glu Glu Tyr Gln Arg Arg Leu Arg Glu Ser Tyr Thr Gly

```
    370                 375                 380

Gly Phe Val Lys Glu Pro Glu Lys Gly Leu Trp Glu Asn Ile Val Tyr
385                 390                 395                 400

Leu Asp Phe Arg Ala Leu Tyr Pro Ser Ile Ile Ile Thr His Asn Val
                405                 410                 415

Ser Pro Asp Thr Leu Asn Leu Glu Gly Cys Lys Asn Tyr Asp Ile Ala
            420                 425                 430

Pro Gln Val Gly His Lys Phe Cys Lys Asp Ile Pro Gly Phe Ile Pro
        435                 440                 445

Ser Leu Leu Gly His Leu Leu Glu Glu Arg Gln Lys Ile Lys Thr Lys
    450                 455                 460

Met Lys Glu Thr Gln Asp Pro Ile Glu Lys Ile Leu Leu Asp Tyr Arg
465                 470                 475                 480

Gln Lys Ala Ile Lys Leu Leu Ala Asn Ser Phe Tyr Gly Tyr Tyr Gly
                485                 490                 495

Tyr Ala Lys Ala Arg Trp Tyr Cys Lys Glu Cys Ala Glu Ser Val Thr
            500                 505                 510

Ala Trp Gly Arg Lys Tyr Ile Glu Leu Val Trp Lys Glu Leu Glu Glu
        515                 520                 525

Lys Phe Gly Phe Lys Val Leu Tyr Ile Asp Thr Asp Gly Leu Tyr Ala
    530                 535                 540

Thr Ile Pro Gly Gly Glu Ser Glu Glu Ile Lys Lys Lys Ala Leu Glu
545                 550                 555                 560

Phe Val Lys Tyr Ile Asn Ser Lys Leu Pro Gly Leu Leu Glu Leu Glu
                565                 570                 575

Tyr Glu Gly Phe Tyr Lys Arg Gly Phe Phe Val Thr Lys Lys Arg Tyr
            580                 585                 590

Ala Val Ile Asp Glu Glu Gly Lys Val Ile Thr Arg Gly Leu Glu Ile
        595                 600                 605

Val Arg Arg Asp Trp Ser Glu Ile Ala Lys Glu Thr Gln Ala Arg Val
    610                 615                 620

Leu Glu Thr Ile Leu Lys His Gly Asp Val Glu Glu Ala Val Arg Ile
625                 630                 635                 640

Val Lys Glu Val Ile Gln Lys Leu Ala Asn Tyr Glu Ile Pro Pro Glu
                645                 650                 655

Lys Leu Ala Ile Tyr Glu Gln Ile Thr Arg Pro Leu His Glu Tyr Lys
            660                 665                 670

Ala Ile Gly Pro His Val Ala Val Ala Lys Lys Leu Ala Ala Lys Gly
        675                 680                 685

Val Lys Ile Lys Pro Gly Met Val Ile Gly Tyr Ile Val Leu Arg Gly
    690                 695                 700

Asp Gly Pro Ile Ser Asn Arg Ala Ile Leu Ala Glu Glu Tyr Asp Pro
705                 710                 715                 720

Lys Lys His Lys Tyr Asp Ala Glu Tyr Tyr Ile Glu Asn Gln Val Leu
                725                 730                 735

Pro Ala Val Leu Arg Ile Leu Glu Gly Phe Gly Tyr Arg Lys Glu Asp
            740                 745                 750

Leu Arg Tyr Gln Lys Thr Arg Gln Val Gly Leu Thr Ser Trp Leu Asn
        755                 760                 765

Ile Lys Lys Ser
    770
```

<210> SEQ ID NO 37
<211> LENGTH: 2322

-continued

<212> TYPE: DNA
<213> ORGANISM: Thermococcus gorgonarius
<220> FEATURE:
<221> NAME/KEY: CDS
<222> LOCATION: (1)..(2322)
<220> FEATURE:
<221> NAME/KEY: misc_feature
<222> LOCATION: (277)..(279)
<223> OTHER INFORMATION: Tgo93 (R): nnn = AGA, AGG, CGA, CGC, CGG, CGT; Tgo 93 (E): nnn = GAA, GAG; Tgo93 (D): nnn = GAT, GAC (D) ;Tgo93 (K): nnn = AAA, AAG (K) ; Tgo93 (Q): nnn = CAA, CAG (Q) ; Tgo93 (N): nnn = AAC, AAU (N)

<400> SEQUENCE: 37

```
atg atc ctc gat aca gac tac ata act gag gat gga aag ccc gtc atc       48
Met Ile Leu Asp Thr Asp Tyr Ile Thr Glu Asp Gly Lys Pro Val Ile
1               5                   10                  15

agg atc ttc aag aag gag aac ggc gag ttc aaa ata gac tac gac aga       96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att      144
Asn Phe Glu Pro Tyr Ile Tyr Ala Leu Leu Lys Asp Asp Ser Ala Ile
        35                  40                  45

gag gac gtc aag aag ata act gcc gag agg cac ggc act acc gtt agg      192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata      240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc      288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac      336
Arg Asp Lys Ile Lys Glu His Pro Ala Val Val Asp Ile Tyr Glu Tyr
            100                 105                 110

gac atc ccc ttc gcg aag cgc tac ctc ata gac aaa ggc tta atc ccg      384
Asp Ile Pro Phe Ala Lys Arg Tyr Leu Ile Asp Lys Gly Leu Ile Pro
        115                 120                 125

atg gag ggc gac gag gaa ctt aag atg ctc gcc ttc gac atc gag acg      432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata      480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc      528
Ser Tyr Ala Asp Glu Glu Gly Ala Arg Val Ile Thr Trp Lys Asn Ile
                165                 170                 175

gac ctt ccc tat gtc gac gtc gtt tcc acc gag aag gag atg ata aag      576
Asp Leu Pro Tyr Val Asp Val Val Ser Thr Glu Lys Glu Met Ile Lys
            180                 185                 190

cgc ttc ctc aag gtc gtc aag gaa aag gat ccc gac gtc ctc ata acc      624
Arg Phe Leu Lys Val Val Lys Glu Lys Asp Pro Asp Val Leu Ile Thr
        195                 200                 205

tac aac ggc gac aac ttc gac ttc gcc tac ctc aag aag cgc tcc gag      672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa      720
Lys Leu Gly Val Lys Phe Ile Leu Gly Arg Glu Gly Ser Glu Pro Lys
225                 230                 235                 240

atc cag cgc atg ggc gat cgc ttt gcg gtg gag gtc aag gga agg att      768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act      816
```

-continued

```
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag      864
Tyr Thr Leu Glu Ala Val Tyr Glu Ala Ile Phe Gly Gln Pro Lys Glu
        275                 280                 285

aag gtc tac gct gag gag ata gcg cag gcc tgg gaa acg ggc gag gga      912
Lys Val Tyr Ala Glu Glu Ile Ala Gln Ala Trp Glu Thr Gly Glu Gly
    290                 295                 300

tta gaa agg gtg gcc cgc tac tcg atg gag gac gca aag gta acc tat      960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                325                 330                 335

gta ggc cag agc ctc tgg gat gta tct cgc tcg agt acc gga aac ctc     1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
        355                 360                 365

cca aac aag ccg gac gag agg gag ctg gca aga aga agg gag agc tac     1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc     1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat     1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac     1296
Asn Val Ser Pro Asp Thr Leu Asn Arg Glu Gly Cys Glu Glu Tyr Asp
            420                 425                 430

gtg gct cct cag gta ggc cat aag ttc tgc aag gac ttc ccc ggc ttc     1344
Val Ala Pro Gln Val Gly His Lys Phe Cys Lys Asp Phe Pro Gly Phe
        435                 440                 445

atc cca agc ctc ctc gga gac ctc ttg gag gag aga cag aag gta aag     1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat     1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac     1488
Tyr Arg Gln Arg Ala Ile Lys Ile Leu Ala Asn Ser Phe Tyr Gly Tyr
                485                 490                 495

tac ggc tat gca aag gcc cgc tgg tac tgc aag gag tgc gcc gag agc     1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata     1584
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt     1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca     1680
Phe Ala Thr Ile Pro Gly Ala Asp Ala Glu Thr Val Lys Lys Lys Ala
545                 550                 555                 560

aag gag ttc ctg gac tac atc aac gcc aaa ctg ccc ggc ctg ctc gaa     1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag     1776
```

```
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt     1824
Lys Tyr Ala Val Ile Asp Glu Glu Asp Lys Ile Thr Thr Arg Gly Leu
        595                 600                 605

gaa ata gtt agg cgt gac tgg agc gag ata gcg aag gag acg cag gcg     1872
Glu Ile Val Arg Arg Asp Trp Ser Glu Ile Ala Lys Glu Thr Gln Ala
    610                 615                 620

agg gtt ctt gag gcg ata cta aag cac ggt gac gtt gaa gaa gcg gta     1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca     1968
Arg Ile Val Lys Glu Val Thr Glu Lys Leu Ser Lys Tyr Glu Val Pro
            645                 650                 655

ccg gag aag ctg gtc atc tac gag cag ata acc cgc gac ctg aag gac     2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca     2064
Tyr Lys Ala Thr Gly Pro His Val Ala Val Ala Lys Arg Leu Ala Ala
        675                 680                 685

agg ggg ata aaa atc cgg ccc gga acg gtc ata agc tac atc gtg ctc     2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt     2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag     2208
Asp Pro Ala Lys His Lys Tyr Asp Ala Glu Tyr Tyr Ile Glu Asn Gln
            725                 730                 735

gtt ctt cca gct gtg gag agg att ctg agg gcc ttt ggt tac cgt aaa     2256
Val Leu Pro Ala Val Glu Arg Ile Leu Arg Ala Phe Gly Tyr Arg Lys
            740                 745                 750

gaa gat tta agg tat cag aaa acg cgg cag gtt ggc ttg ggg gcg tgg     2304
Glu Asp Leu Arg Tyr Gln Lys Thr Arg Gln Val Gly Leu Gly Ala Trp
        755                 760                 765

cta aaa cct aag aca tga                                             2322
Leu Lys Pro Lys Thr
    770


<210> SEQ ID NO 38
<211> LENGTH: 773
<212> TYPE: PRT
<213> ORGANISM: Thermococcus gorgonarius
<220> FEATURE:
<221> NAME/KEY: misc_feature
<222> LOCATION: (93)..(93)
<223> OTHER INFORMATION: The 'Xaa' at location 93 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 38

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80
```

-continued

```
Glu Val Trp Lys Leu Tyr Phe Thr His Pro Gln Asp Xaa Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510
```

-continued

```
Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 39
<211> LENGTH: 775
<212> TYPE: PRT
<213> ORGANISM: Pyrococcus furiosus

<400> SEQUENCE: 39

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110
```

-continued

```
Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
```

-continued

```
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 40
<211> LENGTH: 3499
<212> TYPE: DNA
<213> ORGANISM: Pyrococcus furiosus
<220> FEATURE:
<221> NAME/KEY: misc_feature
<222> LOCATION: (2788)..(2789)
<223> OTHER INFORMATION: n= A, T, G or C
<220> FEATURE:
<221> NAME/KEY: misc_feature
<222> LOCATION: (3287)..(3289)
<223> OTHER INFORMATION: n= A, T, G or C
<220> FEATURE:
<221> NAME/KEY: misc_feature
<222> LOCATION: (3290)..(3292)
<223> OTHER INFORMATION: n= A, T, G or C
<220> FEATURE:
<221> NAME/KEY: misc_feature
<222> LOCATION: (3473)..(3473)
<223> OTHER INFORMATION: n= A, T, G or C
<220> FEATURE:
<221> NAME/KEY: misc_feature
<222> LOCATION: (3478)..(3478)
<223> OTHER INFORMATION: n= A, T, G or C

<400> SEQUENCE: 40

ccctggtcct gggtccacat atatgttctt actcgccttt atgaagaatc ccccagtcgc     60

tctaacctgg gttatagtga caaatcttcc tccaccaccg cccaagaagg ttatttctat    120

caactctaca cctcccctat tttctctctt atgagatttt taagtatagt tatagagaag    180
```

-continued

```
gttttatact ccaaactgag ttagtagata tgtggggagc ataatgattt tagatgtgga    240
ttacataact gaagaaggaa aacctgttat taggctattc aaaaaagaga acggaaaatt    300
taagatagag catgatagaa cttttagacc atacatttac gctcttctca gggatgattc    360
aaagattgaa gaagttaaga aaataacggg ggaaaggcat ggaaagattg tgagaattgt    420
tgatgtagag aaggttgaga aaaagtttct cggcaagcct attaccgtgt ggaaacttta    480
tttggaacat ccccaagatg ttcccactat tagagaaaaa gttagagaac atccagcagt    540
tgtggacatc ttcgaatacg atattccatt tgcaaagaga tacctcatcg acaaaggcct    600
aataccaatg gagggggaag aagagctaaa gattcttgcc ttcgatatag aaaccctcta    660
tcacgaagga gaagagtttg gaaaaggccc aattataatg attagttatg cagatgaaaa    720
tgaagcaaag gtgattactt ggaaaaacat agatcttcca tacgttgagg ttgtatcaag    780
cgagagagag atgataaaga gatttctcag gattatcagg gagaaggatc ctgacattat    840
agttacttat aatggagact cattcgactt cccatattta gcgaaaaggg cagaaaaact    900
tgggattaaa ttaaccattg gaagagatgg aagcgagccc aagatgcaga gaataggcga    960
tatgacggct gtagaagtca agggaagaat acatttcgac ttgtatcatg taataacaag   1020
gacaataaat ctcccaacat acacactaga ggctgtatat gaagcaattt ttggaaagcc   1080
aaaggagaag gtatacgccg acgagatagc aaaagcctgg gaaagtggag agaaccttga   1140
gagagttgcc aaatactcga tggaagatgc aaaggcaact tatgaactcg ggaaagaatt   1200
ccttccaatg gaaattcagc tttcaagatt agttggacaa cctttatggg atgtttcaag   1260
gtcaagcaca gggaaccttg tagagtggtt cttacttagg aaagcctacg aaagaaacga   1320
agtagctcca aacaagccaa gtgaagagga gtatcaaaga aggctcaggg agagctacac   1380
aggtggattc gttaaagagc cagaaaaggg gttgtgggaa aacatagtat acctagattt   1440
tagagcccta tatccctcga ttataattac ccacaatgtt tctcccgata ctctaaatct   1500
tgagggatgc aagaactatg atatcgctcc tcaagtaggc cacaagttct gcaaggacat   1560
ccctggtttt ataccaagtc tcttgggaca tttgttagag gaaagacaaa agattaagac   1620
aaaaatgaag gaaactcaag atcctataga aaaaatactc cttgactata gacaaaaagc   1680
gataaaactc ttagcaaatt ctttctacgg atattatggc tatgcaaaag caagatggta   1740
ctgtaaggag tgtgctgaga gcgttactgc ctggggaaga aagtacatcg agttagtatg   1800
gaaggagctc gaagaaaagt ttggatttaa agtcctctac attgacactg atggtctcta   1860
tgcaactatc ccaggaggag aaagtgagga aataaagaaa aaggctctag aatttgtaaa   1920
atacataaat tcaaagctcc ctggactgct agagcttgaa tatgaagggt tttataagag   1980
gggattcttc gttacgaaga agaggtatgc agtaatagat gaagaaggaa aagtcattac   2040
tcgtggttta gagatagtta ggagagattg gagtgaaatt gcaaaagaaa ctcaagctag   2100
agttttggag acaatactaa aacacggaga tgttgaagaa gctgtgagaa tagtaaaaga   2160
agtaatacaa aagcttgcca attatgaaat tccaccagag aagctcgcaa tatatgagca   2220
gataacaaga ccattacatg agtataaggc gataggtcct cacgtagctg ttgcaaagaa   2280
actagctgct aaaggagtta aaataaagcc aggaatggta attggataca tagtacttag   2340
aggcgatggt ccaattagca atagggcaat tctagctgag gaatacgatc ccaaaaagca   2400
caagtatgac gcagaatatt acattgagaa ccaggttctt ccagcggtac ttaggatatt   2460
ggagggattt ggatacagaa aggaagacct cagataccaa aagacaagac aagtcggcct   2520
aacttcctgg cttaacatta aaaaatccta gaaaagcgat agatatcaac ttttattctt   2580
```

-continued

```
tctaaccttt ttctatgaaa gaagaactga gcaggaatta ccagttcttc cgttatttta   2640

tgggtaatta aaaacccatg ctcttgggag aatcttcgaa taaaatccct aacttcaggc   2700

tttgctaagt gaatagaata aacaacatca ctcacttcaa acgccttcgt tagaaatggt   2760

ctatctgcat gcttctctgg ctcggaanng gaggattcat aacaacagta tcaacattct   2820

cagagaattg agaaacatca gaaactttga cttctacaac atttctaact ttgcaactct   2880

tcaagatttt ctaaaagaat tttaacggcc tcctcgtcaa tttcgacgac gtagatcttt   2940

tttgctccaa gcagagccgc tccaatggat aacacccctg ttcccgcacc caagtccgct   3000

acaatttttt ccttgtatct cctaatgtat aagcaagcca aaggagagta gatgctacct   3060

ttccgggagt tttgtattgc tctagccaag gtttgggatt tttgaatcct ttaactctgg   3120

aaagtataat ttcaagctcc ttcttcttca tgacagatga aaaattgttt tgtctctttt   3180

taacttttac agaaataact gtctcaaatt atgacaactc ttgacatttt tacttcatta   3240

ccagggtaat gtttttaagt atgaaatttt tctttcatag aggaggnnnn nngtcctctc   3300

ctcgatttcc ttggttgtgc tccatatgat aagcttccaa agtgggtgtt cagactttta   3360

gacactcaaa taccagacga caatggtgtg ctcactcaag ccccatatgg gttgagaaaa   3420

gtagaagcgg cactactcag atgcttcccc aggaatgagg ttgttgtagc tcntcccnga   3480

aagattgaga tgttcttgg                                                3499
```

<210> SEQ ID NO 41
<211> LENGTH: 25
<212> TYPE: DNA
<213> ORGANISM: Artificial sequence
<220> FEATURE:
<223> OTHER INFORMATION: primer

<400> SEQUENCE: 41

```
ggaatgaagt tatccccgct tcccc                                           25
```

<210> SEQ ID NO 42
<211> LENGTH: 22
<212> TYPE: DNA
<213> ORGANISM: Artificial sequence
<220> FEATURE:
<223> OTHER INFORMATION: primer

<400> SEQUENCE: 42

```
ccagttcatt cagcgtattc ag                                              22
```

<210> SEQ ID NO 43
<211> LENGTH: 31
<212> TYPE: DNA
<213> ORGANISM: Artificial sequence
<220> FEATURE:
<223> OTHER INFORMATION: primer

<400> SEQUENCE: 43

```
gaacatcccc aagataaacc cactattaga g                                    31
```

<210> SEQ ID NO 44
<211> LENGTH: 31
<212> TYPE: DNA
<213> ORGANISM: Artificial sequence
<220> FEATURE:
<223> OTHER INFORMATION: primer

<400> SEQUENCE: 44

```
ctctaatagt gggtttatct tggggatgtt c                                    31
```

-continued

<210> SEQ ID NO 45
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5' phosphate

<400> SEQUENCE: 45
gaacatcccc aagatgcacc cactattaga gaaaaag 37

<210> SEQ ID NO 46
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 46
gaacatcccc aagatgaccc cactattaga gaaaaag 37

<210> SEQ ID NO 47
<211> LENGTH: 38
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 47
gaacatcccc aagattgccc ccactattag agaaaaag 38

<210> SEQ ID NO 48
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 48
gaacatcccc aagatatacc cactattaga gaaaaag 37

<210> SEQ ID NO 49
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 49
gaacatcccc aagatatgcc cactattaga gaaaaag 37

<210> SEQ ID NO 50
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 50
gaacatcccc aagatttccc cactattaga gaaaaag 37

<210> SEQ ID NO 51
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 51
gaacatcccc aagatcctcc cactattaga gaaaaag 37

<210> SEQ ID NO 52
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 52
gaacatcccc aagatagccc cactattaga gaaaaag 37

<210> SEQ ID NO 53
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 53
gaacatcccc aagatacacc cactattaga gaaaaag 37

<210> SEQ ID NO 54
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 54
gaacatcccc aagattaccc cactattaga gaaaaag 37

<210> SEQ ID NO 55
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 55
gaacatcccc aagattggcc cactattaga gaaaaag 37

<210> SEQ ID NO 56
<211> LENGTH: 35
<212> TYPE: DNA
<213> ORGANISM: Artificial sequence
<220> FEATURE:
<223> OTHER INFORMATION: primer

<400> SEQUENCE: 56
ctcatccgca ggaccagcca gcgataaggg acaag 35

<210> SEQ ID NO 57
<211> LENGTH: 35
<212> TYPE: DNA
<213> ORGANISM: Artificial sequence
<220> FEATURE:
<223> OTHER INFORMATION: primer

<400> SEQUENCE: 57
ctcatccgca ggaccgtcca gcgataaggg acaag 35

<210> SEQ ID NO 58
<211> LENGTH: 35
<212> TYPE: DNA
<213> ORGANISM: Artificial sequence
<220> FEATURE:
<223> OTHER INFORMATION: primer

<400> SEQUENCE: 58
ctcatccgca ggacaaacca gcgataaggg acaag 35

<210> SEQ ID NO 59
<211> LENGTH: 35
<212> TYPE: DNA
<213> ORGANISM: Artificial sequence
<220> FEATURE:
<223> OTHER INFORMATION: primer

<400> SEQUENCE: 59
ctcatccgca ggacaatcca gcgataaggg acaag 35

<210> SEQ ID NO 60
<211> LENGTH: 35
<212> TYPE: DNA
<213> ORGANISM: Artificial sequence
<220> FEATURE:
<223> OTHER INFORMATION: primer

<400> SEQUENCE: 60
ctcatccgca ggacgagcca gcgataaggg acaag 35

<210> SEQ ID NO 61
<211> LENGTH: 35

-continued

<212> TYPE: DNA
<213> ORGANISM: Artificial sequence
<220> FEATURE:
<223> OTHER INFORMATION: primer

<400> SEQUENCE: 61
ctcatccgca ggacgatcca gcgataaggg acaag 35

<210> SEQ ID NO 62
<211> LENGTH: 34
<212> TYPE: DNA
<213> ORGANISM: Artificial sequence
<220> FEATURE:
<223> OTHER INFORMATION: primer

<400> SEQUENCE: 62
cacccccagg accaacccgc aatcagggac aagg 34

<210> SEQ ID NO 63
<211> LENGTH: 34
<212> TYPE: DNA
<213> ORGANISM: Artificial sequence
<220> FEATURE:
<223> OTHER INFORMATION: primer

<400> SEQUENCE: 63
cacccccagg acagacccgc aatcagggac aagg 34

<210> SEQ ID NO 64
<211> LENGTH: 34
<212> TYPE: DNA
<213> ORGANISM: Artificial sequence
<220> FEATURE:
<223> OTHER INFORMATION: primer

<400> SEQUENCE: 64
cacccccagg acaatcccgc aatcagggac aagg 34

<210> SEQ ID NO 65
<211> LENGTH: 34
<212> TYPE: DNA
<213> ORGANISM: Artificial sequence
<220> FEATURE:
<223> OTHER INFORMATION: primer

<400> SEQUENCE: 65
cacccccagg acaaacccgc aatcagggac aagg 34

<210> SEQ ID NO 66
<211> LENGTH: 34
<212> TYPE: DNA
<213> ORGANISM: Artificial sequence
<220> FEATURE:
<223> OTHER INFORMATION: primer

<400> SEQUENCE: 66
cacccccagg acgaacccgc aatcagggac aagg 34

<210> SEQ ID NO 67
<211> LENGTH: 34
<212> TYPE: DNA
<213> ORGANISM: Artificial sequence
<220> FEATURE:
<223> OTHER INFORMATION: primer

<400> SEQUENCE: 67
cacccccagg acgaccccgc aatcagggac aagg 34

-continued

<210> SEQ ID NO 68
<211> LENGTH: 33
<212> TYPE: DNA
<213> ORGANISM: Artificial sequence
<220> FEATURE:
<223> OTHER INFORMATION: primer

<400> SEQUENCE: 68
acgcacccgc aggaccaacc ggcaatccgc gac 33

<210> SEQ ID NO 69
<211> LENGTH: 33
<212> TYPE: DNA
<213> ORGANISM: Artificial sequence
<220> FEATURE:
<223> OTHER INFORMATION: primer

<400> SEQUENCE: 69
acgcacccgc aggaccgtcc ggcaatccgc gac 33

<210> SEQ ID NO 70
<211> LENGTH: 33
<212> TYPE: DNA
<213> ORGANISM: Artificial sequence
<220> FEATURE:
<223> OTHER INFORMATION: primer

<400> SEQUENCE: 70
acgcacccgc aggacgagcc ggcaatccgc gac 33

<210> SEQ ID NO 71
<211> LENGTH: 33
<212> TYPE: DNA
<213> ORGANISM: Artificial sequence
<220> FEATURE:
<223> OTHER INFORMATION: primer

<400> SEQUENCE: 71
acgcacccgc aggacgatcc ggcaatccgc gac 33

<210> SEQ ID NO 72
<211> LENGTH: 33
<212> TYPE: DNA
<213> ORGANISM: Artificial sequence
<220> FEATURE:
<223> OTHER INFORMATION: primer

<400> SEQUENCE: 72
acgcacccgc aggacaaacc ggcaatccgc gac 33

<210> SEQ ID NO 73
<211> LENGTH: 28
<212> TYPE: DNA
<213> ORGANISM: Artificial sequence
<220> FEATURE:
<223> OTHER INFORMATION: primer

<400> SEQUENCE: 73
gaacatcccc aagatcccac tattagag 28

<210> SEQ ID NO 74
<211> LENGTH: 22
<212> TYPE: DNA
<213> ORGANISM: Artificial sequence
<220> FEATURE:
<223> OTHER INFORMATION: primer

<400> SEQUENCE: 74
gaacatcccc aaactattag ag 22

<210> SEQ ID NO 75
<211> LENGTH: 25
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (5)..(5)
<223> OTHER INFORMATION: n = U
<220> FEATURE:
<221> NAME/KEY: misc_feature
<222> LOCATION: (10)..(10)
<223> OTHER INFORMATION: n = U
<220> FEATURE:
<221> NAME/KEY: misc_feature
<222> LOCATION: (11)..(11)
<223> OTHER INFORMATION: n = U
<220> FEATURE:
<221> NAME/KEY: misc_feature
<222> LOCATION: (13)..(13)
<223> OTHER INFORMATION: n = U
<220> FEATURE:
<221> NAME/KEY: misc_feature
<222> LOCATION: (20)..(21)
<223> OTHER INFORMATION: n = U

<400> SEQUENCE: 75
ggaangaagn nanccccgcn ncccc 25

<210> SEQ ID NO 76
<211> LENGTH: 20
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n = U
<220> FEATURE:
<221> NAME/KEY: misc_feature
<222> LOCATION: (8)..(8)
<223> OTHER INFORMATION: n = U
<220> FEATURE:
<221> NAME/KEY: misc_feature
<222> LOCATION: (15)..(15)
<223> OTHER INFORMATION: n = U

<400> SEQUENCE: 76
ccaggncncc agcgngccca 20

<210> SEQ ID NO 77
<211> LENGTH: 25
<212> TYPE: DNA
<213> ORGANISM: Artificial sequence
<220> FEATURE:
<223> OTHER INFORMATION: primer

<400> SEQUENCE: 77
ggaatgaagt tatccccgct tcccc 25

<210> SEQ ID NO 78
<211> LENGTH: 20
<212> TYPE: DNA
<213> ORGANISM: Artificial sequence
<220> FEATURE:
<223> OTHER INFORMATION: primer

<400> SEQUENCE: 78
ccaggtctcc agcgtgccca 20

<210> SEQ ID NO 79
<211> LENGTH: 23
<212> TYPE: DNA
<213> ORGANISM: Artificial sequence
<220> FEATURE:
<223> OTHER INFORMATION: primer

<400> SEQUENCE: 79
gaggagagca ggaaaggtgg aac 23

<210> SEQ ID NO 80
<211> LENGTH: 24
<212> TYPE: DNA
<213> ORGANISM: Artificial sequence
<220> FEATURE:
<223> OTHER INFORMATION: primer

<400> SEQUENCE: 80
tgcagagcga ttattcagga atgc 24

<210> SEQ ID NO 81
<211> LENGTH: 23
<212> TYPE: DNA
<213> ORGANISM: Artificial sequence
<220> FEATURE:
<223> OTHER INFORMATION: primer

<400> SEQUENCE: 81
gaggagagca ggaaaggtgg aac 23

<210> SEQ ID NO 82
<211> LENGTH: 32
<212> TYPE: DNA
<213> ORGANISM: Artificial sequence
<220> FEATURE:
<223> OTHER INFORMATION: primer

<400> SEQUENCE: 82
gagcaatggt caaagtcaac gtcatccaca gc 32

<210> SEQ ID NO 83
<211> LENGTH: 774
<212> TYPE: PRT
<213> ORGANISM: Thermococcus litoralis

<400> SEQUENCE: 83

Met Ile Leu Asp Thr Asp Tyr Ile Thr Lys Asp Gly Lys Pro Ile Ile
1 5 10 15

Arg Ile Phe Lys Lys Glu Asn Gly Glu Phe Lys Ile Glu Leu Asp Pro
20 25 30

His Phe Gln Pro Tyr Ile Tyr Ala Leu Leu Lys Asp Asp Ser Ala Ile
35 40 45

Glu Glu Ile Lys Ala Ile Lys Gly Glu Arg His Gly Lys Thr Val Arg
50 55 60

Val Leu Asp Ala Val Lys Val Arg Lys Lys Phe Leu Gly Arg Glu Val
65 70 75 80

Glu Val Trp Lys Leu Ile Phe Glu His Pro Gln Asp Val Pro Ala Met
85 90 95

Arg Gly Lys Ile Arg Glu His Pro Ala Val Val Asp Ile Tyr Glu Tyr

-continued

```
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525
```

-continued

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 84
<211> LENGTH: 1829
<212> TYPE: PRT
<213> ORGANISM: Thermococcus sp.
<220> FEATURE:
<221> NAME/KEY: misc_feature
<222> LOCATION: (1118)..(1118)
<223> OTHER INFORMATION: Xaa can be any naturally occurring amino acid
<220> FEATURE:
<221> NAME/KEY: misc_feature
<222> LOCATION: (1123)..(1123)
<223> OTHER INFORMATION: Xaa can be any naturally occurring amino acid

<400> SEQUENCE: 84

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Asp Glu Ile Lys Ala Ile Lys Gly Glu Arg His Gly Lys Ile Val Arg
    50                  55                  60

Val Val Asp Ala Val Lys Val Lys Lys Lys Phe Leu Gly Arg Asp Val
65                  70                  75                  80

Glu Val Trp Lys Leu Ile Phe Glu His Pro Gln Asp Val Pro Ala Leu

-continued

```
                85                  90                  95

Arg Gly Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Met Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Ile Val Arg Glu Lys Asp Pro Asp Val Leu Ile Thr
        195                 200                 205

Tyr Asn Gly Asp Asn Phe Asp Leu Pro Tyr Leu Ile Lys Arg Ala Glu
    210                 215                 220

Lys Leu Gly Val Thr Leu Leu Leu Gly Arg Asp Lys Glu His Pro Glu
225                 230                 235                 240

Pro Lys Ile His Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Glu Arg Asn Glu
        355                 360                 365

Leu Ala Pro Asn Lys Pro Asp Glu Glu Glu Tyr Arg Arg Arg Leu Arg
    370                 375                 380

Thr Thr Tyr Leu Gly Gly Tyr Val Lys Glu Pro Glu Arg Gly Leu Trp
385                 390                 395                 400

Glu Asn Ile Ala Tyr Leu Asp Phe Arg Cys His Pro Ala Asp Thr Lys
                405                 410                 415

Val Ile Val Lys Gly Lys Gly Ile Val Asn Ile Ser Asp Val Lys Glu
            420                 425                 430

Gly Asp Tyr Ile Leu Gly Ile Asp Gly Trp Gln Arg Val Lys Lys Val
        435                 440                 445

Trp Lys Tyr His Tyr Glu Gly Lys Leu Ile Asn Ile Asn Gly Leu Lys
    450                 455                 460

Cys Thr Pro Asn His Lys Val Pro Val Val Thr Glu Asn Asp Arg Gln
465                 470                 475                 480

Thr Arg Ile Arg Asp Ser Leu Ala Lys Ser Phe Leu Ser Gly Lys Val
                485                 490                 495

Lys Gly Lys Ile Ile Thr Thr Lys Leu Phe Glu Lys Ile Ala Glu Phe
            500                 505                 510
```

```
Glu Lys Asn Lys Pro Ser Glu Glu Glu Ile Leu Lys Gly Glu Leu Ser
        515                 520                 525

Gly Ile Ile Leu Ala Glu Gly Thr Leu Leu Arg Lys Asp Ile Glu Tyr
    530                 535                 540

Phe Asp Ser Ser Arg Gly Lys Lys Arg Ile Ser His Gln Tyr Arg Val
545                 550                 555                 560

Glu Ile Thr Ile Gly Glu Asn Glu Lys Glu Leu Leu Glu Arg Ile Leu
                565                 570                 575

Tyr Ile Phe Asp Lys Leu Phe Gly Ile Arg Pro Ser Val Lys Lys Lys
            580                 585                 590

Gly Asp Thr Asn Ala Leu Lys Ile Thr Thr Ala Lys Lys Ala Val Tyr
        595                 600                 605

Leu Gln Ile Glu Glu Leu Leu Lys Asn Ile Glu Ser Leu Tyr Ala Pro
    610                 615                 620

Ala Val Leu Arg Gly Phe Phe Glu Arg Asp Ala Thr Val Asn Lys Ile
625                 630                 635                 640

Arg Ser Thr Ile Val Val Thr Gln Gly Thr Asn Asn Lys Trp Lys Ile
                645                 650                 655

Asp Ile Val Ala Lys Leu Leu Asp Ser Leu Gly Ile Pro Tyr Ser Arg
            660                 665                 670

Tyr Glu Tyr Lys Tyr Ile Glu Asn Gly Lys Glu Leu Thr Lys His Ile
        675                 680                 685

Leu Glu Ile Thr Gly Arg Asp Gly Leu Ile Leu Phe Gln Thr Leu Val
    690                 695                 700

Gly Phe Ile Ser Ser Glu Lys Asn Glu Ala Leu Glu Lys Ala Ile Glu
705                 710                 715                 720

Val Arg Glu Met Asn Arg Leu Lys Asn Asn Ser Phe Tyr Asn Leu Ser
                725                 730                 735

Thr Phe Glu Val Ser Ser Glu Tyr Tyr Lys Gly Glu Val Tyr Asp Leu
            740                 745                 750

Thr Leu Glu Gly Asn Pro Tyr Tyr Phe Ala Asn Gly Ile Leu Thr His
        755                 760                 765

Asn Ser Leu Tyr Pro Ser Ile Ile Val Thr His Asn Val Ser Pro Asp
    770                 775                 780

Thr Leu Glu Arg Glu Gly Cys Lys Asn Tyr Asp Val Ala Pro Ile Val
785                 790                 795                 800

Gly Tyr Lys Phe Cys Lys Asp Phe Pro Gly Phe Ile Pro Ser Ile Leu
                805                 810                 815

Gly Glu Leu Ile Thr Met Arg Gln Glu Ile Lys Lys Lys Met Lys Ala
            820                 825                 830

Thr Ile Asp Pro Ile Glu Lys Lys Met Leu Asp Tyr Arg Gln Arg Ala
        835                 840                 845

Val Lys Leu Leu Ala Asn Ser Ile Leu Pro Asn Glu Trp Leu Pro Ile
    850                 855                 860

Ile Glu Asn Gly Glu Val Lys Phe Val Lys Ile Gly Glu Phe Ile Asp
865                 870                 875                 880

Arg Tyr Met Glu Glu Gln Lys Asp Lys Val Arg Thr Val Asp Asn Thr
                885                 890                 895

Glu Val Leu Glu Val Asp Asn Ile Phe Ala Phe Ser Leu Asn Lys Glu
            900                 905                 910

Ser Lys Lys Ser Glu Ile Lys Lys Val Lys Ala Leu Ile Arg His Lys
        915                 920                 925

Tyr Lys Gly Glu Ala Tyr Glu Val Glu Leu Asn Ser Gly Arg Lys Ile
    930                 935                 940
```

```
His Ile Thr Arg Gly His Ser Leu Phe Thr Ile Arg Asn Gly Lys Ile
945                 950                 955                 960

Lys Glu Ile Trp Gly Glu Glu Val Lys Val Gly Asp Leu Ile Ile Val
                965                 970                 975

Pro Lys Lys Val Lys Leu Asn Glu Lys Glu Ala Val Ile Asn Ile Pro
            980                 985                 990

Glu Leu Ile Ser Lys Leu Pro Asp  Glu Asp Thr Ala Asp  Val Val Met
        995                 1000                1005

Thr Thr  Pro Val Lys Gly Arg  Lys Asn Phe Phe Lys  Gly Met Leu
    1010                 1015                 1020

Arg Thr  Leu Lys Trp Ile Phe  Gly Glu Glu Ser Lys  Arg Ile Arg
    1025                 1030                 1035

Thr Phe  Asn Arg Tyr Leu Phe  His Leu Glu Glu Leu  Gly Phe Val
    1040                 1045                 1050

Lys Leu  Leu Pro Arg Gly Tyr  Glu Val Thr Asp Trp  Glu Gly Leu
    1055                 1060                 1065

Lys Arg  Tyr Arg Gln Leu Tyr  Glu Lys Leu Val Lys  Asn Leu Arg
    1070                 1075                 1080

Tyr Asn  Gly Asn Lys Arg Glu  Tyr Leu Val Arg Phe  Asn Asp Ile
    1085                 1090                 1095

Lys Asp  Ser Val Ser Cys Phe  Pro Arg Lys Glu Leu  Glu Glu Trp
    1100                 1105                 1110

Lys Ile  Gly Thr Xaa Lys Gly  Phe Arg Xaa Lys Cys  Ile Leu Lys
    1115                 1120                 1125

Val Asp  Glu Asp Phe Gly Lys  Phe Leu Gly Tyr Tyr  Val Ser Glu
    1130                 1135                 1140

Gly Tyr  Ala Gly Ala Gln Lys  Asn Lys Thr Gly Gly  Met Ser Tyr
    1145                 1150                 1155

Ser Val  Lys Leu Tyr Asn Glu  Asn Pro Asn Val Leu  Lys Asp Met
    1160                 1165                 1170

Lys Asn  Ile Ala Glu Lys Phe  Phe Gly Lys Val Arg  Val Gly Lys
    1175                 1180                 1185

Asn Cys  Val Asp Ile Pro Lys  Lys Met Ala Tyr Leu  Leu Ala Lys
    1190                 1195                 1200

Ser Leu  Cys Gly Val Thr Ala  Glu Asn Lys Arg Ile  Pro Ser Ile
    1205                 1210                 1215

Ile Phe  Asp Ser Ser Glu Pro  Val Arg Trp Ala Phe  Leu Arg Ala
    1220                 1225                 1230

Tyr Phe  Val Gly Asp Gly Asp  Ile His Pro Ser Lys  Arg Leu Arg
    1235                 1240                 1245

Leu Ser  Thr Lys Ser Glu Leu  Leu Ala Asn Gln Leu  Val Phe Leu
    1250                 1255                 1260

Leu Asn  Ser Leu Gly Val Ser  Ser Ile Lys Ile Gly  Phe Asp Ser
    1265                 1270                 1275

Gly Val  Tyr Arg Val Tyr Ile  Asn Glu Asp Leu Pro  Phe Leu Gln
    1280                 1285                 1290

Thr Ser  Arg Gln Lys Asn Thr  Tyr Tyr Pro Asn Leu  Ile Pro Lys
    1295                 1300                 1305

Glu Val  Leu Glu Glu Ile Phe  Gly Arg Lys Phe Gln  Lys Asn Ile
    1310                 1315                 1320

Thr Phe  Glu Lys Phe Lys Glu  Leu Ala Asp Ser Gly  Lys Leu Asp
    1325                 1330                 1335

Lys Arg  Lys Val Lys Leu Leu  Asp Phe Leu Leu Asn  Gly Asp Ile
```

```
    1340                1345                1350

Val Leu  Asp Arg Val Lys Asn  Val Glu Lys Arg Glu  Tyr Glu Gly
    1355                1360                1365

Tyr Val  Tyr Asp Leu Ser Val  Glu Asp Asn Glu Asn  Phe Leu Val
    1370                1375                1380

Gly Phe  Gly Leu Leu Tyr Ala  His Asn Ser Tyr Tyr  Gly Tyr Met
    1385                1390                1395

Gly Tyr  Pro Lys Ala Arg Trp  Tyr Ser Lys Glu Cys  Ala Glu Ser
    1400                1405                1410

Val Thr  Ala Trp Gly Arg His  Tyr Ile Glu Met Thr  Ile Lys Glu
    1415                1420                1425

Ile Glu  Glu Lys Phe Gly Phe  Lys Val Leu Tyr Ala  Asp Ser Val
    1430                1435                1440

Thr Gly  Asp Thr Glu Ile Ile  Val Lys Arg Asn Gly  Arg Ile Glu
    1445                1450                1455

Phe Val  Pro Ile Glu Lys Leu  Phe Glu Arg Val Asp  Tyr Arg Ile
    1460                1465                1470

Gly Glu  Lys Glu Tyr Cys Ile  Leu Glu Asp Val Glu  Ala Leu Thr
    1475                1480                1485

Leu Asp  Asn Arg Gly Lys Leu  Ile Trp Lys Lys Val  Pro Tyr Val
    1490                1495                1500

Met Arg  His Arg Ala Lys Lys  Lys Val Tyr Arg Ile  Trp Ile Thr
    1505                1510                1515

Asn Ser  Trp Tyr Ile Asp Val  Thr Glu Asp His Ser  Leu Ile Val
    1520                1525                1530

Ala Glu  Asp Gly Leu Lys Glu  Ala Arg Pro Met Glu  Ile Glu Gly
    1535                1540                1545

Lys Ser  Leu Ile Ala Thr Lys  Asp Asp Leu Ser Gly  Val Glu Tyr
    1550                1555                1560

Ile Lys  Pro His Ala Ile Glu  Glu Ile Ser Tyr Asn  Gly Tyr Val
    1565                1570                1575

Tyr Asp  Ile Glu Val Glu Gly  Thr His Arg Phe Phe  Ala Asn Gly
    1580                1585                1590

Ile Leu  Val His Asn Thr Asp  Gly Phe Tyr Ala Thr  Ile Pro Gly
    1595                1600                1605

Glu Lys  Pro Glu Thr Ile Lys  Lys Lys Ala Lys Glu  Phe Leu Lys
    1610                1615                1620

Tyr Ile  Asn Ser Lys Leu Pro  Gly Leu Leu Glu Leu  Glu Tyr Glu
    1625                1630                1635

Gly Phe  Tyr Leu Arg Gly Phe  Phe Val Ala Lys Lys  Arg Tyr Ala
    1640                1645                1650

Val Ile  Asp Glu Glu Gly Arg  Ile Thr Thr Arg Gly  Leu Glu Val
    1655                1660                1665

Val Arg  Arg Asp Trp Ser Glu  Ile Ala Lys Glu Thr  Gln Ala Lys
    1670                1675                1680

Val Leu  Glu Ala Ile Leu Lys  Glu Asp Ser Val Glu  Lys Ala Val
    1685                1690                1695

Glu Ile  Val Lys Asp Val Val  Glu Glu Ile Ala Lys  Tyr Gln Val
    1700                1705                1710

Pro Leu  Glu Lys Leu Val Ile  His Glu Gln Ile Thr  Lys Asp Leu
    1715                1720                1725

Ser Glu  Tyr Lys Ala Ile Gly  Pro His Val Ala Ile  Ala Lys Arg
    1730                1735                1740
```

Leu Ala Ala Lys Gly Ile Lys Val Arg Pro Gly Thr Ile Ile Ser
    1745                1750                1755

Tyr Ile Val Leu Arg Gly Ser Gly Lys Ile Ser Asp Arg Val Ile
    1760                1765                1770

Leu Leu Ser Glu Tyr Asp Pro Lys Lys His Lys Tyr Asp Pro Asp
    1775                1780                1785

Tyr Tyr Ile Glu Asn Gln Val Leu Pro Ala Val Leu Arg Ile Leu
    1790                1795                1800

Glu Ala Phe Gly Tyr Arg Lys Glu Asp Leu Lys Tyr Gln Ser Ser
    1805                1810                1815

Lys Gln Val Gly Leu Asp Ala Trp Leu Lys Lys
    1820                1825

<210> SEQ ID NO 85
<211> LENGTH: 771
<212> TYPE: PRT
<213> ORGANISM: Pyrococcus abyssi

<400> SEQUENCE: 85

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285

```
Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Arg Gly Phe Lys Val Leu Tyr Ile Asp Thr Asp Gly Leu
    530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720
```

Asp Pro Lys Lys His Lys Tyr Asp Ala Glu Tyr Tyr Ile Glu Asn Gln
725 730 735

Val Leu Pro Ala Val Glu Arg Ile Leu Arg Ala Phe Gly Tyr Arg Lys
740 745 750

Glu Asp Leu Lys Tyr Gln Lys Thr Lys Gln Val Gly Leu Gly Ala Trp
755 760 765

Leu Lys Phe
770

<210> SEQ ID NO 86
<211> LENGTH: 1235
<212> TYPE: PRT
<213> ORGANISM: Pyrococcus horikoshii

<400> SEQUENCE: 86

Met Ile Leu Asp Ala Asp Tyr Ile Thr Glu Asp Gly Lys Pro Ile Ile
1 5 10 15

Arg Ile Phe Lys Lys Glu Asn Gly Glu Phe Lys Val Glu Tyr Asp Arg
20 25 30

Asn Phe Arg Pro Tyr Ile Tyr Ala Leu Leu Arg Asp Asp Ser Ala Ile
35 40 45

Asp Glu Ile Lys Lys Ile Thr Ala Gln Arg His Gly Lys Val Val Arg
50 55 60

Ile Val Glu Thr Glu Lys Ile Gln Arg Lys Phe Leu Gly Arg Pro Ile
65 70 75 80

Glu Val Trp Lys Leu Tyr Leu Glu His Pro Gln Asp Val Pro Ala Ile
85 90 95

Arg Asp Lys Ile Arg Glu His Pro Ala Val Val Asp Ile Phe Glu Tyr
100 105 110

Asp Ile Pro Phe Ala Lys Arg Tyr Leu Ile Asp Lys Gly Leu Thr Pro
115 120 125

Met Glu Gly Asn Glu Lys Leu Thr Phe Leu Ala Val Asp Ile Glu Thr
130 135 140

Leu Tyr His Glu Gly Glu Glu Phe Gly Lys Gly Pro Val Ile Met Ile
145 150 155 160

Ser Tyr Ala Asp Glu Glu Gly Ala Lys Val Ile Thr Trp Lys Lys Ile
165 170 175

Asp Leu Pro Tyr Val Glu Val Val Ser Ser Glu Arg Glu Met Ile Lys
180 185 190

Arg Leu Ile Arg Val Ile Lys Glu Lys Asp Pro Asp Val Ile Ile Thr
195 200 205

Tyr Asn Gly Asp Asn Phe Asp Phe Pro Tyr Leu Leu Lys Arg Ala Glu
210 215 220

Lys Leu Gly Ile Lys Leu Leu Leu Gly Arg Asp Asn Ser Glu Pro Lys
225 230 235 240

Met Gln Lys Met Gly Asp Ser Leu Ala Val Glu Ile Lys Gly Arg Ile
245 250 255

His Phe Asp Leu Phe Pro Val Ile Arg Arg Thr Ile Asn Leu Pro Thr
260 265 270

Tyr Thr Leu Glu Ala Val Tyr Glu Ala Ile Phe Gly Lys Pro Lys Glu
275 280 285

Lys Val Tyr Ala Asp Glu Ile Ala Lys Ala Trp Glu Thr Gly Glu Gly
290 295 300

Leu Glu Arg Val Ala Lys Tyr Ser Met Glu Asp Ala Lys Val Thr Tyr
305 310 315 320

-continued

```
Glu Leu Gly Arg Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Glu Glu Tyr
            420                 425                 430

Asp Val Ala Pro Lys Val Gly His Arg Phe Cys Lys Asp Phe Pro Gly
        435                 440                 445

Phe Ile Pro Ser Leu Leu Gly Gln Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Ile Leu Pro
                485                 490                 495

Asp Glu Trp Leu Pro Ile Val Glu Asn Glu Lys Val Arg Phe Val Lys
            500                 505                 510

Ile Gly Asp Phe Ile Asp Arg Glu Ile Glu Glu Asn Ala Glu Arg Val
        515                 520                 525

Lys Arg Asp Gly Glu Thr Glu Ile Leu Glu Val Lys Asp Leu Lys Ala
    530                 535                 540

Leu Ser Phe Asn Arg Glu Thr Lys Lys Ser Glu Leu Lys Lys Val Lys
545                 550                 555                 560

Ala Leu Ile Arg His Arg Tyr Ser Gly Lys Val Tyr Ser Ile Lys Leu
                565                 570                 575

Lys Ser Gly Arg Arg Ile Lys Ile Thr Ser Gly His Ser Leu Phe Ser
            580                 585                 590

Val Lys Asn Gly Lys Leu Val Lys Val Arg Gly Asp Glu Leu Lys Pro
        595                 600                 605

Gly Asp Leu Val Val Val Pro Gly Arg Leu Lys Leu Pro Glu Ser Lys
    610                 615                 620

Gln Val Leu Asn Leu Val Glu Leu Leu Leu Lys Leu Pro Glu Glu Glu
625                 630                 635                 640

Thr Ser Asn Ile Val Met Met Ile Pro Val Lys Gly Arg Lys Asn Phe
                645                 650                 655

Phe Lys Gly Met Leu Lys Thr Leu Tyr Trp Ile Phe Gly Glu Gly Glu
            660                 665                 670

Arg Pro Arg Thr Ala Gly Arg Tyr Leu Lys His Leu Glu Arg Leu Gly
        675                 680                 685

Tyr Val Lys Leu Lys Arg Arg Gly Cys Glu Val Leu Asp Trp Glu Ser
    690                 695                 700

Leu Lys Arg Tyr Arg Lys Leu Tyr Glu Thr Leu Ile Lys Asn Leu Lys
705                 710                 715                 720

Tyr Asn Gly Asn Ser Arg Ala Tyr Met Val Glu Phe Asn Ser Leu Arg
                725                 730                 735

Asp Val Val Ser Leu Met Pro Ile Glu Glu Leu Lys Glu Trp Ile Ile
```

-continued

```
            740                 745                 750

Gly Glu Pro Arg Gly Pro Lys Ile Gly Thr Phe Ile Asp Val Asp Asp
        755                 760                 765

Ser Phe Ala Lys Leu Leu Gly Tyr Tyr Ile Ser Ser Gly Asp Val Glu
    770                 775                 780

Lys Asp Arg Val Lys Phe His Ser Lys Asp Gln Asn Val Leu Glu Asp
785                 790                 795                 800

Ile Ala Lys Leu Ala Glu Lys Leu Phe Gly Lys Val Arg Arg Gly Arg
                805                 810                 815

Gly Tyr Ile Glu Val Ser Gly Lys Ile Ser His Ala Ile Phe Arg Val
            820                 825                 830

Leu Ala Glu Gly Lys Arg Ile Pro Glu Phe Ile Phe Thr Ser Pro Met
        835                 840                 845

Asp Ile Lys Val Ala Phe Leu Lys Gly Leu Asn Gly Asn Ala Glu Glu
    850                 855                 860

Leu Thr Phe Ser Thr Lys Ser Glu Leu Leu Val Asn Gln Leu Ile Leu
865                 870                 875                 880

Leu Leu Asn Ser Ile Gly Val Ser Asp Ile Lys Ile Glu His Glu Lys
                885                 890                 895

Gly Val Tyr Arg Val Tyr Ile Asn Lys Lys Glu Ser Ser Asn Gly Asp
            900                 905                 910

Ile Val Leu Asp Ser Val Glu Ser Ile Glu Val Glu Lys Tyr Glu Gly
        915                 920                 925

Tyr Val Tyr Asp Leu Ser Val Glu Asp Asn Glu Asn Phe Leu Val Gly
    930                 935                 940

Phe Gly Leu Leu Tyr Ala His Asn Ser Tyr Tyr Gly Tyr Tyr Gly Tyr
945                 950                 955                 960

Ala Lys Ala Arg Trp Tyr Cys Lys Glu Cys Ala Glu Ser Val Thr Ala
                965                 970                 975

Trp Gly Arg Gln Tyr Ile Asp Leu Val Arg Arg Glu Leu Glu Ala Arg
            980                 985                 990

Gly Phe Lys Val Leu Tyr Ile Asp  Thr Asp Gly Leu Tyr  Ala Thr Ile
        995                 1000                1005

Pro Gly  Val Lys Asp Trp Glu  Glu Val Lys Arg Arg  Ala Leu Glu
    1010                1015                1020

Phe Val  Asp Tyr Ile Asn Ser  Lys Leu Pro Gly Val  Leu Glu Leu
    1025                1030                1035

Glu Tyr  Glu Gly Phe Tyr Ala  Arg Gly Phe Phe Val  Thr Lys Lys
    1040                1045                1050

Lys Tyr  Ala Leu Ile Asp Glu  Glu Gly Lys Ile Val  Thr Arg Gly
    1055                1060                1065

Leu Glu  Ile Val Arg Arg Asp  Trp Ser Glu Ile Ala  Lys Glu Thr
    1070                1075                1080

Gln Ala  Arg Val Leu Glu Ala  Ile Leu Lys His Gly  Asn Val Glu
    1085                1090                1095

Glu Ala  Val Lys Ile Val Lys  Asp Val Thr Glu Lys  Leu Thr Asn
    1100                1105                1110

Tyr Glu  Val Pro Pro Glu Lys  Leu Val Ile Tyr Glu  Gln Ile Thr
    1115                1120                1125

Arg Pro  Ile Asn Glu Tyr Lys  Ala Ile Gly Pro His  Val Ala Val
    1130                1135                1140

Ala Lys  Arg Leu Met Ala Arg  Gly Ile Lys Val Lys  Pro Gly Met
    1145                1150                1155
```

```
Val Ile  Gly Tyr Ile Val Leu  Arg Gly Asp Gly Pro  Ile Ser Lys
    1160                 1165                 1170

Arg Ala  Ile Ser Ile Glu Glu  Phe Asp Pro Arg Lys  His Lys Tyr
    1175                 1180                 1185

Asp Ala  Glu Tyr Tyr Ile Glu  Asn Gln Val Leu Pro  Ala Val Glu
    1190                 1195                 1200

Arg Ile  Leu Lys Ala Phe Gly  Tyr Lys Arg Glu Asp  Leu Arg Trp
    1205                 1210                 1215

Gln Lys  Thr Lys Gln Val Gly  Leu Gly Ala Trp Ile  Lys Val Lys
    1220                 1225                 1230

Lys Ser
    1235
```

<210> SEQ ID NO 87
<211> LENGTH: 771
<212> TYPE: PRT
<213> ORGANISM: Pyrococcus sp.

<400> SEQUENCE: 87

```
Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285
```

```
Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Ser Gly Phe Lys Val Leu Tyr Ile Asp Thr Asp Gly Leu
    530                 535                 540

Tyr Ala Thr Ile Pro Gly Ala Lys Pro Asn Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720
```

```
Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Phe
    770


<210> SEQ ID NO 88
<211> LENGTH: 775
<212> TYPE: PRT
<213> ORGANISM: Pyrococcus sp.

<400> SEQUENCE: 88

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320
```

-continued

```
Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
```

```
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775


<210> SEQ ID NO 89
<211> LENGTH: 775
<212> TYPE: PRT
<213> ORGANISM: Pyrococcus furiosus

<400> SEQUENCE: 89

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
```

```
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765
```

```
Trp Leu Asn Ile Lys Lys Ser
    770                 775


<210> SEQ ID NO 90
<211> LENGTH: 776
<212> TYPE: PRT
<213> ORGANISM: Thermococcus sp. JDF-3

<400> SEQUENCE: 90

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

-continued

```
Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
    770                 775
```

<210> SEQ ID NO 91

<211> LENGTH: 775
<212> TYPE: PRT
<213> ORGANISM: Thermococcus sp.

<400> SEQUENCE: 91

Met Ile Leu Asp Thr Asp Tyr Ile Thr Glu Asn Gly Lys Pro Val Ile
1 5 10 15

Arg Val Phe Lys Lys Glu Asn Gly Glu Phe Lys Ile Glu Tyr Asp Arg
20 25 30

Thr Phe Glu Pro Tyr Phe Tyr Ala Leu Leu Lys Asp Asp Ser Ala Ile
35 40 45

Glu Asp Val Lys Lys Val Thr Ala Lys Arg His Gly Thr Val Val Lys
50 55 60

Val Lys Arg Ala Glu Lys Val Gln Lys Lys Phe Leu Gly Arg Pro Ile
65 70 75 80

Glu Val Trp Lys Leu Tyr Phe Asn His Pro Gln Asp Val Pro Ala Ile
85 90 95

Arg Asp Arg Ile Arg Ala His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Thr Met Leu Ala Phe Asp Ile Glu Thr
130 135 140

Leu Tyr His Glu Gly Glu Glu Phe Gly Thr Gly Pro Ile Leu Met Ile
145 150 155 160

Ser Tyr Ala Asp Gly Ser Glu Ala Arg Val Ile Thr Trp Lys Lys Ile
165 170 175

Asp Leu Pro Tyr Val Asp Val Val Ser Thr Glu Lys Glu Met Ile Lys
180 185 190

Arg Phe Leu Arg Val Val Arg Glu Lys Asp Pro Asp Val Leu Ile Thr
195 200 205

Tyr Asn Gly Asp Asn Phe Asp Phe Ala Tyr Leu Lys Lys Arg Cys Glu
210 215 220

Glu Leu Gly Ile Lys Phe Thr Leu Gly Arg Asp Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Val Phe Gly Lys Pro Lys Glu
275 280 285

Lys Val Tyr Ala Glu Glu Ile Ala Gln Ala Trp Glu Ser Gly Glu Gly
290 295 300

Leu Glu Arg Val Ala Arg Tyr Ser Met Glu Asp Ala Lys Val Thr Tyr
305 310 315 320

Glu Leu Gly Arg Glu Phe Phe Pro Met Glu Ala Gln Leu Ser Arg Leu
325 330 335

Ile Gly Gln Ser Leu Trp Asp Val Ser Arg Ser Ser Thr Gly Asn Leu
340 345 350

Val Glu Trp Phe Leu Leu Arg Lys Ala Tyr Lys Arg Asn Glu Leu Ala
355 360 365

Pro Asn Lys Pro Asp Glu Arg Glu Leu Ala Arg Arg Arg Gly Gly Tyr
370 375 380

Ala Gly Gly Tyr Val Lys Glu Pro Glu Arg Gly Leu Trp Asp Asn Ile
385 390 395 400

-continued

```
Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775
```

<210> SEQ ID NO 92
<211> LENGTH: 1671
<212> TYPE: PRT
<213> ORGANISM: Pyrococcus sp.

<400> SEQUENCE: 92

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Cys His Pro Ala Asp Thr Lys Val Val Val
                405                 410                 415

Lys Gly Lys Gly Ile Ile Asn Ile Ser Glu Val Gln Glu Gly Asp Tyr
```

-continued

```
            420                 425                 430

Val Leu Gly Ile Asp Gly Trp Gln Arg Val Arg Lys Val Trp Glu Tyr
        435                 440                 445

Asp Tyr Lys Gly Glu Leu Val Asn Ile Asn Gly Leu Lys Cys Thr Pro
    450                 455                 460

Asn His Lys Leu Pro Val Val Thr Lys Asn Glu Arg Gln Thr Arg Ile
465                 470                 475                 480

Arg Asp Ser Leu Ala Lys Ser Phe Leu Thr Lys Lys Val Lys Gly Lys
                485                 490                 495

Ile Ile Thr Thr Pro Leu Phe Tyr Glu Ile Gly Arg Ala Thr Ser Glu
            500                 505                 510

Asn Ile Pro Glu Glu Glu Val Leu Lys Gly Glu Leu Ala Gly Ile Leu
        515                 520                 525

Leu Ala Glu Gly Thr Leu Leu Arg Lys Asp Val Glu Tyr Phe Asp Ser
    530                 535                 540

Ser Arg Lys Lys Arg Arg Ile Ser His Gln Tyr Arg Val Glu Ile Thr
545                 550                 555                 560

Ile Gly Lys Asp Glu Glu Glu Phe Arg Asp Arg Ile Thr Tyr Ile Phe
                565                 570                 575

Glu Arg Leu Phe Gly Ile Thr Pro Ser Ile Ser Glu Lys Lys Gly Thr
            580                 585                 590

Asn Ala Val Thr Leu Lys Val Ala Lys Lys Asn Val Tyr Leu Lys Val
        595                 600                 605

Lys Glu Ile Met Asp Asn Ile Glu Ser Leu His Ala Pro Ser Val Leu
    610                 615                 620

Arg Gly Phe Phe Glu Gly Asp Gly Ser Val Asn Arg Val Arg Arg Ser
625                 630                 635                 640

Ile Val Ala Thr Gln Gly Thr Lys Asn Glu Trp Lys Ile Lys Leu Val
                645                 650                 655

Ser Lys Leu Leu Ser Gln Leu Gly Ile Pro His Gln Thr Tyr Thr Tyr
            660                 665                 670

Gln Tyr Gln Glu Asn Gly Lys Asp Arg Ser Arg Tyr Ile Leu Glu Ile
        675                 680                 685

Thr Gly Lys Asp Gly Leu Ile Leu Phe Gln Thr Leu Ile Gly Phe Ile
    690                 695                 700

Ser Glu Arg Lys Asn Ala Leu Leu Asn Lys Ala Ile Ser Gln Arg Glu
705                 710                 715                 720

Met Asn Asn Leu Glu Asn Asn Gly Phe Tyr Arg Leu Ser Glu Phe Asn
                725                 730                 735

Val Ser Thr Glu Tyr Tyr Glu Gly Lys Val Tyr Asp Leu Thr Leu Glu
            740                 745                 750

Gly Thr Pro Tyr Tyr Phe Ala Asn Gly Ile Leu Thr His Asn Ser Leu
        755                 760                 765

Tyr Pro Ser Ile Ile Ile Thr His Asn Val Ser Pro Asp Thr Leu Asn
    770                 775                 780

Arg Glu Gly Cys Lys Glu Tyr Asp Val Ala Pro Gln Val Gly His Arg
785                 790                 795                 800

Phe Cys Lys Asp Phe Pro Gly Phe Ile Pro Ser Leu Leu Gly Asp Leu
                805                 810                 815

Leu Glu Glu Arg Gln Lys Ile Lys Lys Lys Met Lys Ala Thr Ile Asp
            820                 825                 830

Pro Ile Glu Arg Lys Leu Leu Asp Tyr Arg Gln Arg Ala Ile Lys Ile
        835                 840                 845
```

-continued

```
Leu Ala Asn Ser Ile Leu Pro Glu Glu Trp Leu Pro Val Leu Glu Glu
    850                 855                 860

Gly Glu Val His Phe Val Arg Ile Gly Glu Leu Ile Asp Arg Met Met
865                 870                 875                 880

Glu Glu Asn Ala Gly Lys Val Lys Arg Glu Gly Glu Thr Glu Val Leu
                885                 890                 895

Glu Val Ser Gly Leu Glu Val Pro Ser Phe Asn Arg Arg Thr Asn Lys
            900                 905                 910

Ala Glu Leu Lys Arg Val Lys Ala Leu Ile Arg His Asp Tyr Ser Gly
        915                 920                 925

Lys Val Tyr Thr Ile Arg Leu Lys Ser Gly Arg Arg Ile Lys Ile Thr
    930                 935                 940

Ser Gly His Ser Leu Phe Ser Val Arg Asn Gly Glu Leu Val Glu Val
945                 950                 955                 960

Thr Gly Asp Glu Leu Lys Pro Gly Asp Leu Val Ala Val Pro Arg Arg
                965                 970                 975

Leu Glu Leu Pro Glu Arg Asn His Val Leu Asn Leu Val Glu Leu Leu
            980                 985                 990

Leu Gly Thr Pro Glu Glu Glu Thr  Leu Asp Ile Val Met  Thr Ile Pro
        995                 1000                1005

Val Lys  Gly Lys Lys Asn Phe  Phe Lys Gly Met Leu  Arg Thr Leu
    1010                1015                1020

Arg Trp  Ile Phe Gly Glu Glu  Lys Arg Pro Arg Thr  Ala Arg Arg
    1025                1030                1035

Tyr Leu  Arg His Leu Glu Asp  Leu Gly Tyr Val Arg  Leu Lys Lys
    1040                1045                1050

Ile Gly  Tyr Glu Val Leu Asp  Trp Asp Ser Leu Lys  Asn Tyr Arg
    1055                1060                1065

Arg Leu  Tyr Glu Ala Leu Val  Glu Asn Val Arg Tyr  Asn Gly Asn
    1070                1075                1080

Lys Arg  Glu Tyr Leu Val Glu  Phe Asn Ser Ile Arg  Asp Ala Val
    1085                1090                1095

Gly Ile  Met Pro Leu Lys Glu  Leu Lys Glu Trp Lys  Ile Gly Thr
    1100                1105                1110

Leu Asn  Gly Phe Arg Met Arg  Lys Leu Ile Glu Val  Asp Glu Ser
    1115                1120                1125

Leu Ala  Lys Leu Leu Gly Tyr  Tyr Val Ser Glu Gly  Tyr Ala Arg
    1130                1135                1140

Lys Gln  Arg Asn Pro Lys Asn  Gly Trp Ser Tyr Ser  Val Lys Leu
    1145                1150                1155

Tyr Asn  Glu Asp Pro Glu Val  Leu Asp Asp Met Glu  Arg Leu Ala
    1160                1165                1170

Ser Arg  Phe Phe Gly Lys Val  Arg Arg Gly Arg Asn  Tyr Val Glu
    1175                1180                1185

Ile Pro  Lys Lys Ile Gly Tyr  Leu Leu Phe Glu Asn  Met Cys Gly
    1190                1195                1200

Val Leu  Ala Glu Asn Lys Arg  Ile Pro Glu Phe Val  Phe Thr Ser
    1205                1210                1215

Pro Lys  Gly Val Arg Leu Ala  Phe Leu Glu Gly Tyr  Phe Ile Gly
    1220                1225                1230

Asp Gly  Asp Val His Pro Asn  Lys Arg Leu Arg Leu  Ser Thr Lys
    1235                1240                1245

Ser Glu  Leu Leu Ala Asn Gln  Leu Val Leu Leu Leu  Asn Ser Val
    1250                1255                1260
```

-continued

```
Gly Val  Ser Ala Val Lys Leu  Gly His Asp Ser Gly  Val Tyr Arg
    1265                 1270                 1275

Val Tyr  Ile Asn Glu Glu Leu  Pro Phe Val Lys Leu  Asp Lys Lys
    1280                 1285                 1290

Lys Asn  Ala Tyr Tyr Ser His  Val Ile Pro Lys Glu  Val Leu Ser
    1295                 1300                 1305

Glu Val  Phe Gly Lys Val Phe  Gln Lys Asn Val Ser  Pro Gln Thr
    1310                 1315                 1320

Phe Arg  Lys Met Val Glu Asp  Gly Arg Leu Asp Pro  Glu Lys Ala
    1325                 1330                 1335

Gln Arg  Leu Ser Trp Leu Ile  Glu Gly Asp Val Val  Leu Asp Arg
    1340                 1345                 1350

Val Glu  Ser Val Asp Val Glu  Asp Tyr Asp Gly Tyr  Val Tyr Asp
    1355                 1360                 1365

Leu Ser  Val Glu Asp Asn Glu  Asn Phe Leu Val Gly  Phe Gly Leu
    1370                 1375                 1380

Val Tyr  Ala His Asn Ser Tyr  Tyr Gly Tyr Tyr Gly  Tyr Ala Arg
    1385                 1390                 1395

Ala Arg  Trp Tyr Cys Lys Glu  Cys Ala Glu Ser Val  Thr Ala Trp
    1400                 1405                 1410

Gly Arg  Glu Tyr Ile Thr Met  Thr Ile Lys Glu Ile  Glu Glu Lys
    1415                 1420                 1425

Tyr Gly  Phe Lys Val Ile Tyr  Ser Asp Thr Asp Gly  Phe Phe Ala
    1430                 1435                 1440

Thr Ile  Pro Gly Ala Asp Ala  Glu Thr Val Lys Lys  Lys Ala Met
    1445                 1450                 1455

Glu Phe  Leu Lys Tyr Ile Asn  Ala Lys Leu Pro Gly  Ala Leu Glu
    1460                 1465                 1470

Leu Glu  Tyr Glu Gly Phe Tyr  Lys Arg Gly Phe Phe  Val Thr Lys
    1475                 1480                 1485

Lys Lys  Tyr Ala Val Ile Asp  Glu Glu Gly Lys Ile  Thr Thr Arg
    1490                 1495                 1500

Gly Leu  Glu Ile Val Arg Arg  Asp Trp Ser Glu Ile  Ala Lys Glu
    1505                 1510                 1515

Thr Gln  Ala Arg Val Leu Glu  Ala Leu Leu Lys Asp  Gly Asp Val
    1520                 1525                 1530

Glu Lys  Ala Val Arg Ile Val  Lys Glu Val Thr Glu  Lys Leu Ser
    1535                 1540                 1545

Lys Tyr  Glu Val Pro Pro Glu  Lys Leu Val Ile His  Glu Gln Ile
    1550                 1555                 1560

Thr Arg  Asp Leu Lys Asp Tyr  Lys Ala Thr Gly Pro  His Val Ala
    1565                 1570                 1575

Val Ala  Lys Arg Leu Ala Ala  Arg Gly Val Lys Ile  Arg Pro Gly
    1580                 1585                 1590

Thr Val  Ile Ser Tyr Ile Val  Leu Lys Gly Ser Gly  Arg Ile Gly
    1595                 1600                 1605

Asp Arg  Ala Ile Pro Phe Asp  Glu Phe Asp Pro Thr  Lys His Lys
    1610                 1615                 1620

Tyr Asp  Ala Glu Tyr Tyr Ile  Glu Asn Gln Val Leu  Pro Ala Val
    1625                 1630                 1635

Glu Arg  Ile Leu Arg Ala Phe  Gly Tyr Arg Lys Glu  Asp Leu Arg
    1640                 1645                 1650

Tyr Gln  Lys Thr Arg Gln Val  Gly Leu Ser Ala Trp  Leu Lys Pro
```

-continued 1655 1660 1665

Lys Gly Thr
1670

<210> SEQ ID NO 93
<211> LENGTH: 773
<212> TYPE: PRT
<213> ORGANISM: Thermococcus sp.

<400> SEQUENCE: 93

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

Asn Phe Glu Pro Tyr Ile Tyr Ala Leu Leu Lys Asp Asp Ser Ala Ile
35 40 45

Glu Asp Val Lys Lys Ile Thr Ala Glu Arg His Gly Thr Thr Val Arg
50 55 60

Val Val Arg Ala Glu Lys Val Lys Lys Lys Phe Leu Gly Arg Pro Ile
65 70 75 80

Glu Val Trp Lys Leu Tyr Phe Thr His Pro Gln Asp Val Pro Ala Ile
85 90 95

Arg Asp Lys Ile Lys Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Met Leu Ala Phe Asp Ile Glu Thr
130 135 140

Leu Tyr His Glu Gly Glu Glu Phe Ala Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Asp Val Val Ser Thr Glu Lys Glu Met Ile Lys
180 185 190

Arg Phe Leu Lys Val Val Lys Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Lys Leu Gly Val Lys Phe Ile Leu Gly Arg Glu Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Ile Phe Gly Gln Pro Lys Glu
275 280 285

Lys Val Tyr Ala Glu Glu Ile Ala Gln Ala Trp Glu Thr Gly Glu Gly
290 295 300

Leu Glu Arg Val Ala Arg Tyr Ser Met Glu Asp Ala Lys Val Thr Tyr
305 310 315 320

Glu Leu Gly Lys Glu Phe Phe Pro Met Glu Ala Gln Leu Ser Arg Leu
325 330 335

Val Gly Gln Ser Leu Trp Asp Val Ser Arg Ser Ser Thr Gly Asn Leu
340 345 350

Val Glu Trp Phe Leu Leu Arg Lys Ala Tyr Glu Arg Asn Glu Leu Ala

-continued

```
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

-continued

<210> SEQ ID NO 94
<211> LENGTH: 1523
<212> TYPE: PRT
<213> ORGANISM: Thermococcus fumicolans

<400> SEQUENCE: 94

```
Met Ile Leu Asp Thr Asp Tyr Ile Thr Glu Asp Gly Arg Pro Val Ile
1               5                   10                  15

Arg Val Phe Lys Lys Glu Asn Gly Glu Phe Lys Ile Glu Tyr Asp Arg
            20                  25                  30

Asp Phe Glu Pro Tyr Ile Tyr Ala Leu Leu Lys Asp Asp Ser Ala Ile
        35                  40                  45

Glu Asp Val Lys Lys Ile Thr Ala Ser Arg His Gly Thr Thr Val Arg
    50                  55                  60

Val Val Arg Ala Gly Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg His Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Ser Phe Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Ser Gly Arg Glu Leu Glu Arg Arg Arg Gly Gly Tyr
    370                 375                 380
```

-continued

```
Ala Gly Gly Tyr Val Lys Glu Pro Glu Arg Gly Leu Trp Glu Asn Ile
385                 390                 395                 400

Ala Tyr Leu Asp Phe Arg Cys His Pro Ala Asp Thr Lys Val Ile Val
                405                 410                 415

Lys Gly Lys Gly Val Val Asn Ile Ser Glu Val Arg Glu Gly Asp Tyr
            420                 425                 430

Val Leu Gly Ile Asp Gly Trp Gln Lys Val Gln Arg Val Trp Glu Tyr
        435                 440                 445

Asp Tyr Glu Gly Glu Leu Val Asn Ile Asn Gly Leu Lys Cys Thr Pro
    450                 455                 460

Asn His Lys Leu Pro Val Val Arg Arg Thr Glu Arg Gln Thr Ala Ile
465                 470                 475                 480

Arg Asp Ser Leu Ala Lys Ser Phe Leu Thr Lys Lys Val Lys Gly Lys
                485                 490                 495

Leu Ile Thr Thr Pro Leu Phe Glu Lys Ile Gly Lys Ile Glu Arg Glu
            500                 505                 510

Asp Val Pro Glu Glu Glu Ile Leu Lys Gly Glu Leu Ala Gly Ile Ile
        515                 520                 525

Leu Ala Glu Gly Thr Leu Leu Arg Lys Asp Val Glu Tyr Phe Asp Ser
    530                 535                 540

Ser Arg Gly Lys Lys Arg Val Ser His Gln Tyr Arg Val Glu Ile Thr
545                 550                 555                 560

Val Gly Ala Gln Glu Glu Asp Phe Gln Arg Arg Ile Val Tyr Ile Phe
                565                 570                 575

Glu Arg Leu Phe Gly Val Thr Pro Ser Val Tyr Arg Lys Lys Asn Thr
            580                 585                 590

Asn Ala Ile Thr Phe Lys Val Ala Lys Lys Glu Val Tyr Leu Arg Val
        595                 600                 605

Arg Glu Ile Met Asp Gly Ile Glu Asn Leu His Ala Pro Ser Val Leu
    610                 615                 620

Arg Gly Phe Phe Glu Gly Asp Gly Ser Val Asn Lys Val Arg Lys Thr
625                 630                 635                 640

Val Val Val Asn Gln Gly Thr Asn Asn Glu Trp Lys Ile Glu Val Val
                645                 650                 655

Ser Lys Leu Leu Asn Lys Leu Gly Ile Pro His Arg Arg Tyr Thr Tyr
            660                 665                 670

Asp Tyr Thr Glu Arg Glu Lys Thr Met Thr Thr His Ile Leu Glu Ile
        675                 680                 685

Ala Gly Arg Asp Gly Leu Ile Leu Phe Gln Thr Ile Val Gly Phe Ile
    690                 695                 700

Ser Thr Glu Lys Asn Met Ala Leu Glu Glu Ala Ile Arg Asn Arg Glu
705                 710                 715                 720

Val Asn Arg Leu Glu Asn Asn Ala Phe Tyr Thr Leu Ala Asp Phe Thr
                725                 730                 735

Ala Lys Thr Glu Tyr Tyr Lys Gly Lys Val Tyr Asp Leu Thr Leu Glu
            740                 745                 750

Gly Thr Pro Tyr Tyr Phe Ala Asn Gly Ile Leu Thr His Asn Ser Leu
        755                 760                 765

Tyr Pro Ser Ile Ile Ile Ser His Asn Val Ser Pro Asp Thr Leu Asn
    770                 775                 780

Arg Glu Gly Cys Gly Glu Tyr Asp Glu Ala Pro Gln Val Gly His Arg
785                 790                 795                 800

Phe Cys Lys Asp Phe Pro Gly Phe Ile Pro Ser Leu Leu Gly Asp Leu
                805                 810                 815
```

```
Leu Asp Glu Arg Gln Lys Val Lys Lys His Met Lys Ala Thr Val Asp
            820                 825                 830

Pro Ile Glu Lys Lys Leu Leu Asp Tyr Arg Gln Arg Ala Ile Lys Ile
        835                 840                 845

Leu Ala Asn Ser Phe Tyr Gly Tyr Tyr Gly Tyr Ala Lys Ala Arg Trp
    850                 855                 860

Tyr Cys Lys Glu Cys Ala Glu Ser Val Thr Ala Trp Gly Arg Gln Tyr
865                 870                 875                 880

Ile Glu Thr Thr Met Arg Glu Ile Glu Glu Lys Phe Gly Phe Lys Val
                885                 890                 895

Leu Tyr Ala Asp Ser Val Thr Gly Asp Thr Glu Val Thr Ile Arg Arg
            900                 905                 910

Asn Gly Arg Ile Glu Phe Val Pro Ile Glu Lys Leu Phe Glu Arg Val
        915                 920                 925

Asp His Arg Val Gly Glu Lys Glu Tyr Cys Val Leu Gly Gly Val Glu
    930                 935                 940

Ala Leu Thr Leu Asp Asn Arg Gly Arg Leu Val Trp Lys Lys Val Pro
945                 950                 955                 960

Tyr Val Met Arg His Lys Thr Asp Lys Arg Ile Tyr Arg Val Trp Phe
                965                 970                 975

Thr Asn Ser Trp Tyr Leu Asp Val Thr Glu Asp His Ser Leu Ile Gly
            980                 985                 990

Tyr Leu Asn Thr Ser Lys Val Lys  Pro Gly Lys Pro Leu  Lys Glu Arg
        995                 1000                1005

Leu Val  Glu Val Lys Pro Glu  Glu Leu Gly Gly Lys  Val Lys Ser
    1010                1015                1020

Leu Ile  Thr Pro Asn Arg Pro  Ile Ala Arg Thr Ile  Lys Ala Asn
    1025                1030                1035

Pro Ile  Ala Val Lys Leu Trp  Glu Leu Ile Gly Leu  Leu Val Gly
    1040                1045                1050

Asp Gly  Asn Trp Gly Gly Gln  Ser Asn Trp Ala Lys  Tyr Tyr Val
    1055                1060                1065

Gly Leu  Ser Cys Gly Leu Asp  Lys Ala Glu Ile Glu  Arg Lys Val
    1070                1075                1080

Leu Asn  Pro Leu Arg Glu Ala  Ser Val Ile Ser Asn  Tyr Tyr Asp
    1085                1090                1095

Lys Ser  Lys Lys Gly Asp Val  Ser Ile Leu Ser Lys  Trp Leu Ala
    1100                1105                1110

Gly Phe  Met Val Lys Tyr Phe  Lys Asp Glu Asn Gly  Asn Lys Ala
    1115                1120                1125

Ile Pro  Ser Phe Met Phe Asn  Leu Pro Arg Glu Tyr  Ile Glu Ala
    1130                1135                1140

Phe Leu  Arg Gly Leu Phe Ser  Ala Asp Gly Thr Val  Ser Leu Arg
    1145                1150                1155

Arg Gly  Ile Pro Glu Ile Arg  Leu Thr Ser Val Asn  Arg Glu Leu
    1160                1165                1170

Ser Asp  Ala Val Arg Lys Leu  Leu Trp Leu Val Gly  Val Ser Asn
    1175                1180                1185

Ser Leu  Phe Thr Glu Thr Lys  Pro Asn Arg Tyr Leu  Glu Lys Glu
    1190                1195                1200

Ser Gly  Thr His Ser Ile His  Val Arg Ile Lys Asn  Lys His Arg
    1205                1210                1215

Phe Ala  Asp Arg Ile Gly Phe  Leu Ile Asp Arg Lys  Ser Thr Lys
```

-continued

```
    1220                1225                1230

Leu Ser  Glu Asn Leu Gly Gly  His Thr Asn Lys Lys  Arg Ala Tyr
    1235                1240                1245

Lys Tyr  Asp Phe Asp Leu Val  Tyr Pro Arg Lys Ile  Glu Glu Ile
    1250                1255                1260

Thr Tyr  Asp Gly Tyr Val Tyr  Asp Ile Glu Val Glu  Gly Thr His
    1265                1270                1275

Arg Phe  Phe Ala Asn Gly Ile  Leu Val His Asn Thr  Asp Gly Phe
    1280                1285                1290

Phe Ala  Thr Ile Pro Gly Ala  Asp Ala Glu Thr Val  Lys Lys Lys
    1295                1300                1305

Ala Arg  Glu Phe Leu Asn Tyr  Ile Asn Pro Lys Leu  Pro Gly Leu
    1310                1315                1320

Leu Glu  Leu Glu Tyr Glu Gly  Phe Tyr Arg Arg Gly  Phe Phe Val
    1325                1330                1335

Thr Lys  Lys Lys Tyr Ala Val  Ile Asp Glu Glu Gly  Lys Ile Thr
    1340                1345                1350

Thr Arg  Gly Leu Glu Ile Val  Arg Arg Asp Trp Ser  Glu Val Ala
    1355                1360                1365

Lys Glu  Thr Gln Ala Arg Val  Leu Glu Ala Ile Leu  Arg His Gly
    1370                1375                1380

Asp Val  Glu Glu Ala Val Arg  Ile Val Lys Glu Val  Thr Glu Lys
    1385                1390                1395

Leu Ser  Lys Tyr Glu Val Pro  Pro Glu Lys Leu Val  Ile His Glu
    1400                1405                1410

Gln Ile  Thr Arg Glu Leu Lys  Asp Tyr Lys Ala Thr  Gly Pro His
    1415                1420                1425

Val Ala  Ile Ala Lys Arg Leu  Ala Ala Arg Gly Ile  Lys Val Arg
    1430                1435                1440

Pro Gly  Thr Val Ile Ser Tyr  Ile Val Leu Lys Gly  Ser Gly Arg
    1445                1450                1455

Ile Gly  Asp Arg Thr Ile Pro  Phe Asp Glu Phe Asp  Pro Thr Lys
    1460                1465                1470

His Arg  Tyr Asp Ala Glu Tyr  Tyr Ile Glu Asn Gln  Val Leu Pro
    1475                1480                1485

Ala Val  Glu Arg Ile Leu Lys  Ala Phe Gly Tyr Lys  Lys Glu Asp
    1490                1495                1500

Leu Arg  Tyr Gln Lys Thr Arg  Gln Val Gly Leu Gly  Ala Trp Leu
    1505                1510                1515

Lys Met  Gly Lys Lys
    1520


<210> SEQ ID NO 95
<211> LENGTH: 586
<212> TYPE: PRT
<213> ORGANISM: Methanobacterium thermoautotrophicum

<400> SEQUENCE: 95

Met Glu Asp Tyr Arg Met Val Leu Leu Asp Ile Asp Tyr Val Thr Val
1               5                   10                  15

Asp Glu Val Pro Val Ile Arg Leu Phe Gly Lys Asp Lys Ser Gly Gly
            20                  25                  30

Asn Glu Pro Ile Ile Ala His Asp Arg Ser Phe Arg Pro Tyr Ile Tyr
        35                  40                  45

Ala Ile Pro Thr Asp Leu Asp Glu Cys Leu Arg Glu Leu Glu Glu Leu
```

-continued

```
    50                  55                  60

Glu Leu Glu Lys Leu Glu Val Lys Glu Met Arg Asp Leu Gly Arg Pro
65                  70                  75                  80

Thr Glu Val Ile Arg Ile Glu Phe Arg His Pro Gln Asp Val Pro Lys
                85                  90                  95

Ile Arg Asp Arg Ile Arg Asp Leu Glu Ser Val Arg Asp Ile Arg Glu
            100                 105                 110

His Asp Ile Pro Phe Tyr Arg Arg Tyr Leu Ile Asp Lys Ser Ile Val
        115                 120                 125

Pro Met Glu Glu Leu Glu Phe Gln Gly Val Glu Val Asp Ser Ala Pro
    130                 135                 140

Ser Val Thr Thr Asp Val Arg Thr Val Glu Val Thr Gly Arg Val Gln
145                 150                 155                 160

Ser Thr Gly Ser Gly Ala His Gly Leu Asp Ile Leu Ser Phe Asp Ile
                165                 170                 175

Glu Val Arg Asn Pro His Gly Met Pro Asp Pro Glu Lys Asp Glu Ile
            180                 185                 190

Val Met Ile Gly Val Ala Gly Asn Met Gly Tyr Glu Ser Val Ile Ser
        195                 200                 205

Thr Ala Gly Asp His Leu Asp Phe Val Glu Val Val Glu Asp Glu Arg
    210                 215                 220

Glu Leu Leu Glu Arg Phe Ala Glu Ile Val Ile Asp Lys Lys Pro Asp
225                 230                 235                 240

Ile Leu Val Gly Tyr Asn Ser Asp Asn Phe Asp Phe Pro Tyr Ile Thr
                245                 250                 255

Arg Arg Ala Ala Ile Leu Gly Ala Glu Leu Asp Leu Gly Trp Asp Gly
            260                 265                 270

Ser Lys Ile Arg Thr Met Arg Arg Gly Phe Ala Asn Ala Thr Ala Ile
        275                 280                 285

Lys Gly Thr Val His Val Asp Leu Tyr Pro Val Met Arg Arg Tyr Met
    290                 295                 300

Asn Leu Asp Arg Tyr Thr Leu Glu Arg Val Tyr Gln Glu Leu Phe Gly
305                 310                 315                 320

Glu Glu Lys Ile Asp Leu Pro Gly Asp Arg Leu Trp Glu Tyr Trp Asp
                325                 330                 335

Arg Asp Glu Leu Arg Asp Glu Leu Phe Arg Tyr Ser Leu Asp Asp Val
            340                 345                 350

Val Ala Thr His Arg Ile Ala Glu Lys Ile Leu Pro Leu Asn Leu Glu
        355                 360                 365

Leu Thr Arg Leu Val Gly Gln Pro Leu Phe Asp Ile Ser Arg Met Ala
    370                 375                 380

Thr Gly Gln Gln Ala Glu Trp Phe Leu Val Arg Lys Ala Tyr Gln Tyr
385                 390                 395                 400

Gly Glu Leu Val Pro Asn Lys Pro Ser Gln Ser Asp Phe Ser Ser Arg
                405                 410                 415

Arg Gly Arg Arg Ala Val Gly Gly Tyr Val Lys Glu Pro Glu Lys Gly
            420                 425                 430

Leu His Glu Asn Ile Val Gln Phe Asp Phe Arg Ser Leu Tyr Pro Ser
        435                 440                 445

Ile Ile Ile Ser Lys Asn Ile Ser Pro Asp Thr Leu Thr Asp Asp Glu
    450                 455                 460

Glu Ser Glu Cys Tyr Val Ala Pro Glu Tyr Gly Tyr Arg Phe Arg Lys
465                 470                 475                 480
```

Ser Pro Arg Gly Phe Val Pro Ser Val Ile Gly Glu Ile Leu Ser Glu
485 490 495

Arg Val Arg Ile Lys Glu Glu Met Lys Gly Ser Asp Asp Pro Met Glu
500 505 510

Arg Lys Ile Leu Asn Val Gln Gln Glu Ala Leu Lys Arg Leu Ala Asn
515 520 525

Thr Met Tyr Gly Val Tyr Gly Tyr Ser Arg Phe Arg Trp Tyr Ser Met
530 535 540

Glu Cys Ala Glu Ala Ile Thr Ala Trp Gly Arg Asp Tyr Ile Lys Lys
545 550 555 560

Thr Ile Lys Thr Ala Glu Glu Phe Gly Phe His Thr Val Tyr Ala Asp
565 570 575

Thr Asp Gly Phe Tyr Ala Thr Tyr Arg Gly
580 585

<210> SEQ ID NO 96
<211> LENGTH: 1634
<212> TYPE: PRT
<213> ORGANISM: Methanococcus jannaschii

<400> SEQUENCE: 96

Met Gly Met Ser Met Gly Lys Ile Lys Ile Asp Ala Leu Ile Asp Asn
1 5 10 15

Thr Tyr Lys Thr Ile Glu Asp Lys Ala Val Ile Tyr Leu Tyr Leu Ile
20 25 30

Asn Ser Ile Leu Lys Asp Arg Asp Phe Lys Pro Tyr Phe Tyr Val Glu
35 40 45

Leu His Lys Glu Lys Val Glu Asn Glu Asp Ile Glu Lys Ile Lys Glu
50 55 60

Phe Leu Leu Lys Asn Asp Leu Leu Lys Phe Val Glu Asn Ile Glu Val
65 70 75 80

Val Lys Lys Ile Ile Leu Arg Lys Glu Lys Glu Val Ile Lys Ile Ile
85 90 95

Ala Thr His Pro Gln Lys Val Pro Lys Leu Arg Lys Ile Lys Glu Cys
100 105 110

Glu Ile Val Lys Glu Ile Tyr Glu His Asp Ile Pro Phe Ala Lys Arg
115 120 125

Tyr Leu Ile Asp Asn Glu Ile Ile Pro Met Thr Tyr Trp Asp Phe Glu
130 135 140

Asn Lys Lys Pro Val Ser Ile Glu Ile Pro Lys Leu Lys Ser Val Ala
145 150 155 160

Phe Asp Met Glu Val Tyr Asn Arg Asp Thr Glu Pro Asn Pro Glu Arg
165 170 175

Asp Pro Ile Leu Met Ala Ser Phe Trp Asp Glu Asn Gly Gly Lys Val
180 185 190

Ile Thr Tyr Lys Glu Phe Asn His Pro Asn Ile Glu Val Val Lys Asn
195 200 205

Glu Lys Glu Leu Ile Lys Lys Ile Ile Glu Thr Leu Lys Glu Tyr Asp
210 215 220

Val Ile Tyr Thr Tyr Asn Gly Asp Asn Phe Asp Phe Pro Tyr Leu Lys
225 230 235 240

Ala Arg Ala Lys Ile Tyr Gly Ile Asp Ile Asn Leu Gly Lys Asp Gly
245 250 255

Glu Glu Leu Lys Ile Lys Arg Gly Gly Met Glu Tyr Arg Ser Tyr Ile
260 265 270

-continued

```
Pro Gly Arg Val His Ile Asp Leu Tyr Pro Ile Ser Arg Arg Leu Leu
        275                 280                 285

Lys Leu Thr Lys Tyr Thr Leu Glu Asp Val Val Tyr Asn Leu Phe Gly
    290                 295                 300

Ile Glu Lys Leu Lys Ile Pro His Thr Lys Ile Val Asp Tyr Trp Ala
305                 310                 315                 320

Asn Asn Asp Lys Thr Leu Ile Glu Tyr Ser Leu Gln Asp Ala Lys Tyr
                325                 330                 335

Thr Tyr Lys Ile Gly Lys Tyr Phe Phe Pro Leu Glu Val Met Phe Ser
            340                 345                 350

Arg Ile Val Asn Gln Thr Pro Phe Glu Ile Thr Arg Met Ser Ser Gly
        355                 360                 365

Gln Met Val Glu Tyr Leu Leu Met Lys Arg Ala Phe Lys Glu Asn Met
    370                 375                 380

Ile Val Pro Asn Lys Pro Asp Glu Glu Glu Tyr Arg Arg Arg Val Leu
385                 390                 395                 400

Thr Thr Tyr Glu Gly Gly Tyr Val Lys Glu Pro Glu Lys Gly Met Phe
                405                 410                 415

Glu Asp Ile Ile Ser Met Asp Phe Arg Cys His Pro Lys Gly Thr Lys
            420                 425                 430

Val Val Val Lys Gly Lys Gly Ile Val Asn Ile Glu Asp Val Lys Glu
        435                 440                 445

Gly Asn Tyr Val Leu Gly Ile Asp Gly Trp Gln Lys Val Lys Lys Val
    450                 455                 460

Trp Lys Tyr Glu Tyr Glu Gly Glu Leu Ile Asn Val Asn Gly Leu Lys
465                 470                 475                 480

Cys Thr Pro Asn His Lys Ile Pro Leu Arg Tyr Lys Ile Lys His Lys
                485                 490                 495

Lys Ile Asn Lys Asn Asp Tyr Leu Val Arg Asp Ile Tyr Ala Lys Ser
            500                 505                 510

Leu Leu Thr Lys Phe Lys Gly Glu Gly Lys Leu Ile Leu Cys Lys Asp
        515                 520                 525

Phe Glu Thr Ile Gly Asn Tyr Glu Lys Tyr Ile Asn Asp Met Asp Glu
    530                 535                 540

Asp Phe Ile Leu Lys Ser Glu Leu Ile Gly Ile Leu Leu Ala Glu Gly
545                 550                 555                 560

His Leu Leu Arg Arg Asp Ile Glu Tyr Phe Asp Ser Ser Arg Gly Lys
                565                 570                 575

Lys Arg Ile Ser His Gln Tyr Arg Val Glu Ile Thr Val Asn Glu Asp
            580                 585                 590

Glu Lys Asp Phe Ile Glu Lys Ile Lys Tyr Ile Phe Lys Lys Leu Phe
        595                 600                 605

Asn Tyr Glu Leu Tyr Val Arg Arg Lys Lys Gly Thr Lys Ala Ile Thr
    610                 615                 620

Leu Gly Cys Ala Lys Lys Asp Ile Tyr Leu Lys Ile Glu Glu Ile Leu
625                 630                 635                 640

Lys Asn Lys Glu Lys Tyr Leu Pro Asn Ala Ile Leu Arg Gly Phe Phe
                645                 650                 655

Glu Gly Asp Gly Tyr Val Asn Thr Val Arg Arg Ala Val Val Val Asn
            660                 665                 670

Gln Gly Thr Asn Asn Tyr Asp Lys Ile Lys Phe Ile Ala Ser Leu Leu
        675                 680                 685

Asp Arg Leu Gly Ile Lys Tyr Ser Phe Tyr Thr Tyr Ser Tyr Glu Glu
    690                 695                 700
```

-continued

```
Arg Gly Lys Lys Leu Lys Arg Tyr Val Ile Glu Ile Phe Ser Lys Gly
705                 710                 715                 720

Asp Leu Ile Lys Phe Ser Ile Leu Ile Ser Phe Ile Ser Arg Arg Lys
                725                 730                 735

Asn Asn Leu Leu Asn Glu Ile Ile Arg Gln Lys Thr Leu Tyr Lys Ile
            740                 745                 750

Gly Asp Tyr Gly Phe Tyr Asp Leu Asp Asp Val Cys Val Ser Leu Glu
        755                 760                 765

Ser Tyr Lys Gly Glu Val Tyr Asp Leu Thr Leu Glu Gly Arg Pro Tyr
    770                 775                 780

Tyr Phe Ala Asn Gly Ile Leu Thr His Asn Ser Leu Tyr Pro Ser Ile
785                 790                 795                 800

Ile Ile Ser Tyr Asn Ile Ser Pro Asp Thr Leu Asp Cys Glu Cys Cys
                805                 810                 815

Lys Asp Val Ser Glu Lys Ile Leu Gly His Trp Phe Cys Lys Lys Lys
            820                 825                 830

Glu Gly Leu Ile Pro Lys Thr Leu Arg Asn Leu Ile Glu Arg Arg Ile
        835                 840                 845

Asn Ile Lys Arg Arg Met Lys Lys Met Ala Glu Ile Gly Glu Ile Asn
    850                 855                 860

Glu Glu Tyr Asn Leu Leu Asp Tyr Glu Gln Lys Ser Leu Lys Ile Leu
865                 870                 875                 880

Ala Asn Ser Ile Leu Pro Asp Glu Tyr Leu Thr Ile Ile Glu Glu Asp
                885                 890                 895

Gly Ile Lys Val Val Lys Ile Gly Glu Tyr Ile Asp Asp Leu Met Arg
            900                 905                 910

Lys His Lys Asp Lys Ile Lys Phe Ser Gly Ile Ser Glu Ile Leu Glu
        915                 920                 925

Thr Lys Asn Leu Lys Thr Phe Ser Phe Asp Lys Ile Thr Lys Lys Cys
    930                 935                 940

Glu Ile Lys Lys Val Lys Ala Leu Ile Arg His Pro Tyr Phe Gly Lys
945                 950                 955                 960

Ala Tyr Lys Ile Lys Leu Arg Ser Gly Arg Thr Ile Lys Val Thr Arg
                965                 970                 975

Gly His Ser Leu Phe Lys Tyr Glu Asn Gly Lys Ile Val Glu Val Lys
            980                 985                 990

Gly Asp Asp Val Arg Phe Gly Asp  Leu Ile Val Val Pro  Lys Lys Leu
        995                 1000                 1005

Thr Cys  Val Asp Lys Glu Val  Val Ile Asn Ile Pro  Lys Arg Leu
    1010                 1015                 1020

Ile Asn  Ala Asp Glu Glu Glu  Ile Lys Asp Leu Val  Ile Thr Lys
    1025                 1030                 1035

His Lys  Asp Lys Ala Phe Phe  Val Lys Leu Lys Lys  Thr Leu Glu
    1040                 1045                 1050

Asp Ile  Glu Asn Asn Lys Leu  Lys Val Ile Phe Asp  Asp Cys Ile
    1055                 1060                 1065

Leu Tyr  Leu Lys Glu Leu Gly  Leu Ile Asp Tyr Asn  Ile Ile Lys
    1070                 1075                 1080

Lys Ile  Asn Lys Val Asp Ile  Lys Ile Leu Asp Glu  Glu Lys Phe
    1085                 1090                 1095

Lys Ala  Tyr Lys Lys Tyr Phe  Asp Thr Val Ile Glu  His Gly Asn
    1100                 1105                 1110

Phe Lys  Lys Gly Arg Cys Asn  Ile Gln Tyr Ile Lys  Ile Lys Asp
```

1115 1120 1125

Tyr Ile Ala Asn Ile Pro Asp Lys Glu Phe Glu Asp Cys Glu Ile
1130 1135 1140

Gly Ala Tyr Ser Gly Lys Ile Asn Ala Leu Leu Lys Leu Asp Glu
1145 1150 1155

Lys Leu Ala Lys Phe Leu Gly Phe Phe Val Thr Arg Gly Arg Leu
1160 1165 1170

Lys Lys Gln Lys Leu Lys Gly Glu Thr Val Tyr Glu Ile Ser Val
1175 1180 1185

Tyr Lys Ser Leu Pro Glu Tyr Gln Lys Glu Ile Ala Glu Thr Phe
1190 1195 1200

Lys Glu Val Phe Gly Ala Gly Ser Met Val Lys Asp Lys Val Thr
1205 1210 1215

Met Asp Asn Lys Ile Val Tyr Leu Val Leu Lys Tyr Ile Phe Lys
1220 1225 1230

Cys Gly Asp Lys Asp Lys Lys His Ile Pro Glu Glu Leu Phe Leu
1235 1240 1245

Ala Ser Glu Ser Val Ile Lys Ser Phe Leu Asp Gly Phe Leu Lys
1250 1255 1260

Ala Lys Lys Asn Ser His Lys Gly Thr Ser Thr Phe Met Ala Lys
1265 1270 1275

Asp Glu Lys Tyr Leu Asn Gln Leu Met Ile Leu Phe Asn Leu Val
1280 1285 1290

Gly Ile Pro Thr Arg Phe Thr Pro Val Lys Asn Lys Gly Tyr Lys
1295 1300 1305

Leu Thr Leu Asn Pro Lys Tyr Gly Thr Val Lys Asp Leu Met Leu
1310 1315 1320

Asp Glu Val Lys Glu Ile Glu Ala Phe Glu Tyr Ser Gly Tyr Val
1325 1330 1335

Tyr Asp Leu Ser Val Glu Asp Asn Glu Asn Phe Leu Val Asn Asn
1340 1345 1350

Ile Tyr Ala His Asn Ser Val Tyr Gly Tyr Leu Ala Phe Pro Arg
1355 1360 1365

Ala Arg Phe Tyr Ser Arg Glu Cys Ala Glu Ile Val Thr Tyr Leu
1370 1375 1380

Gly Arg Lys Tyr Ile Leu Glu Thr Val Lys Glu Ala Glu Lys Phe
1385 1390 1395

Gly Phe Lys Val Leu Tyr Ile Asp Thr Asp Gly Phe Tyr Ala Ile
1400 1405 1410

Trp Lys Glu Lys Ile Ser Lys Glu Glu Leu Ile Lys Lys Ala Met
1415 1420 1425

Glu Phe Val Glu Tyr Ile Asn Ser Lys Leu Pro Gly Thr Met Glu
1430 1435 1440

Leu Glu Phe Glu Gly Tyr Phe Lys Arg Gly Ile Phe Val Thr Lys
1445 1450 1455

Lys Arg Tyr Ala Leu Ile Asp Glu Asn Gly Arg Val Thr Val Lys
1460 1465 1470

Gly Leu Glu Phe Val Arg Arg Asp Trp Ser Asn Ile Ala Lys Ile
1475 1480 1485

Thr Gln Arg Arg Val Leu Glu Ala Leu Leu Val Glu Gly Ser Ile
1490 1495 1500

Glu Lys Ala Lys Lys Ile Ile Gln Asp Val Ile Lys Asp Leu Arg
1505 1510 1515

Glu Lys Lys Ile Lys Lys Glu Asp Leu Ile Ile Tyr Thr Gln Leu
1520 1525 1530

Thr Lys Asp Pro Lys Glu Tyr Lys Thr Thr Ala Pro His Val Glu
1535 1540 1545

Ile Ala Lys Lys Leu Met Arg Glu Gly Lys Arg Ile Lys Val Gly
1550 1555 1560

Asp Ile Ile Gly Tyr Ile Ile Val Lys Gly Thr Lys Ser Ile Ser
1565 1570 1575

Glu Arg Ala Lys Leu Pro Glu Glu Val Asp Ile Asp Asp Ile Asp
1580 1585 1590

Val Asn Tyr Tyr Ile Asp Asn Gln Ile Leu Pro Pro Val Leu Arg
1595 1600 1605

Ile Met Glu Ala Val Gly Val Ser Lys Asn Glu Leu Lys Lys Glu
1610 1615 1620

Gly Ala Gln Leu Thr Leu Asp Lys Phe Phe Lys
1625 1630

<210> SEQ ID NO 97
<211> LENGTH: 803
<212> TYPE: PRT
<213> ORGANISM: Pyrodictium occultum

<400> SEQUENCE: 97

Met Thr Glu Thr Ile Glu Phe Val Leu Leu Asp Ser Ser Tyr Glu Ile
1 5 10 15

Leu Gly Lys Glu Pro Val Val Ile Leu Trp Gly Ile Thr Leu Asp Gly
20 25 30

Lys Arg Val Val Leu Leu Asp His Arg Phe Arg Pro Tyr Phe Tyr Ala
35 40 45

Leu Ile Ala Arg Gly Tyr Glu Asp Met Val Glu Glu Ile Ala Ala Ser
50 55 60

Ile Arg Arg Leu Ser Val Val Lys Ser Pro Ile Ile Asp Ala Lys Pro
65 70 75 80

Leu Asp Lys Arg Tyr Phe Gly Arg Pro Arg Lys Ala Val Lys Ile Thr
85 90 95

Thr Met Ile Pro Glu Ser Val Arg His Tyr Arg Glu Ala Val Lys Lys
100 105 110

Ile Glu Gly Val Glu Asp Ser Leu Glu Ala Asp Ile Arg Phe Ala Met
115 120 125

Arg Tyr Leu Ile Asp Lys Arg Leu Tyr Pro Phe Thr Val Tyr Arg Ile
130 135 140

Pro Val Glu Asp Ala Gly Arg Asn Pro Gly Phe Arg Val Asp Arg Val
145 150 155 160

Tyr Lys Val Ala Gly Asp Pro Glu Pro Leu Ala Asp Ile Thr Arg Ile
165 170 175

Asp Leu Pro Pro Met Arg Leu Val Ala Phe Asp Ile Glu Val Tyr Ser
180 185 190

Arg Arg Gly Ser Pro Asn Pro Ala Arg Asp Pro Val Ile Ile Val Ser
195 200 205

Leu Arg Asp Ser Glu Gly Lys Glu Arg Leu Ile Glu Ala Glu Gly His
210 215 220

Asp Asp Arg Arg Val Leu Arg Glu Phe Val Glu Tyr Val Arg Ala Phe
225 230 235 240

Asp Pro Asp Ile Ile Val Gly Tyr Asn Ser Asn His Phe Asp Trp Pro
245 250 255

-continued

```
Tyr Leu Met Glu Arg Ala Arg Arg Leu Gly Ile Lys Leu Asp Val Thr
            260                 265                 270

Arg Arg Val Gly Ala Glu Pro Thr Thr Ser Val Tyr Gly His Val Ser
        275                 280                 285

Val Gln Gly Arg Leu Asn Val Asp Leu Tyr Asp Tyr Ala Glu Glu Met
    290                 295                 300

Pro Glu Ile Lys Met Lys Thr Leu Glu Glu Val Ala Glu Tyr Leu Gly
305                 310                 315                 320

Val Met Lys Lys Ser Glu Arg Val Ile Ile Glu Trp Trp Arg Ile Pro
                325                 330                 335

Glu Tyr Trp Asp Asp Glu Lys Lys Arg Gln Leu Leu Glu Arg Tyr Ala
            340                 345                 350

Leu Asp Asp Val Arg Ala Thr Tyr Gly Leu Ala Glu Lys Met Leu Pro
        355                 360                 365

Phe Ala Ile Gln Leu Ser Thr Val Thr Gly Val Pro Leu Asp Gln Val
    370                 375                 380

Gly Ala Met Gly Val Gly Phe Arg Leu Glu Trp Tyr Leu Met Arg Ala
385                 390                 395                 400

Ala Tyr Asp Met Asn Glu Leu Val Pro Asn Arg Val Glu Arg Arg Gly
                405                 410                 415

Glu Ser Tyr Lys Gly Ala Val Val Leu Lys Pro Leu Lys Gly Val His
            420                 425                 430

Glu Asn Val Val Val Leu Asp Phe Ser Ser Met Tyr Pro Ser Ile Met
        435                 440                 445

Ile Lys Tyr Asn Val Gly Pro Asp Thr Ile Val Asp Asp Pro Ser Glu
    450                 455                 460

Cys Pro Lys Tyr Gly Gly Cys Tyr Val Ala Pro Glu Val Gly His Arg
465                 470                 475                 480

Phe Arg Arg Ser Pro Pro Gly Phe Phe Lys Thr Val Leu Glu Asn Leu
                485                 490                 495

Leu Lys Leu Arg Arg Gln Val Lys Glu Lys Met Lys Glu Phe Pro Pro
            500                 505                 510

Asp Ser Pro Glu Tyr Arg Leu Tyr Asp Glu Arg Gln Lys Ala Leu Lys
        515                 520                 525

Val Leu Ala Asn Ala Ser Tyr Gly Tyr Met Gly Trp Ser His Ala Arg
    530                 535                 540

Trp Tyr Cys Lys Arg Cys Ala Glu Ala Val Thr Ala Trp Gly Arg Asn
545                 550                 555                 560

Leu Ile Leu Thr Ala Ile Glu Tyr Ala Arg Lys Leu Gly Leu Lys Val
                565                 570                 575

Ile Tyr Gly Asp Thr Asp Ser Leu Phe Val Val Tyr Asp Lys Glu Lys
            580                 585                 590

Val Glu Lys Leu Ile Glu Phe Val Glu Lys Glu Leu Gly Phe Glu Ile
        595                 600                 605

Lys Ile Asp Lys Ile Tyr Lys Lys Val Phe Phe Thr Glu Ala Lys Lys
    610                 615                 620

Arg Tyr Val Gly Leu Leu Glu Asp Gly Arg Ile Asp Ile Val Gly Phe
625                 630                 635                 640

Glu Ala Val Arg Gly Asp Trp Cys Glu Leu Ala Lys Glu Val Gln Glu
                645                 650                 655

Lys Ala Ala Glu Ile Val Leu Asn Thr Gly Asn Val Asp Lys Ala Ile
            660                 665                 670

Ser Tyr Ile Arg Glu Val Ile Lys Gln Leu Arg Glu Gly Lys Val Pro
        675                 680                 685
```

Ile Thr Lys Leu Ile Ile Trp Lys Thr Leu Ser Lys Arg Ile Glu Glu
    690                 695                 700

Tyr Glu His Asp Ala Pro His Val Met Ala Ala Arg Arg Met Lys Glu
705                 710                 715                 720

Ala Gly Tyr Glu Val Ser Pro Gly Asp Lys Val Gly Tyr Val Ile Val
                725                 730                 735

Lys Gly Ser Gly Ser Val Ser Ser Arg Ala Tyr Pro Tyr Phe Met Val
            740                 745                 750

Asp Pro Ser Thr Ile Asp Val Asn Tyr Tyr Ile Asp His Gln Ile Val
        755                 760                 765

Pro Ala Ala Leu Arg Ile Leu Ser Tyr Phe Gly Val Thr Glu Lys Gln
    770                 775                 780

Leu Lys Ala Ala Ala Thr Val Gln Arg Ser Leu Phe Asp Phe Phe Ala
785                 790                 795                 800

Ser Lys Lys

<210> SEQ ID NO 98
<211> LENGTH: 784
<212> TYPE: PRT
<213> ORGANISM: Aeropyrum pernix

<400> SEQUENCE: 98

Met Arg Gly Ser Thr Pro Val Ile Ile Leu Trp Gly Arg Gly Ala Asp
1               5                   10                  15

Gly Ser Arg Val Val Val Phe Tyr Gly Glu Phe Arg Pro Tyr Phe Tyr
            20                  25                  30

Val Leu Pro Asp Gly Ser Val Gly Leu Asp Gln Leu Ala Ala Met Ile
        35                  40                  45

Arg Arg Leu Ser Arg Pro Ser Ser Pro Ile Leu Ser Val Glu Arg Val
    50                  55                  60

Arg Arg Arg Phe Ile Gly Arg Glu Val Glu Ala Leu Lys Val Thr Thr
65                  70                  75                  80

Leu Val Pro Ala Ser Val Arg Glu Tyr Arg Glu Ala Val Arg Arg Leu
                85                  90                  95

Gly Gly Val Arg Asp Val Leu Glu Ala Asp Ile Pro Phe Ala Leu Arg
            100                 105                 110

Phe Ile Ile Asp Phe Asn Leu Tyr Pro Met Arg Trp Tyr Val Ala Glu
        115                 120                 125

Val Arg Glu Val Ala Val Pro His Gly Tyr Ser Val Asp Arg Ala Tyr
    130                 135                 140

Thr Leu Ser Gly Asp Ile Arg Glu Asp Glu Thr Arg Ile Gln Glu Asp
145                 150                 155                 160

Pro Leu Lys Gly Leu Arg Val Met Ala Phe Asp Ile Glu Val Tyr Ser
                165                 170                 175

Lys Met Arg Thr Pro Asp Pro Lys Lys Asp Pro Val Ile Met Ile Gly
            180                 185                 190

Leu Gln Gln Ala Gly Gly Glu Ile Glu Ile Leu Glu Ala Glu Asp Arg
        195                 200                 205

Ser Asp Lys Lys Val Ile Ala Gly Phe Val Glu Arg Val Lys Ser Ile
    210                 215                 220

Asp Pro Asp Val Ile Val Gly Tyr Asn Gln Asn Arg Phe Asp Trp Pro
225                 230                 235                 240

Tyr Leu Val Glu Arg Ala Arg Val Leu Gly Val Lys Leu Ala Val Gly
                245                 250                 255

```
Arg Arg Ser Val Glu Pro Gln Pro Gly Leu Tyr Gly His Tyr Ser Val
            260                 265                 270

Ser Gly Arg Leu Asn Val Asp Leu Leu Asp Phe Ala Glu Glu Leu His
        275                 280                 285

Glu Val Lys Val Lys Thr Leu Glu Glu Val Ala Asp Tyr Leu Gly Val
    290                 295                 300

Val Lys Ile Gly Glu Arg Val Thr Leu Glu Trp Trp Gln Ile Gly Glu
305                 310                 315                 320

Tyr Trp Asp Asp Pro Ser Lys Arg Glu Ile Leu Arg Lys Tyr Leu Arg
                325                 330                 335

Asp Asp Val Arg Ser Thr Met Gly Leu Ala Glu Lys Phe Leu Pro Phe
            340                 345                 350

Gly Ala Glu Leu Ser Gln Val Ser Gly Leu Pro Leu Asp Gln Val Met
        355                 360                 365

Ala Ala Ser Val Gly Phe Arg Leu Glu Trp Arg Leu Ile Arg Glu Ala
    370                 375                 380

Ala Lys Leu Gly Glu Leu Val Pro Asn Arg Val Glu Arg Ser Glu Gly
385                 390                 395                 400

Arg Tyr Ala Gly Ala Ile Val Leu Arg Pro Lys Pro Gly Val His Glu
                405                 410                 415

Asp Ile Ala Val Leu Asp Phe Ala Ser Met Tyr Pro Asn Ile Met Val
            420                 425                 430

Lys Tyr Asn Val Gly Pro Asp Thr Leu Val Arg Pro Gly Glu Glu Tyr
        435                 440                 445

Gly Glu Glu Glu Val Tyr Thr Ala Pro Glu Val Gly His Lys Phe Arg
    450                 455                 460

Lys Ser Pro Pro Gly Phe Phe Lys Lys Ile Leu Glu Arg Phe Leu Ser
465                 470                 475                 480

Trp Arg Arg Gln Ile Arg Ser Glu Met Lys Lys His Pro Pro Asp Ser
                485                 490                 495

Pro Glu Tyr Lys Leu Leu Asp Glu Arg Gln Lys Ala Ile Lys Leu Leu
            500                 505                 510

Ala Asn Ala Ser Tyr Gly Tyr Met Gly Trp Pro His Ala Arg Trp Tyr
        515                 520                 525

Cys Arg Glu Cys Ala Glu Ala Val Thr Ala Trp Gly Arg Ser Ile Ile
    530                 535                 540

Arg Thr Ala Ile Arg Lys Ala Gly Glu Leu Gly Leu Glu Val Ile Tyr
545                 550                 555                 560

Gly Asp Thr Asp Ser Leu Phe Val Lys Asn Asp Pro Glu Lys Val Glu
                565                 570                 575

Arg Leu Ile Arg Phe Val Glu Glu Glu Leu Gly Phe Asp Ile Lys Val
            580                 585                 590

Asp Lys Val Tyr Arg Arg Val Phe Phe Thr Glu Ala Lys Lys Arg Tyr
        595                 600                 605

Val Gly Leu Thr Val Asp Gly Lys Ile Asp Val Val Gly Phe Glu Ala
    610                 615                 620

Val Arg Gly Asp Trp Ser Glu Leu Ala Lys Glu Thr Gln Phe Lys Val
625                 630                 635                 640

Ala Glu Ile Val Leu Lys Thr Gly Ser Val Asp Glu Ala Val Asp Tyr
                645                 650                 655

Val Arg Asn Ile Ile Glu Lys Leu Arg Arg Gly Gln Val Asp Met Arg
            660                 665                 670

Lys Leu Val Ile Trp Lys Thr Leu Thr Arg Pro Pro Ser Met Tyr Glu
        675                 680                 685
```

Ala Arg Gln Pro His Val Thr Ala Ala Leu Leu Met Glu Arg Ala Gly
690 695 700

Ile Lys Val Glu Pro Gly Ala Lys Ile Gly Tyr Val Val Thr Lys Gly
705 710 715 720

Ser Gly Pro Leu Tyr Thr Arg Ala Lys Pro Tyr Phe Met Ala Ser Lys
725 730 735

Glu Glu Val Asp Val Glu Tyr Tyr Val Asp Lys Gln Val Val Pro Ala
740 745 750

Ala Leu Arg Ile Leu Gln Tyr Phe Gly Val Thr Glu Lys Arg Leu Lys
755 760 765

Gly Gly Gly Arg Gln Ser Thr Leu Leu Asp Phe Met Arg Arg Gly Lys
770 775 780

<210> SEQ ID NO 99
<211> LENGTH: 781
<212> TYPE: PRT
<213> ORGANISM: Archaeoglobus fulgidus

<400> SEQUENCE: 99

Met Glu Arg Val Glu Gly Trp Leu Ile Asp Ala Asp Tyr Glu Thr Ile
1 5 10 15

Gly Gly Lys Ala Val Val Arg Leu Trp Cys Lys Asp Asp Gln Gly Ile
20 25 30

Phe Val Ala Tyr Asp Tyr Asn Phe Asp Pro Tyr Phe Tyr Val Ile Gly
35 40 45

Val Asp Glu Asp Ile Leu Lys Asn Ala Ala Thr Ser Thr Arg Arg Glu
50 55 60

Val Ile Lys Leu Lys Ser Phe Glu Lys Ala Gln Leu Lys Thr Leu Gly
65 70 75 80

Arg Glu Val Glu Gly Tyr Ile Val Tyr Ala His His Pro Gln His Val
85 90 95

Pro Lys Leu Arg Asp Tyr Leu Ser Gln Phe Gly Asp Val Arg Glu Ala
100 105 110

Asp Ile Pro Phe Ala Tyr Arg Tyr Leu Ile Asp Lys Asp Leu Ala Cys
115 120 125

Met Asp Gly Ile Ala Ile Glu Gly Glu Lys Gln Gly Gly Val Ile Arg
130 135 140

Ser Tyr Lys Ile Glu Lys Val Glu Arg Ile Pro Arg Met Glu Phe Pro
145 150 155 160

Glu Leu Lys Met Leu Val Phe Asp Cys Glu Met Leu Ser Ser Phe Gly
165 170 175

Met Pro Glu Pro Glu Lys Asp Pro Ile Ile Val Ile Ser Val Lys Thr
180 185 190

Asn Asp Asp Asp Glu Ile Ile Leu Thr Gly Asp Glu Arg Lys Ile Ile
195 200 205

Ser Asp Phe Val Lys Leu Ile Lys Ser Tyr Asp Pro Asp Ile Ile Val
210 215 220

Gly Tyr Asn Gln Asp Ala Phe Asp Trp Pro Tyr Leu Arg Lys Arg Ala
225 230 235 240

Glu Arg Trp Asn Ile Pro Leu Asp Val Gly Arg Asp Gly Ser Asn Val
245 250 255

Val Phe Arg Gly Gly Arg Pro Lys Ile Thr Gly Arg Leu Asn Val Asp
260 265 270

Leu Tyr Asp Ile Ala Met Arg Ile Ser Asp Ile Lys Ile Lys Lys Leu
275 280 285

```
Glu Asn Val Ala Glu Phe Leu Gly Thr Lys Ile Glu Ile Ala Asp Ile
    290                 295                 300

Glu Ala Lys Asp Ile Tyr Arg Tyr Trp Ser Arg Gly Glu Lys Glu Lys
305                 310                 315                 320

Val Leu Asn Tyr Ala Arg Gln Asp Ala Ile Asn Thr Tyr Leu Ile Ala
                325                 330                 335

Lys Glu Leu Leu Pro Met His Tyr Glu Leu Ser Lys Met Ile Arg Leu
            340                 345                 350

Pro Val Asp Asp Val Thr Arg Met Gly Arg Gly Lys Gln Val Asp Trp
        355                 360                 365

Leu Leu Leu Ser Glu Ala Lys Lys Ile Gly Glu Ile Ala Pro Asn Pro
    370                 375                 380

Pro Glu His Ala Glu Ser Tyr Glu Gly Ala Phe Val Leu Glu Pro Glu
385                 390                 395                 400

Arg Gly Leu His Glu Asn Val Ala Cys Leu Asp Phe Ala Ser Met Tyr
                405                 410                 415

Pro Ser Ile Met Ile Ala Phe Asn Ile Ser Pro Asp Thr Tyr Gly Cys
            420                 425                 430

Arg Asp Asp Cys Tyr Glu Ala Pro Glu Val Gly His Lys Phe Arg Lys
        435                 440                 445

Ser Pro Asp Gly Phe Phe Lys Arg Ile Leu Arg Met Leu Ile Glu Lys
    450                 455                 460

Arg Arg Glu Leu Lys Val Glu Leu Lys Asn Leu Ser Pro Glu Ser Ser
465                 470                 475                 480

Glu Tyr Lys Leu Leu Asp Ile Lys Gln Gln Thr Leu Lys Val Leu Thr
                485                 490                 495

Asn Ser Phe Tyr Gly Tyr Met Gly Trp Asn Leu Ala Arg Trp Tyr Cys
            500                 505                 510

His Pro Cys Ala Glu Ala Thr Thr Ala Trp Gly Arg His Phe Ile Arg
        515                 520                 525

Thr Ser Ala Lys Ile Ala Glu Ser Met Gly Phe Lys Val Leu Tyr Gly
    530                 535                 540

Asp Thr Asp Ser Ile Phe Val Thr Lys Ala Gly Met Thr Lys Glu Asp
545                 550                 555                 560

Val Asp Arg Leu Ile Asp Lys Leu His Glu Glu Leu Pro Ile Gln Ile
                565                 570                 575

Glu Val Asp Glu Tyr Tyr Ser Ala Ile Phe Phe Val Glu Lys Lys Arg
            580                 585                 590

Tyr Ala Gly Leu Thr Glu Asp Gly Arg Leu Val Val Lys Gly Leu Glu
        595                 600                 605

Val Arg Arg Gly Asp Trp Cys Glu Leu Ala Lys Lys Val Gln Arg Glu
    610                 615                 620

Val Ile Glu Val Ile Leu Lys Glu Lys Asn Pro Glu Lys Ala Leu Ser
625                 630                 635                 640

Leu Val Lys Asp Val Ile Leu Arg Ile Lys Glu Gly Lys Val Ser Leu
                645                 650                 655

Glu Glu Val Val Ile Tyr Lys Gly Leu Thr Lys Lys Pro Ser Lys Tyr
            660                 665                 670

Glu Ser Met Gln Ala His Val Lys Ala Ala Leu Lys Ala Arg Glu Met
        675                 680                 685

Gly Ile Ile Tyr Pro Val Ser Ser Lys Ile Gly Tyr Val Ile Val Lys
    690                 695                 700

Gly Ser Gly Asn Ile Gly Asp Arg Ala Tyr Pro Ile Asp Leu Ile Glu
```

705 710 715 720

Asp Phe Asp Gly Glu Asn Leu Arg Ile Lys Thr Lys Ser Gly Ile Glu
725 730 735

Ile Lys Lys Leu Asp Lys Asp Tyr Tyr Ile Asp Asn Gln Ile Ile Pro
740 745 750

Ser Val Leu Arg Ile Leu Glu Arg Phe Gly Tyr Thr Glu Ala Ser Leu
755 760 765

Lys Gly Ser Ser Gln Met Ser Leu Asp Ser Phe Phe Ser
770 775 780

<210> SEQ ID NO 100
<211> LENGTH: 773
<212> TYPE: PRT
<213> ORGANISM: Desulfurococcus saccharovorans

<400> SEQUENCE: 100

Met Ile Leu Asp Ala Asp Tyr Ile Thr Glu Asp Gly Lys Pro Val Ile
1 5 10 15

Arg Val Phe Lys Lys Glu Lys Gly Glu Phe Lys Ile Asp Tyr Asp Arg
20 25 30

Asp Phe Glu Pro Tyr Ile Tyr Ala Leu Leu Lys Asp Asp Ser Ala Ile
35 40 45

Glu Asp Ile Lys Lys Ile Thr Ala Glu Arg His Gly Thr Thr Val Arg
50 55 60

Val Thr Arg Ala Glu Arg Val Lys Lys Lys Phe Leu Gly Arg Pro Val
65 70 75 80

Glu Val Trp Lys Leu Tyr Phe Thr His Pro Gln Asp Val Pro Ala Ile
85 90 95

Arg Asp Lys Ile Arg Glu His Pro Ala Val Val Asp Ile Tyr Glu Tyr
100 105 110

Asp Ile Pro Phe Ala Lys Arg Tyr Leu Ile Asp Arg Gly Leu Ile Pro
115 120 125

Met Glu Gly Asp Glu Glu Leu Arg Met Leu Ala Phe Asp Ile Glu Thr
130 135 140

Leu Tyr His Glu Gly Glu Glu Phe Gly Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Glu Ser Val Ser Thr Glu Lys Glu Met Ile Lys
180 185 190

Arg Phe Leu Lys Val Ile Gln Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Met Leu Gly Val Lys Phe Ile Leu Gly Arg Asp Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Thr Val Tyr Glu Pro Val Phe Gly Gln Pro Lys Glu
275 280 285

Lys Val Tyr Ala Glu Glu Ile Ala Arg Ala Trp Glu Ser Gly Glu Gly
290 295 300

Leu Glu Arg Val Ala Arg Tyr Ser Met Glu Asp Ala Lys Ala Thr Tyr

```
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Asp Val Ala
        355                 360                 365

Pro Asn Lys Pro Asp Glu Arg Glu Leu Ala Arg Arg Thr Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Ala Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Asn Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg His Glu Val Pro
                645                 650                 655

Pro Glu Lys Leu Val Ile Tyr Glu Gln Ile Thr Arg Asp Leu Arg Ser
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735
```

Val Leu Pro Ala Val Glu Arg Ile Leu Arg Ala Phe Gly Tyr Arg Lys
740 745 750

Glu Asp Leu Arg Tyr Gln Lys Thr Lys Gln Ala Gly Leu Gly Ala Trp
755 760 765

Leu Lys Pro Lys Thr
770

<210> SEQ ID NO 101
<211> LENGTH: 775
<212> TYPE: PRT
<213> ORGANISM: Thermococcus sp.

<400> SEQUENCE: 101

Met Ile Leu Asp Thr Asp Tyr Ile Thr Glu Asn Gly Lys Pro Val Ile
1 5 10 15

Arg Val Phe Lys Lys Glu Asn Gly Glu Phe Lys Ile Glu Tyr Asp Arg
20 25 30

Thr Phe Glu Pro Tyr Phe Tyr Ala Leu Leu Lys Asp Asp Ser Ala Ile
35 40 45

Glu Asp Val Lys Lys Val Thr Ala Lys Arg His Gly Thr Val Val Lys
50 55 60

Val Lys Arg Ala Glu Lys Val Gln Lys Lys Phe Leu Gly Arg Pro Ile
65 70 75 80

Glu Val Trp Lys Leu Tyr Phe Asn His Pro Gln Asp Val Pro Ala Ile
85 90 95

Arg Asp Arg Ile Arg Ala His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Thr Met Leu Ala Phe Asp Ile Glu Thr
130 135 140

Leu Tyr His Glu Gly Glu Glu Phe Gly Thr Gly Pro Ile Leu Met Ile
145 150 155 160

Ser Tyr Ala Asp Gly Ser Glu Ala Arg Val Ile Thr Trp Lys Lys Ile
165 170 175

Asp Leu Pro Tyr Val Asp Val Val Ser Thr Glu Lys Glu Met Ile Lys
180 185 190

Arg Phe Leu Arg Val Val Arg Glu Lys Asp Pro Asp Val Leu Ile Thr
195 200 205

Tyr Asn Gly Asp Asn Phe Asp Phe Ala Tyr Leu Lys Lys Arg Cys Glu
210 215 220

Glu Leu Gly Ile Lys Phe Thr Leu Gly Arg Asp Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Val Phe Gly Lys Pro Lys Glu
275 280 285

Lys Val Tyr Ala Glu Glu Ile Ala Gln Ala Trp Glu Ser Gly Glu Gly
290 295 300

Leu Glu Arg Val Ala Arg Tyr Ser Met Glu Asp Ala Lys Val Thr Tyr
305 310 315 320

Glu Leu Gly Arg Glu Phe Phe Pro Met Glu Ala Gln Leu Ser Arg Leu
325 330 335

```
Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765
```

```
Leu Lys Val Lys Gly Lys Lys
    770                 775


<210> SEQ ID NO 102
<211> LENGTH: 781
<212> TYPE: PRT
<213> ORGANISM: Archaeoglobus fulgidus

<400> SEQUENCE: 102

Met Glu Arg Val Glu Gly Trp Leu Ile Asp Ala Asp Tyr Glu Thr Ile
1               5                   10                  15

Gly Gly Lys Ala Val Val Arg Leu Trp Cys Lys Asp Asp Gln Gly Ile
            20                  25                  30

Phe Val Ala Tyr Asp Tyr Asn Phe Asp Pro Tyr Phe Tyr Val Ile Gly
        35                  40                  45

Val Asp Glu Asp Ile Leu Lys Asn Ala Ala Thr Ser Thr Arg Arg Glu
    50                  55                  60

Val Ile Lys Leu Lys Ser Phe Glu Lys Ala Gln Leu Lys Thr Leu Gly
65                  70                  75                  80

Arg Glu Val Glu Gly Tyr Ile Val Tyr Ala His His Pro Gln His Val
                85                  90                  95

Pro Lys Leu Arg Asp Tyr Leu Ser Gln Phe Gly Asp Val Arg Glu Ala
            100                 105                 110

Asp Ile Pro Phe Ala Tyr Arg Tyr Leu Ile Asp Lys Asp Leu Ala Cys
        115                 120                 125

Met Asp Gly Ile Ala Ile Glu Gly Glu Lys Gln Gly Gly Val Ile Arg
    130                 135                 140

Ser Tyr Lys Ile Glu Lys Val Glu Arg Ile Pro Arg Met Glu Phe Pro
145                 150                 155                 160

Glu Leu Lys Met Leu Val Phe Asp Cys Glu Met Leu Ser Ser Phe Gly
                165                 170                 175

Met Pro Glu Pro Glu Lys Asp Pro Ile Ile Val Ile Ser Val Lys Thr
            180                 185                 190

Asn Asp Asp Asp Glu Ile Ile Leu Thr Gly Asp Glu Arg Lys Ile Ile
        195                 200                 205

Ser Asp Phe Val Lys Leu Ile Lys Ser Tyr Asp Pro Asp Ile Ile Val
    210                 215                 220

Gly Tyr Asn Gln Asp Ala Phe Asp Trp Pro Tyr Leu Arg Lys Arg Ala
225                 230                 235                 240

Glu Arg Trp Asn Ile Pro Leu Asp Val Gly Arg Asp Gly Ser Asn Val
                245                 250                 255

Val Phe Arg Gly Gly Arg Pro Lys Ile Thr Gly Arg Leu Asn Val Asp
            260                 265                 270

Leu Tyr Asp Ile Ala Met Arg Ile Ser Asp Ile Lys Ile Lys Lys Leu
        275                 280                 285

Glu Asn Val Ala Glu Phe Leu Gly Thr Lys Ile Glu Ile Ala Asp Ile
    290                 295                 300

Glu Ala Lys Asp Ile Tyr Arg Tyr Trp Ser Arg Gly Glu Lys Glu Lys
305                 310                 315                 320

Val Leu Asn Tyr Ala Arg Gln Asp Ala Ile Asn Thr Tyr Leu Ile Ala
                325                 330                 335

Lys Glu Leu Leu Pro Met His Tyr Glu Leu Ser Lys Met Ile Arg Leu
            340                 345                 350

Pro Val Asp Asp Val Thr Arg Met Gly Arg Gly Lys Gln Val Asp Trp
        355                 360                 365
```

-continued

```
Leu Leu Leu Ser Glu Ala Lys Lys Ile Gly Glu Ile Ala Pro Asn Pro
    370                 375                 380

Pro Glu His Ala Glu Ser Tyr Glu Gly Ala Phe Val Leu Glu Pro Glu
385                 390                 395                 400

Arg Gly Leu His Glu Asn Val Ala Cys Leu Asp Phe Ala Ser Met Tyr
                405                 410                 415

Pro Ser Ile Met Ile Ala Phe Asn Ile Ser Pro Asp Thr Tyr Gly Cys
            420                 425                 430

Arg Asp Asp Cys Tyr Glu Ala Pro Glu Val Gly His Lys Phe Arg Lys
        435                 440                 445

Ser Pro Asp Gly Phe Phe Lys Arg Ile Leu Arg Met Leu Ile Glu Lys
    450                 455                 460

Arg Arg Glu Leu Lys Val Glu Leu Lys Asn Leu Ser Pro Glu Ser Ser
465                 470                 475                 480

Glu Tyr Lys Leu Leu Asp Ile Lys Gln Gln Thr Leu Lys Val Leu Thr
                485                 490                 495

Asn Ser Phe Tyr Gly Tyr Met Gly Trp Asn Leu Ala Arg Trp Tyr Cys
            500                 505                 510

His Pro Cys Ala Glu Ala Thr Thr Ala Trp Gly Arg His Phe Ile Arg
        515                 520                 525

Thr Ser Ala Lys Ile Ala Glu Ser Met Gly Phe Lys Val Leu Tyr Gly
    530                 535                 540

Asp Thr Asp Ser Ile Phe Val Thr Lys Ala Gly Met Thr Lys Glu Asp
545                 550                 555                 560

Val Asp Arg Leu Ile Asp Lys Leu His Glu Glu Leu Pro Ile Gln Ile
                565                 570                 575

Glu Val Asp Glu Tyr Tyr Ser Ala Ile Phe Phe Val Glu Lys Lys Arg
            580                 585                 590

Tyr Ala Gly Leu Thr Glu Asp Gly Arg Leu Val Val Lys Gly Leu Glu
        595                 600                 605

Val Arg Arg Gly Asp Trp Cys Glu Leu Ala Lys Lys Val Gln Arg Glu
    610                 615                 620

Val Ile Glu Val Ile Leu Lys Glu Lys Asn Pro Glu Lys Ala Leu Ser
625                 630                 635                 640

Leu Val Lys Asp Val Ile Leu Arg Ile Lys Glu Gly Lys Val Ser Leu
                645                 650                 655

Glu Glu Val Val Ile Tyr Lys Gly Leu Thr Lys Lys Pro Ser Lys Tyr
            660                 665                 670

Glu Ser Met Gln Ala His Val Lys Ala Ala Leu Lys Ala Arg Glu Met
        675                 680                 685

Gly Ile Ile Tyr Pro Val Ser Ser Lys Ile Gly Tyr Val Ile Val Lys
    690                 695                 700

Gly Ser Gly Asn Ile Gly Asp Arg Ala Tyr Pro Ile Asp Leu Ile Glu
705                 710                 715                 720

Asp Phe Asp Gly Glu Asn Leu Arg Ile Lys Thr Lys Ser Gly Ile Glu
                725                 730                 735

Ile Lys Lys Leu Asp Lys Asp Tyr Tyr Ile Asp Asn Gln Ile Ile Pro
            740                 745                 750

Ser Val Leu Arg Ile Leu Glu Arg Phe Gly Tyr Thr Glu Ala Ser Leu
        755                 760                 765

Lys Gly Ser Ser Gln Met Ser Leu Asp Ser Phe Phe Ser
    770                 775                 780
```

<210> SEQ ID NO 103
<211> LENGTH: 824
<212> TYPE: PRT
<213> ORGANISM: Methanococcus voltae

<400> SEQUENCE: 103

Met Asp Leu Asp Tyr Asn Ser Lys Asp Leu Cys Ile Asp Met Tyr Tyr
1               5                   10                  15

Lys Asn Cys Gly Leu Lys Lys Pro Glu Ile Asn Leu Gln Lys Glu Cys
            20                  25                  30

Glu Phe Lys Pro Tyr Phe Tyr Val Asp Thr Ser Glu Pro Lys Glu Ile
        35                  40                  45

Tyr Asp Tyr Leu Asp Gly Leu Asn Gln Glu Ile Asp Leu Lys Lys Leu
    50                  55                  60

Glu Pro Glu Phe Glu Asn Asn Thr Ser Leu Lys Val Gln Asp Leu Ile
65                  70                  75                  80

Thr Asn Ile Glu Ile Ile Glu Lys Ile Val Tyr Ser Asp Tyr Ile Leu
                85                  90                  95

Asn Gly Lys Asp Ile Ser Glu Val Ser Asp Phe Lys Asn Lys Lys Glu
            100                 105                 110

Arg Lys Ile Cys Lys Val Tyr Val Lys Tyr Pro Asn His Val Lys Ile
        115                 120                 125

Ile Arg Glu Tyr Phe Lys Glu Phe Gly Lys Ser Tyr Glu Phe Asp Ile
    130                 135                 140

Pro Phe Leu Arg Arg Tyr Met Ile Asp Gln Asp Ile Val Pro Ser Ala
145                 150                 155                 160

Lys Tyr Ser Glu Asp Asn Lys Ile Asp Asn Ser Ile Pro Glu Leu Asn
                165                 170                 175

Cys Ile Ala Phe Asp Met Glu Leu Tyr Cys Lys Lys Glu Pro Asn Ala
            180                 185                 190

Lys Lys Asp Pro Ile Ile Met Val Asn Leu Phe Ser Lys Asp Tyr Gln
        195                 200                 205

Lys Val Ile Thr Tyr Lys Lys Phe Glu Asn Ser Glu Tyr Asn Gly Cys
    210                 215                 220

Val Asp Tyr Val Lys Asp Glu Lys Glu Leu Ile Gln Lys Thr Ile Glu
225                 230                 235                 240

Ile Leu Lys Gln Tyr Asp Val Ile Tyr Thr Tyr Asn Gly Asp Asn Phe
                245                 250                 255

Asp Phe Pro Tyr Leu Lys Lys Arg Ala Asn Ile Tyr Glu Ile Glu Leu
            260                 265                 270

Asp Phe Asp Asn Ala Ser Asn Ser Gln Gln Pro Gln Ile Ile Lys Ile
        275                 280                 285

Ser Lys Gly Gly Ile Asn Arg Lys Ser Lys Ile Pro Gly Ile Ile His
    290                 295                 300

Ile Asp Leu Tyr Pro Ile Ala Arg Lys Leu Leu Asn Leu Thr Lys Tyr
305                 310                 315                 320

Lys Leu Glu Asn Val Val Gln Glu Leu Phe Lys Ile Asn Lys Glu Ala
                325                 330                 335

Val Asp Tyr Gly Asp Ile Pro Lys Met Trp Glu Thr Glu Asp Thr Thr
            340                 345                 350

Leu Leu Arg Tyr Ala Tyr Glu Asp Ala Leu Tyr Thr Tyr Lys Met Gly
        355                 360                 365

Asn Tyr Phe Leu Pro Leu Glu Ile Met Phe Ser Arg Ile Val Asn Gln
    370                 375                 380

Pro Leu Tyr Asp Thr Ser Arg Met Asn Ser Ser Gln Met Val Glu Phe

-continued

```
385                 390                 395                 400

Leu Leu Leu Lys Arg Ser Phe Glu Gln Asn Met Ile Ser Pro Asn Arg
                405                 410                 415

Pro Ser Ser Ser Ser Tyr Arg Glu Arg Ala Lys Phe Ser Tyr Glu Gly
            420                 425                 430

Gly Tyr Val Arg Glu Pro Leu Lys Gly Ile Gln Glu Asp Ile Val Ser
        435                 440                 445

Leu Asp Phe Met Ser Leu Tyr Pro Ser Ile Leu Ile Ser His Asn Ile
    450                 455                 460

Ser Pro Glu Thr Val Ile Tyr Glu Glu Lys Glu Arg Glu Asn Met Glu
465                 470                 475                 480

Leu Gly Ile Ile Pro Lys Thr Leu Asn Glu Leu Leu Ser Arg Arg Lys
                485                 490                 495

His Ile Lys Met Leu Leu Lys Asp Lys Ile Gln Lys Asn Glu Phe Asp
            500                 505                 510

Glu Glu Tyr Ser Arg Leu Glu His Glu Gln Lys Ser Ile Lys Val Leu
        515                 520                 525

Ala Asn Ser His Tyr Gly Tyr Leu Ala Phe Pro Met Ala Arg Trp Tyr
    530                 535                 540

Ser Asp Lys Cys Ala Glu Met Val Thr Gly Leu Gly Arg Lys Tyr Ile
545                 550                 555                 560

Gln Glu Thr Ile Glu Lys Ala Glu Glu Phe Gly Phe Lys Val Ile Tyr
                565                 570                 575

Ala Asp Thr Asp Gly Phe Tyr Ala Lys Trp Asp Tyr Asp Lys Leu Gln
            580                 585                 590

Lys Gly Lys Lys Glu Glu Asn Asp Lys Ser Asp Lys Leu Ser Asn Leu
        595                 600                 605

Pro Lys Leu Ser Lys Glu Glu Leu Ile Ile Leu Thr Lys Lys Phe Leu
    610                 615                 620

Lys Gly Ile Asn Glu Glu Leu Pro Glu Gly Met Glu Leu Glu Phe Glu
625                 630                 635                 640

Gly His Phe Lys Arg Gly Leu Phe Val Thr Lys Lys Lys Tyr Ala Leu
                645                 650                 655

Ile Glu Asp Asp Gly His Ile Val Val Lys Gly Leu Glu Val Val Arg
            660                 665                 670

Arg Asp Trp Ser Asn Ile Ala Lys Asp Thr Gln Gln Ala Val Ile Arg
        675                 680                 685

Ala Leu Leu Glu Asp Gly Asp Val Asn Leu Ala Lys Lys Ile Ile Lys
    690                 695                 700

Asn Thr Ile Asp Asn Leu Lys Lys Gly Asn Ile Asp Lys Asn Asp Leu
705                 710                 715                 720

Leu Ile His Thr Gln Leu Thr Lys Asn Ile Glu Glu Tyr Lys Ser Thr
                725                 730                 735

Ala Pro His Ile Glu Val Ala Lys Lys Ile Lys Gln Arg Gly Asp Ser
            740                 745                 750

Val Arg Val Gly Asp Val Ile Ser Tyr Ile Ile Val Lys Gly Ser Arg
        755                 760                 765

Ser Ile Ser Glu Arg Ala Glu Leu Leu Glu Tyr Ala Gly Asp Tyr Asp
    770                 775                 780

Ile Asn Tyr Tyr Ile Asp Asn Gln Val Leu Pro Pro Val Ile Arg Ile
785                 790                 795                 800

Met Glu Ser Leu Gly Ile Ser Glu Asp Glu Leu Lys Asn Ser Gly Lys
                805                 810                 815
```

```
Gln Phe Lys Leu Asp Gln Phe Met
            820


<210> SEQ ID NO 104
<211> LENGTH: 785
<212> TYPE: PRT
<213> ORGANISM: Pyrobaculum islandicum

<400> SEQUENCE: 104

Met Glu Leu Lys Val Trp Pro Leu Asp Ile Thr Tyr Ala Val Val Gly
1               5                   10                  15

Ser Val Pro Glu Ile Arg Ile Phe Gly Ile Leu Ser Ser Gly Glu Arg
            20                  25                  30

Val Val Leu Ile Asp Arg Ser Phe Lys Pro Tyr Phe Tyr Val Asp Cys
        35                  40                  45

Ala Val Cys Glu Pro Ala Ala Leu Lys Thr Ala Leu Ser Arg Val Ala
    50                  55                  60

Pro Ile Asp Asp Val Gln Ile Val Glu Arg Arg Phe Leu Gly Arg Ser
65                  70                  75                  80

Lys Lys Phe Leu Lys Val Ile Ala Lys Ile Pro Glu Asp Val Arg Lys
                85                  90                  95

Leu Arg Glu Ala Ala Met Ser Ile Pro Arg Val Ser Gly Val Tyr Glu
            100                 105                 110

Ala Asp Ile Arg Phe Tyr Met Arg Tyr Met Ile Asp Met Gly Val Val
        115                 120                 125

Pro Cys Ser Trp Asn Val Ala Glu Val Glu Glu Gly Gly Arg Leu Gly
    130                 135                 140

Gly Ile Pro Thr Tyr Val Val Ser Gln Trp Tyr Gly Ile Asp Glu Gly
145                 150                 155                 160

Phe Pro Pro Ser Leu Lys Val Met Ala Phe Asp Ile Glu Val Tyr Asn
                165                 170                 175

Glu Arg Gly Ser Pro Asp Pro Ile Arg Asp Pro Val Val Met Leu Ala
            180                 185                 190

Ile Lys Thr Asn Asp Gly His Glu Glu Val Phe Glu Ala Ser Gly Lys
        195                 200                 205

Asp Asp Arg Gly Val Val Arg Ala Phe Val Asp Phe Ile Arg Ser Tyr
    210                 215                 220

Asp Pro Asp Val Ile Val Gly Tyr Asn Ser Asn Gly Phe Asp Trp Pro
225                 230                 235                 240

Tyr Leu Val Glu Arg Ala Lys Ala Val Gly Val Pro Leu Lys Val Asp
                245                 250                 255

Arg Leu Ser Asn Pro Pro Gln Gln Ser Val Tyr Gly His Trp Ser Ile
            260                 265                 270

Val Gly Arg Ala Asn Val Asp Leu Tyr Asn Ile Val Glu Glu Phe Pro
        275                 280                 285

Glu Ile Lys Leu Lys Thr Leu Asp Arg Val Ala Glu Tyr Phe Gly Val
    290                 295                 300

Met Lys Arg Glu Glu Arg Val Leu Ile Pro Gly His Lys Ile Tyr Glu
305                 310                 315                 320

Tyr Trp Lys Asp Pro Asn Lys Arg Pro Leu Leu Lys Arg Tyr Val Leu
                325                 330                 335

Asp Asp Val Arg Ser Thr Leu Gly Leu Ala Asp Lys Leu Leu Pro Phe
            340                 345                 350

Leu Ile Gln Leu Ser Ser Val Ser Gly Leu Pro Leu Asp Gln Val Ala
        355                 360                 365
```

```
Ala Ala Ser Val Gly Asn Arg Val Glu Trp Met Leu Leu Arg Tyr Ala
    370                 375                 380

Tyr Arg Leu Gly Glu Val Ala Pro Asn Arg Glu Glu Arg Glu Tyr Glu
385                 390                 395                 400

Pro Tyr Lys Gly Ala Ile Val Leu Glu Pro Lys Pro Gly Met Tyr Glu
                405                 410                 415

Asp Val Leu Val Leu Asp Phe Ser Ser Met Tyr Pro Asn Ile Met Met
            420                 425                 430

Lys Tyr Asn Leu Ser Pro Asp Thr Tyr Leu Glu Pro Gly Glu Pro Asp
        435                 440                 445

Pro Pro Glu Gly Val Asn Val Ala Pro Glu Val Gly His Arg Phe Arg
    450                 455                 460

Arg Ser Pro Pro Gly Phe Val Pro Gln Val Leu Lys Ser Leu Val Glu
465                 470                 475                 480

Leu Arg Lys Ala Val Arg Glu Glu Ala Lys Lys Tyr Pro Pro Asp Ser
                485                 490                 495

Pro Glu Phe Lys Ile Leu Asp Glu Arg Gln Arg Ala Leu Lys Val Met
            500                 505                 510

Ala Asn Ala Ile Tyr Gly Tyr Leu Gly Trp Val Gly Ala Arg Trp Tyr
        515                 520                 525

Lys Arg Glu Val Ala Glu Ser Val Thr Ala Phe Ala Arg Ala Ile Leu
    530                 535                 540

Lys Asp Val Ile Glu Gln Ala Arg Arg Leu Gly Ile Val Val Val Tyr
545                 550                 555                 560

Gly Asp Thr Asp Ser Leu Phe Val Lys Lys His Gly Asp Val Asp Lys
                565                 570                 575

Leu Ile Lys Tyr Val Glu Glu Lys Tyr Gly Ile Asp Ile Lys Val Asp
            580                 585                 590

Lys Asp Tyr Ala Lys Val Leu Phe Thr Glu Ala Lys Lys Arg Tyr Ala
        595                 600                 605

Gly Leu Leu Arg Asp Gly Arg Ile Asp Ile Val Gly Phe Glu Val Val
    610                 615                 620

Arg Gly Asp Trp Ser Glu Leu Ala Lys Asp Val Gln Leu Arg Val Ile
625                 630                 635                 640

Glu Ile Ile Leu Lys Ser Arg Asp Ile Val Glu Ala Arg His Gly Val
                645                 650                 655

Ile Lys Tyr Ile Arg Glu Ile Ile Glu Arg Leu Lys Asn Tyr Lys Phe
            660                 665                 670

Asn Ile Asp Asp Leu Ile Ile Trp Lys Thr Leu Asp Lys Glu Leu Asp
        675                 680                 685

Glu Tyr Lys Ala Tyr Pro Pro His Val His Ala Ala Gln Ile Leu Lys
    690                 695                 700

Arg His Gly Tyr Arg Val Gly Lys Gly Thr Thr Ile Gly Tyr Val Ile
705                 710                 715                 720

Val Lys Gly Gly Glu Lys Val Ser Glu Arg Ala Leu Pro Tyr Ile Leu
                725                 730                 735

Leu Asp Asp Ile Lys Lys Ile Asp Ile Asp Tyr Tyr Ile Glu Arg Gln
            740                 745                 750

Ile Ile Pro Ala Ala Leu Arg Ile Ala Glu Val Ile Gly Val Lys Glu
        755                 760                 765

Ser Asp Leu Lys Thr Gly Arg Met Glu Arg Ser Leu Leu Asp Phe Leu
    770                 775                 780

Ser
785
```

<210> SEQ ID NO 105
<211> LENGTH: 844
<212> TYPE: PRT
<213> ORGANISM: Cenarchaeum symbiosum

<400> SEQUENCE: 105

Met Thr Val Gln Asp Ala Val Glu Ile Pro Pro Ser Leu Leu Val Ser
1               5                   10                  15

Ala Thr Tyr Asp Ser Gln Ala Gly Ala Val Val Leu Lys Phe Tyr Glu
            20                  25                  30

Pro Glu Ser Gln Lys Ile Val His Trp Thr Asp Asn Thr Gly His Lys
        35                  40                  45

Pro Tyr Cys Tyr Thr Arg Gln Pro Pro Ser Glu Leu Gly Glu Leu Glu
    50                  55                  60

Gly Arg Glu Asp Val Leu Gly Thr Glu Gln Val Met Arg His Asp Leu
65                  70                  75                  80

Ile Ala Asp Lys Asp Val Pro Val Thr Lys Ile Thr Val Ala Asp Pro
                85                  90                  95

Leu Ala Ile Gly Gly Thr Asn Ser Glu Lys Ser Ile Arg Asn Ile Met
            100                 105                 110

Asp Thr Trp Glu Ser Asp Ile Lys Tyr Tyr Glu Asn Tyr Leu Tyr Asp
        115                 120                 125

Lys Ser Leu Val Val Gly Arg Tyr Tyr Ser Val Ser Gly Gly Lys Val
    130                 135                 140

Ile Pro His Asp Met Pro Ile Ser Asp Glu Val Lys Leu Ala Leu Lys
145                 150                 155                 160

Ser Leu Leu Trp Asp Lys Val Val Asp Glu Gly Met Ala Asp Arg Lys
                165                 170                 175

Glu Phe Arg Glu Phe Ile Ala Gly Trp Ala Asp Leu Leu Asn Gln Pro
            180                 185                 190

Ile Pro Arg Ile Arg Arg Leu Ser Phe Asp Ile Glu Val Asp Ser Glu
        195                 200                 205

Glu Gly Arg Ile Pro Asp Pro Lys Ile Ser Asp Arg Arg Val Thr Ala
    210                 215                 220

Val Gly Phe Ala Ala Thr Asp Gly Leu Lys Gln Val Phe Val Leu Arg
225                 230                 235                 240

Ser Gly Ala Glu Glu Gly Glu Asn Gly Val Thr Pro Gly Val Glu Val
                245                 250                 255

Val Phe Tyr Asp Lys Glu Ala Asp Met Ile Arg Asp Ala Leu Ser Val
            260                 265                 270

Ile Gly Ser Tyr Pro Phe Val Leu Thr Tyr Asn Gly Asp Asp Phe Asp
        275                 280                 285

Met Pro Tyr Met Leu Asn Arg Ala Arg Arg Leu Gly Val Ser Asp Ser
    290                 295                 300

Asp Ile Pro Leu Tyr Met Met Arg Asp Ser Ala Thr Leu Arg His Gly
305                 310                 315                 320

Val His Leu Asp Leu Tyr Arg Thr Phe Ser Asn Arg Ser Phe Gln Leu
                325                 330                 335

Tyr Ala Phe Ala Ala Lys Tyr Thr Asp Tyr Ser Leu Asn Ser Val Thr
            340                 345                 350

Lys Ala Met Leu Gly Glu Gly Lys Val Asp Tyr Gly Val Lys Leu Gly
        355                 360                 365

Asp Leu Thr Leu Tyr Gln Thr Ala Asn Tyr Cys Tyr His Asp Ala Arg
    370                 375                 380

-continued

```
Leu Thr Leu Glu Leu Ser Thr Phe Gly Asn Glu Ile Leu Met Asp Leu
385                 390                 395                 400

Leu Val Val Thr Ser Arg Ile Ala Arg Met Pro Ile Asp Asp Met Ser
                405                 410                 415

Arg Met Gly Val Ser Gln Trp Ile Arg Ser Leu Leu Tyr Tyr Glu His
            420                 425                 430

Arg Gln Arg Asn Ala Leu Ile Pro Arg Arg Asp Glu Leu Glu Gly Arg
        435                 440                 445

Ser Arg Glu Val Ser Asn Asp Ala Val Ile Lys Asp Lys Lys Phe Arg
    450                 455                 460

Gly Gly Leu Val Val Glu Pro Glu Glu Gly Ile His Phe Asp Val Thr
465                 470                 475                 480

Val Met Asp Phe Ala Ser Leu Tyr Pro Ser Ile Ile Lys Val Arg Asn
                485                 490                 495

Leu Ser Tyr Glu Thr Val Arg Cys Val His Ala Glu Cys Lys Lys Asn
            500                 505                 510

Thr Ile Pro Asp Thr Asn His Trp Val Cys Thr Lys Asn Asn Gly Leu
        515                 520                 525

Thr Ser Met Ile Ile Gly Ser Leu Arg Asp Leu Arg Val Asn Tyr Tyr
    530                 535                 540

Lys Ser Leu Ser Lys Ser Thr Ser Ile Thr Glu Glu Gln Arg Gln Gln
545                 550                 555                 560

Tyr Thr Val Ile Ser Gln Ala Leu Lys Val Val Leu Asn Ala Ser Tyr
                565                 570                 575

Gly Val Met Gly Ala Glu Ile Phe Pro Leu Tyr Phe Leu Pro Ala Ala
            580                 585                 590

Glu Ala Thr Thr Ala Val Gly Arg Tyr Ile Ile Met Gln Thr Ile Ser
        595                 600                 605

His Cys Glu Gln Met Gly Val Arg Val Leu Tyr Gly Asp Thr Asp Ser
    610                 615                 620

Leu Phe Ile Lys Asp Pro Glu Glu Arg Gln Ile His Glu Ile Val Glu
625                 630                 635                 640

His Ala Lys Lys Glu His Gly Val Glu Leu Glu Val Asp Lys Glu Tyr
                645                 650                 655

Arg Tyr Val Val Leu Ser Asn Arg Lys Lys Asn Tyr Phe Gly Val Thr
            660                 665                 670

Arg Ala Gly Lys Val Asp Val Lys Gly Leu Thr Gly Lys Lys Ser His
        675                 680                 685

Thr Pro Pro Phe Ile Lys Glu Leu Phe Tyr Ser Leu Leu Asp Ile Leu
    690                 695                 700

Ser Gly Val Glu Ser Glu Asp Glu Phe Glu Ser Ala Lys Met Arg Ile
705                 710                 715                 720

Ser Lys Ala Ile Ala Ala Cys Gly Lys Arg Leu Glu Glu Arg Gln Ile
                725                 730                 735

Pro Leu Val Asp Leu Ala Phe Asn Val Met Ile Ser Lys Ala Pro Ser
            740                 745                 750

Glu Tyr Val Lys Thr Val Pro Gln His Ile Arg Ala Ala Arg Leu Leu
        755                 760                 765

Glu Asn Ala Arg Glu Val Lys Lys Gly Asp Ile Ile Ser Tyr Val Lys
    770                 775                 780

Val Met Asn Lys Thr Gly Val Lys Pro Val Glu Met Ala Arg Ala Gly
785                 790                 795                 800

Glu Val Asp Thr Ser Lys Tyr Leu Glu Phe Met Glu Ser Thr Leu Asp
```

```
                805                 810                 815

Gln Leu Thr Ser Ser Met Gly Leu Asp Phe Asp Glu Ile Leu Gly Lys
            820                 825                 830

Pro Lys Gln Thr Gly Met Glu Gln Phe Phe Phe Lys
        835                 840


<210> SEQ ID NO 106
<211> LENGTH: 875
<212> TYPE: PRT
<213> ORGANISM: Sulfolobus acidocaldarius

<400> SEQUENCE: 106

Met Ser Lys Gln Ala Thr Leu Phe Asp Phe Ser Ile Lys Lys Asn Glu
1               5                   10                  15

Ser Lys Glu Gln Thr Asn Gln Glu Ser Val Glu Val Pro Lys Gln Thr
            20                  25                  30

Ala Asn Arg Thr Lys Ile Glu Trp Ile Lys Glu Ala Glu Asp Gly Lys
        35                  40                  45

Val Tyr Phe Leu Leu Gln Val Asp Tyr Asp Gly Lys Lys Ser Arg Ala
    50                  55                  60

Val Cys Lys Leu Tyr Asp Lys Glu Gly Lys Lys Ile Tyr Ile Met Gln
65                  70                  75                  80

Asp Glu Ser Gly His Lys Pro Tyr Phe Leu Thr Asp Ile Asp Pro Asp
                85                  90                  95

Lys Val Asn Lys Ile Thr Lys Val Val Arg Asp Pro Ser Phe Asp His
            100                 105                 110

Leu Glu Leu Ile Asn Lys Val Asp Pro Tyr Thr Gly Lys Lys Ile Arg
        115                 120                 125

Leu Thr Lys Ile Val Val Lys Asp Pro Leu Ala Val Arg Arg Met Arg
    130                 135                 140

Ser Ser Leu Pro Lys Ala Tyr Glu Ala His Ile Lys Tyr Tyr Asn Asn
145                 150                 155                 160

Tyr Val Tyr Asp Asn Gly Leu Ile Pro Gly Leu Ile Tyr Lys Val Asn
                165                 170                 175

Lys Gly Lys Leu Thr Gln Leu Asn Pro Glu Leu Lys Gly Glu Glu Ile
            180                 185                 190

Asn Glu Ile Lys Lys Leu Ser Asp Ala Tyr Glu Met Thr Lys Glu Thr
        195                 200                 205

Val Asn Asp Trp Ile Pro Ile Leu Glu Thr Glu Val Pro Asp Ile Lys
    210                 215                 220

Arg Val Ser Leu Asp Ile Glu Val Tyr Thr Pro Asn Arg Gly Arg Ile
225                 230                 235                 240

Pro Asp Pro Glu Arg Ala Glu Phe Pro Ile Ile Ser Val Ala Leu Ala
                245                 250                 255

Gly Asn Asp Gly Ser Lys Ile Val Leu Ala Leu Lys Arg Glu Asp Val
            260                 265                 270

Asn Ser Asp Phe Ser Lys Lys Asp Gly Val Gln Val Glu Ile Phe Asp
        275                 280                 285

Ser Glu Lys Lys Leu Leu Ala Arg Leu Phe Glu Ile Ile Arg Glu Tyr
    290                 295                 300

Pro Met Leu Leu Thr Phe Asn Gly Asp Asp Phe Asp Ile Pro Tyr Ile
305                 310                 315                 320

Tyr Phe Arg Ala Leu Arg Leu Asn Phe Ser Pro Glu Glu Val Pro Leu
                325                 330                 335

Asp Val Val Ser Gly Glu Gly Lys Phe Leu Ala Gly Ile His Ile Asp
```

-continued

```
            340                 345                 350

Leu Tyr Lys Phe Phe Phe Asn Arg Ala Val Ser Ile Tyr Ala Phe Glu
        355                 360                 365

Gly Lys Tyr Ser Glu Tyr Ser Leu Tyr Ala Val Ala Thr Ala Leu Leu
    370                 375                 380

Gly Ile Ser Lys Val Lys Leu Asp Thr Phe Ile Ser Phe Met Asp Ile
385                 390                 395                 400

Asp Lys Leu Ile Glu Tyr Asn Leu Arg Asp Ala Glu Ile Thr Leu Lys
                405                 410                 415

Leu Thr Thr Phe Asn Asn Asn Leu Val Leu Lys Leu Met Val Leu Leu
            420                 425                 430

Ala Arg Ile Ser Lys Leu Gly Leu Glu Glu Leu Thr Arg Thr Glu Val
        435                 440                 445

Ser Thr Trp Ile Lys Asn Leu Tyr Tyr Trp Glu His Arg Lys Arg Asn
    450                 455                 460

Trp Leu Ile Pro Leu Lys Glu Glu Ile Leu Val Arg Ser Asn Gln Val
465                 470                 475                 480

Lys Thr Ala Ala Val Ile Lys Gly Lys Lys Tyr Lys Gly Ala Val Val
                485                 490                 495

Ile Asp Pro Pro Ala Gly Val Tyr Phe Asn Val Val Val Leu Asp Phe
            500                 505                 510

Ala Ser Leu Tyr Pro Ser Ile Ile Lys Asn Trp Asn Ile Ser Tyr Glu
        515                 520                 525

Thr Ile Glu Ile Asp Glu Cys Thr Lys Lys Val Trp Val Glu Asp Glu
    530                 535                 540

Thr Gly Glu Lys Leu His Tyr Val Cys Met Asp Lys Pro Gly Ile Thr
545                 550                 555                 560

Ala Val Tyr Gln Gly Leu Ile Arg Asp Phe Arg Val Lys Val Tyr Lys
                565                 570                 575

Lys Lys Ala Lys Tyr Ser Asn Ile Ser Glu Glu Gln Arg Ser Leu Tyr
            580                 585                 590

Asp Val Val Gln Arg Ala Met Lys Val Phe Ile Asn Ala Thr Tyr Gly
        595                 600                 605

Val Phe Gly Ala Glu Asn Phe Pro Leu Tyr Ala Pro Ala Val Ala Glu
    610                 615                 620

Ser Val Thr Ala Ile Gly Arg Tyr Ile Ile Thr Thr Thr Tyr Lys Gln
625                 630                 635                 640

Ala Glu Lys Leu Asn Leu Lys Val Ile Tyr Gly Asp Thr Asp Ser Leu
                645                 650                 655

Phe Leu Tyr Asn Pro Thr Lys Asp Lys Leu Glu Glu Leu Ile Lys Phe
            660                 665                 670

Val Lys Gln Asn Phe Asn Leu Asp Leu Glu Val Asp Asn Thr Tyr Lys
        675                 680                 685

Tyr Val Ala Tyr Ser Gly Leu Lys Lys Asn Tyr Phe Gly Val Tyr Pro
    690                 695                 700

Asp Gly Lys Thr Glu Ile Lys Gly Met Leu Ala Lys Lys Arg Asn Thr
705                 710                 715                 720

Pro Glu Phe Ile Lys Lys Glu Phe Ala Glu Ile Lys Asn Met Leu Ala
                725                 730                 735

Ser Leu Asn Ser Pro Asn Asp Ile Pro Glu Val Lys Asn Lys Leu Glu
            740                 745                 750

Ile Lys Ile Lys Asp Ile Tyr Tyr Lys Leu Arg Asn Lys Gly Tyr Asn
        755                 760                 765
```

Leu Asp Asp Leu Ala Phe Arg Ile Met Leu Ser Lys Pro Leu Asp Ser
    770                 775                 780

Tyr Thr Lys Asn Thr Pro Gln His Val Lys Ala Gly Leu Gln Leu Arg
785                 790                 795                 800

Ala Phe Gly Val Asn Val Leu Pro Arg Asp Val Ile Met Phe Val Lys
                805                 810                 815

Val Lys Ser Lys Asp Gly Val Lys Ala Tyr Gln Leu Ala Lys Ile Ser
            820                 825                 830

Glu Ile Asp Ile Glu Lys Tyr Val Glu Thr Leu Arg Thr Thr Phe Glu
        835                 840                 845

Gln Ile Leu Lys Ala Phe Gly Ile Ser Trp Asp Glu Ile Val Ser Thr
    850                 855                 860

Ile Ser Ile Asp Ser Phe Phe Gly Ser Lys Lys
865                 870                 875

<210> SEQ ID NO 107
<211> LENGTH: 872
<212> TYPE: PRT
<213> ORGANISM: Sulfurisphaera ohwakuensis

<400> SEQUENCE: 107

Met Ala Arg Gln Ile Thr Leu Phe Asp Phe Thr Leu Lys Lys Glu Gln
1               5                   10                  15

Asn Lys Asp Glu Ser Arg Lys Glu Glu Ile Pro His Ala Asn Ile Asn
            20                  25                  30

Glu Glu Arg Arg Lys Pro Lys Glu Trp Ile Lys Glu Ala Glu Glu Gly
        35                  40                  45

Lys Ser Tyr Phe Leu Leu Gln Val Asp Tyr Asp Gly Lys Lys Ser Lys
    50                  55                  60

Ala Ile Cys Lys Leu Tyr Asp Lys Glu Thr Lys Lys Ile Tyr Ile Leu
65                  70                  75                  80

Tyr Asp Asn Thr Gly His Lys Pro Tyr Phe Leu Thr Asp Ile Asp Pro
                85                  90                  95

Glu Lys Val Asn Lys Ile Pro Lys Val Val Arg Asp Pro Ser Phe Asp
            100                 105                 110

His Leu Glu Thr Val Ile Lys Ile Asp Pro Tyr Ser Gly Asn Lys Ile
        115                 120                 125

Lys Leu Thr Lys Ile Val Val Lys Asp Pro Leu Ala Val Arg Arg Met
    130                 135                 140

Arg Asn Ser Val Pro Lys Ala Tyr Glu Ala His Ile Lys Tyr Phe Asn
145                 150                 155                 160

Asn Tyr Ile Tyr Asp Leu Gly Leu Ile Pro Gly Leu Pro Tyr Val Val
                165                 170                 175

Lys Lys Gly Lys Leu Glu Gln Leu Arg Pro Glu Leu Lys Gly Glu Glu
            180                 185                 190

Val Asp Glu Ile Arg Lys Ala Phe Ala Asp Ser Asp Glu Met Thr Lys
        195                 200                 205

Glu Ala Val Asn Asp Trp Ile Pro Ile Phe Glu Ser Glu Val Pro Asp
    210                 215                 220

Val Lys Arg Val Ala Ile Asp Ile Glu Val Tyr Thr Pro Ile Lys Gly
225                 230                 235                 240

Arg Ile Pro Asp Pro Glu Lys Ala Glu Phe Pro Ile Ile Ser Ile Ser
                245                 250                 255

Leu Ala Gly Asn Asp Gly Thr Lys Arg Val Leu Val Leu Leu Arg Glu
            260                 265                 270

-continued

```
Asp Val Asn Ser Gln Ile Thr Lys His Asp Val Ile Val Glu Thr Phe
        275                 280                 285

Lys Ser Glu Arg Glu Leu Ile Arg Arg Phe Phe Asp Ile Ile Leu Asp
    290                 295                 300

Tyr Pro Ile Ile Leu Thr Phe Asn Gly Asp Asp Phe Asp Ile Pro Tyr
305                 310                 315                 320

Ile Tyr Tyr Arg Ala Leu Lys Leu Asn Phe Thr Pro Glu Glu Ile Pro
                325                 330                 335

Phe Asp Ile Ile Asn Asp Glu Gly Lys Tyr Leu Ala Gly Ile His Ile
            340                 345                 350

Asp Leu Tyr Lys Phe Phe Phe Asn Arg Ala Ile Arg Asn Tyr Ala Phe
        355                 360                 365

Glu Gly Lys Tyr Asn Glu Tyr Asn Leu Asp Ala Val Ala Thr Ala Leu
    370                 375                 380

Leu Gly Met Ser Lys Val Lys Leu Asp Thr Leu Ile Ser Phe Leu Asp
385                 390                 395                 400

Leu Asp Lys Leu Ile Glu Tyr Asn Ser Arg Asp Ala Glu Ile Thr Leu
                405                 410                 415

Lys Leu Thr Thr Phe Asn Asn Asn Leu Val Trp Lys Leu Ile Ile Leu
            420                 425                 430

Leu Ala Arg Ile Ser Lys Met Gly Leu Glu Glu Leu Thr Arg Thr Glu
        435                 440                 445

Val Ser Thr Trp Ile Lys Asn Leu Tyr Tyr Trp Glu His Arg Arg Arg
    450                 455                 460

Asn Trp Leu Ile Pro Leu Lys Glu Glu Ile Leu Thr Arg Ser Ser Gln
465                 470                 475                 480

Ile Lys Thr Ala Ala Ile Ile Lys Gly Lys Arg Tyr Lys Gly Ala Val
                485                 490                 495

Val Ile Asp Pro Pro Ala Gly Val Phe Phe Asn Val Val Val Leu Asp
            500                 505                 510

Phe Ala Ser Leu Tyr Pro Ser Ile Ile Arg Asn Trp Asn Ile Ser Tyr
        515                 520                 525

Glu Thr Val Asp Val Glu Asn Cys Lys Asn Lys Glu Tyr Val Arg Asp
    530                 535                 540

Glu Thr Gly Glu Val Leu His Tyr Ile Cys Lys Asp Lys Pro Gly Ile
545                 550                 555                 560

Thr Ala Val Ile Thr Gly Leu Leu Arg Asp Phe Arg Val Lys Val Tyr
                565                 570                 575

Lys Lys Lys Ala Lys Ser Gln Asn Ile Ser Glu Glu Gln Arg Ser Val
            580                 585                 590

Tyr Asp Val Val Gln Arg Ala Met Lys Val Phe Ile Asn Ala Thr Tyr
        595                 600                 605

Gly Val Phe Gly Ala Glu Asn Phe Pro Leu Tyr Ala Pro Ala Val Ala
    610                 615                 620

Glu Ser Val Thr Ala Ile Gly Arg Tyr Val Ile Thr Thr Thr Val Asn
625                 630                 635                 640

Tyr Cys Arg Ser Ile Gly Leu Gln Val Leu Tyr Gly Asp Thr Asp Ser
                645                 650                 655

Met Phe Leu Trp Asn Pro Ser Lys Glu Lys Leu Glu Glu Ile Ile Lys
            660                 665                 670

Phe Val Lys Gly Lys Phe Gly Leu Asp Leu Glu Val Asp Lys Val Tyr
        675                 680                 685

Lys Phe Val Ala Phe Ser Gly Leu Lys Lys Asn Tyr Leu Gly Val Tyr
    690                 695                 700
```

Pro Asp Gly Lys Thr Asp Ile Lys Gly Met Leu Ala Lys Lys Arg Asn
705 710 715 720

Thr Pro Glu Phe Ile Lys Lys Glu Phe Asn Glu Val Lys Gln Leu Val
725 730 735

Thr Thr Ile Asn Ser Pro Asp Asp Ile Pro Lys Ile Arg Asp Gln Leu
740 745 750

Glu Tyr Lys Ile Lys Glu Ile Tyr Glu Lys Leu Arg His Lys Gly Tyr
755 760 765

Asn Leu Asp Glu Leu Ala Phe Arg Val Met Leu Ser Lys Pro Leu Glu
770 775 780

Ser Tyr Thr Lys Asn Thr Pro Gln His Val Lys Ala Ala Leu Gln Leu
785 790 795 800

Arg Ser Tyr Gly Val Met Val Leu Pro Arg Asp Ile Ile Met Phe Val
805 810 815

Lys Val Lys Ser Lys Asp Gly Val Lys Pro Val Gln Leu Ala Lys Leu
820 825 830

Ser Glu Ile Asp Val Asp Lys Tyr Ile Asp Ala Val Arg Ser Thr Phe
835 840 845

Glu Gln Ile Leu Lys Ala Phe Gly Leu Ile Gly Ala Asn Leu Leu Gln
850 855 860

Leu Leu Ser Ile Leu Ser Leu Thr
865 870

<210> SEQ ID NO 108
<211> LENGTH: 882
<212> TYPE: PRT
<213> ORGANISM: Sulfolobus solfataricus

<400> SEQUENCE: 108

Met Thr Lys Gln Leu Thr Leu Phe Asp Ile Pro Ser Ser Lys Pro Ala
1 5 10 15

Lys Ser Glu Gln Asn Thr Gln Gln Ser Gln Gln Ser Ala Pro Val Glu
20 25 30

Glu Lys Lys Val Val Arg Arg Glu Trp Leu Glu Glu Ala Gln Glu Asn
35 40 45

Lys Ile Tyr Phe Leu Leu Gln Val Asp Tyr Asp Gly Lys Lys Gly Lys
50 55 60

Ala Val Cys Lys Leu Phe Asp Lys Glu Thr Gln Lys Ile Tyr Ala Leu
65 70 75 80

Tyr Asp Asn Thr Gly His Lys Pro Tyr Phe Leu Val Asp Leu Glu Pro
85 90 95

Asp Lys Val Gly Lys Ile Pro Lys Ile Val Arg Asp Pro Ser Phe Asp
100 105 110

His Ile Glu Thr Val Ser Lys Ile Asp Pro Tyr Thr Trp Asn Lys Phe
115 120 125

Lys Leu Thr Lys Ile Val Val Arg Asp Pro Leu Ala Val Arg Arg Leu
130 135 140

Arg Asn Asp Val Pro Lys Ala Tyr Glu Ala His Ile Lys Tyr Phe Asn
145 150 155 160

Asn Tyr Met Tyr Asp Ile Gly Leu Ile Pro Gly Met Pro Tyr Val Val
165 170 175

Lys Asn Gly Lys Leu Glu Ser Val Tyr Leu Ser Leu Asp Glu Lys Asp
180 185 190

Val Glu Glu Ile Lys Lys Ala Phe Ala Asp Ser Asp Glu Met Thr Arg
195 200 205

```
Gln Met Ala Val Asp Trp Leu Pro Ile Phe Glu Thr Glu Ile Pro Lys
    210                 215                 220

Ile Lys Arg Val Ala Ile Asp Ile Glu Val Tyr Thr Pro Val Lys Gly
225                 230                 235                 240

Arg Ile Pro Asp Ser Gln Lys Ala Glu Phe Pro Ile Ile Ser Ile Ala
                245                 250                 255

Leu Ala Gly Ser Asp Gly Leu Lys Lys Val Leu Val Leu Asn Arg Asn
            260                 265                 270

Asp Val Asn Glu Gly Ser Val Lys Leu Asp Gly Ile Ser Val Glu Arg
        275                 280                 285

Phe Asn Thr Glu Tyr Glu Leu Leu Gly Arg Phe Phe Asp Ile Leu Leu
    290                 295                 300

Glu Tyr Pro Ile Val Leu Thr Phe Asn Gly Asp Asp Phe Asp Leu Pro
305                 310                 315                 320

Tyr Ile Tyr Phe Arg Ala Leu Lys Leu Gly Tyr Phe Pro Glu Glu Ile
                325                 330                 335

Pro Ile Asp Val Ala Gly Lys Asp Glu Ala Lys Tyr Leu Ala Gly Leu
            340                 345                 350

His Ile Asp Leu Tyr Lys Phe Phe Phe Asn Lys Ala Val Arg Asn Tyr
        355                 360                 365

Ala Phe Glu Gly Lys Tyr Asn Glu Tyr Asn Leu Asp Ala Val Ala Lys
    370                 375                 380

Ala Leu Leu Gly Thr Ser Lys Val Lys Val Asp Thr Leu Ile Ser Phe
385                 390                 395                 400

Leu Asp Val Glu Lys Leu Ile Glu Tyr Asn Phe Arg Asp Ala Glu Ile
                405                 410                 415

Thr Leu Gln Leu Thr Thr Phe Asn Asn Asp Leu Thr Met Lys Leu Ile
            420                 425                 430

Val Leu Phe Ser Arg Ile Ser Arg Leu Gly Ile Glu Glu Leu Thr Arg
        435                 440                 445

Thr Glu Ile Ser Thr Trp Val Lys Asn Leu Tyr Tyr Trp Glu His Arg
    450                 455                 460

Lys Arg Asn Trp Leu Ile Pro Leu Lys Glu Glu Ile Leu Ala Lys Ser
465                 470                 475                 480

Ser Asn Ile Arg Thr Ser Ala Leu Ile Lys Gly Lys Gly Tyr Lys Gly
                485                 490                 495

Ala Val Val Ile Asp Pro Pro Ala Gly Ile Phe Phe Asn Ile Thr Val
            500                 505                 510

Leu Asp Phe Ala Ser Leu Tyr Pro Ser Ile Ile Arg Thr Trp Asn Leu
        515                 520                 525

Ser Tyr Glu Thr Val Asp Ile Gln Gln Cys Lys Lys Pro Tyr Glu Val
    530                 535                 540

Lys Asp Glu Thr Gly Glu Val Leu His Ile Val Cys Met Asp Arg Pro
545                 550                 555                 560

Gly Ile Thr Ala Val Ile Thr Gly Leu Leu Arg Asp Phe Arg Val Lys
                565                 570                 575

Ile Tyr Lys Lys Lys Ala Lys Asn Pro Asn Asn Ser Glu Glu Gln Lys
            580                 585                 590

Leu Leu Tyr Asp Val Val Gln Arg Ala Met Lys Val Phe Ile Asn Ala
        595                 600                 605

Thr Tyr Gly Val Phe Gly Ala Glu Thr Phe Pro Leu Tyr Ala Pro Ala
    610                 615                 620

Val Ala Glu Ser Val Thr Ala Leu Gly Arg Tyr Val Ile Thr Ser Thr
```

-continued

```
625                 630                 635                 640

Val Lys Lys Ala Arg Glu Glu Gly Leu Thr Val Leu Tyr Gly Asp Thr
                645                 650                 655

Asp Ser Leu Phe Leu Leu Asn Pro Pro Lys Asn Ser Leu Glu Asn Ile
            660                 665                 670

Ile Lys Trp Val Lys Thr Thr Phe Asn Leu Asp Leu Glu Val Asp Lys
        675                 680                 685

Thr Tyr Lys Phe Val Ala Phe Ser Gly Leu Lys Lys Asn Tyr Phe Gly
    690                 695                 700

Val Tyr Gln Asp Gly Lys Val Asp Ile Lys Gly Met Leu Val Lys Lys
705                 710                 715                 720

Arg Asn Thr Pro Glu Phe Val Lys Lys Val Phe Asn Glu Val Lys Glu
                725                 730                 735

Leu Met Ile Ser Ile Asn Ser Pro Asn Asp Val Lys Glu Ile Lys Arg
            740                 745                 750

Lys Ile Val Asp Val Val Lys Gly Ser Tyr Glu Lys Leu Lys Asn Lys
        755                 760                 765

Gly Tyr Asn Leu Asp Glu Leu Ala Phe Lys Val Met Leu Ser Lys Pro
    770                 775                 780

Leu Asp Ala Tyr Lys Lys Asn Thr Pro Gln His Val Lys Ala Ala Leu
785                 790                 795                 800

Gln Leu Arg Pro Phe Gly Val Asn Val Leu Pro Arg Asp Ile Ile Tyr
                805                 810                 815

Tyr Val Lys Val Arg Ser Lys Asp Gly Val Lys Pro Val Gln Leu Ala
            820                 825                 830

Lys Val Thr Glu Ile Asp Ala Glu Lys Tyr Leu Glu Ala Leu Arg Ser
        835                 840                 845

Thr Phe Glu Gln Ile Leu Arg Ala Phe Gly Val Ser Trp Asp Glu Ile
    850                 855                 860

Ala Ala Thr Met Ser Ile Asp Ser Phe Phe Ser Tyr Pro Ser Lys Gly
865                 870                 875                 880

Asn Ser


<210> SEQ ID NO 109
<211> LENGTH: 30
<212> TYPE: DNA
<213> ORGANISM: Artificial
<220> FEATURE:
<223> OTHER INFORMATION: PCR primer

<400> SEQUENCE: 109

gggaaacata tgatccttga cgttgattac                                        30


<210> SEQ ID NO 110
<211> LENGTH: 31
<212> TYPE: DNA
<213> ORGANISM: Artificial
<220> FEATURE:
<223> OTHER INFORMATION: PCR primer

<400> SEQUENCE: 110

gggaaaggat cctcacttct tcttcccctt c                                      31
```